(12) United States Patent
Li et al.

(10) Patent No.: US 10,177,323 B2
(45) Date of Patent: Jan. 8, 2019

(54) TETRADENTATE PLATINUM (II) AND PALLADIUM (II) COMPLEXES AND OCTAHEDRAL IRIDIUM COMPLEXES EMPLOYING AZEPINE FUNCTIONAL GROUPS AND THEIR ANALOGUES

(71) Applicant: Arizona Board of Regents on behalf of Arizona State University, Scottsdale, AZ (US)

(72) Inventors: Jian Li, Tempe, AZ (US); Zhi-Qiang Zhu, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/625,082

(22) Filed: Jun. 16, 2017

(65) Prior Publication Data
US 2018/0053904 A1 Feb. 22, 2018

Related U.S. Application Data

(60) Provisional application No. 62/377,883, filed on Aug. 22, 2016, provisional application No. 62/377,884, filed on Aug. 22, 2016.

(51) Int. Cl.
*C09K 11/06* (2006.01)
*H01L 51/00* (2006.01)
(Continued)

(52) U.S. Cl.
CPC ........ *H01L 51/0087* (2013.01); *C07F 15/006* (2013.01); *C07F 15/0033* (2013.01);
(Continued)

(58) Field of Classification Search
CPC .................................................... H01L 51/87
See application file for complete search history.

(56) References Cited

U.S. PATENT DOCUMENTS 4,769,292 A 9/1988 Tang et al.
5,707,745 A 1/1998 Forrest et al.
(Continued)

FOREIGN PATENT DOCUMENTS

CN 1680366 A 10/2005
CN 1777663 5/2006
(Continued)

OTHER PUBLICATIONS

Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligans," Helvetica Chimica Acta, vol. 71, Issue 5, Aug. 10, 1988, pp. 1053-1059.

U.S. Appl. No. 61/945,940, filed Feb. 28, 2014, Jian Li, Chiral Metal Complexes As Emitters for Organic Polarized Electroluminescent Devices.

U.S. Appl. No. 15/119,961, filed Aug. 18, 2016, Jian Li, Chiral Metal Complexes As Emitters for Organic Polarized Electroluminescent Devices.

(Continued)

*Primary Examiner* — Paul V Ward
(74) *Attorney, Agent, or Firm* — Fish & Richardson P.C.

(57) ABSTRACT

Platinum (II) and palladium (II) complexes of Formulas A and B and iridium (III) complexes of Formula C having azepine functional groups and their analogs as emitters for full color displays and lighting applications.

10 Claims, 1 Drawing Sheet

Formula A

Formula B

Formula C

(51) Int. Cl.
  *C07F 15/00* (2006.01)
  *H05B 33/14* (2006.01)
  *H01L 51/50* (2006.01)
  *H01L 51/42* (2006.01)
(52) U.S. Cl.
  CPC .......... *C07F 15/0086* (2013.01); *C09K 11/06* (2013.01); *H01L 51/0084* (2013.01); *H01L 51/0085* (2013.01); *H05B 33/14* (2013.01); *C09K 2211/1022* (2013.01); *C09K 2211/1044* (2013.01); *C09K 2211/185* (2013.01); *H01L 51/42* (2013.01); *H01L 51/5016* (2013.01)

(56) References Cited

U.S. PATENT DOCUMENTS

| | | |
|---|---|---|
| 5,844,363 A | 12/1998 | Gu et al. |
| 6,200,695 B1 | 3/2001 | Arai |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,064,228 B1 | 6/2006 | Yu et al. |
| 7,268,485 B2 | 9/2007 | Tyan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,854,513 B2 | 12/2010 | Quach |
| 7,947,383 B2 | 5/2011 | Ise et al. |
| 8,133,597 B2 | 3/2012 | Yasukawa et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,221,857 B2 | 12/2015 | Li et al. |
| 9,224,963 B2 | 12/2015 | Li et al. |
| 9,238,668 B2 | 1/2016 | Li et al. |
| 9,312,502 B2 | 4/2016 | Li et al. |
| 9,312,505 B2 | 4/2016 | Brooks et al. |
| 9,318,725 B2 | 4/2016 | Li |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,461,254 B2 | 10/2016 | Tsai |
| 9,550,801 B2 | 1/2017 | Li et al. |
| 9,617,291 B2 | 4/2017 | Li et al. |
| 9,673,409 B2 | 6/2017 | Li |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,818,959 B2 | 11/2017 | Li |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li et al. |
| 2001/0019782 A1 | 9/2001 | Iqarashi et al. |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2004/0230061 A1 | 11/2004 | Seo et al. |
| 2005/0170207 A1 | 8/2005 | Ma et al. |
| 2005/0260446 A1 | 11/2005 | Mackenzie et al. |
| 2006/0024522 A1 | 2/2006 | Thompson |
| 2006/0073359 A1 | 4/2006 | Ise et al. |
| 2006/0094875 A1 | 5/2006 | Itoh et al. |
| 2006/0127696 A1 | 6/2006 | Stossel et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0255721 A1 | 11/2006 | Igarashi et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0153045 A1 | 6/2009 | Kinoshita |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0141127 A1 | 6/2010 | Xia et al. |
| 2010/0171111 A1 | 7/2010 | Takada et al. |
| 2010/0171418 A1 | 7/2010 | Kinoshita et al. |
| 2010/0270540 A1 | 10/2010 | Chung et al. |
| 2011/0049496 A1 | 3/2011 | Fukuzaki |
| 2011/0062858 A1 | 3/2011 | Yersin et al. |
| 2011/0227058 A1 | 9/2011 | Masui |
| 2012/0095232 A1 | 4/2012 | Li et al. |
| 2012/0181528 A1 | 7/2012 | Takada et al. |
| 2012/0199823 A1 | 8/2012 | Molt et al. |
| 2012/0215001 A1 | 8/2012 | Li et al. |
| 2012/0223634 A1 | 9/2012 | Xia et al. |
| 2012/0264938 A1 | 10/2012 | Li et al. |
| 2012/0273736 A1 | 11/2012 | James et al. |
| 2012/0302753 A1 | 11/2012 | Li |
| 2013/0048963 A1 | 2/2013 | Beers et al. |
| 2013/0082245 A1 | 4/2013 | Kottas |
| 2013/0168656 A1 | 7/2013 | Tsai et al. |
| 2013/0172561 A1 | 7/2013 | Tsai |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li |
| 2015/0349279 A1* | 12/2015 | Li ................... H01L 51/0087 252/301.16 |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197285 A1 | 7/2016 | Zeng et al. |
| 2016/0197291 A1 | 7/2016 | Xia et al. |
| 2016/0285015 A1 | 9/2016 | Li et al. |

(56) References Cited

U.S. PATENT DOCUMENTS

| | | |
|---|---|---|
| 2016/0359120 A1 | 12/2016 | Li |
| 2016/0359125 A1 | 12/2016 | Li |
| 2017/0005278 A1 | 1/2017 | Li et al. |
| 2017/0012224 A1 | 1/2017 | Li et al. |
| 2017/0040555 A1 | 2/2017 | Li et al. |
| 2017/0047533 A1 | 2/2017 | Li et al. |
| 2017/0066792 A1 | 3/2017 | Li et al. |
| 2017/0069855 A1 | 3/2017 | Li et al. |
| 2017/0267923 A1 | 9/2017 | Li |
| 2017/0271611 A1 | 9/2017 | Li et al. |
| 2017/0301871 A1 | 10/2017 | Li |
| 2017/0305881 A1 | 10/2017 | Li et al. |
| 2017/0331056 A1 | 11/2017 | Li et al. |
| 2017/0373260 A1 | 12/2017 | Li |
| 2018/0006246 A1 | 1/2018 | Li |

FOREIGN PATENT DOCUMENTS

| | | |
|---|---|---|
| CN | 1894269 | 1/2007 |
| CN | 101667626 | 3/2010 |
| CN | 102449108 A | 5/2012 |
| CN | 102892860 | 1/2013 |
| CN | 102971396 | 3/2013 |
| CN | 103102372 | 5/2013 |
| CN | 104232076 | 12/2014 |
| CN | 104377231 | 2/2015 |
| CN | 104693243 | 6/2015 |
| CN | 105367605 | 3/2016 |
| CN | 105418591 | 3/2016 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2002105055 A | 4/2002 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 A | 2/2007 |
| JP | 2007042875 | 2/2007 |
| JP | 2007051243 A1 | 3/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007099765 A | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 A | 4/2009 |
| JP | 2009161524 A1 | 7/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2010171205 A1 | 8/2010 |
| JP | 2011071452 A1 | 4/2011 |
| JP | 2012079895 A1 | 4/2012 |
| JP | 2012079898 A1 | 4/2012 |
| JP | 2012222255 | 11/2012 |
| JP | 2012231135 A1 | 11/2012 |
| JP | 2013023500 A1 | 2/2013 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| KR | 101338250 | 12/2013 |
| TW | 200701835 | 1/2007 |
| TW | 201307365 | 2/2013 |
| TW | 201710277 | 3/2017 |
| WO | WO2008054578 | 5/2000 |
| WO | WO2000070655 | 11/2000 |
| WO | WO2004003108 | 1/2004 |
| WO | WO2004085450 | 10/2004 |
| WO | WO2004108857 | 12/2004 |
| WO | WO2005042444 | 5/2005 |
| WO | WO2005042550 | 5/2005 |
| WO | WO2005113704 | 12/2005 |
| WO | WO2006033440 | 3/2006 |
| WO | WO2006067074 | 6/2006 |
| WO | WO2006098505 | 9/2006 |
| WO | WO2006113106 | 10/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008101842 | 8/2008 |
| WO | WO2008117889 | 10/2008 |
| WO | WO2008123540 | 10/2008 |
| WO | WO2009017211 | 2/2009 |
| WO | WO2009023667 | 2/2009 |
| WO | WO2010007098 | 1/2010 |
| WO | WO2010056669 | 5/2010 |
| WO | WO2010093176 | 8/2010 |
| WO | WO2010118026 | 10/2010 |
| WO | WO2011064335 | 6/2011 |
| WO | WO2011070989 | 6/2011 |
| WO | WO2011089163 | 7/2011 |
| WO | WO2011137429 | 11/2011 |
| WO | WO2011137431 | 11/2011 |
| WO | WO2012112853 | 8/2012 |
| WO | WO2012116231 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 | 1/2014 |
| WO | WO2014031977 | 2/2014 |
| WO | WO2014047616 | 3/2014 |
| WO | WO2014109814 | 7/2014 |
| WO | WO2014208271 | 12/2014 |

(56) References Cited

FOREIGN PATENT DOCUMENTS

| WO | WO2015027060 | 2/2015 |
|---|---|---|
| WO | WO2015131158 | 9/2015 |
| WO | WO2016025921 | 2/2016 |
| WO | WO2016029137 | 2/2016 |
| WO | WO2016029186 | 2/2016 |
| WO | WO2016197019 | 12/2016 |

OTHER PUBLICATIONS

U.S. Appl. No. 62/037,802, filed Aug. 15, 2014, Jian Li, Liang Huang, Tyler Fleetham, Non-Platinum Metal Complexes for Excimer Based Single Dopant White Organic Light Emitting Diodes.

U.S. Appl. No. 15/503,690, filed Feb. 13, 2017, Jian Li, Liang Huang, Tyler Fleetham, Non-Platinum Metal Complexes for Excimer Based Single Dopant White Organic Light Emitting Diodes.

U.S. Appl. No. 62/040,470, filed Aug. 22, 2014, Jian Li, Tyler Fleetham, Organic Light-Emitting Diodes With Fluorescent and Phosphorescent Emitters.

U.S. Appl. No. 15/505,527, filed Feb. 21, 2017, Jian Li, Tyler Fleetham, Organic Light-Emitting Diodes With Fluorescent and Phosphorescent Emitters.

U.S. Appl. No. 62/040,727, filed Aug. 22, 2014, Jian Li, Metal-Assisted Delayed Fluorescent Materials As Co-Host Materials for Fluorescent OLEDs.

U.S. Appl. No. 15/505,544, filed Feb. 21, 2017, Jian Li, Metal-Assisted Delayed Fluorescent Materials As Co-Host Materials for Fluorescent OLEDs.

U.S. Appl. No. 62/050,243, filed Sep. 15, 2014, C. Austen Angell, Leigang Xue, Ionic Liquid Catholyte.

U.S. Appl. No. 62/138,710, filed Mar. 26, 2015, Charles Austen Angell, Leigang Xue, Ionic Liquid Catholytes and Electrochemical Devices Containing Same.

U.S. Appl. No. 15/508,032, filed Mar. 1, 2017, Charles Austen Angell, Leigang Xue, Ionic Liquid Catholytes and Electrochemical Devices Containing Same.

U.S. Appl. No. 62/170,809, filed Jun. 4, 2015, Jian Li, Transparent Electroluminescent Devices With Controlled One-Side Emissive Displays.

U.S. Appl. No. 15/577,655, filed Nov. 28, 2017, Jian Li, Transparent Electroluminescent Devices With Controlled One-Side Emissive Displays.

U.S. Appl. No. 62/323,383, filed Apr. 15, 2016, Jian Li, OLED With Doped Electron Blocking Layer.

U.S. Appl. No. 62/377,747, filed Aug. 22, 2016, Jian Li, OLED With Multi-Emissive Material Layer.

U.S. Appl. No. 62/407,020, filed Oct. 12, 2016, Jian Li, Qunbo Mei, Narrow Band Red Phosphorescent Tetradentate Platinum (II) Complexes.

U.S. Appl. No. 62/435,455, filed Dec. 16, 2016, Jian Li, Kody George Klimes, Organic Light Emitting Diode With Split Emissive Layer.

U.S. Appl. No. 14/437,963, filed Apr. 23, 2015, Eric Turner, Jian Li, Metal Complexes, Methods, and Uses Thereof.

U.S. Appl. No. 15/905,385, filed Feb. 26, 2018, Eric Turner, Jian Li, Metal Complexes, Methods, and Uses Thereof.

U.S. Appl. No. 61/166,901, filed Apr. 6, 2009, Eric Turner, Jian Li, Zixing Wang, Synthesis of Four Coordinated Platinum Complexes and Their Applications in Light Emitting Devices Thereof.

U.S. Appl. No. 13/263,096, filed Jan. 3, 2014, Eric Turner, Jian Li, Zixing Wang, Synthesis of Four Coordinated Platinum Complexes and Their Applications in Light Emitting Devices Thereof.

U.S. Appl. No. 14/611,654, filed Feb. 2, 2015, Eric Turner, Jian Li, Zixing Wang, Synthesis of Four Coordinated Platinum Complexes and Their Applications in Light Emitting Devices Thereof.

U.S. Appl. No. 61/329,687, filed Apr. 30, 2010, Eric Turner, Jian Li, Synthesis of Four Coordinated Gold Complexes and Their Applications in Light Emitting Devices Thereof.

U.S. Appl. No. 13/695,338, filed May 16, 2013, Eric Turner, Jian Li, Synthesis of Four Coordinated Gold Complexes and Their Applications in Light Emitting Devices Thereof.

U.S. Appl. No. 61/913,552, filed Dec. 9, 2013, Jian Li, Guijie Li, Stable Emitters.

U.S. Appl. No. 61/969,729, filed Mar. 24, 2014, Jian Li, Guijie Li, Efficient Pure Blue OLEDs Employing Tetradentate Pt Complexes with Narrow Spectral Bandwidth.

U.S. Appl. No. 62/021,488, filed Jul. 7, 2014, Jian Li, Guijie Li, Stable and Efficient Platinum Complexes as Red Phosphorescent Emitters.

U.S. Appl. No. 14/562,195, filed Dec. 5, 2014, Jian Li, Guijie Li, Stable Emitters.

U.S. Appl. No. 61/329,684, filed Apr. 30, 2010, Eric Turner, Jian Li, Synthesis of Four Coordinated Palladium Complexes and Their Applications in Light Emitting Devices Thereof.

U.S. Appl. No. 13/695,337, filed Mar. 13, 2013, Eric Turner, Jian Li, Synthesis of Four Coordinated Palladium Complexes and Their Applications in Light Emitting Devices Thereof.

U.S. Appl. No. 14/145,461, filed Dec. 31, 2013, Eric Turner, Jian Li, Synthesis of Four Coordinated Palladium Complexes and Their Applications in Light Emitting Devices Thereof.

U.S. Appl. No. 15/202,058, filed Jul. 5, 2016, Eric Turner, Jian Li, Synthesis of Four Coordinated Palladium Complexes and Their Applications in Light Emitting Devices Thereof.

U.S. Appl. No. 15/692,660, filed Aug. 31, 2017, Eric Turner, Jian Li, Synthesis of Four Coordinated Palladium Complexes and Their Applications in Light Emitting Devices Thereof.

U.S. Appl. No. 61/444,387, filed Feb. 18, 2011, Eric Turner, Jian Li, Xiaochun Hang, Four Coordinated Platinum and Palladium Complexes With Geometrically Distorted Charge Transfer State and Their Applications in Light Emitting Devices.

U.S. Appl. No. 13/399,252, filed Feb. 17, 2012, Eric Turner, Jian Li, Xiaochun Hang, Four Coordinated Platinum and Palladium Complexes With Geometrically Disorted Charge Transfer State and Their Applications in Light Emitting Devices.

U.S. Appl. No. 14/332,610, filed Jul. 16, 2014, Eric Turner, Jian Li, Xiaochun Hang, Four Coordinated Platinum and Palladium Complexes With Geometrically Disorted Charge Transfer State and Their Applications in Light Emitting Devices.

U.S. Appl. No. 14/589,599, filed Jan. 5, 2015, Eric Turner, Jian Li, Xiaochun Hang, Four Coordinated Platinum and Palladium Complexes With Geometrically Disorted Charge Transfer State and Their Applications in Light Emitting Devices.

U.S. Appl. No. 15/243,801, filed Aug. 22, 2016, Eric Turner, Jian Li, Xiaochun Hang, Four Coordinated Platinum and Palladium Complexes With Geometrically Disorted Charge Transfer State and Their Applications in Light Emitting Devices.

U.S. Appl. No. 61/490,111, filed May 26, 2011, Eric Turner, Jian Li, Synthesis of Platinum and Palladium Complexes As Narrow-Band Phosphorescent Emitters for Full Color Displays.

U.S. Appl. No. 13/479,921, filed May 24, 2012, Eric Turner, Jian Li, Synthesis of Platinum and Palladium Complexes as Narrow-Band Phosphorescent Emitters for Full Color Displays.

U.S. Appl. No. 14/996,522, filed Jan. 15, 2016, Eric Turner, Jian Li, Synthesis of Platinum and Palladium Complexes As Narrow-Band Phosphorescent Emitters for Full Color Displays.

U.S. Appl. No. 15/640,686, filed Jul. 3, 2017, Eric Turner, Jian Li, Synthesis of Platinum and Palladium Complexes As Narrow-Band Phosphorescent Emitters for Full Color Displays.

U.S. Appl. No. 61/704,880, filed Sep. 24, 2012, Guijie Li, Jian Li, Tetradentate Cyclometalated Metal Complexes.

U.S. Appl. No. 14/430,454, filed Mar. 23, 2015, Guijie Li, Jian Li, Metal Compounds, Methods, and Uses Thereof.

U.S. Appl. No. 15/882,358, filed Jan. 29, 2018, Guijie Li, Jian Li, Metal Compounds, Methods, and Uses Thereof.

U.S. Appl. No. 61/833,091, filed Jun. 10, 2013, Guijie Li, Jason Brooks, Jian Li, Phosphorescent Tetradentate Metal Complexes Having Modified Emission Spectra.

U.S. Appl. No. 61/868,411, filed Aug. 21, 2013, Jian Li, Highly Efficient Organic Electrophosphorescent Devices With "Quantum Dot" Like Emission.

U.S. Appl. No. 14/913,306, filed Feb. 19, 2016, Guijie Li, Jason Brooks, Jian Li, Phosphorescent Tetradentate Metal Complexes Having Modified Emission Spectra.

(56) References Cited

OTHER PUBLICATIONS

U.S. Appl. No. 14/513,506, filed Oct. 14, 2014, Guijie Li, Jason Brooks, Jian Li, Platinum Complexes and Devices.
U.S. Appl. No. 15/202,111, filed Jul. 5, 2016, Guijie Li, Jason Brooks, Jian Li, Platinum Complexes and Devices.
U.S. Appl. No. 15/615,566, filed Jun. 6, 2017, Guijie Li, Jason Brooks, Jian Li, Jason Brooks, Phosphorescent Tetradentate Metal Complexes Having Modified Emission Spectra.
U.S. Appl. No. 15/900,260, filed Feb. 20, 2018, Guijie Li, Jason Brooks, Jian Li, Jason Brooks, Phosphorescent Tetradentate Metal Complexes Having Modified Emission Spectra.
U.S. Appl. No. 61/890,545, filed Oct. 14, 2013, Guijie Li, Jason Brooks, Jian Li, Platinum Complexes, Devices, and Uses Thereof.
U.S. Appl. No. 61/890,580, filed Oct. 14, 2013, Guijie Li, Jason Brooks, Jian Li, Platinum Complexes, Devices, and Uses Thereof.
U.S. Appl. No. 61/924,462, filed Jan. 7, 2014, Guijie Li, Jian Li, Delayed Fluorescent Emitters Containing Phenyl-Pyrazole and Its Analogues.
U.S. Appl. No. 14/591,188, filed Jan. 7, 2015, Guijie Li, Jian Li, Tetradentate Plantinum and Palladium Complex Emitters Containing Phenyl-Pyrazole and Its Analogues.
U.S. Appl. No. 61/897,065, filed Oct. 29, 2013, Guijie Li, Jian Li, Efficient and Stable Blue and White Organic Light Emitting Diodes.
U.S. Appl. No. 62/006,509, filed Jun. 2, 2014, Guijie Li, Jian Li, Zhi-Qiang Zhu, Tetradentate Cyclometalated Platinum Complexes Containing 9, 10-Dihydroacridine and Its Analogues.
U.S. Appl. No. 14/728,848, filed Jun. 2, 2015, Guijie Li, Jian Li, Zhi-Qiang Zhu, Tetradentate Cyclometalated Platinum Complexes Containing 9, 10-Dihydroacridine and Its Analogues.
U.S. Appl. No. 62/030,235, filed Jul. 29, 2014, Guijie Li, Jian Li, Metal-Assisted Delayed Fluorescent Emitters Containing Tridentated Ligands.
U.S. Appl. No. 14/809,981, filed Jul. 27, 2015, Guijie Li, Jian Li, Metal-Assisted Delayed Fluorescent Emitters Containing Tridentated Ligands.
U.S. Appl. No. 15/711,525, filed Sep. 21, 2017, Guijie Li, Jian Li, Metal-Assisted Delayed Fluorescent Emitters Containing Tridentate Ligands.
U.S. Appl. No. 62/028,562, filed Jul. 24, 2014, Jian Li, Zhi-Qiang Zhu, Tetradentate Platinum (II) Complexes Cyclometalated With Functionalized Phenyl Carbene Ligands and Their Analogues.
U.S. Appl. No. 14/805,691, filed Jul. 22, 2015, Jian Li, Zhi-Qiang Zhu, Tetradentate Platinum (II) Complexes Cyclometalated With Functionalized Phenyl Carbene Ligands and Their Analogues.
U.S. Appl. No. 62/040,133, filed Aug. 21, 2014, Jian Li, Efficient Cyclometalated Platinum Complexes for Displays and Lighting Applications.
U.S. Appl. No. 62/077,431, filed Nov. 10, 2014, Guijie Li, Jian Li, Tetradentate Metal Complexes With Carbon Group Bridging Ligands.
U.S. Appl. No. 14/937,318, filed Nov. 10, 2015, Guijie Li, Jian Li, Tetradentate Metal Complexes With Carbon Group Bridging Ligands.
U.S. Appl. No. 62/170,283, filed Jun. 3, 2015, Guijie Li, Jian Li, Tetradentate Metal Complexes Containing Napthyridinocarbazole and Its Analogues.
U.S. Appl. No. 62/254,011, filed Nov. 11, 2015, Guijie Li, Jian Li, Tetradentate and Octahedral Metal Complexes Containing Naphthyridinocarbazole and Its Analogues.
U.S. Appl. No. 15/168,942, filed May 31, 2016, Guijie Li, Jian Li, Tetradentate and Octahedral Metal Complexes Containing Naphthyridinocarbazole and Its Analogues.
U.S. Appl. No. 15/354,280, filed Nov. 17, 2016, Guijie Li, Jian Li, Tetradentate and Octahedral Metal Complexes Containing Naphthyridinocarbazole and Its Analogues.
U.S. Appl. No. 15/882,267, filed Jan. 29, 2018, Guijie Li, Jian Li, Tetradentate and Octahedral Metal Complexes Containing Naphthyridinocarbazole and Its Analogues.
U.S. Appl. No. 62/170,049, filed Jun. 2, 2015, Jian Li, Tetradentate Metal Complexes Containing Indoloacridine and Its Analogues.
U.S. Appl. No. 62/274,456, filed Jan. 4, 2016, Jian Li, Tetradentate Metal Complexes Containing Indoloacridine and Its Analogues.
U.S. Appl. No. 15/168,910, filed May 31, 2016, Jian Li, Tetradentate Metal Complexes Containing Indoloacridine and Its Analogues.
U.S. Appl. No. 15/651,972, filed Jul. 17, 2017, Jian Li, Tetradentate Metal Complexes Containing Indoloacridine and Its Analogues.
U.S. Appl. No. 62/200,960, filed Aug. 4, 2015, Jian Li, Zhi-Qiang Zhu, Novel Cyclic Tetradentate Platinum (II) and Palladium (II) Complexes.
U.S. Appl. No. 15/228,401, filed Aug. 4, 2016, Jian Li, Zhi-Qiang Zhu, Tetradentate Platinum (II) and Palladium (II) Complexes, Devices, and Uses Thereof.
U.S. Appl. No. 62/377,883, filed Aug. 22, 2016, Jian Li, Zhi-Qiang Zhu, Octahedral Iridium (III) Complexes Employing Azepine Functional Group and Their Analogues.
U.S. Appl. No. 62/377,884, filed Aug. 22, 2016, Jian Li, Zhi-Qiang Zhu, Tetradentate Platinum (II) and Palladium (II) Complexes Employing Azepine Functional Group and Their Analogues.
U.S. Appl. No. 62/451,574, filed Jan. 27, 2017, Jian Li, Yunlong Ji, Metal-Assisted Delayed Fluorescent Emitters Employing Pyrido-Pyrrolo-Acridine and Analogues.
U.S. Appl. No. 15/487,476, filed Apr. 14, 2017, Jian Li, OLED With Multi-Emissive Material Layer.
U.S. Appl. No. 62/508,560, filed May 19, 2017, Jian Li, Yunlong Ji, Metal-Assisted Delayed Fluorescent Emttters Employing Benzo-Imidazo-Phenanthridine and Analogues.
U.S. Appl. No. 62/508,849, filed May 19, 2017, Jian Li, Zhiqiang Zhu, Tetradentate Platinum and Palladium Complexes Based on Biscarbazole and Analogues.
U.S. Appl. No. 62/573,596, filed Oct. 17, 2017, Jian Li, Hole-Blocking Materials for Organic Light Emitting Diodes.
U.S. Appl. No. 62/573,472, filed Oct. 17, 2017, Jian Li, Phosphorescent Excimers With Preferred Molecular Orientation As Monochromatic Emitters for Display and Lighting Applications.
U.S. Appl. No. 62/573,639, filed Oct. 17, 2017, Jian Li, Phosphorescent Excimers With Preferred Molecular Orientation As Monochromatic Emitters for Display and Lighting Applications.
U.S. Appl. No. 62/573,462, filed Oct. 17, 2017, Jian Li, Single-Doped White OLED With Extraction Layer Doped With Down-Conversion Red Phosphors.
U.S. Appl. No. 15/845,575, filed Dec. 18, 2017, Jian Li, Kody George Klimes, Organic Light Emitting Diode With Split Emissive Layer.
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).

(56) References Cited

OTHER PUBLICATIONS

Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate OÔNÔCÔN Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate OÔNÔCÔN ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.
Zhi-Qiang Zhu et.al., "Harvesting All Electrogenerated Excitons through Metal Assisted Delayed Fluorescent Materials," Adv. Mater. 27 (2015) 2533-2537.
Zhi-Qiang Zhu et. al.. "Efficient Cyclometalated Platinum(II) Complex with Superior Operational Stability," Adv. Mater. 29 (2017) 1605002.
Chew, S. et al.: Photoluminescence and electroluminescence of a new blue-emitting homoleptic iridium complex. Applied Phys. Letters; 2006, vol. 88, pp. 093510-1-093510-3.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Christoph Ulbricht et al., "Synthesis and Characterization of Oxetane-Functionalized Phosphorescent Ir(III)-Complexes", Macromol. Chem. Phys. 2009, 210, pp. 531-541.
Dan Wang et al., "Carbazole and arylamine functionalized iridium complexes for efficient electro-phosphorescent light-emitting diodes", Inorganica Chimica Acta 370 (2011) pp. 340-345.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.
Jack W. Levell et al., "Carbazole/iridium dendrimer side-chain phosphorescent copolymers for efficient light emitting devices", New J. Chem., 2012, 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Zhaowu Xu et al., "Synthesis and properties of iridium complexes based 1,3,4-oxadiazoles derivatives", Tetrahedron 64 (2008) pp. 1860-1867.
D.F. O'Brien et al., "Improved energy transfer in electrophosphorescent devices," Appl. Phys. Lett., vol. 74, No. 3, Jan. 18, 1999, pp. 442-444.

(56) References Cited

OTHER PUBLICATIONS

Vadim Adamovich et al., "High efficiency single dopant white electrophosphorescent light emitting diodes," New J. Chem., 2002, 26, pp. 1171-1178.
Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.
Matthew J. Jurow et al., "Understanding and predicting the orientation of heteroleptic phosphors in organic light-emitting materials", Nature Materials, vol. 15, Jan. 2016, pp. 85-93.
Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.

* cited by examiner

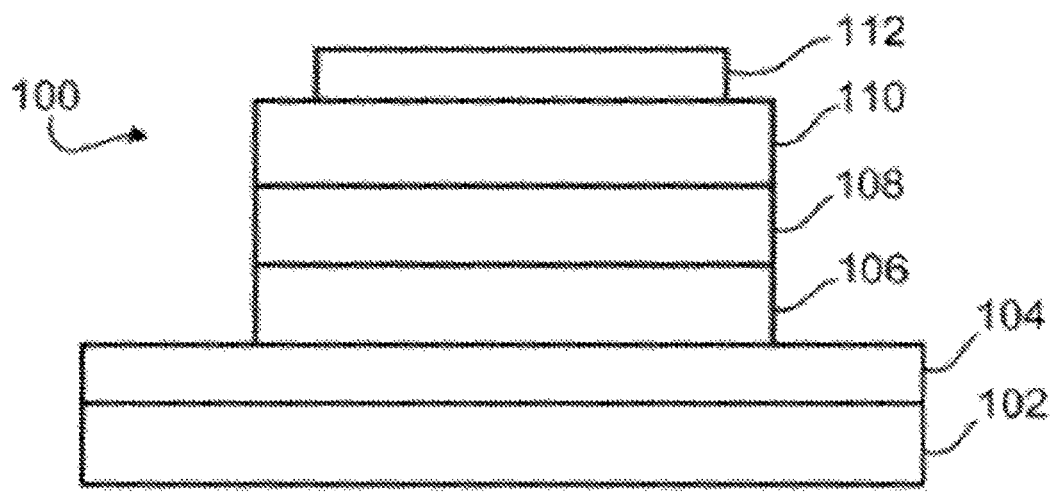

TETRADENTATE PLATINUM (II) AND PALLADIUM (II) COMPLEXES AND OCTAHEDRAL IRIDIUM COMPLEXES EMPLOYING AZEPINE FUNCTIONAL GROUPS AND THEIR ANALOGUES

CROSS-REFERENCE TO RELATED APPLICATIONS

This application claims the benefit of U.S. Application Ser. Nos. 62/377,883 and 62/377,884, both filed on Aug. 22, 2016, and both of which are incorporated herein by reference in their entirety.

TECHNICAL FIELD

The present disclosure relates to platinum (II), palladium (II), and iridium (III) complexes having azepine functional groups and their analogues as emitters for organic light emitting diodes (OLEDs).

BACKGROUND

Compounds capable of absorbing and/or emitting light can be ideally suited for use in a wide variety of optical and electroluminescent devices, including, for example, photo-absorbing devices such as solar- and photo-sensitive devices, OLEDs, and photo-emitting devices. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in OLEDs, lighting and advanced displays), many currently available materials exhibit a number of disadvantages, including poor processing ability, inefficient emission or absorption, and less than ideal stability, among others.

SUMMARY

Complexes disclosed herein include platinum, palladium, and iridium complexes that are useful for full color displays and lighting applications. Provided herein are complexes of Formulas A, B, and C:

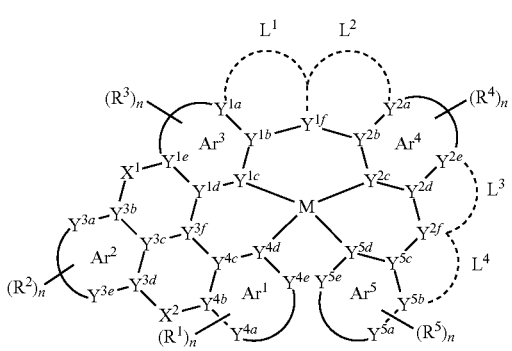

Formula A

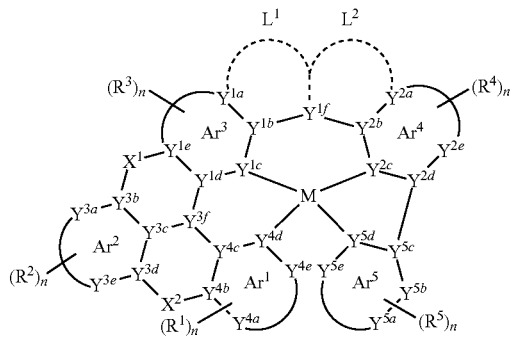

Formula B

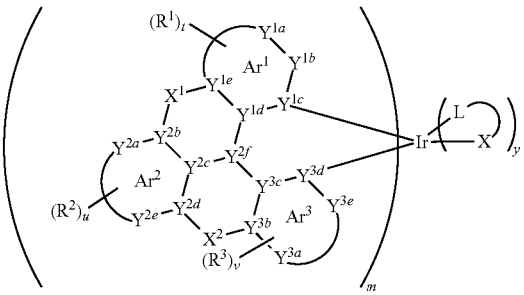

Formula C where the constituent variables are defined herein.

Light emitting devices including complexes represented by Formulas A, B, and C are described. Examples of light emitting devices include OLEDs (e.g., phosphorescent OLED devices), photovoltaic devices, luminescent display devices, and the like.

Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

BRIEF DESCRIPTION OF THE DRAWINGS

FIG. 1 depicts a cross section of an exemplary OLED.

DETAILED DESCRIPTION

Platinum (II), palladium (II), and iridium (III) complexes of the present disclosure provide improvements in color purity, enhanced operational stability, and eliminate potential intermolecular interactions, making them suitable for full color displays and lighting applications.

This disclosure relates to the complexes represented by Formulas A, B, and C, each of which is described below. Complexes of Formula A are represented as:

Formula A

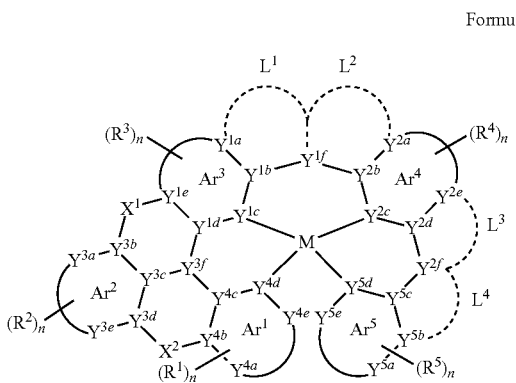

where:

M represents $Pt^{2+}$ or $Pd^{2+}$;

$Ar^1$, $Ar^2$, $Ar^3$, $Ar^4$, and $Ar^4$ each independently represents an aryl or heteroaryl;

$R^1$, $R^2$, $R^3$, $R^4$, and $R^5$ each independently represents hydrogen, halogen, hydroxyl, nitro, thiol, or substituted or unsubstituted $C_1$-$C_4$ alkyl, alkoxy, amino, or aryl;

each n is 0, 1, 2, 3, 4, or 5, valency permitting;

$Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{2e}$, $Y^{3a}$, $Y^{3b}$, $Y^{3c}$, $Y^{3d}$, $Y^{3e}$ $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, and $Y^{5e}$ each independently represents C, N, Si, O, or S;

$Y^{1f}$, $Y^{2f}$, and $Y^{3f}$, valency permitting, each independently represents N, P, N=O, P=O, NR, PR, CR, SiR, $CR_2$, $SiR_2O$, or S;

at least one of $X^1$ and $X^2$ independently represents one of the following moieties:

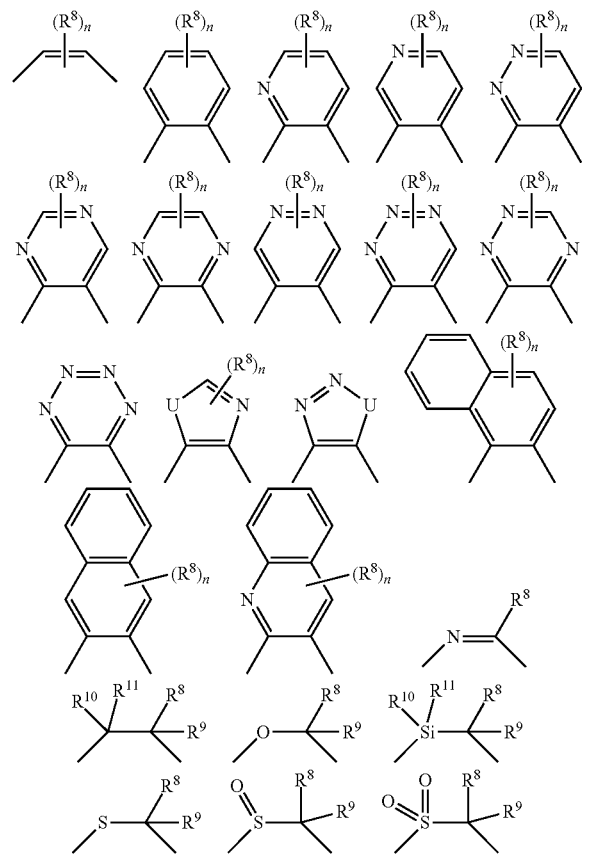

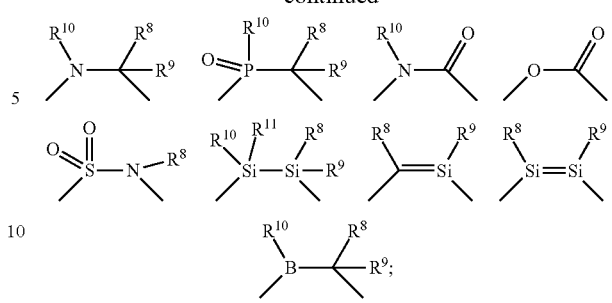

and the other of $X^1$ and $X^2$, if not one of the moieties above, is independently present or absent, and each $X^1$ and $X^2$ present independently represents a single bond, NR, PR, BR, CRR', SiRR', O, S, S=O, O=S=O, Se, Se=O, or O=Se=O;

each of R and R' is independently present or absent, and each R and R' present independently represents substituted or unsubstituted $C_1$-$C_4$ alkyl, aryl, or heteroaryl;

$R^8$, $R^9$, $R^{10}$, and $R^{11}$ each independently represents hydrogen, halogen, hydroxyl, nitro, thiol, or substituted or unsubstituted $C_1$-$C_4$ alkyl, alkoxy, amino, or aryl;

each of $L^1$, $L^2$, $L^3$, and $L^4$ is independently present or absent, and each $L^1$, $L^2$, $L^3$, and $L^4$ present represents a linking atom or linking group.

The linking atom can optionally, if valency permits, have other chemical moieties attached. Suitable chemical moieties include hydroxy, amide, thiol, or substituted or unsubstituted alkyl, alkoxy, alkenyl, alkynyl, amino, aryl, heteroaryl, cycloalkyl, and heterocyclyl.

Embodiments of Formula A include:

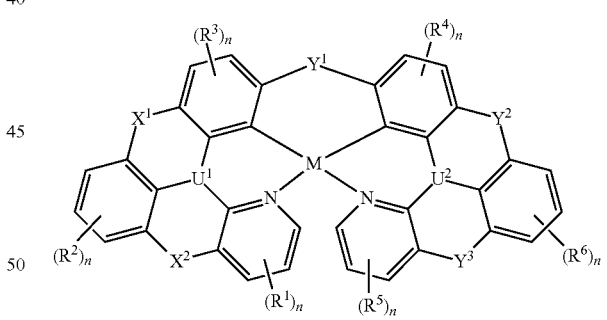

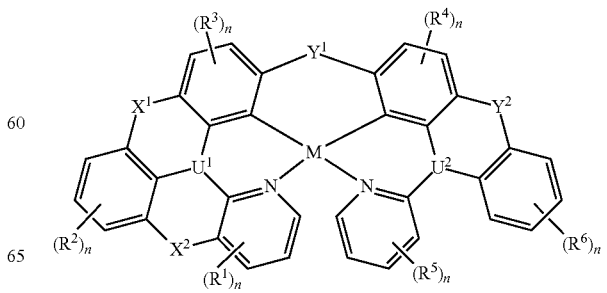

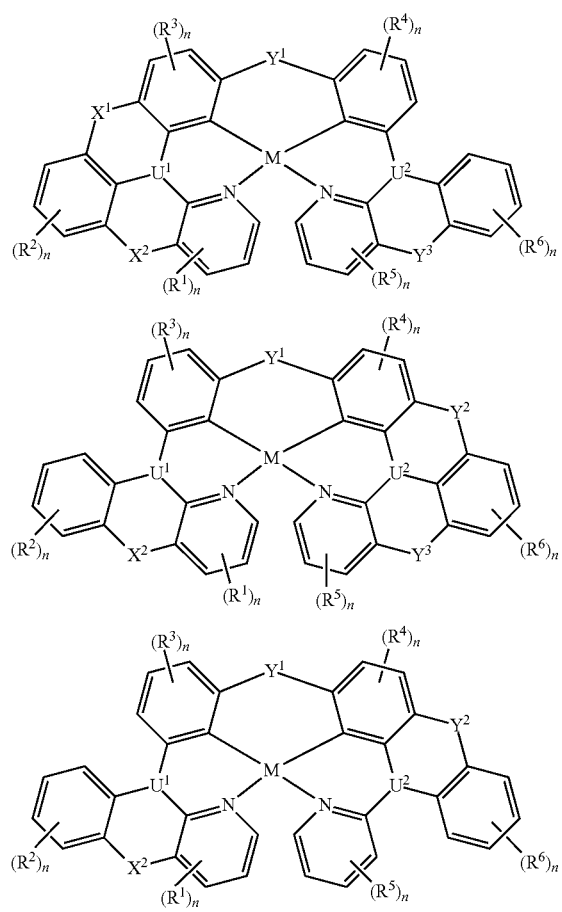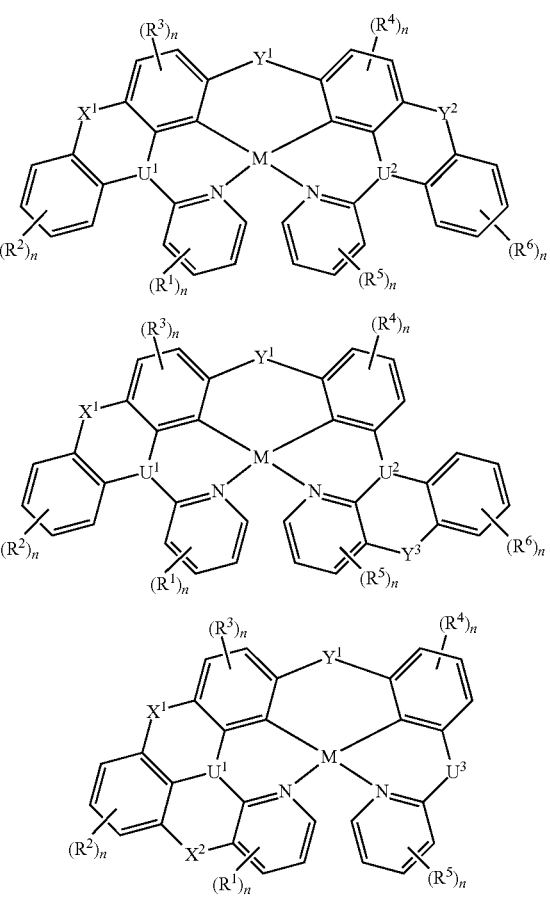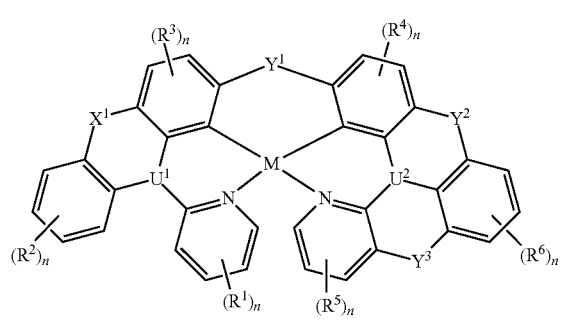

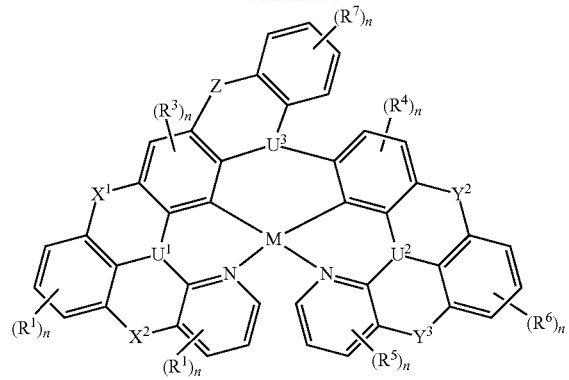
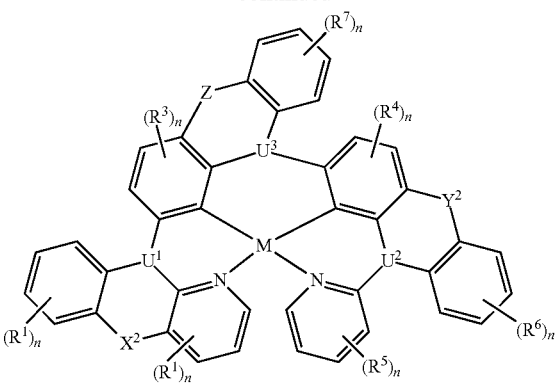
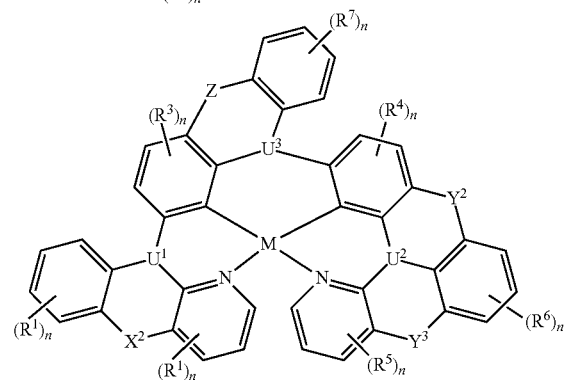
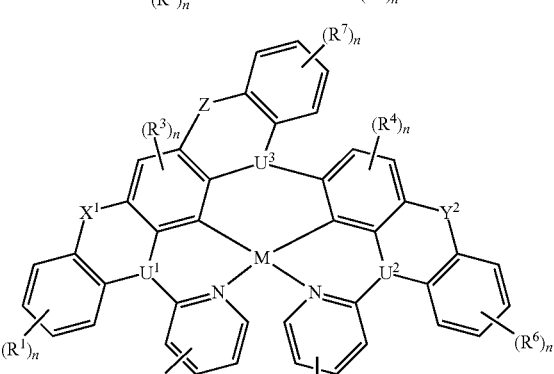
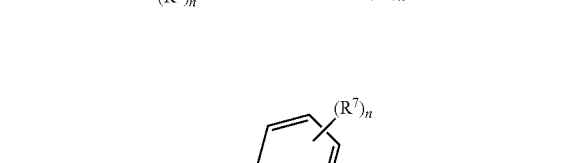
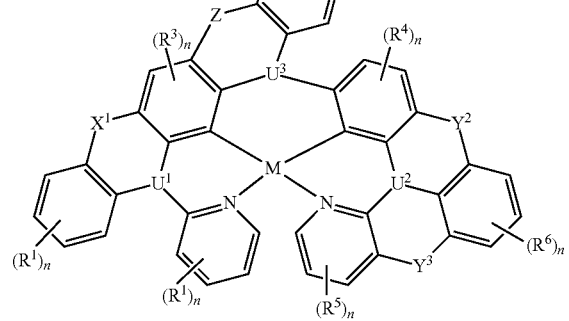
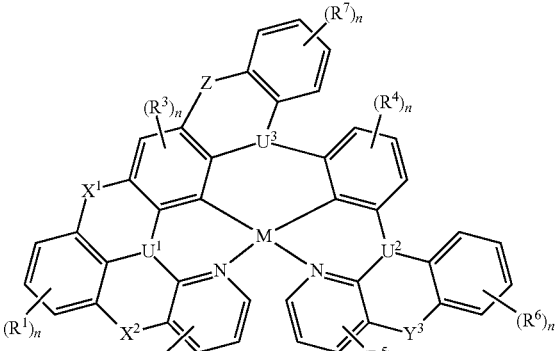
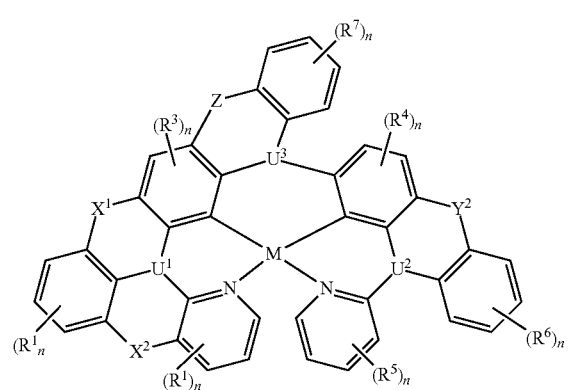
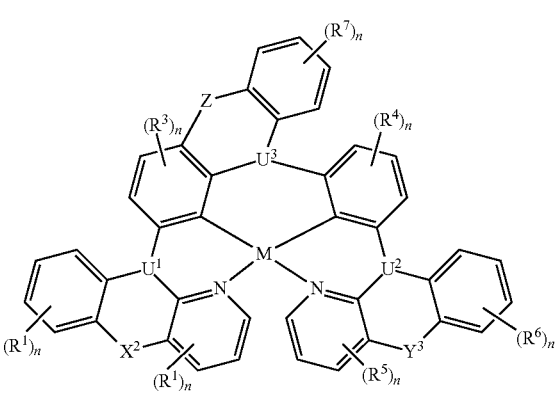

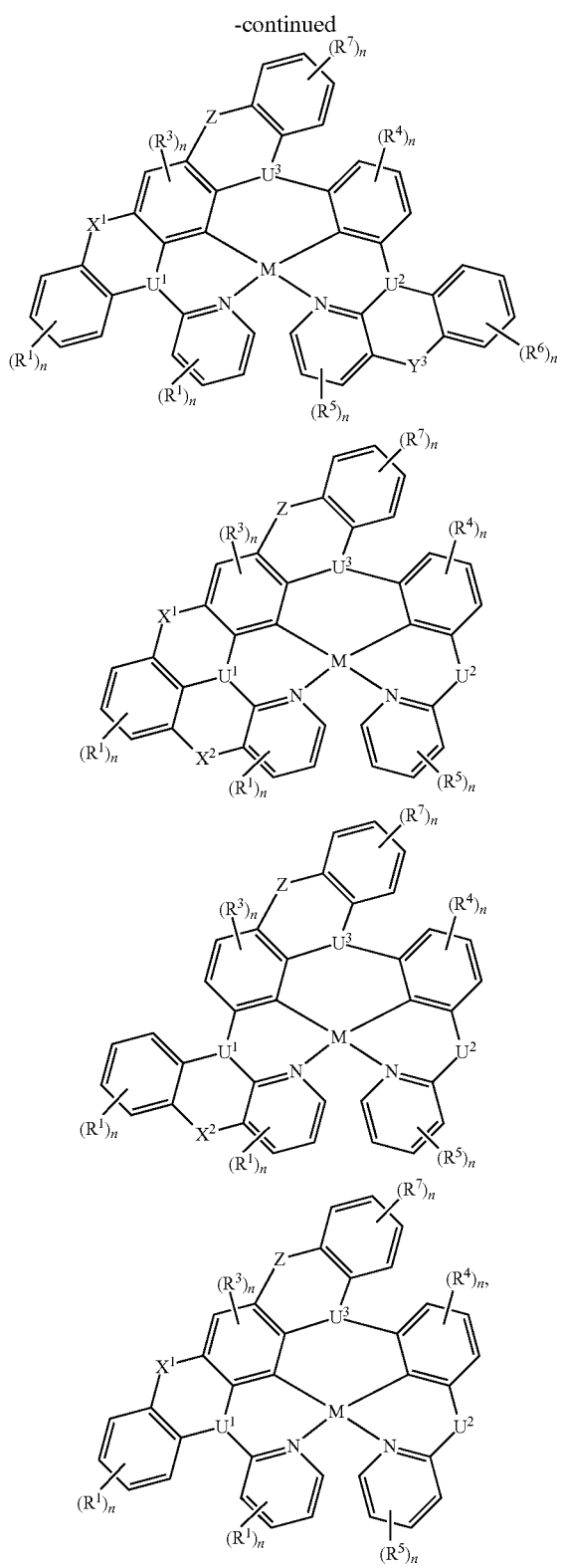

where:
U represents O, S, NR, or PR;
$U^1$ represents N, P, As, B, NO, PO, or AsO;
Z represents O, S, SO, $S(O)_2$, NR, PR, $CR_2$, $SiR_2$, or BR;
$Z^1$ represents C or N;
$Z^2$ represents C or N, and each R independently represents substituted or unsubstituted $C_1$-$C_4$ alkyl, aryl, or heteroaryl.

Complexes of Formula B are represented as:

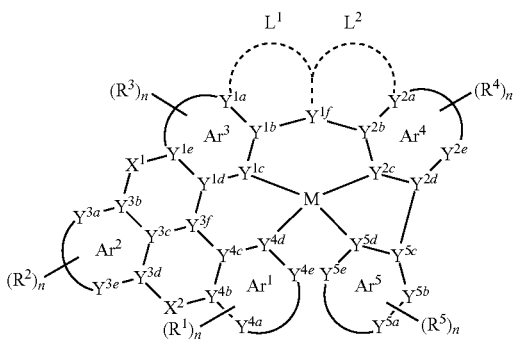

Formula B where:
$Ar^1$, $Ar^2$, $Ar^3$, $Ar^4$, and $Ar^5$ each independently represents an aryl or heteroaryl;
M represents $Pt^{2+}$ or $Pd^{2+}$;
$R^1$, $R^2$, $R^3$, $R^4$, and $R^5$ each independently represents hydrogen, halogen, hydroxyl, nitro, thiol, or substituted or unsubstituted $C_1$-$C_4$ alkyl, alkoxy, amino, or aryl;
each n is independently 0, 1, 2, 3, 4, or 5, valency permitting;
$Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{2e}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, and $Y^{5e}$ each independently represents C, N, Si, O, or S;
$Y^{1f}$, and $Y^{3f}$, valency permitting, each independently represents N, P, N=O, P=O, NR, PR, CR, SiR, $CR_2$, $SiR_2O$, or S;
at least one of $X^1$ and $X^2$ independently represents the following moieties:

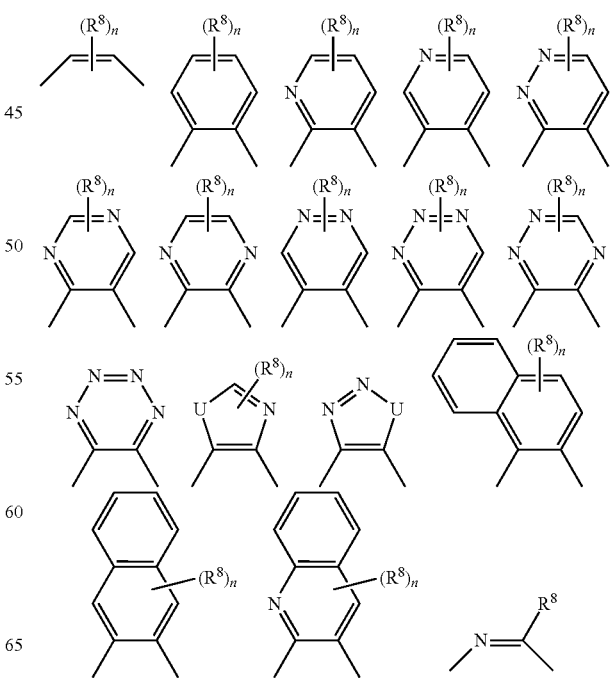

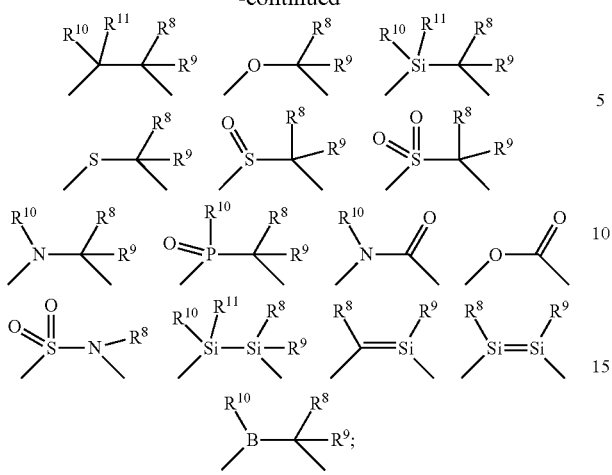

and the other $X^1$ and $X^2$, if not one of the moieties above, is independently present or absent, and each $X^1$ and $X^2$ present independently represents a single bond, NR, PR, BR, CRR', SiRR', O, S, S=O, O=S=O, Se, Se=O, or O=Se=O;

each of R and R' is independently present or absent, and each R and R' present represents substituted or unsubstituted $C_1$-$C_4$ alkyl, aryl, or heteroaryl;

$R^8$, $R^9$, $R^{10}$, and $R^{11}$ each independently represents hydrogen, halogen, hydroxyl, nitro, thiol, or substituted or unsubstituted $C_1$-$C_4$ alkyl, alkoxy, amino, or aryl;

each of $L^1$ and $L^2$ is independently present or absent, and each $L^1$ and $L^2$ present represents a linking atom or linking group.

The linking atom can optionally, if valency permits, have other chemical moieties attached. Suitable chemical moieties include hydroxy, amide, thiol, or substituted or unsubstituted alkyl, alkoxy, alkenyl, alkynyl, amino, aryl, heteroaryl, cycloalkyl, and heterocyclyl.

Embodiments of Formula B include:

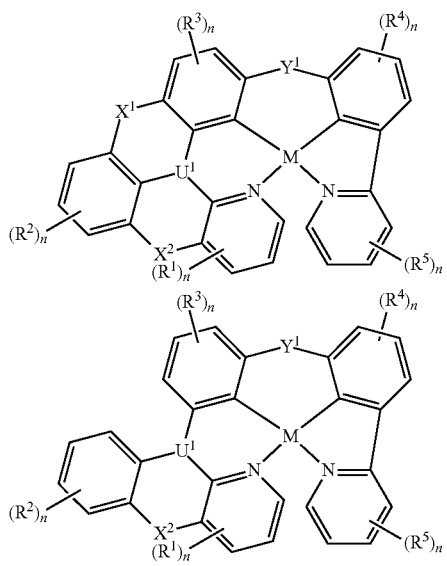

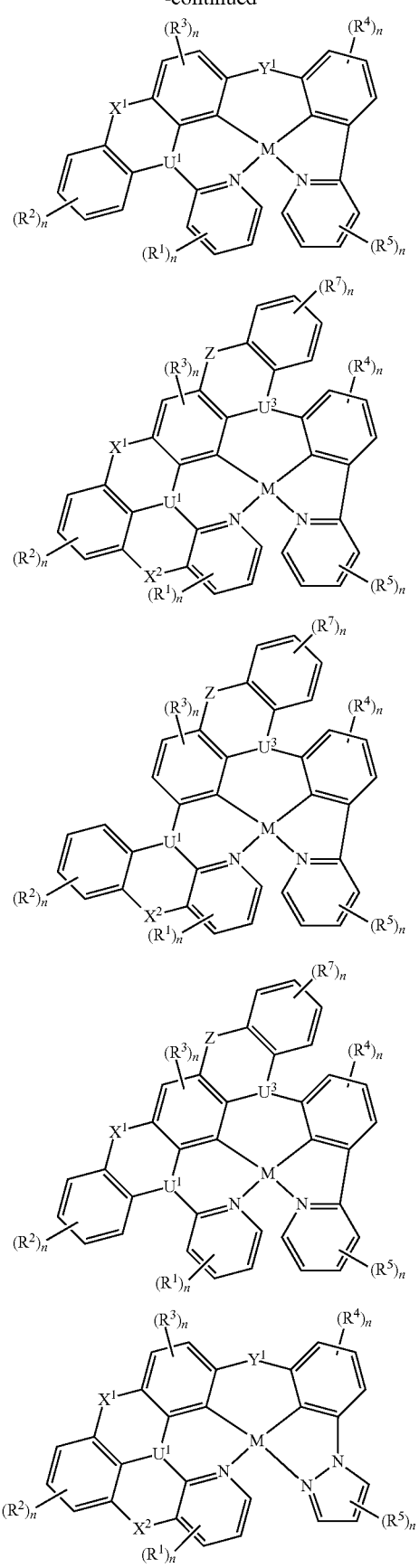

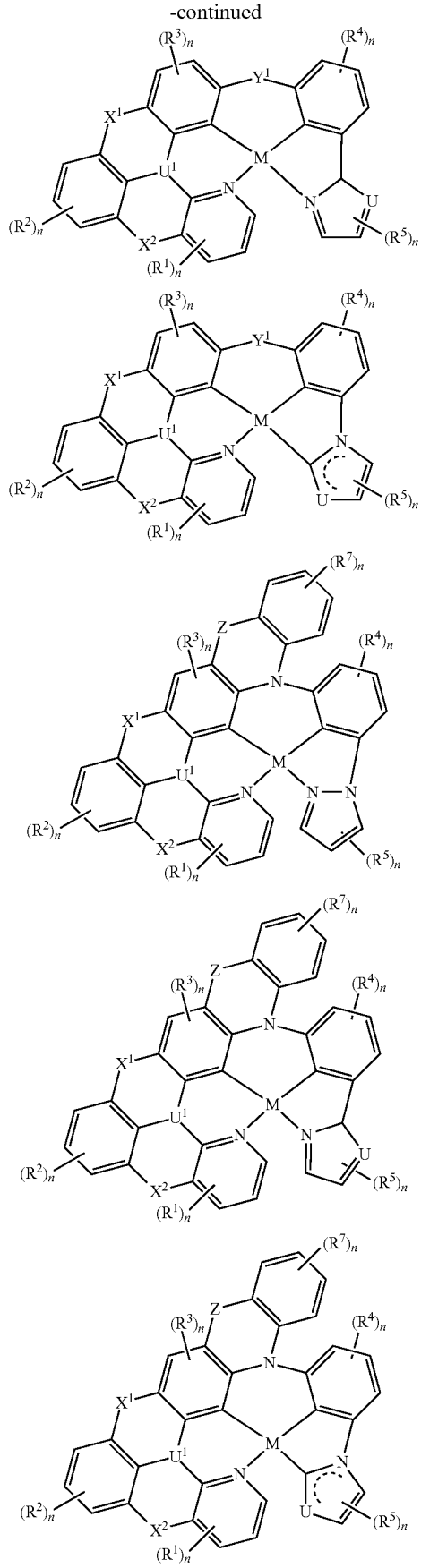
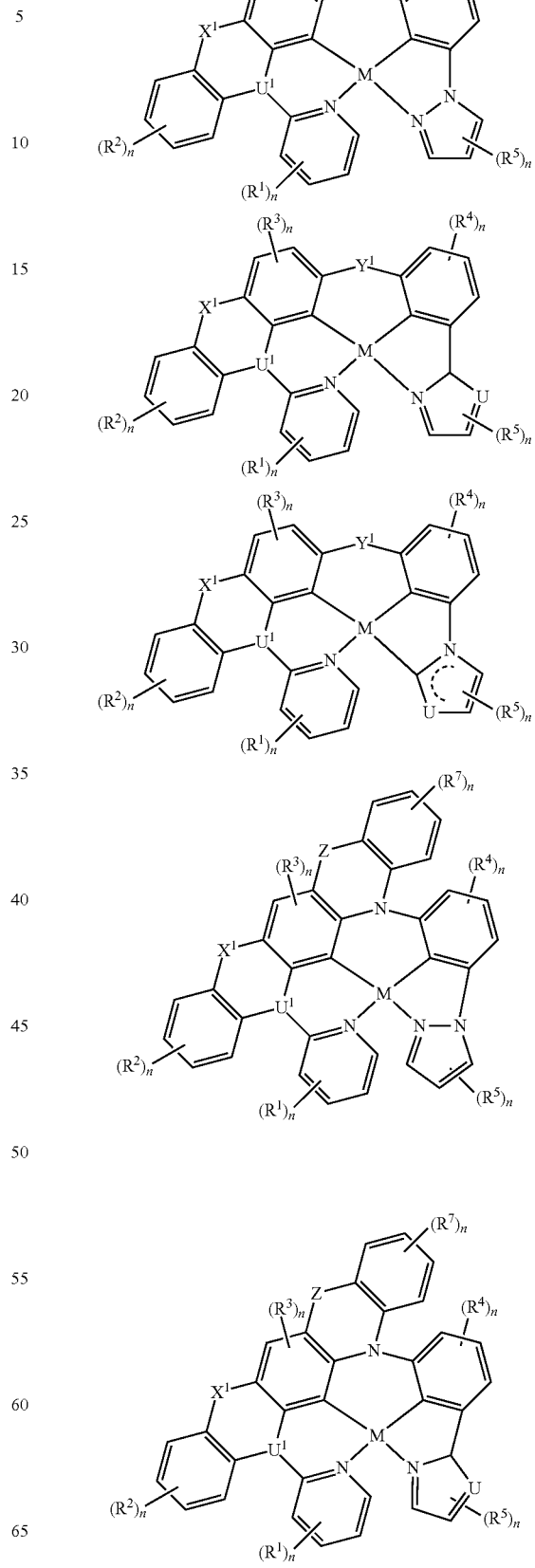

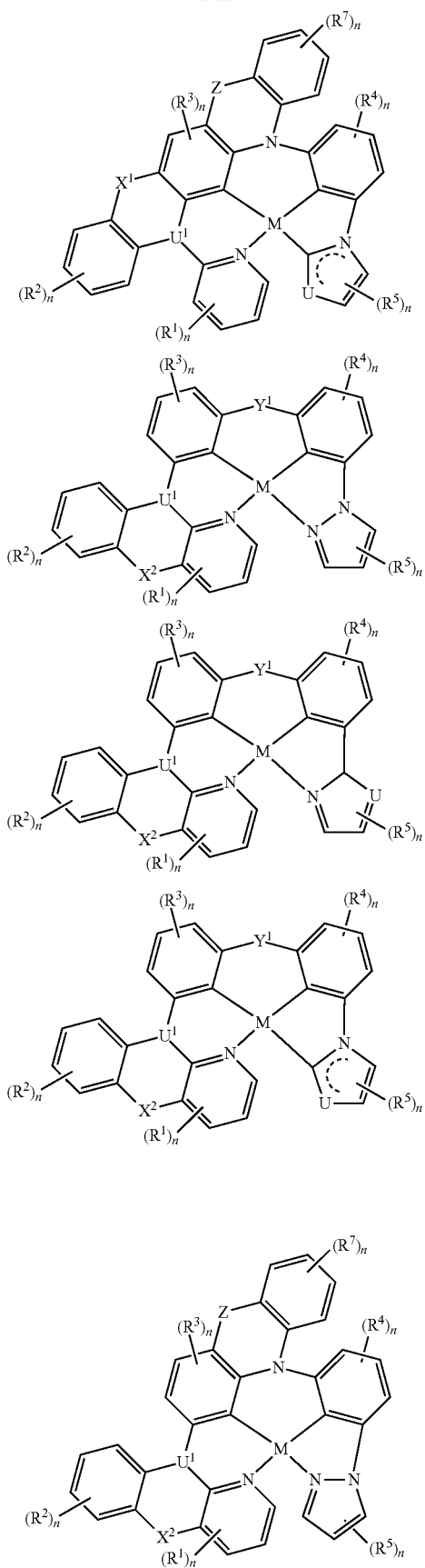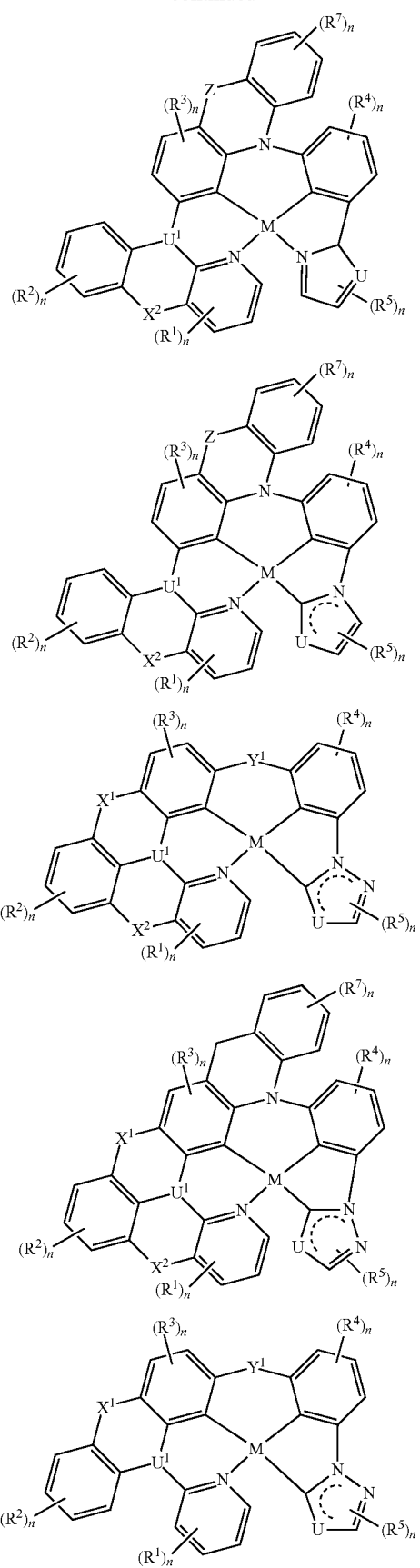

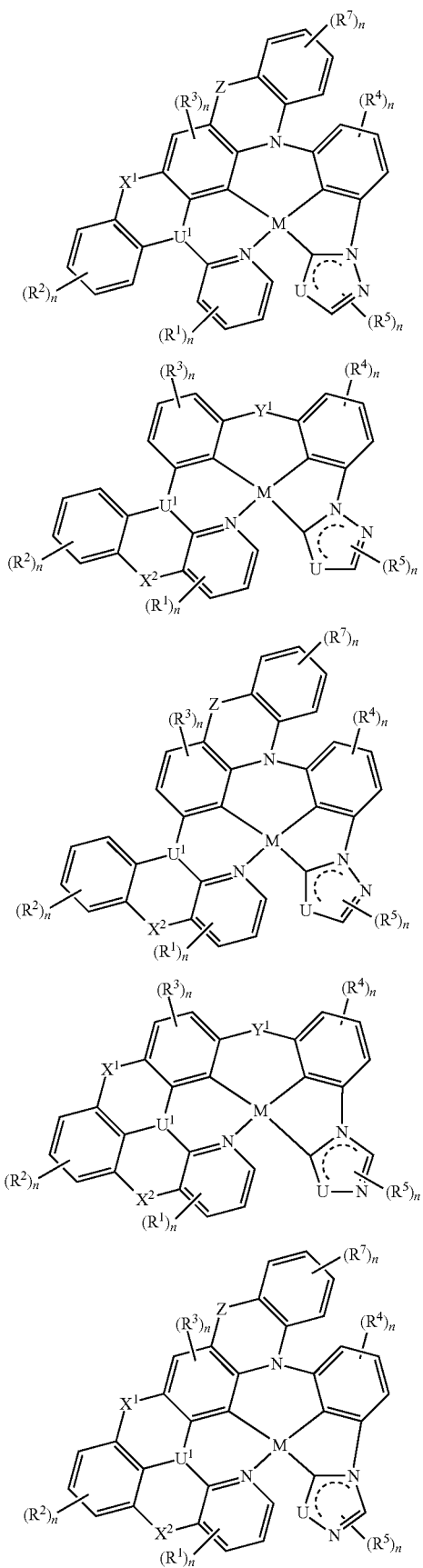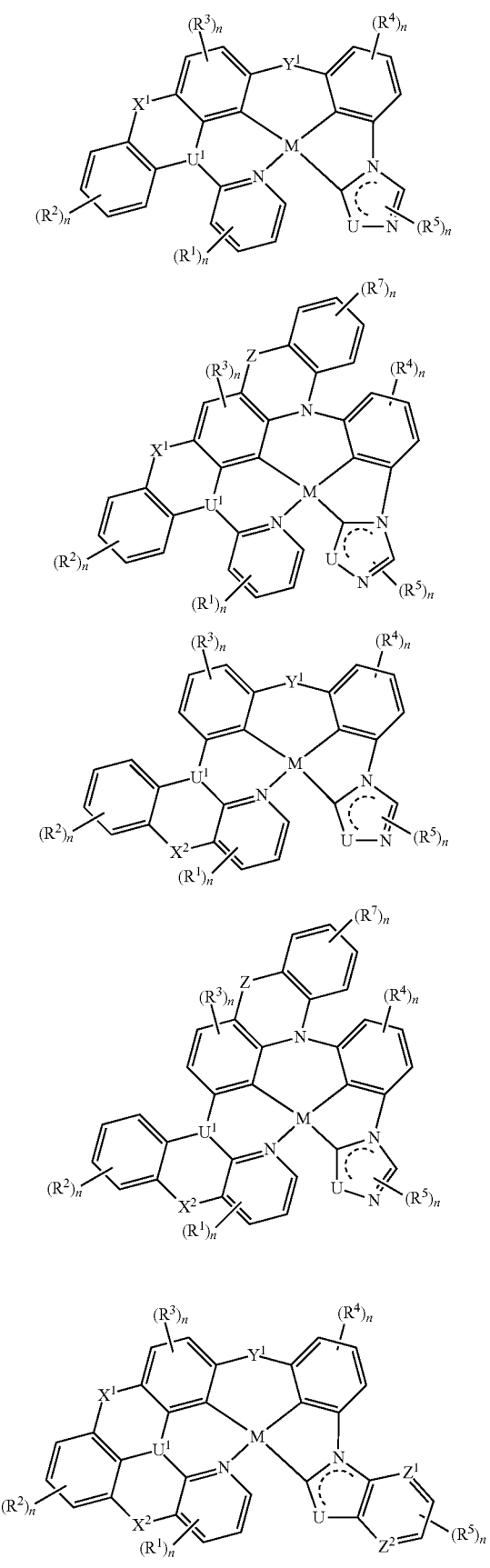

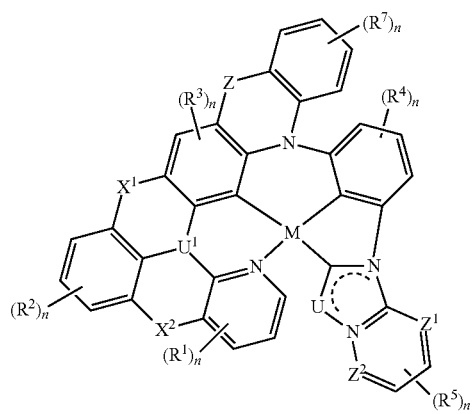
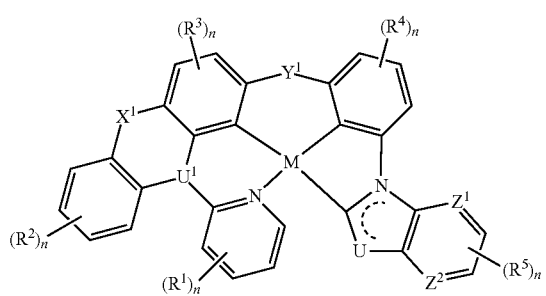
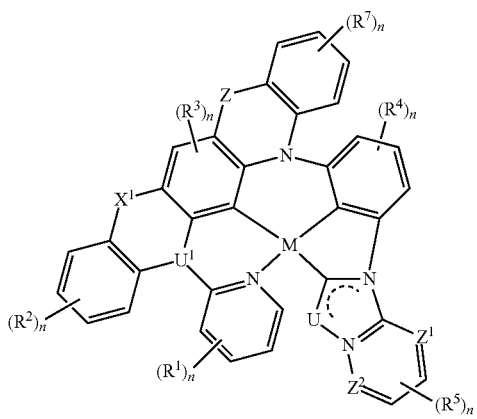
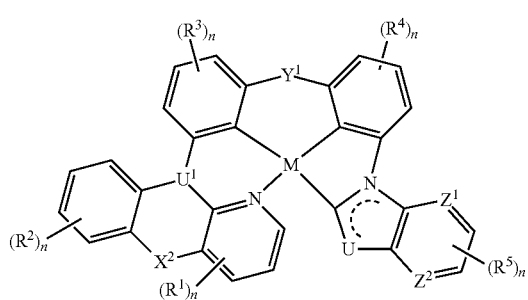
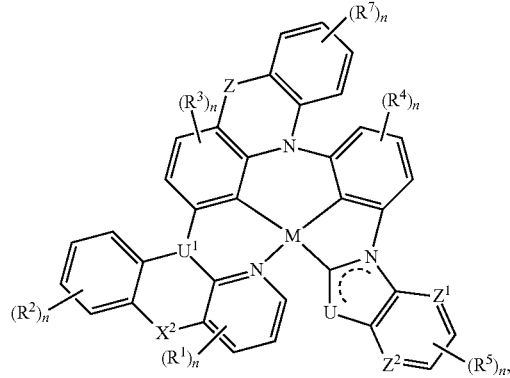
where:
U represents O, S, NR, or PR;
U¹ represents N, P, As, B, NO, PO, or AsO;
Z represents O, S, SO, S(O)$_2$, NR, PR, CR$_2$, SiR$_2$, or BR;
Z¹ represents C or N;
Z² represents C or N; and
each R independently represents substituted or unsubstituted C$_1$-C$_4$ alkyl, aryl, or heteroaryl.
Examples of complexes of Formula A and Formula B include the following:
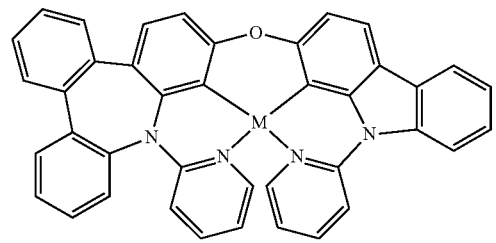
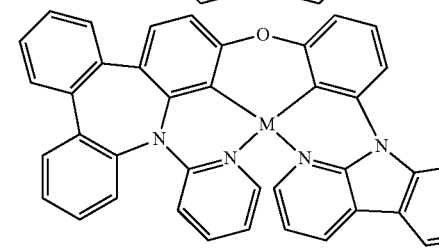
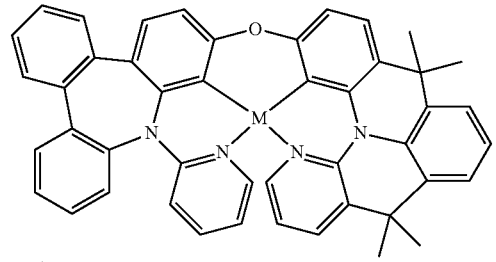
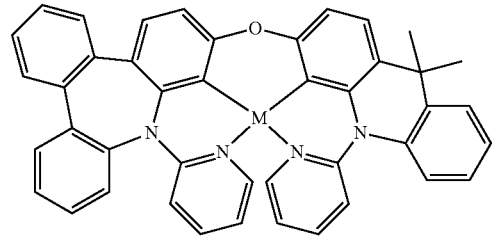

21
-continued
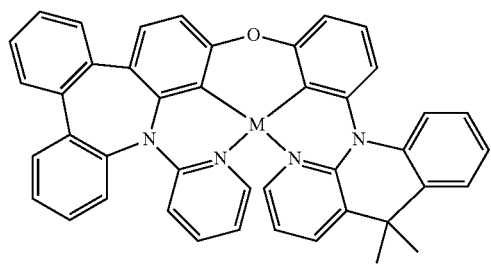
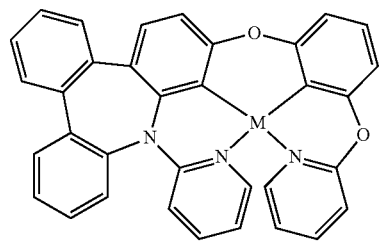
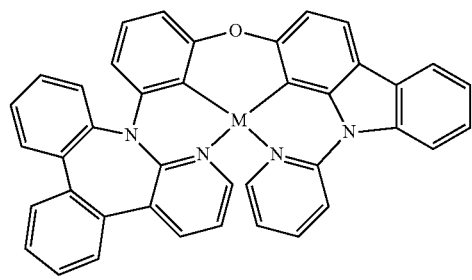
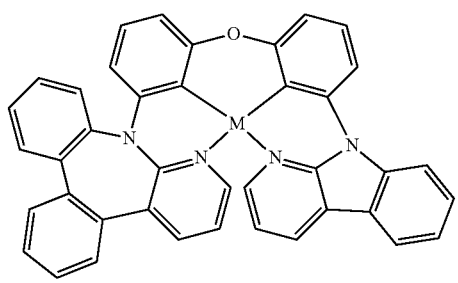
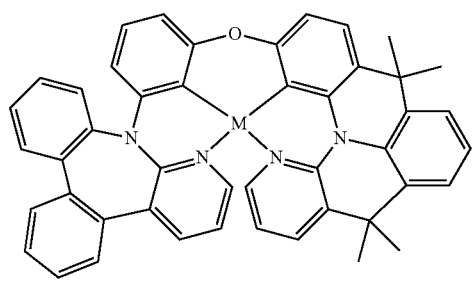
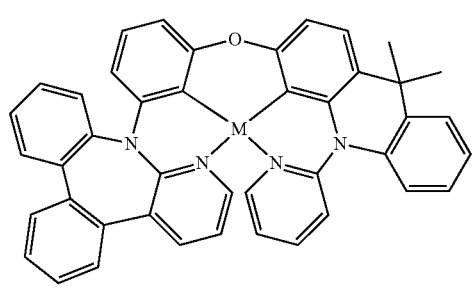
22
-continued
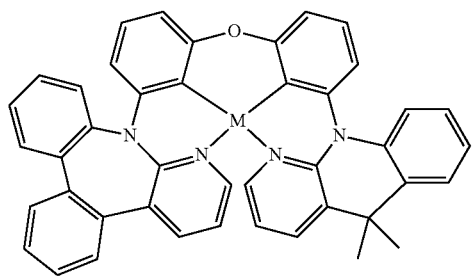
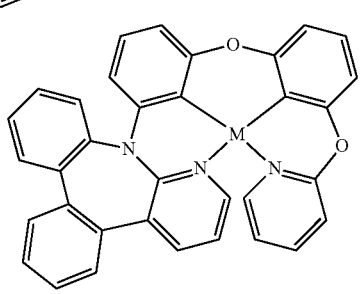
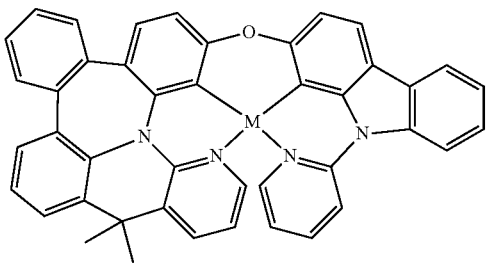
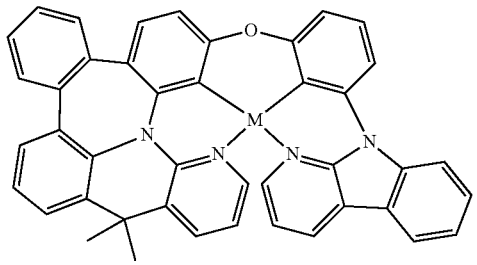
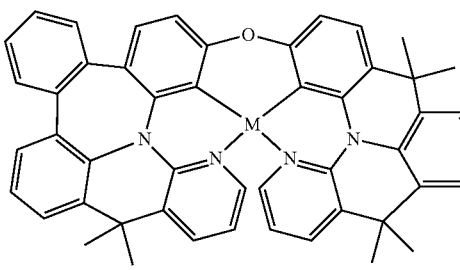
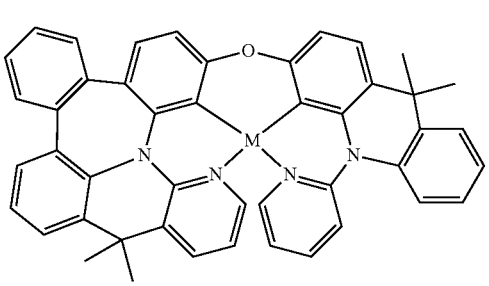

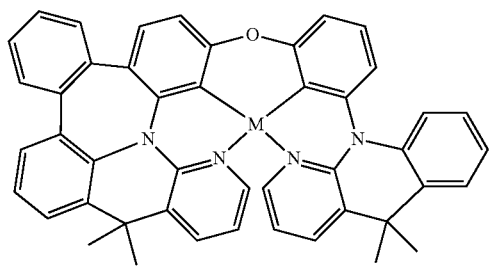
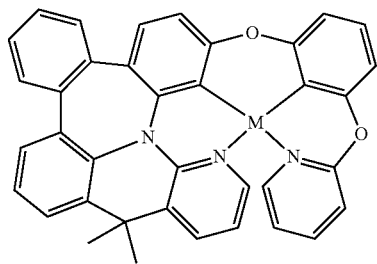
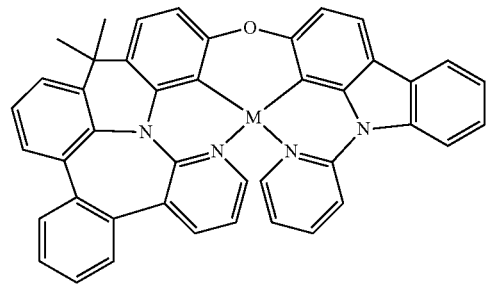
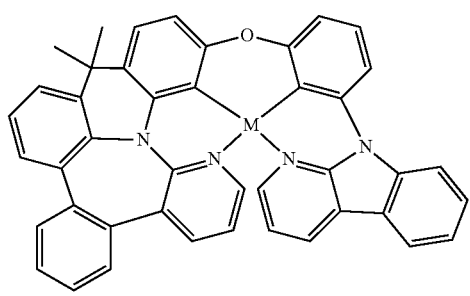
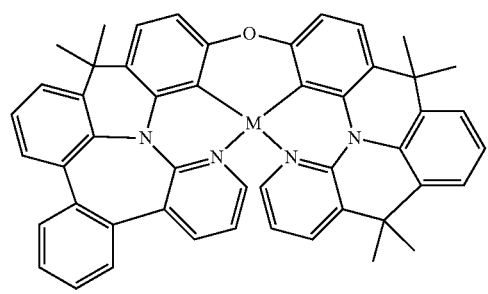
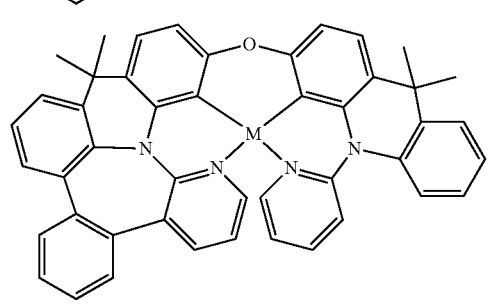
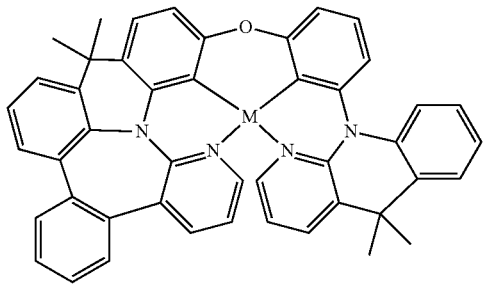
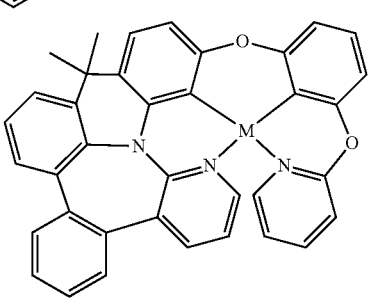
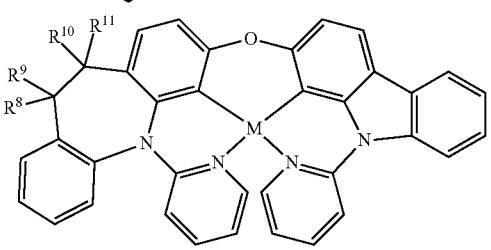
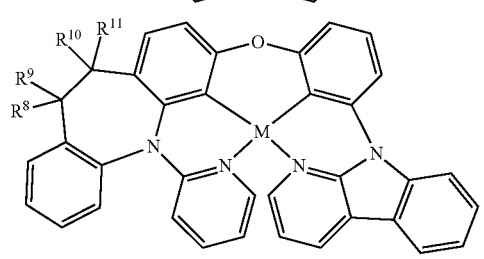
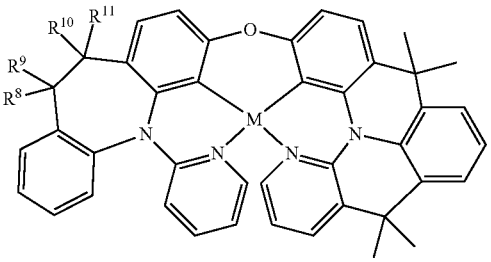
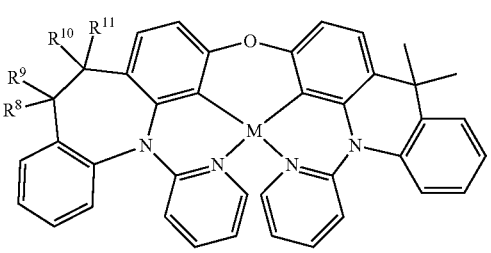

25
-continued
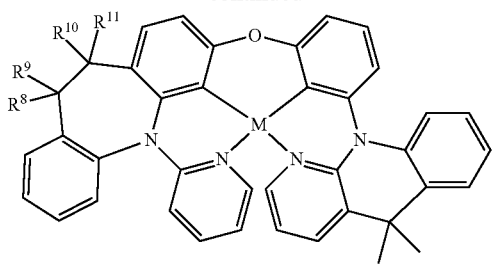
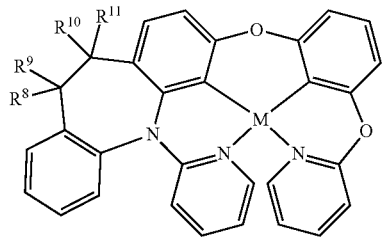
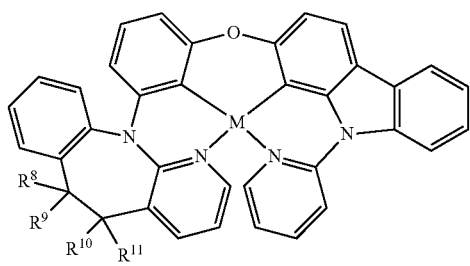
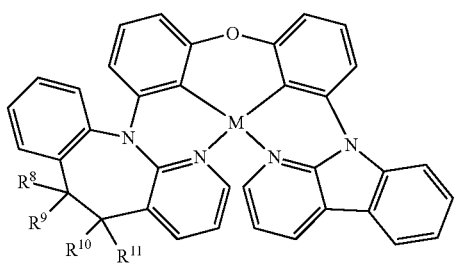
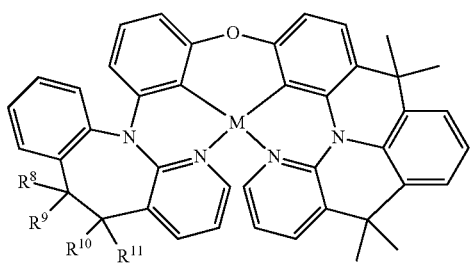
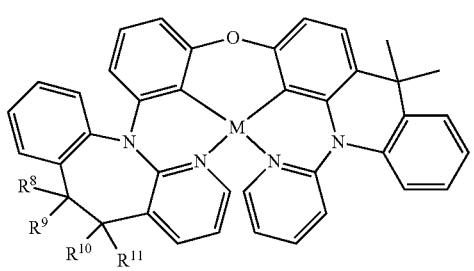
26
-continued
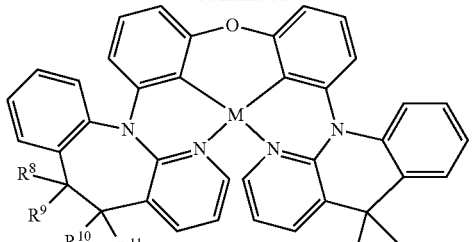
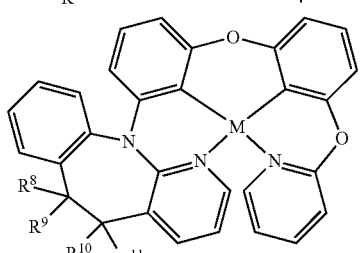
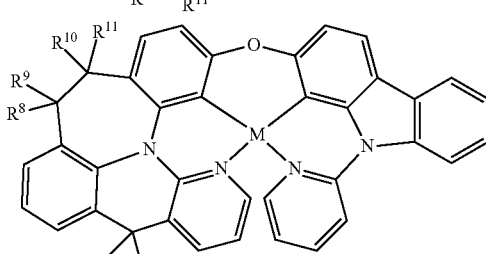
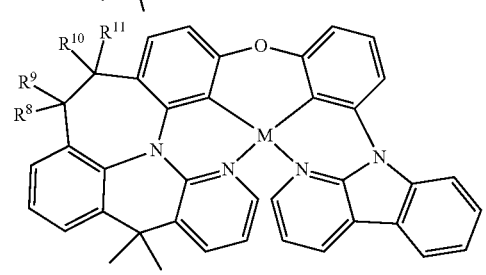
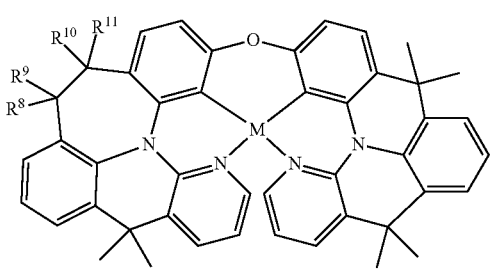
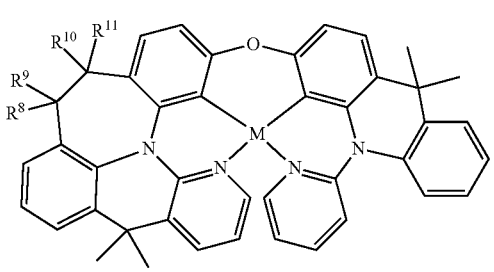

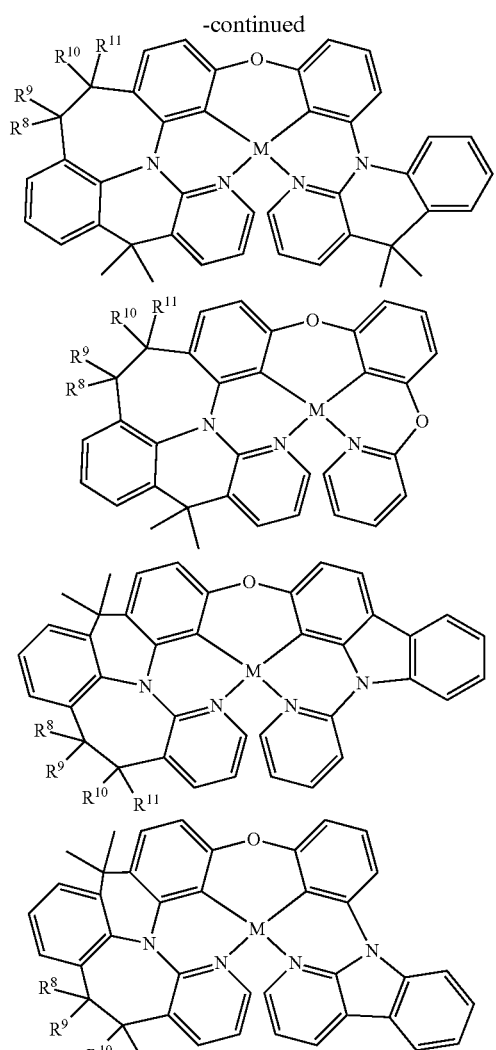
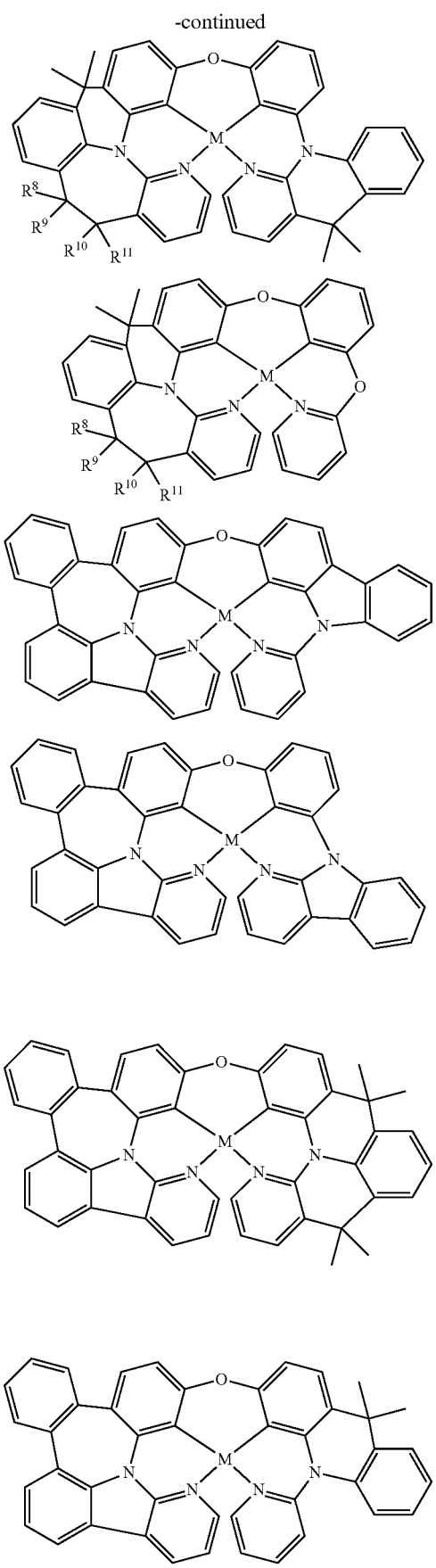

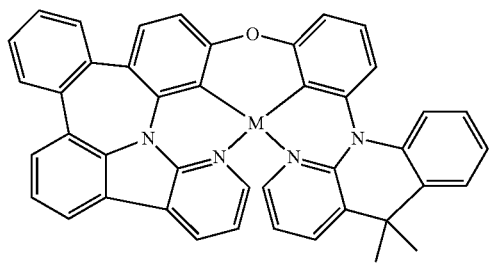
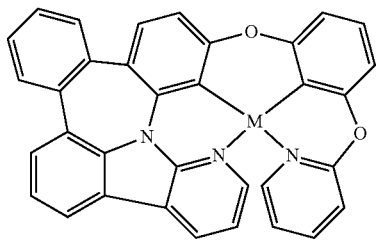
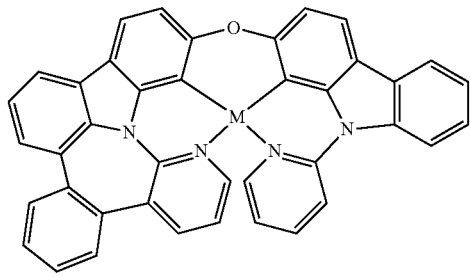
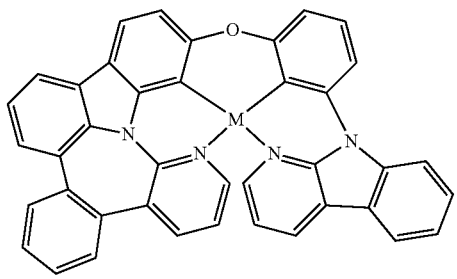
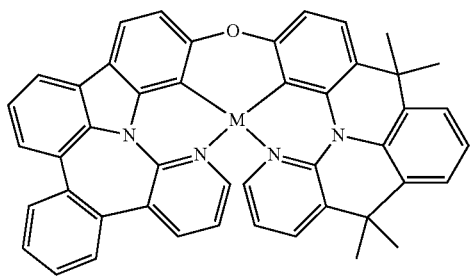
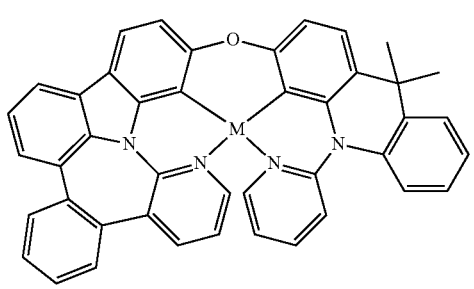
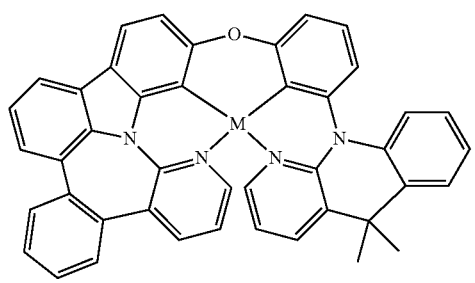
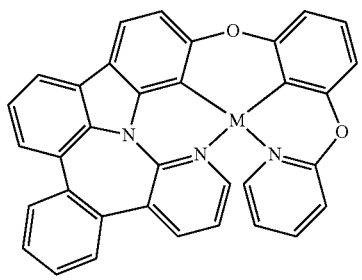
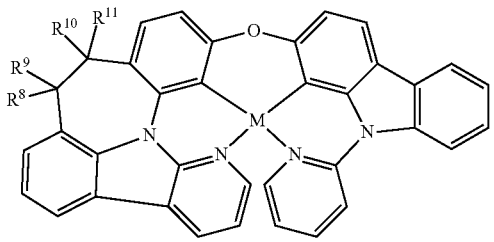
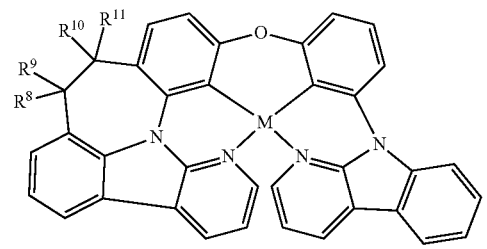
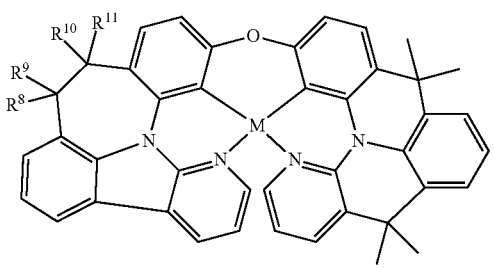
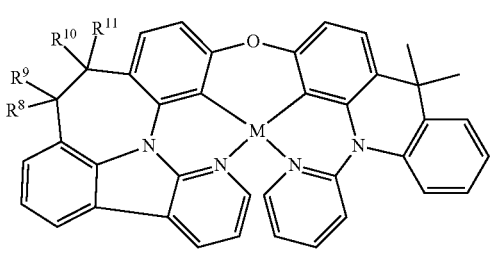

31
-continued
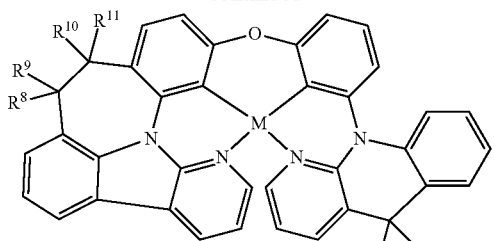
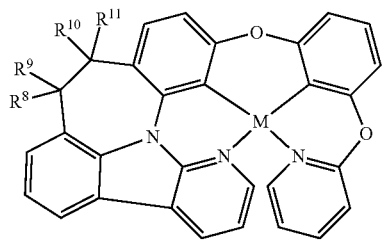
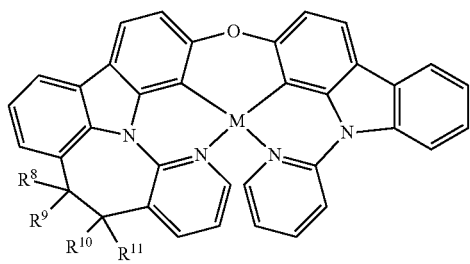
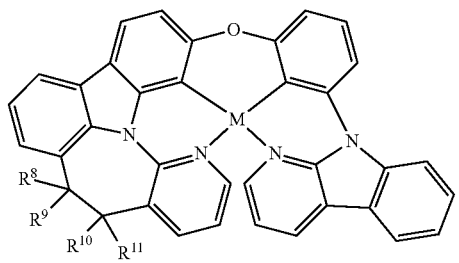
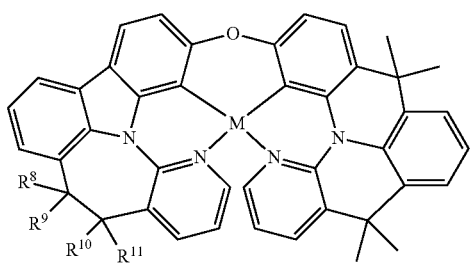
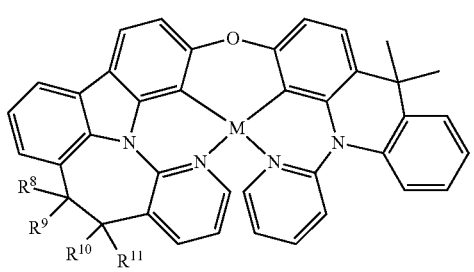
32
-continued
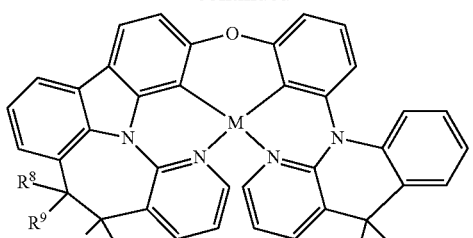
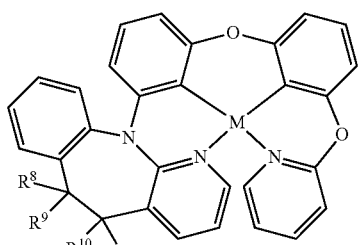
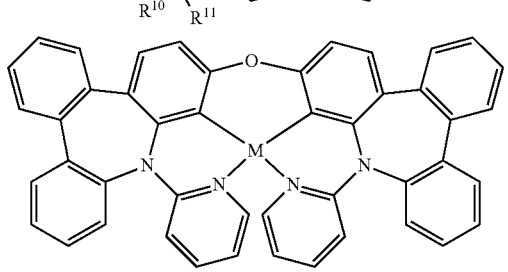
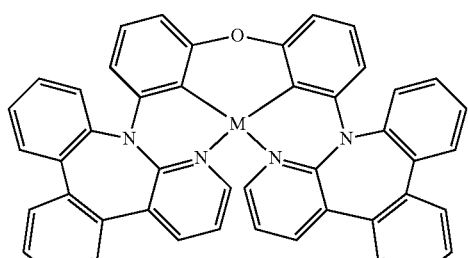
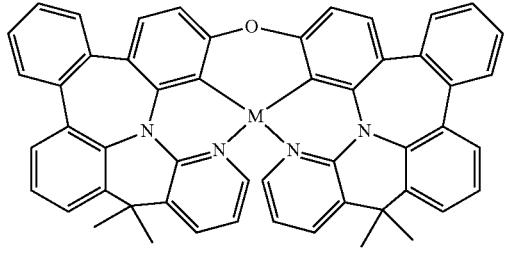
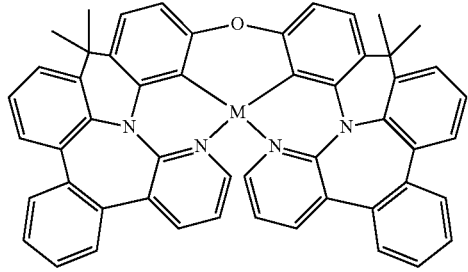

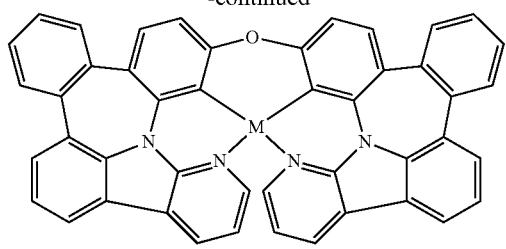
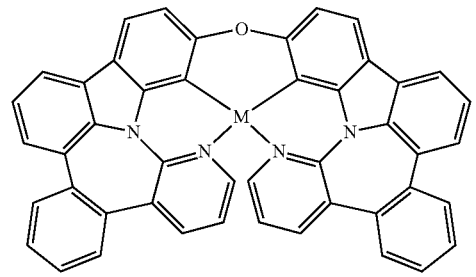
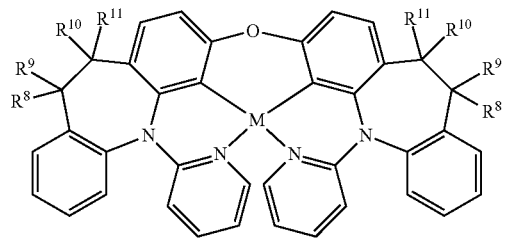
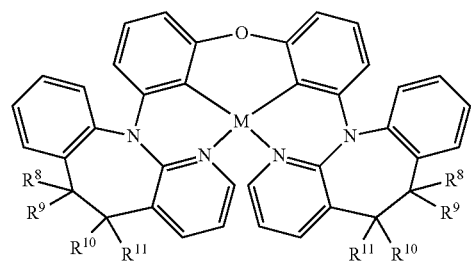
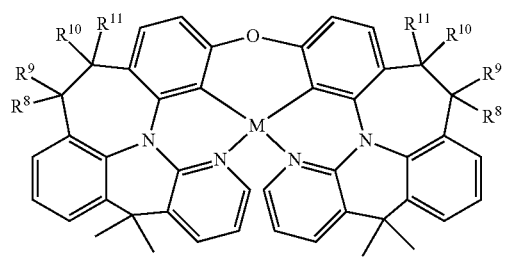
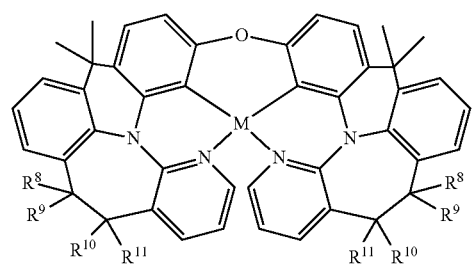
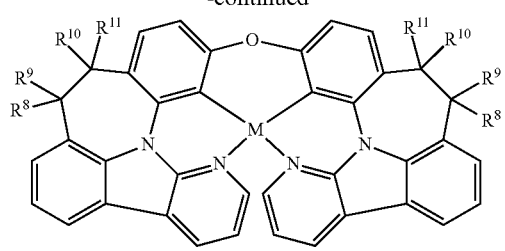
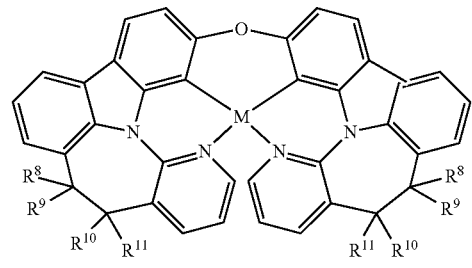
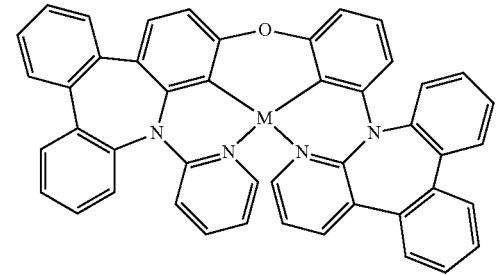
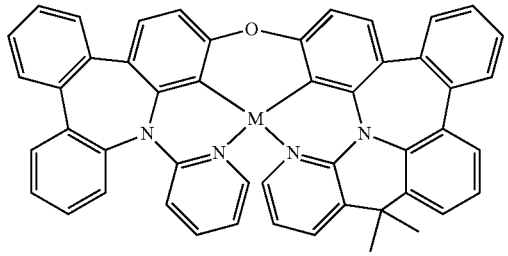
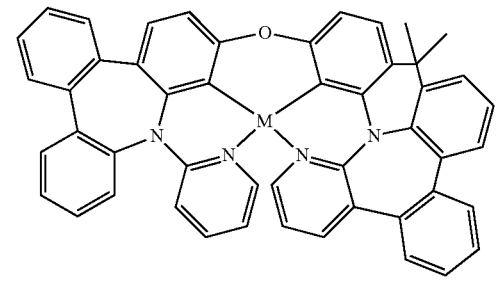
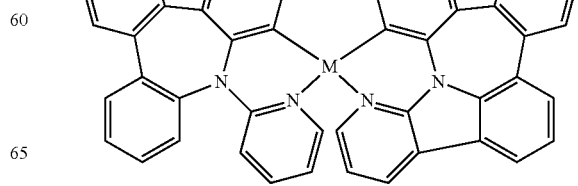

35
-continued
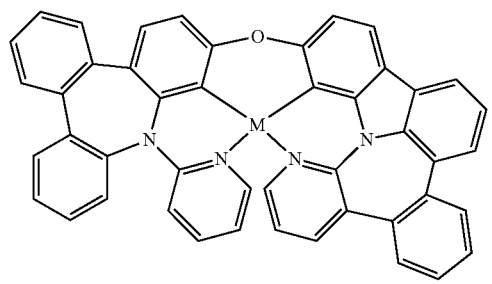
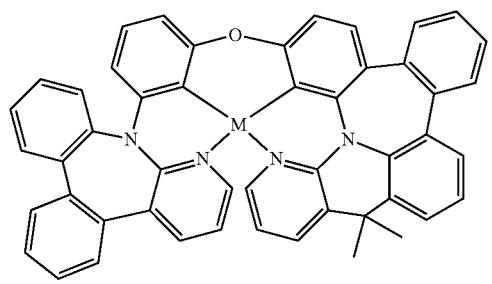
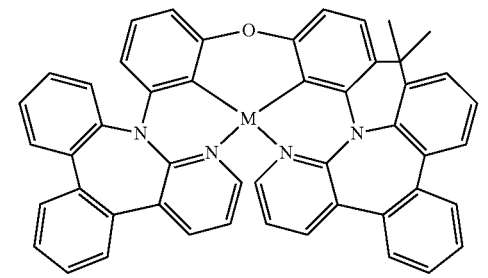
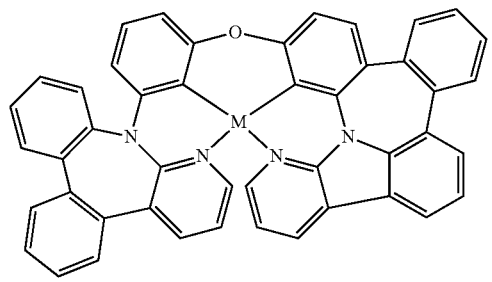
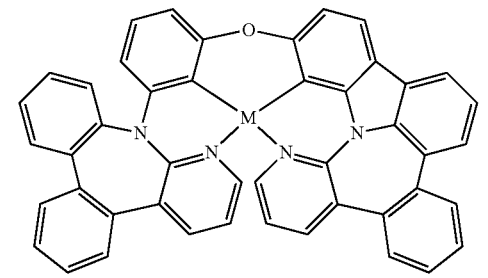
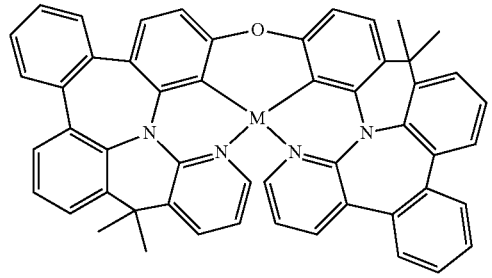
36
-continued
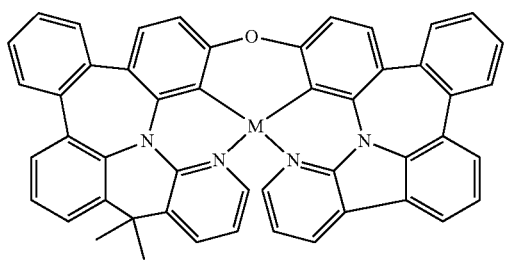
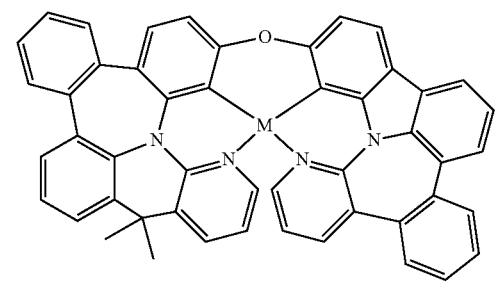
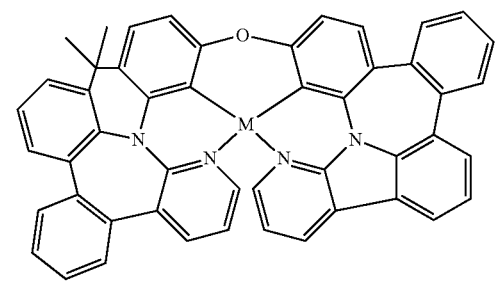
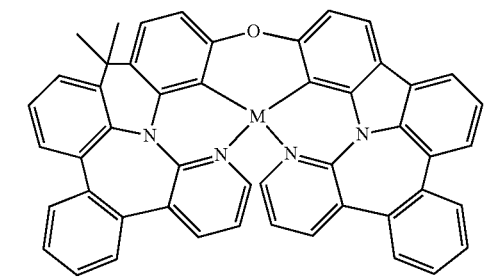
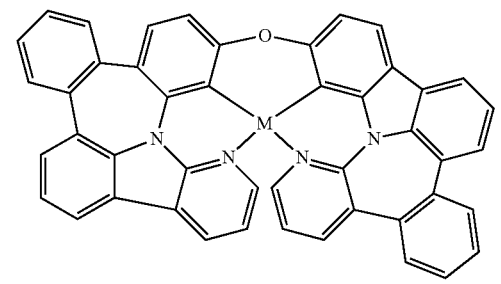
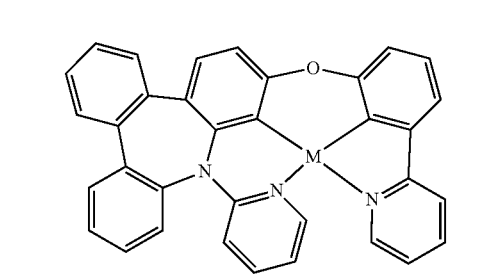

-continued
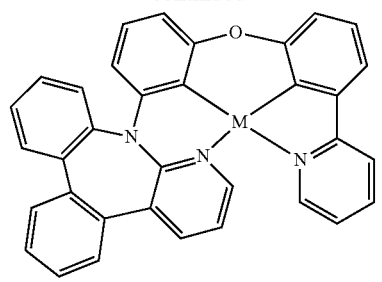
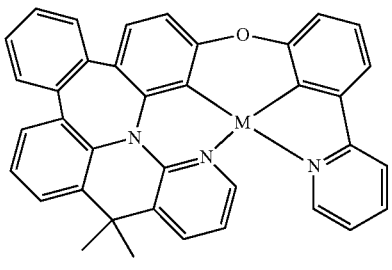
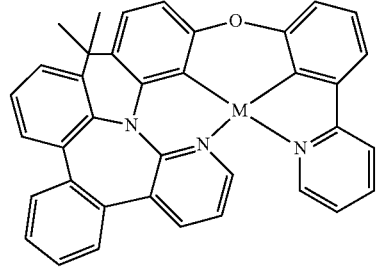
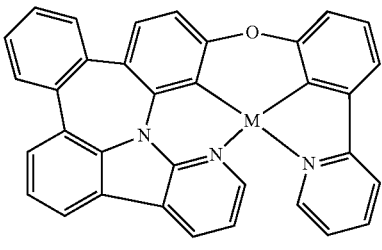
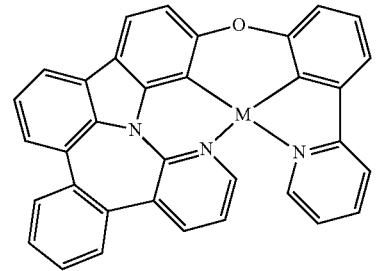
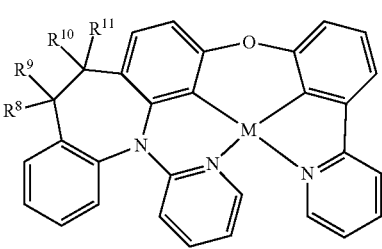
-continued
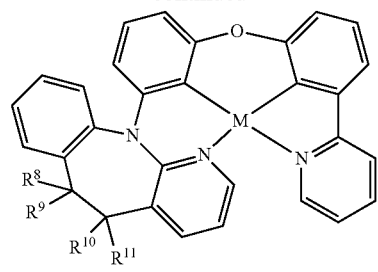
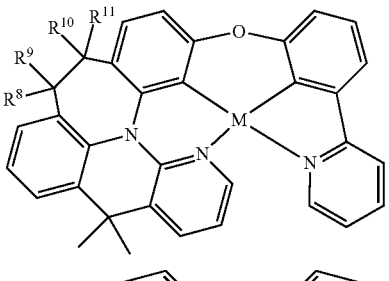
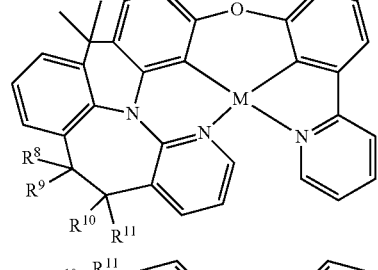
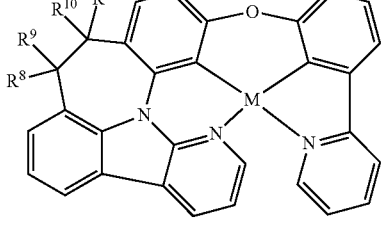
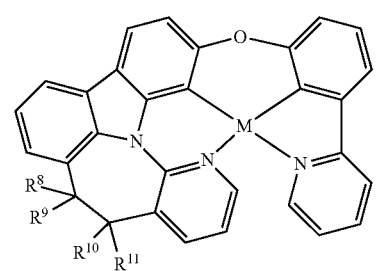
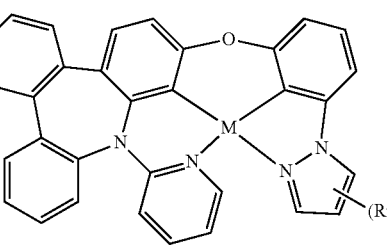

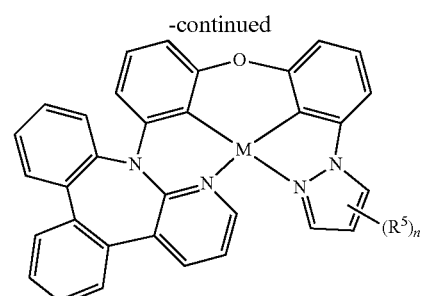
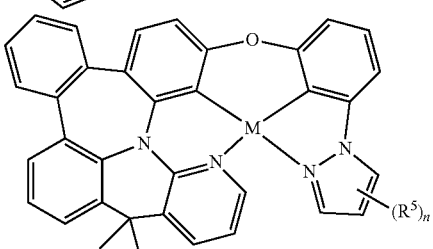
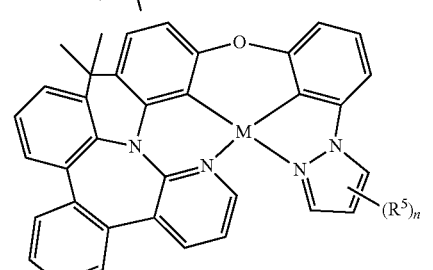
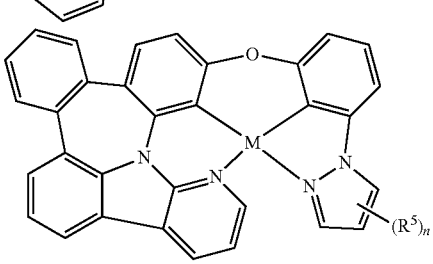
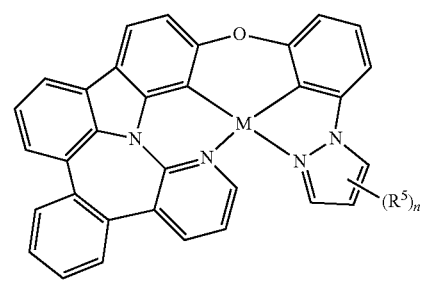
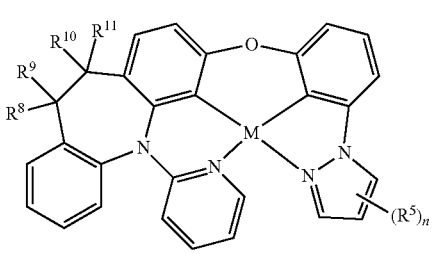
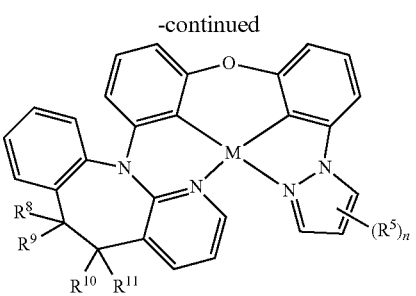
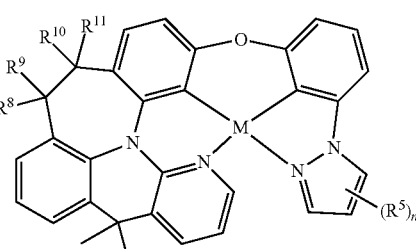
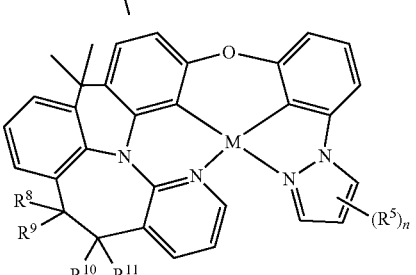
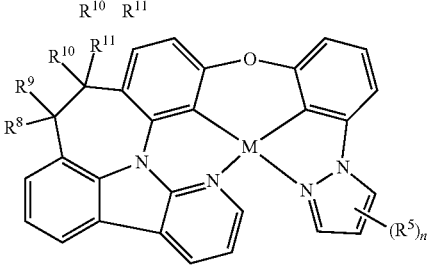
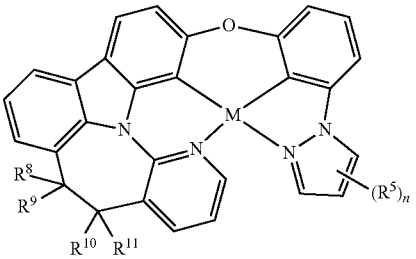
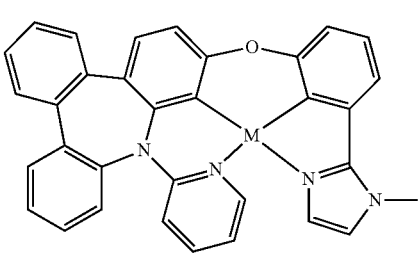

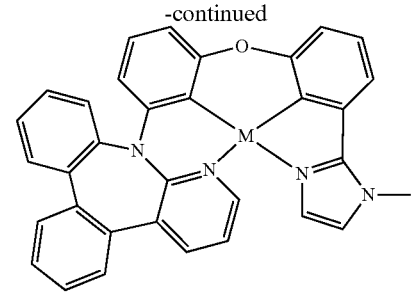
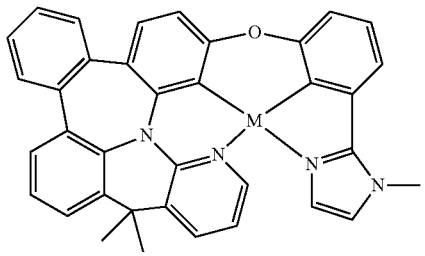
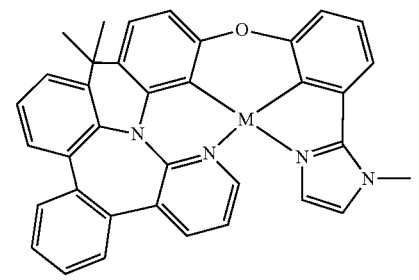
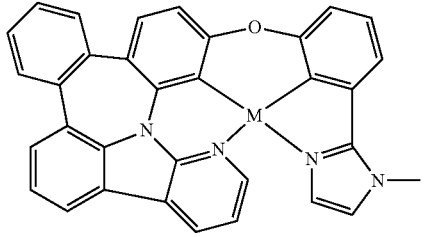
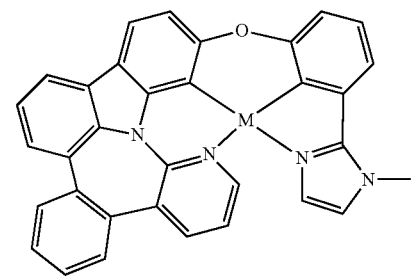
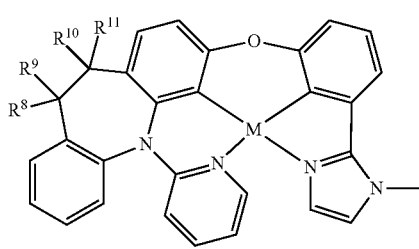
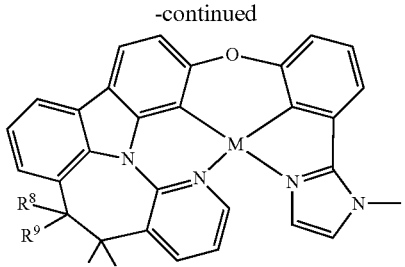
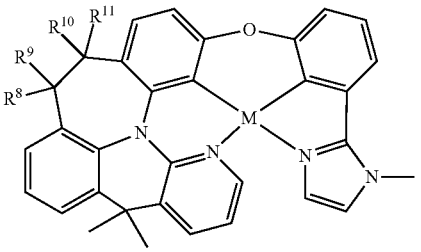
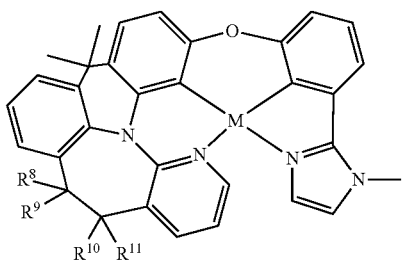
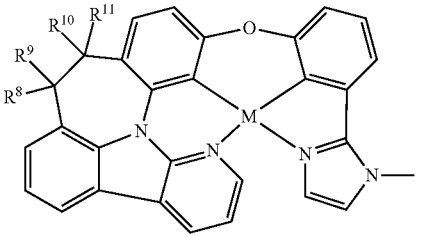
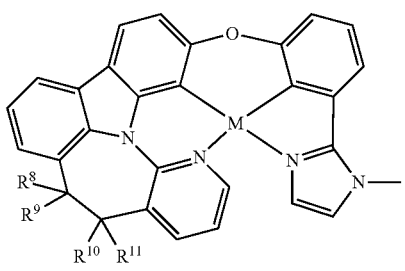
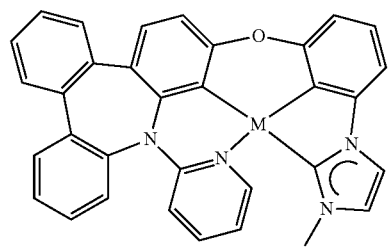

-continued
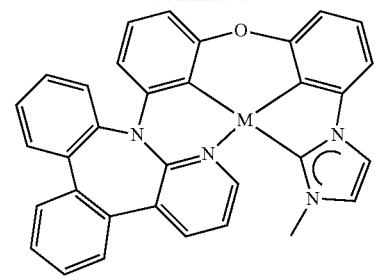
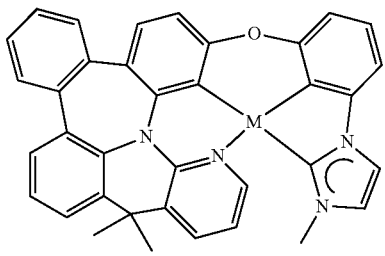
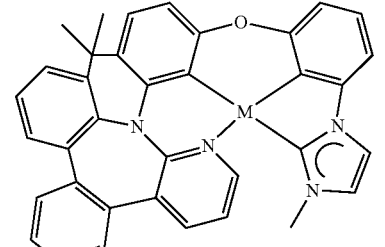
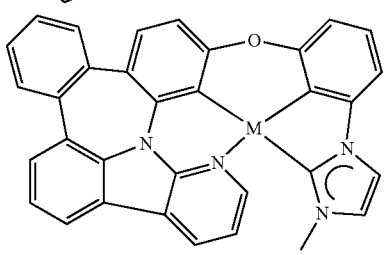
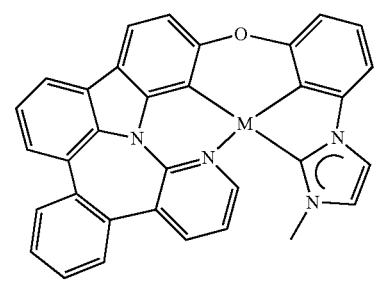
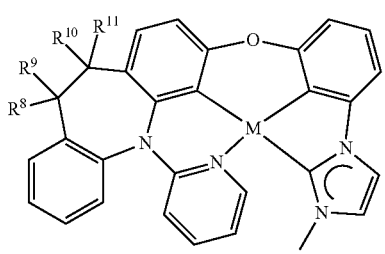
-continued
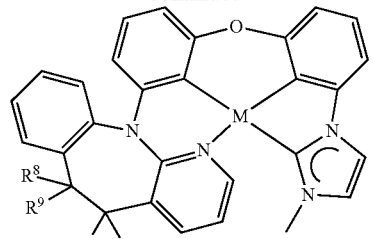
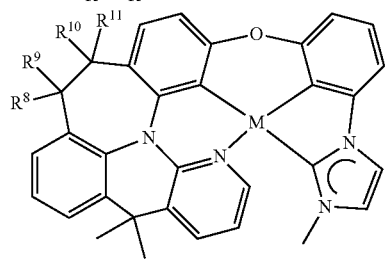
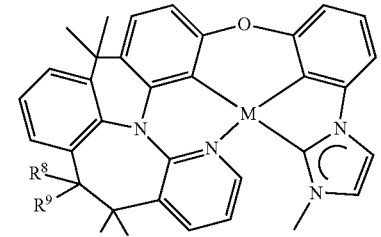
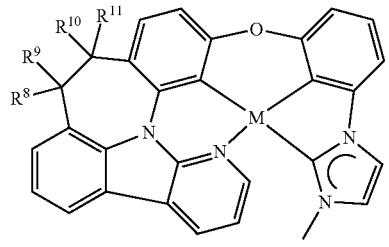
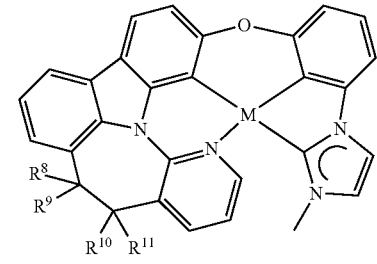
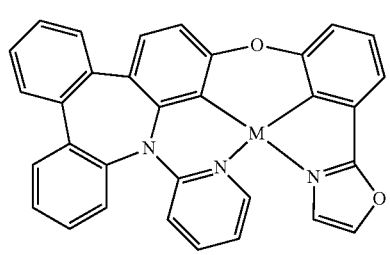

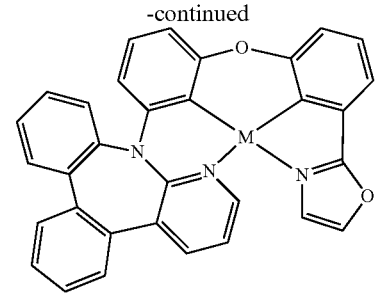
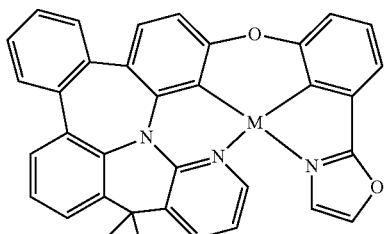
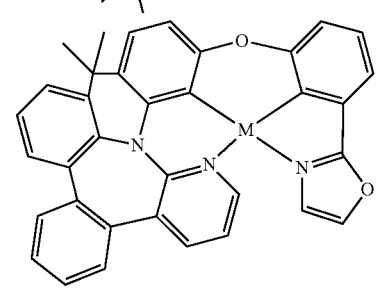
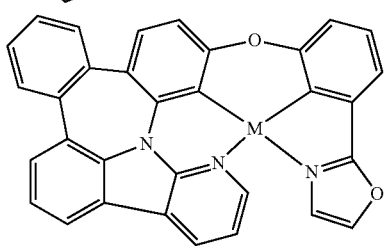
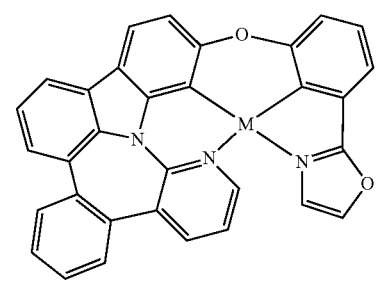
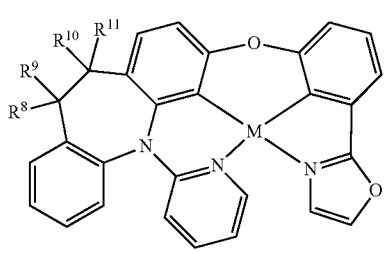
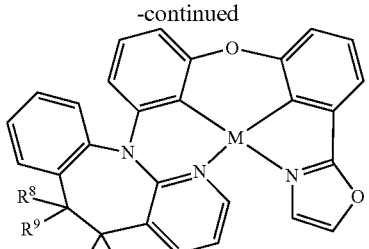
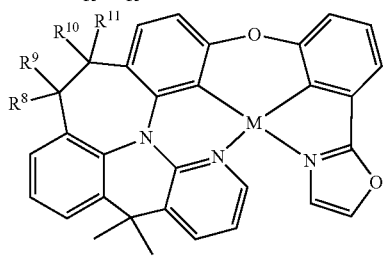
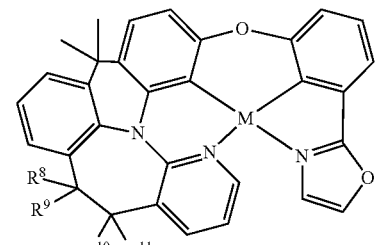
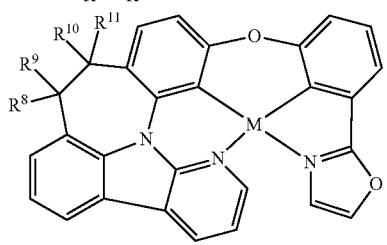
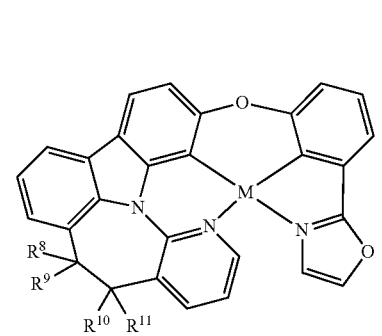
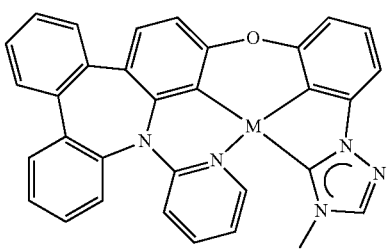

-continued
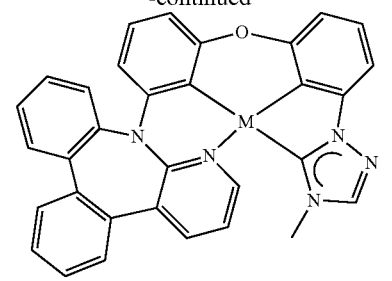
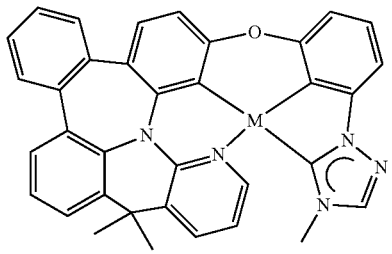
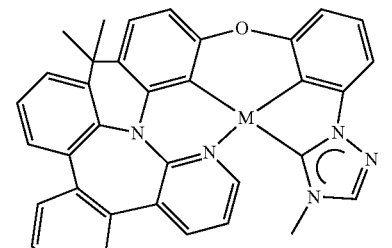
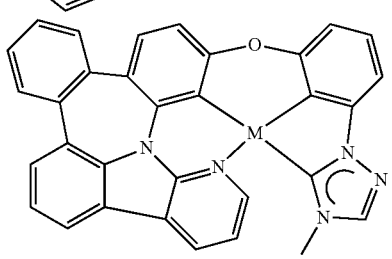
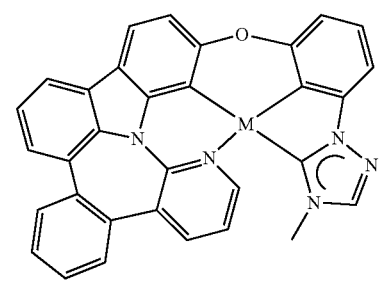
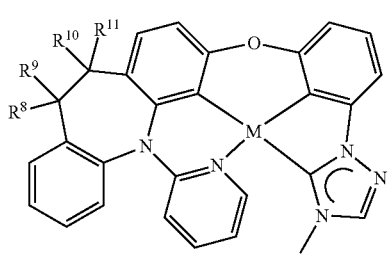
-continued
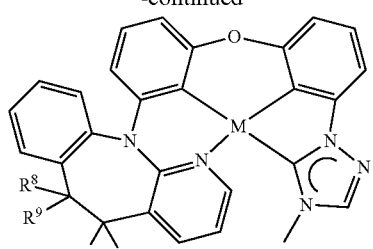
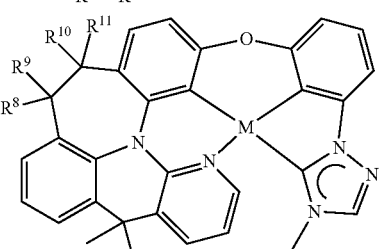
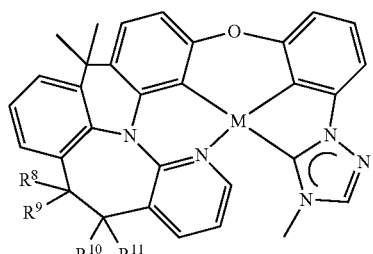
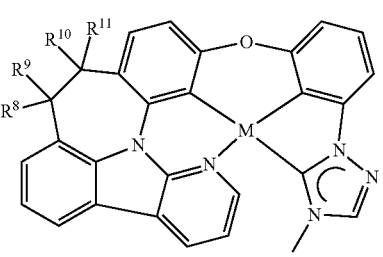
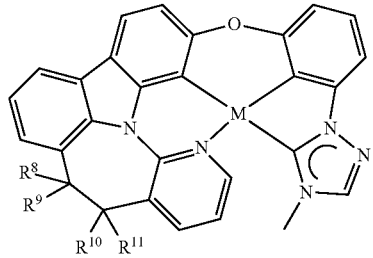
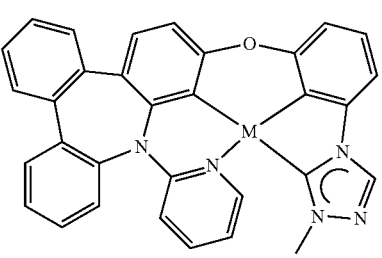

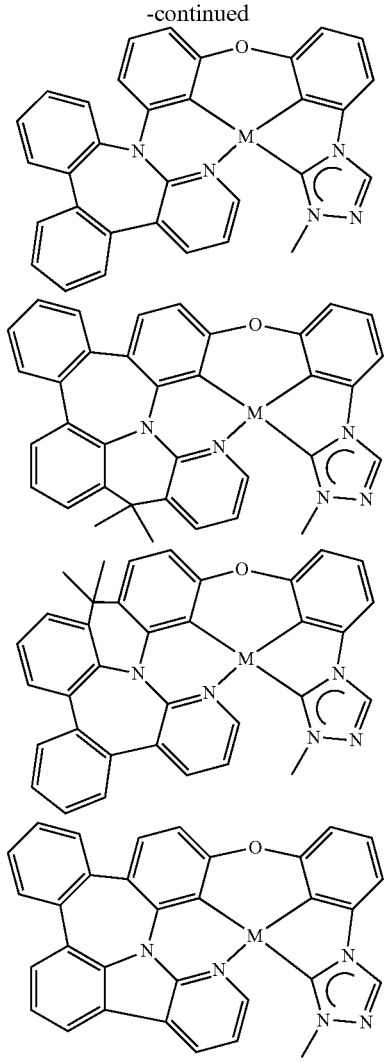
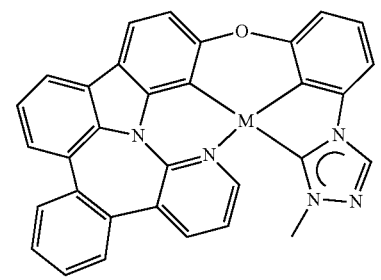
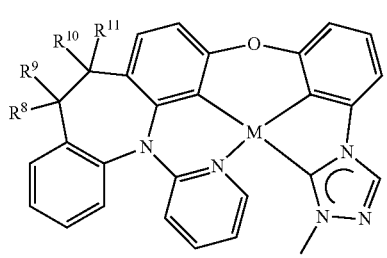
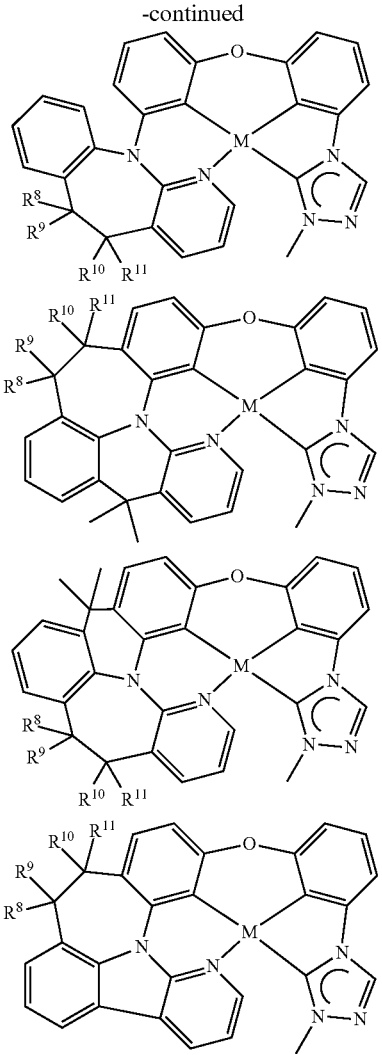
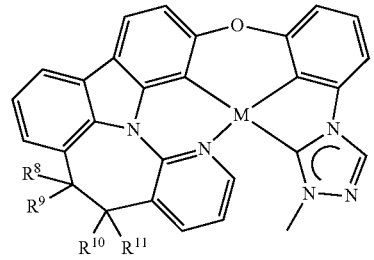
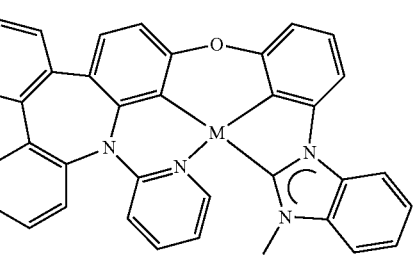

51
-continued
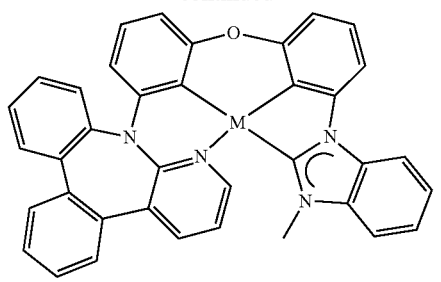
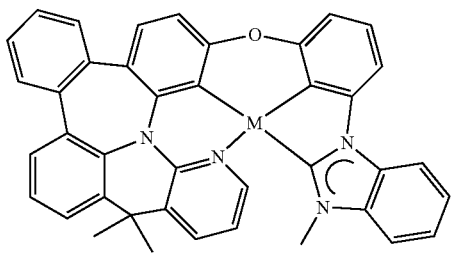
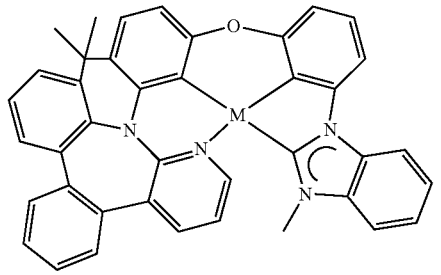
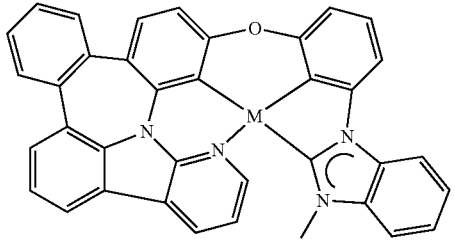
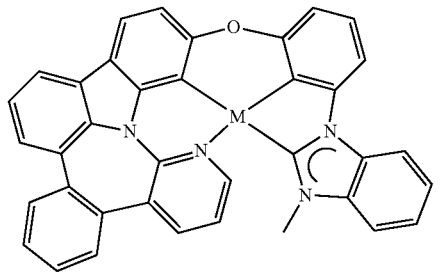
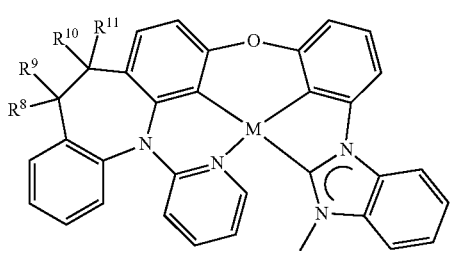
52
-continued
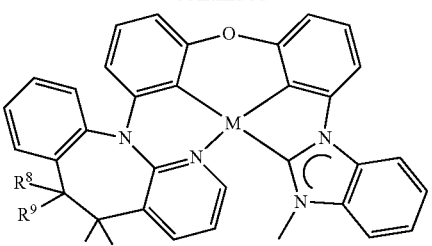
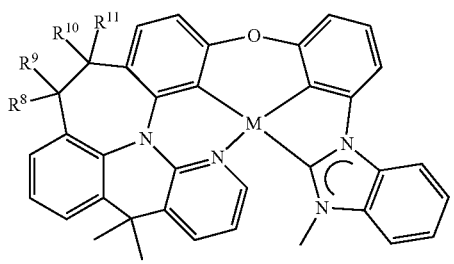
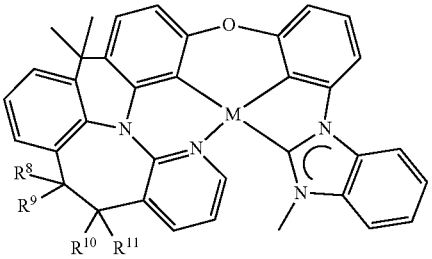
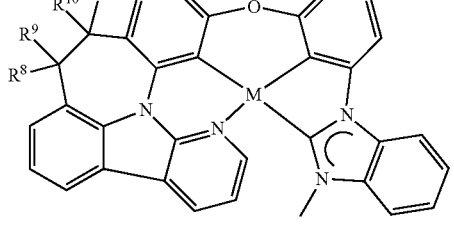
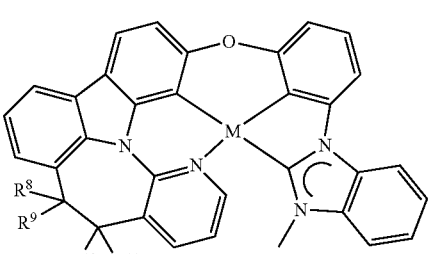
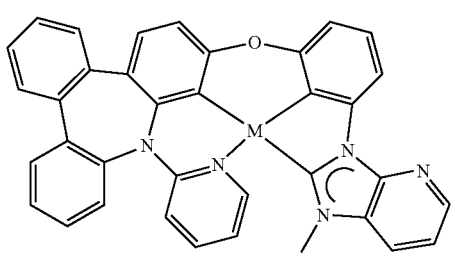

53
-continued
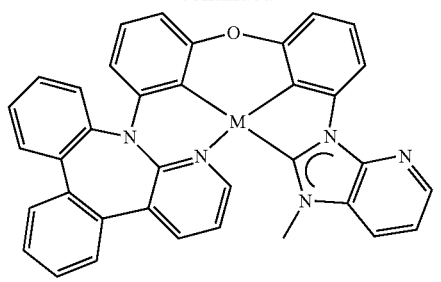
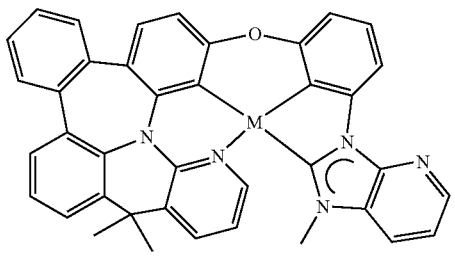
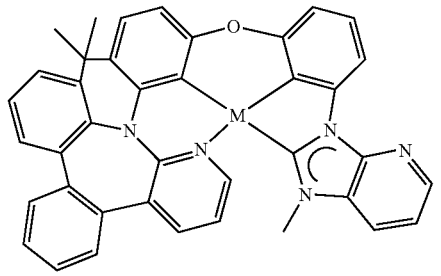
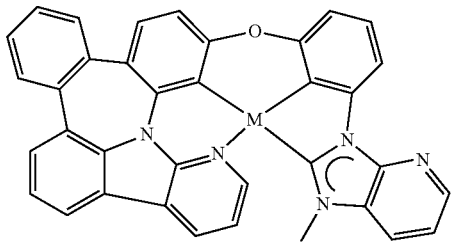
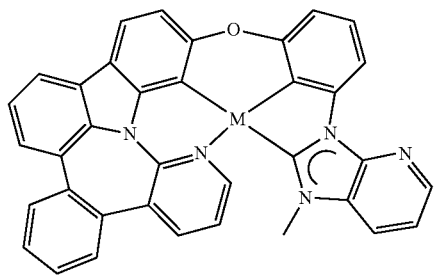
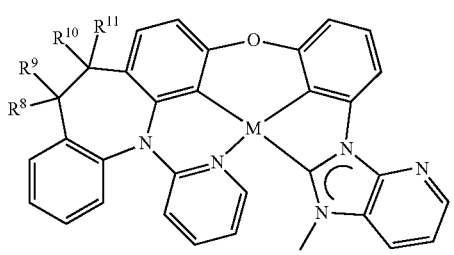
54
-continued
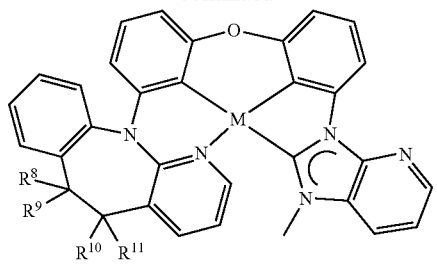
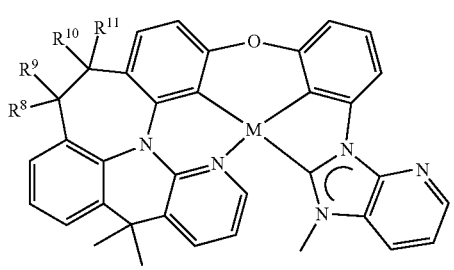
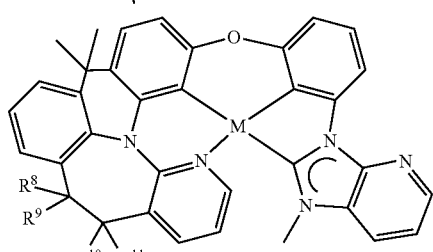
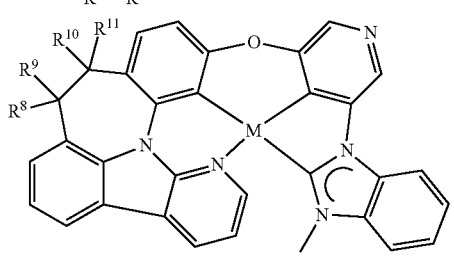
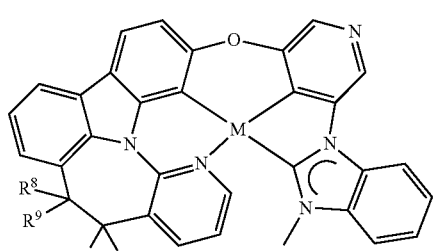
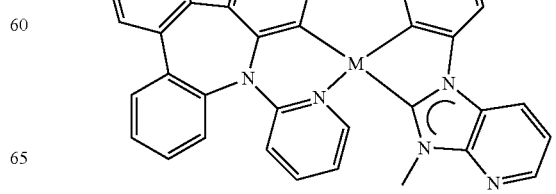

-continued
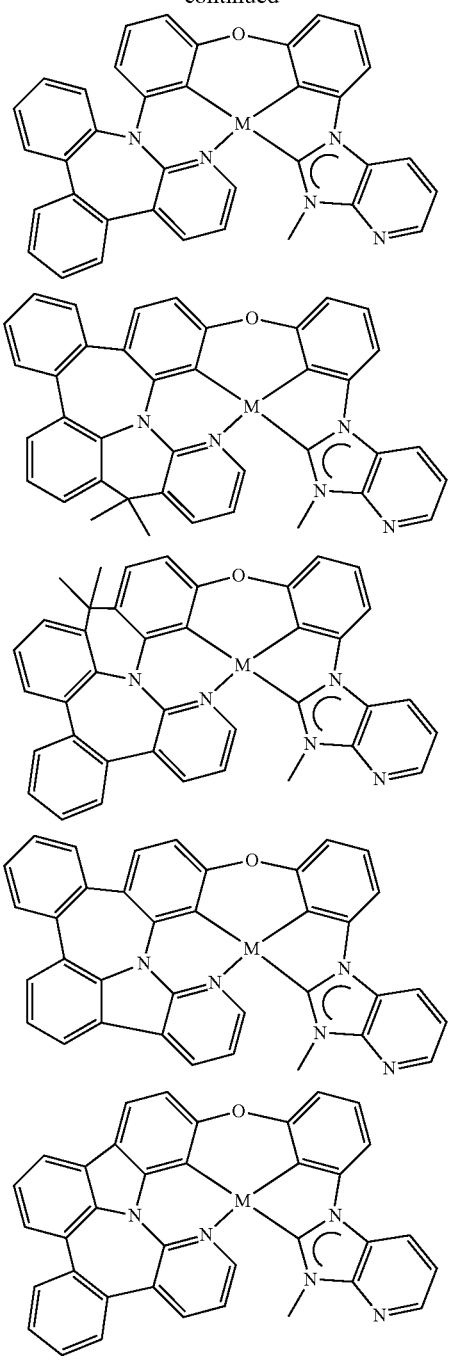
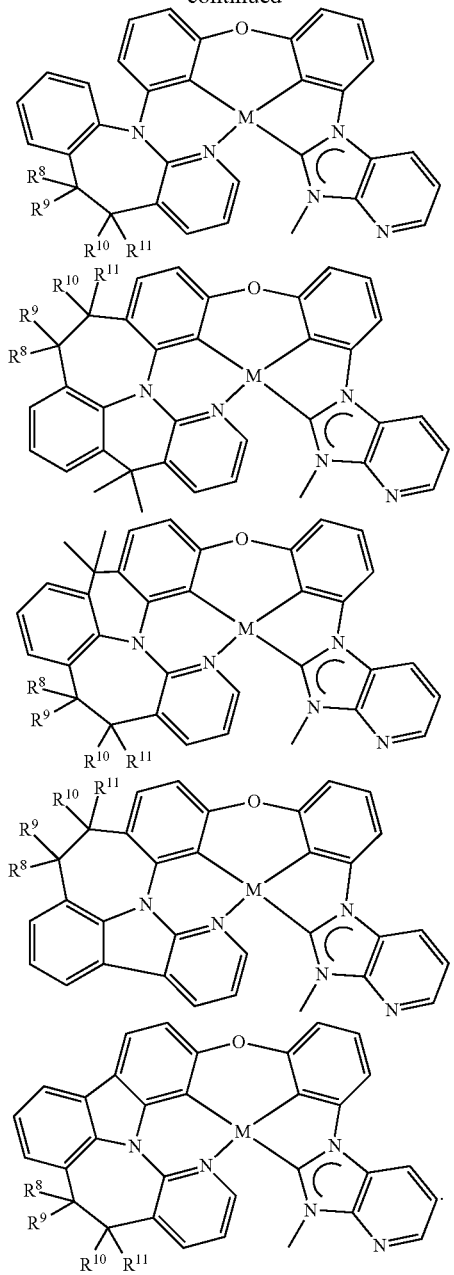
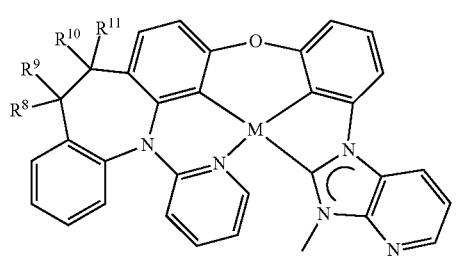
Complexes of Formula C are represented as:
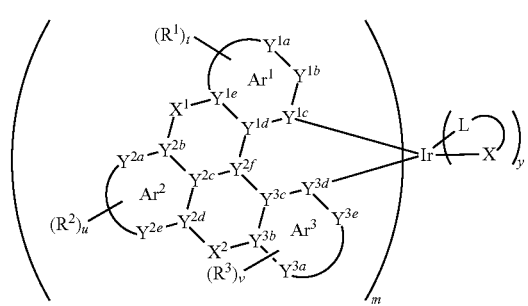

where:

$R^1$, $R^2$, and $R^3$ each independently represents hydrogen, halogen, hydroxyl, nitro, thiol, or substituted or unsubstituted $C_1$-$C_4$ alkyl, alkoxy, amino, or aryl;

$Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{2e}$, $Y^{3a}$, $Y^{3b}$, $Y^{3c}$, $Y^{3d}$, and $Y^{3e}$ each independently represents C, N, Si, O, or S;

$Ar^1$, $Ar^2$, and $Ar^3$ each independently represents an aryl or heteroaryl;

$Y^2f$, valency permitting, represents N, P, N=O, P=O, NR, PR, CR, SiR, $CR_2$, $SiR_2O$, or S;

m is 1, 2, or 3;

y is 0, 1, or 2;

the sum of m and y is 3;

each of t, u, and v is independently 0, 1, 2, 3, 4, or 5, valency permitting;

at least one of $X^1$ and $X^2$ independently represents one of the following moieties:

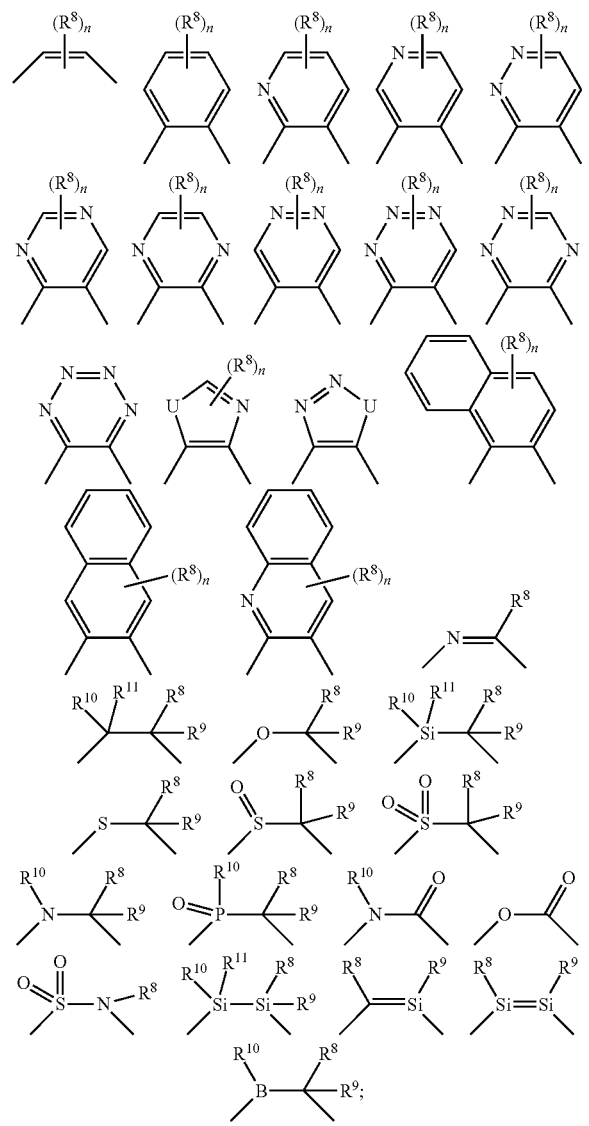

and the other $X^1$ and $X^2$, if not one of the moieties above, is independently absent or represents single bond, NR, PR, BR, CRR', SiRR', O, S, S=O, O=S=O, Se, Se=O, or O=Se=O;

$R^8$, $R^9$, $R^{10}$, and $R^{11}$ each independently represents hydrogen, halogen, hydroxyl, nitro, thiol, or substituted or unsubstituted $C_1$-$C_4$ alkyl, alkoxy, amino, or aryl;

each n is independently 1, 2, 3, 4, 5, or 6, valency permitting;

each of R and R' is independently present or absent, and each R and R' present represents substituted or unsubstituted $C_1$-$C_4$ alkyl, aryl, or heteroaryl;

each

present independently represents one of the following moieties:

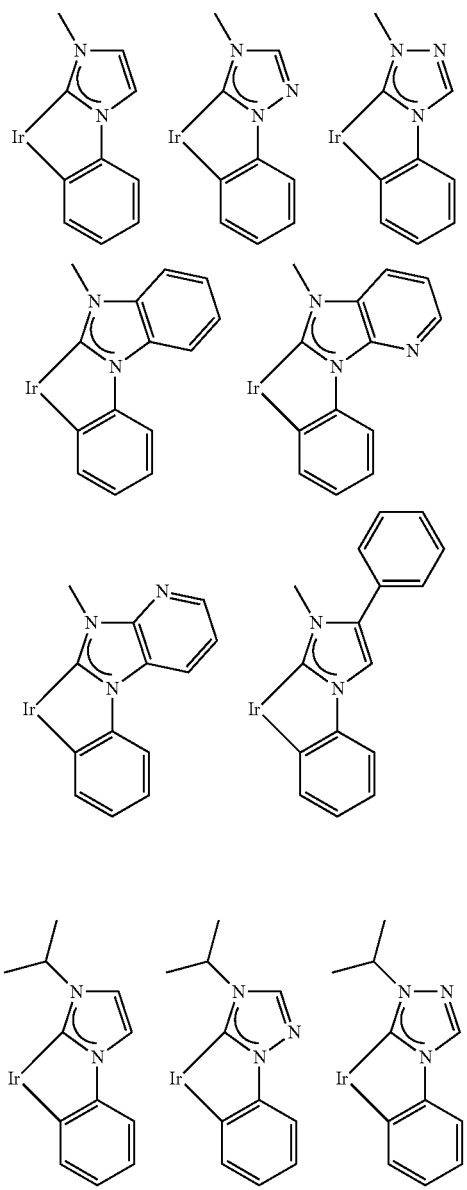

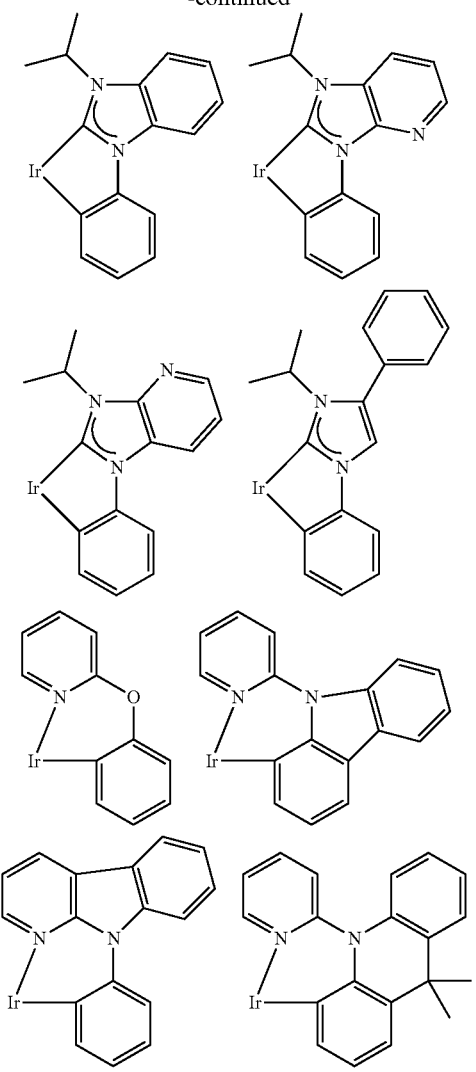
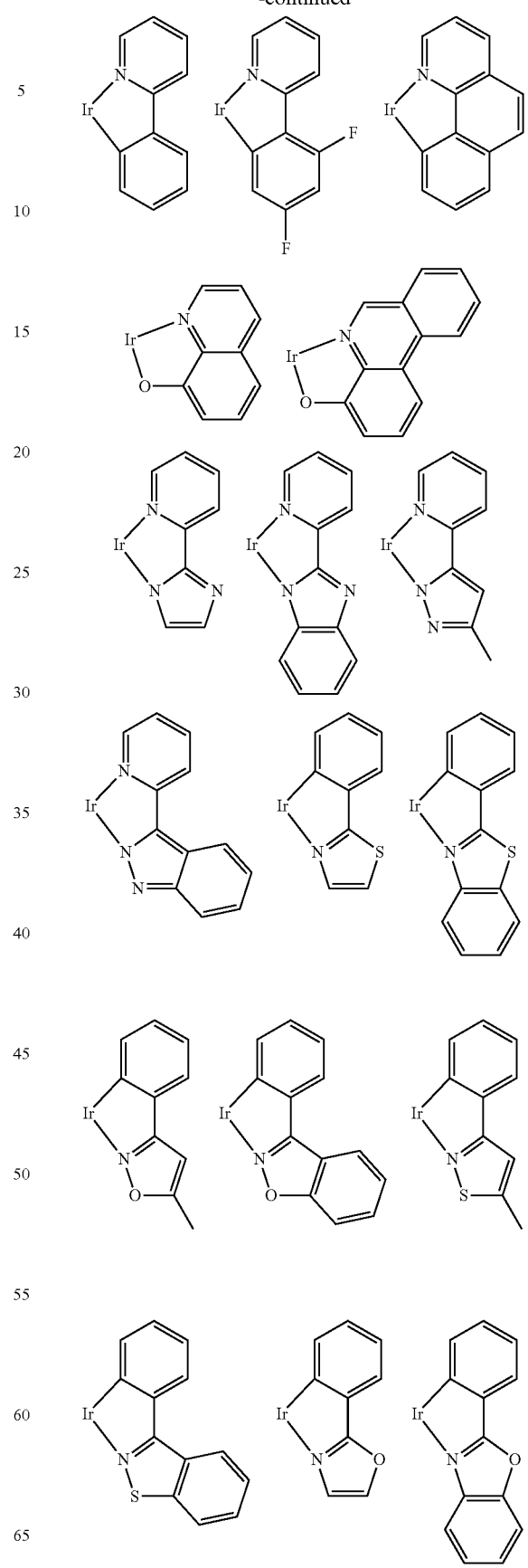

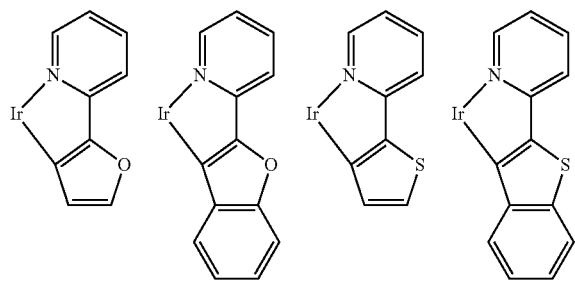
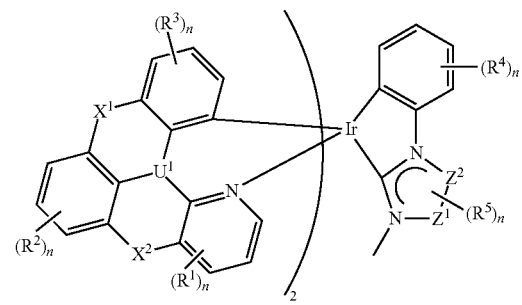
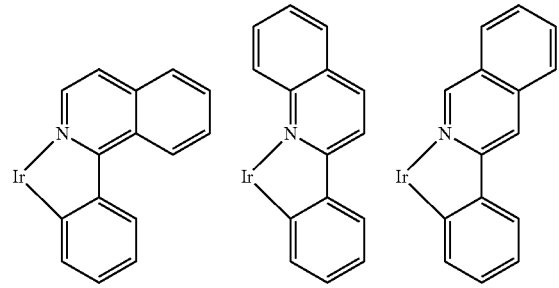
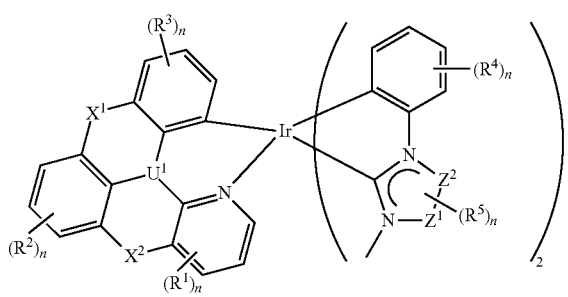
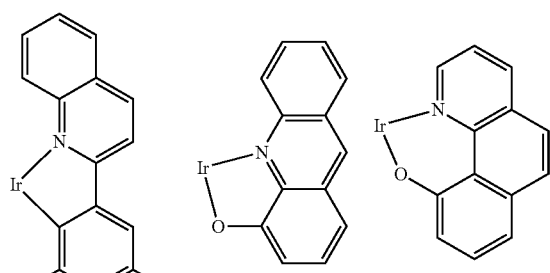
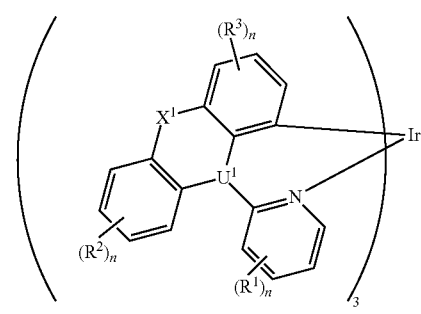
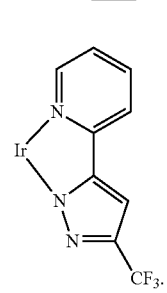
Embodiments of Formula C include the following:
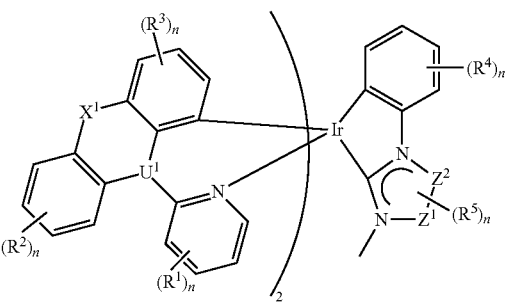
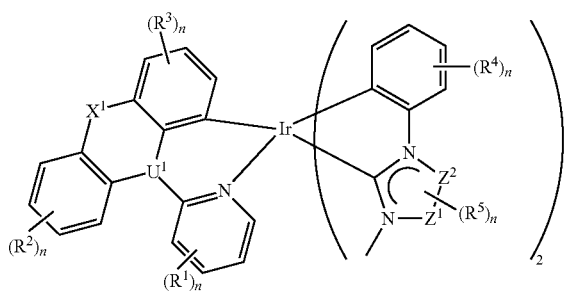

-continued
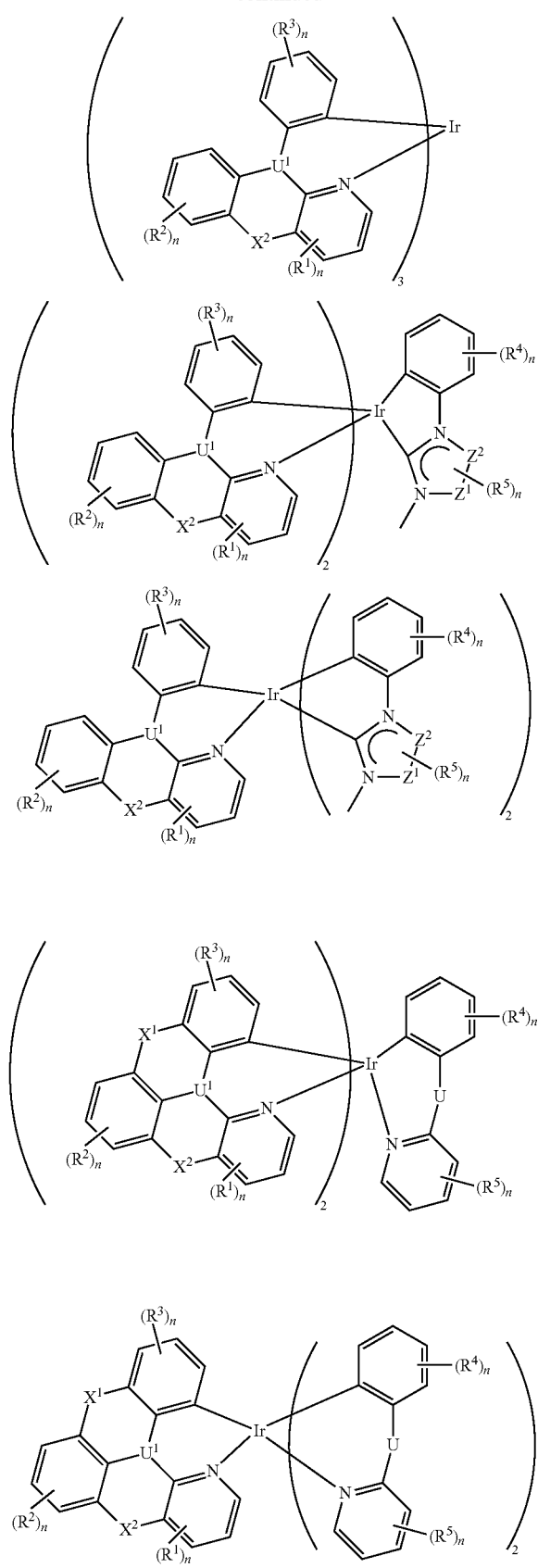
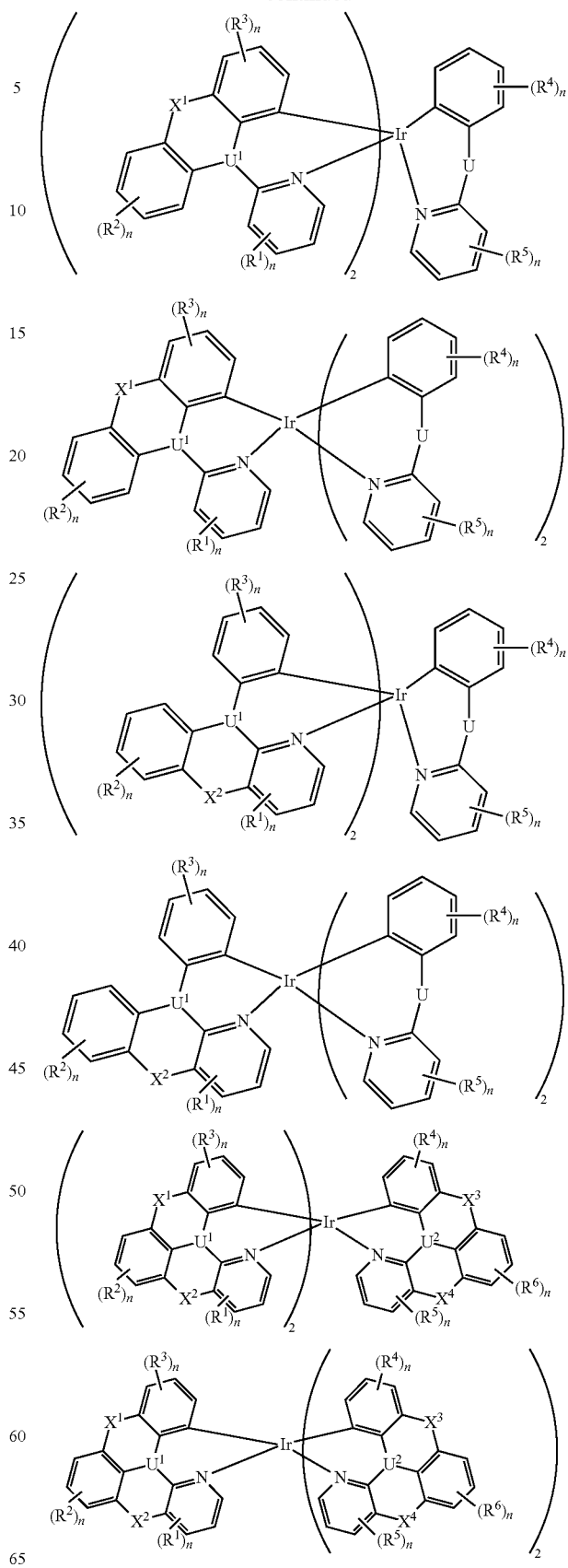

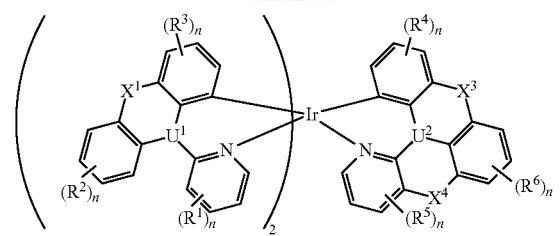
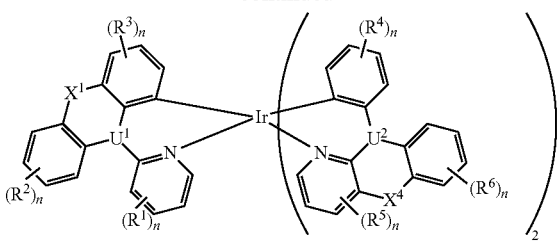
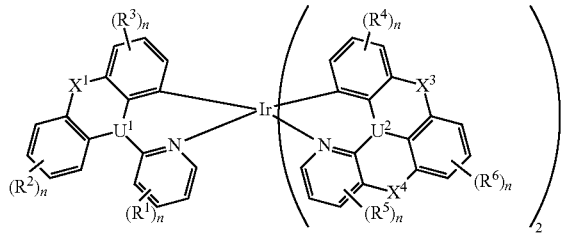
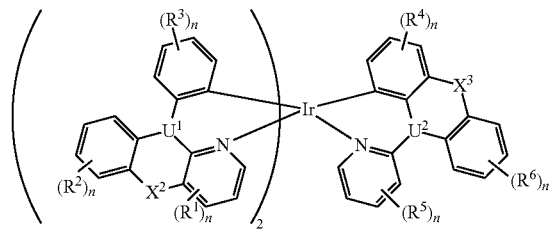
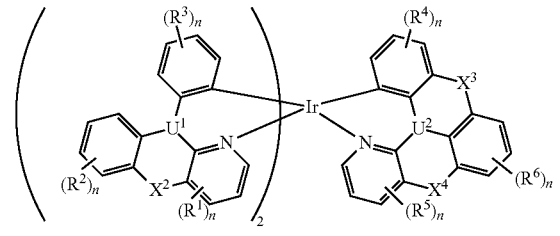
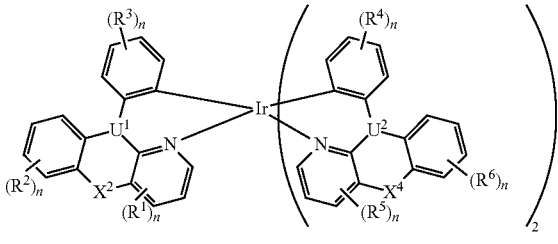
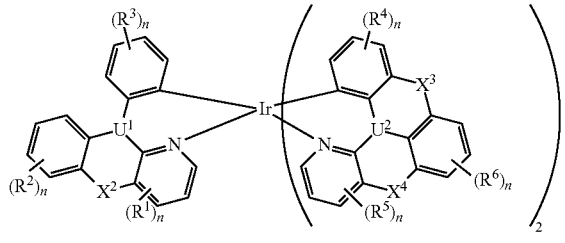
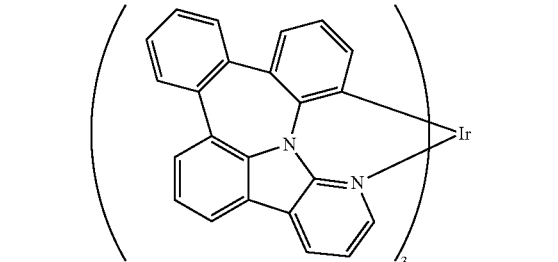
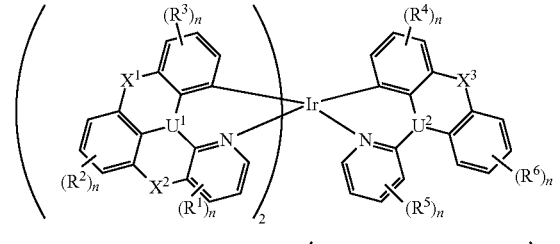
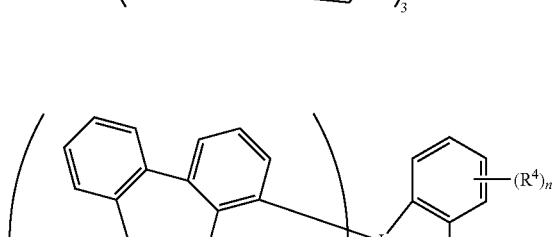
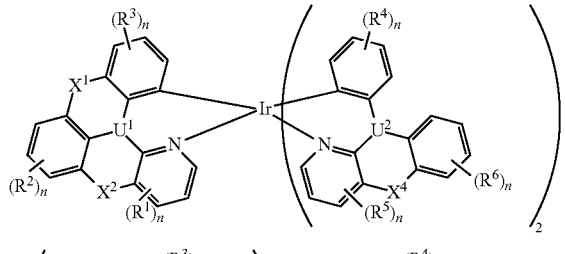
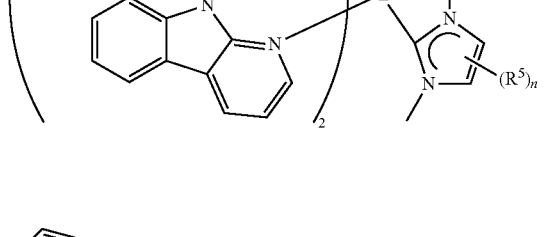
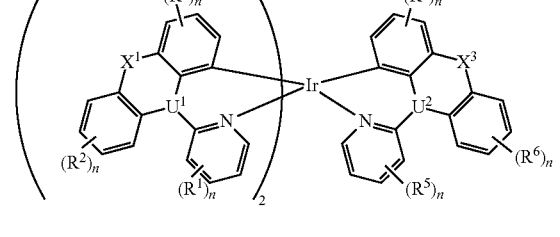
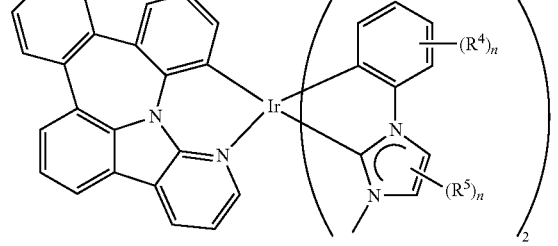

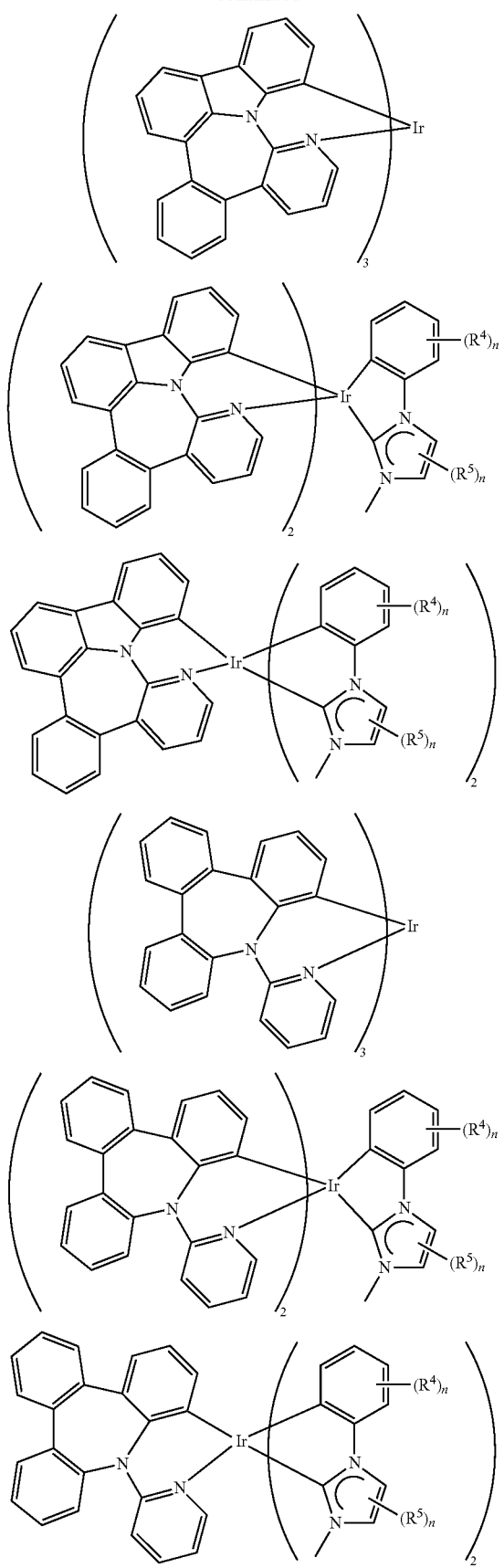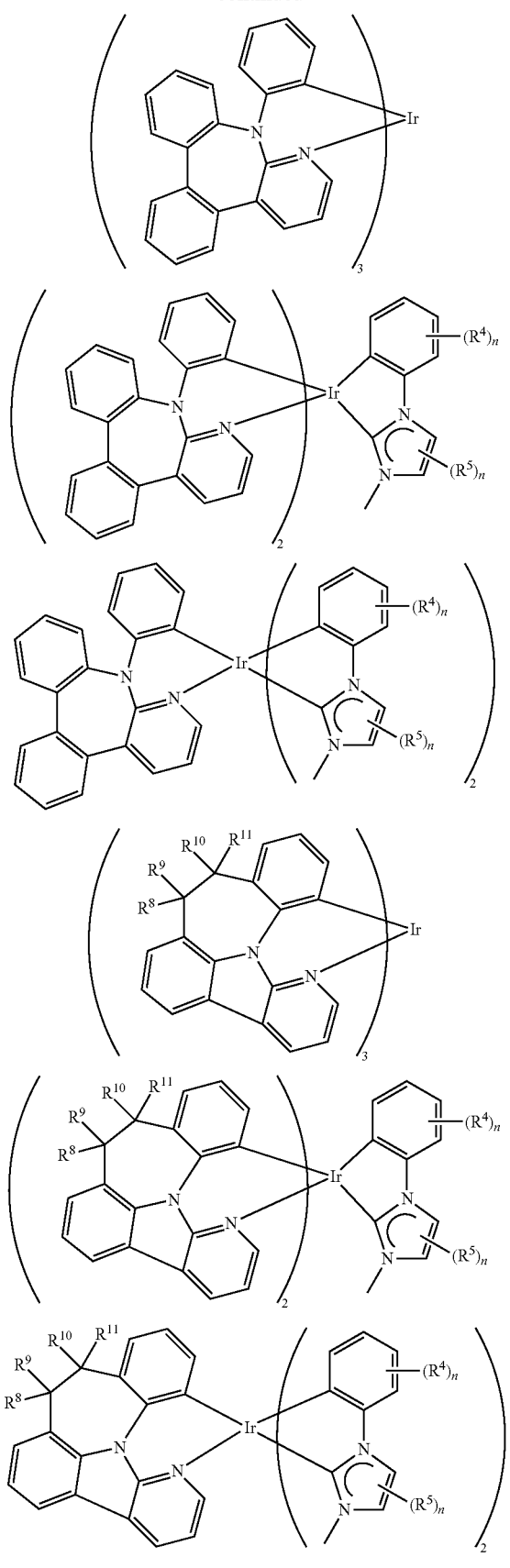

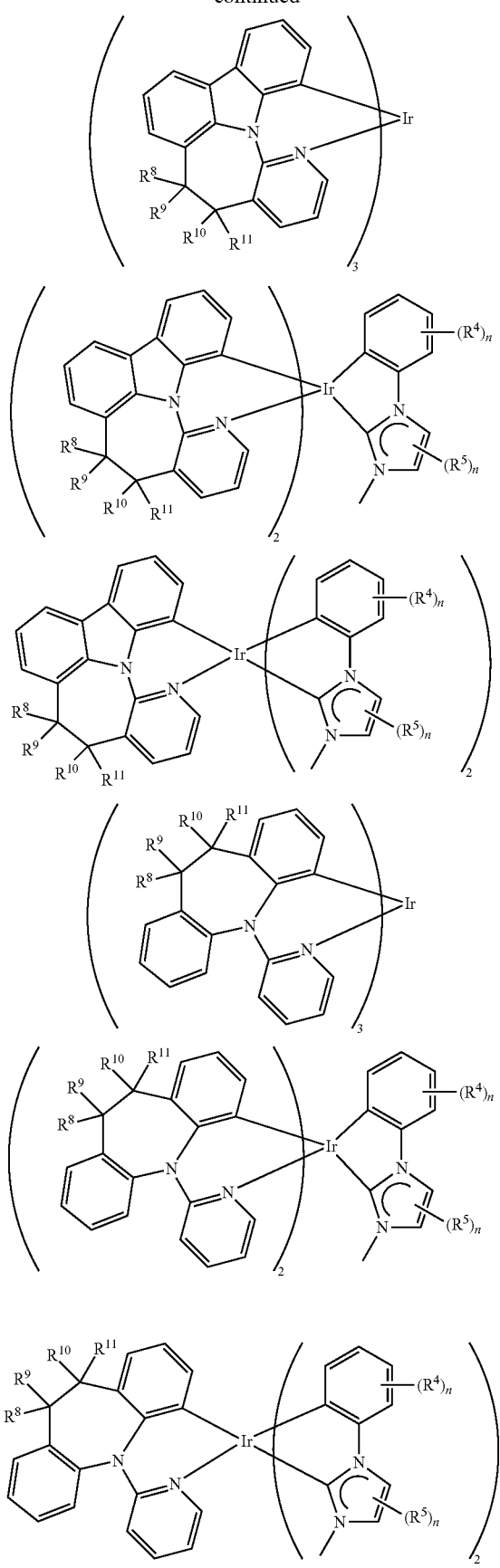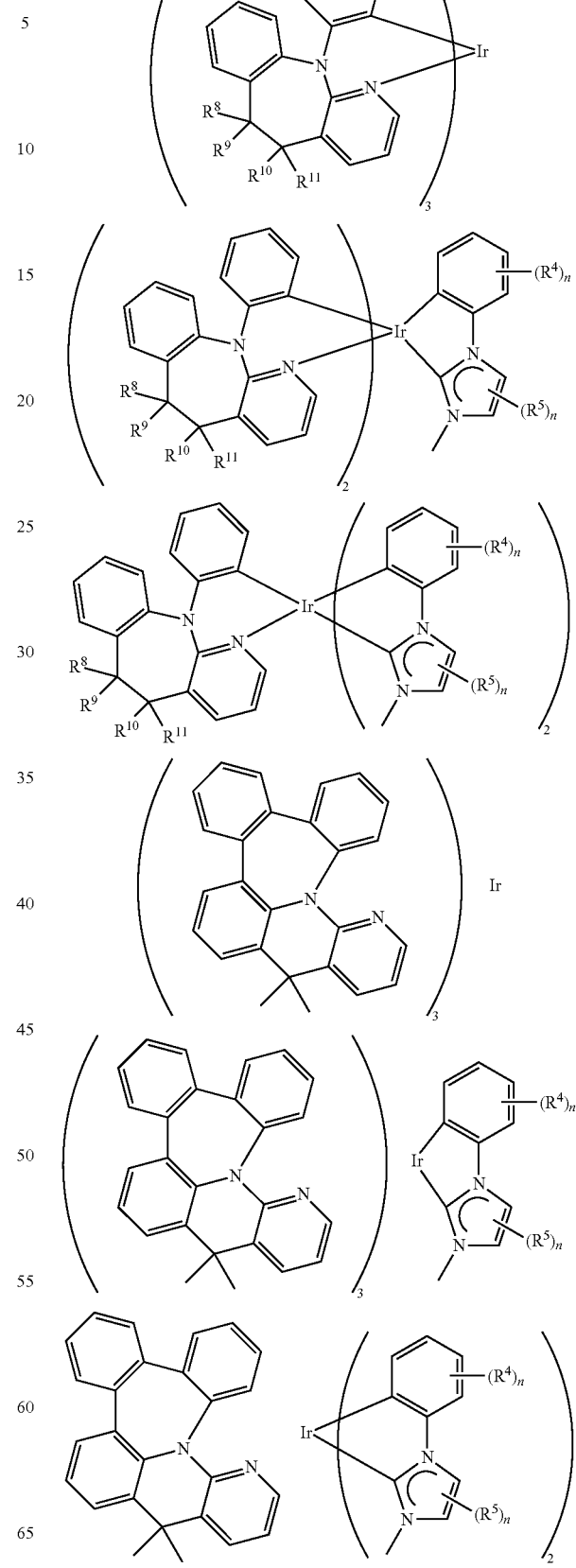

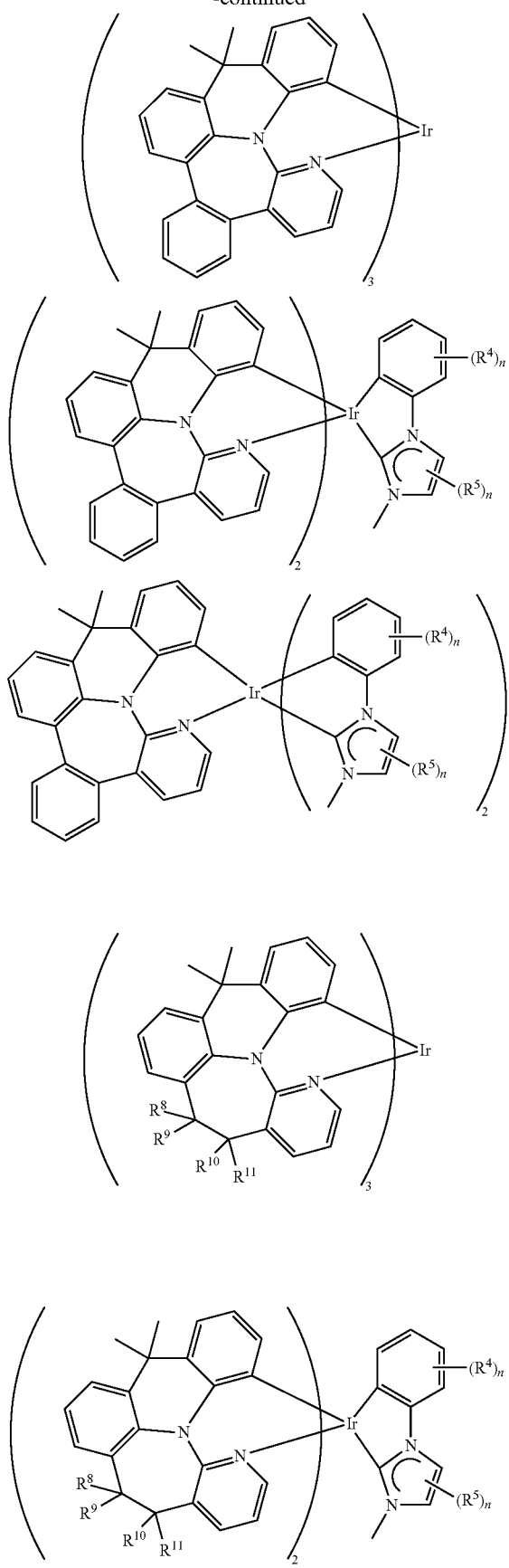
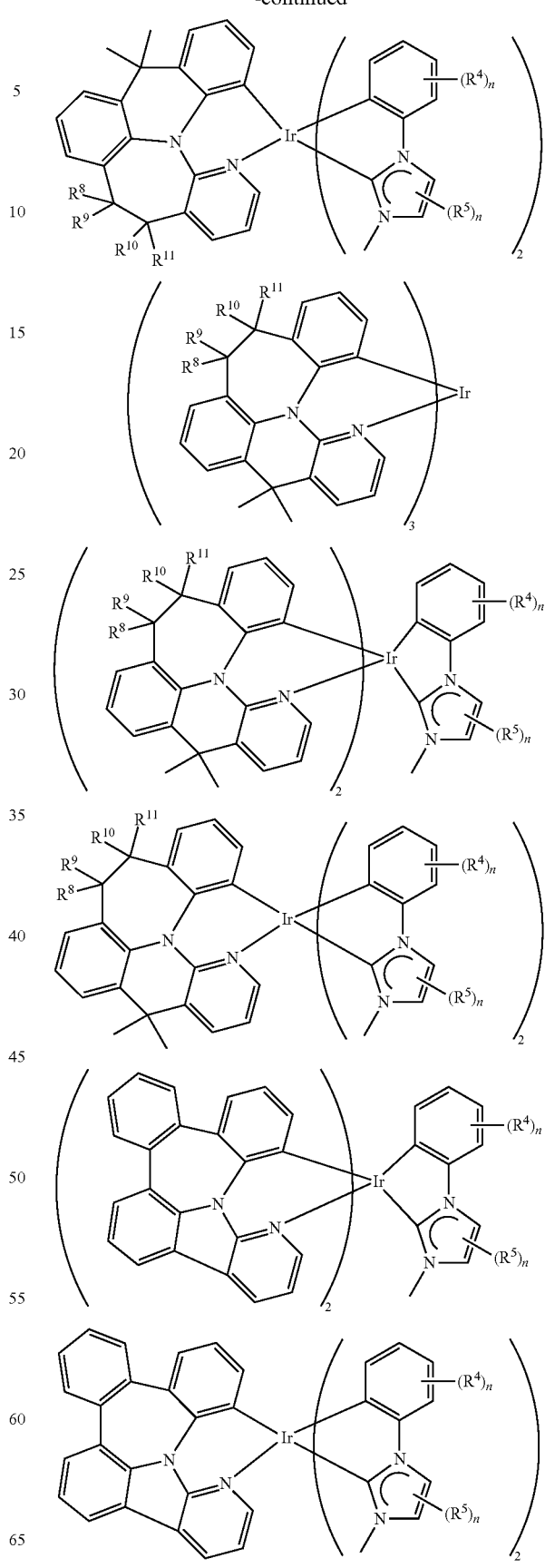

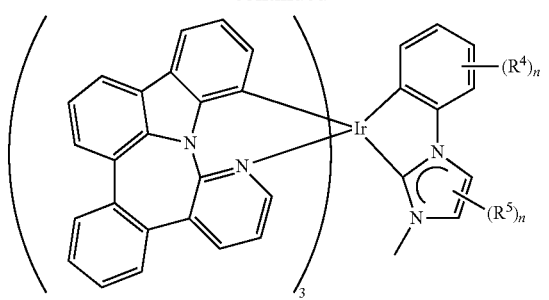
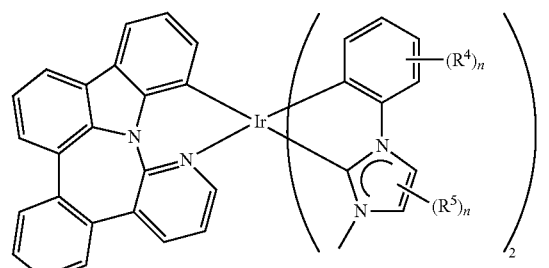
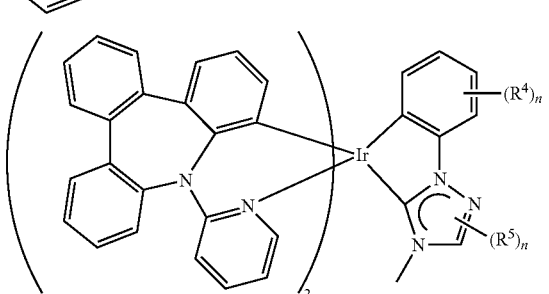
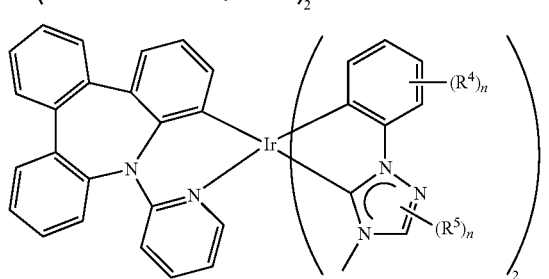
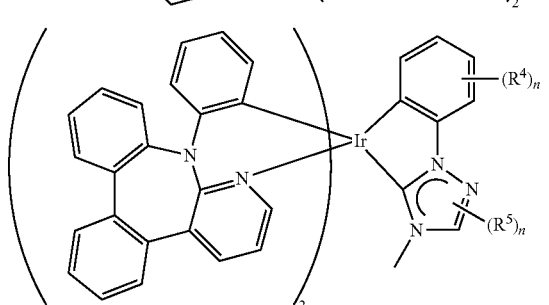
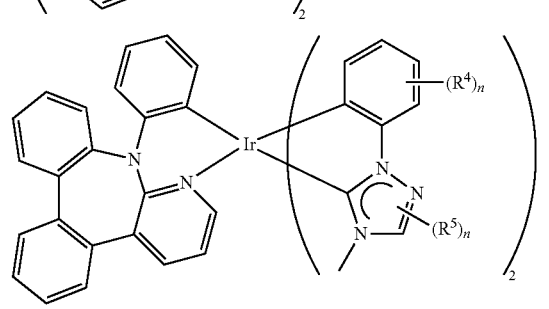
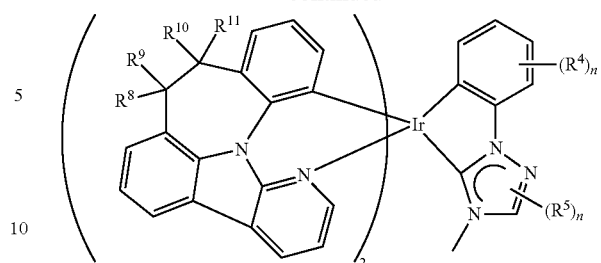
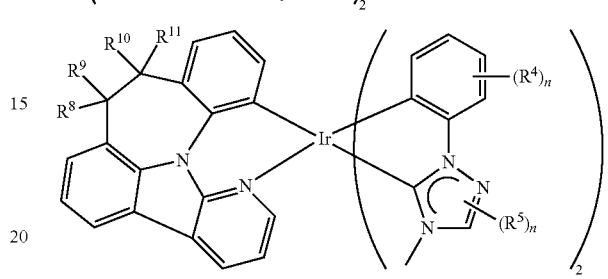
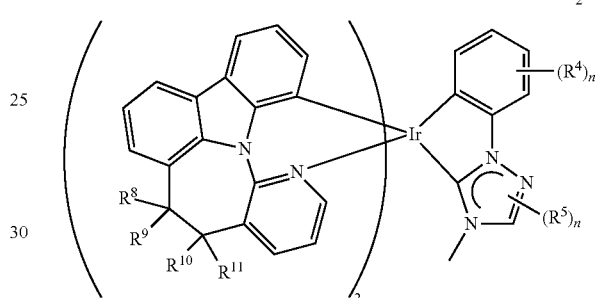
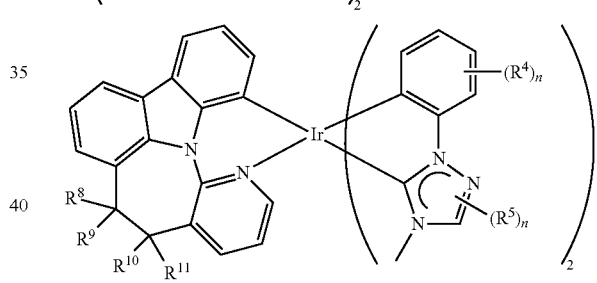
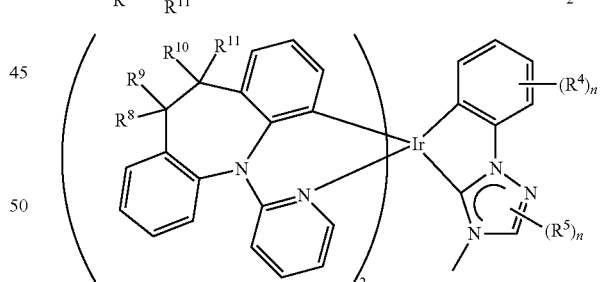
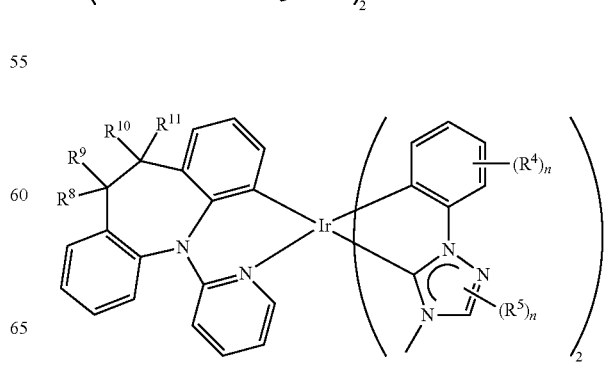

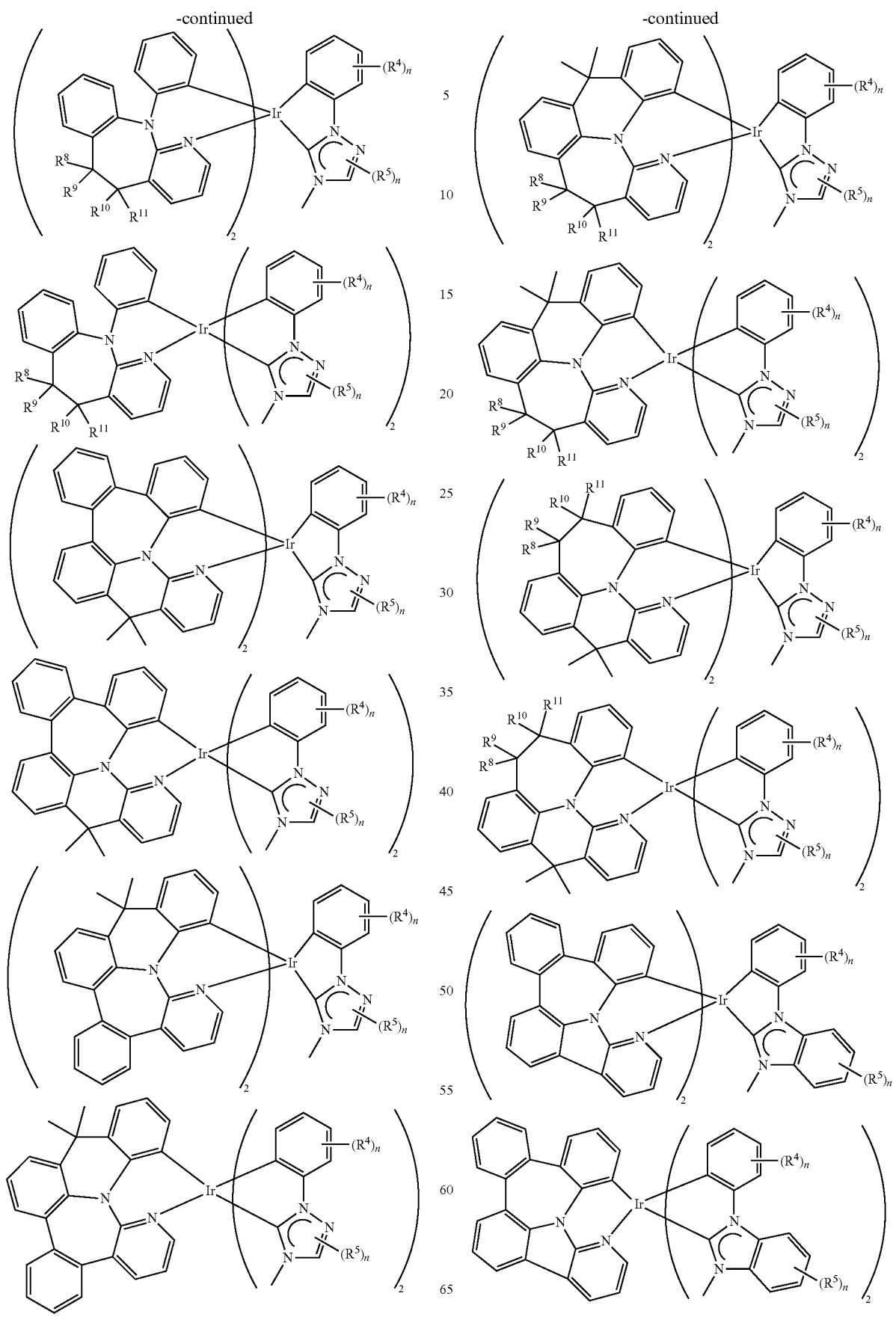

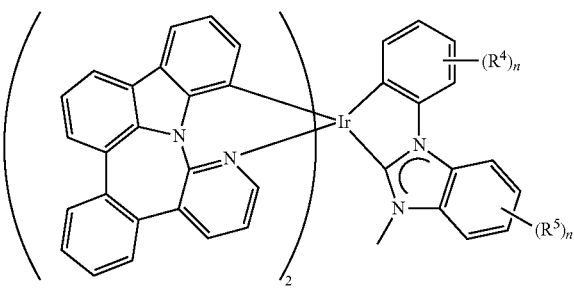
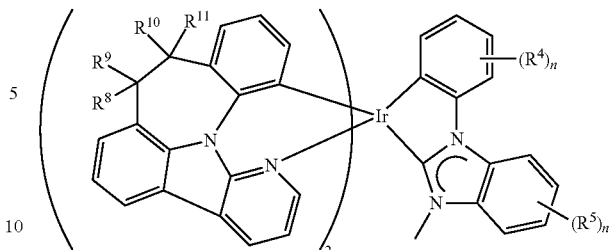
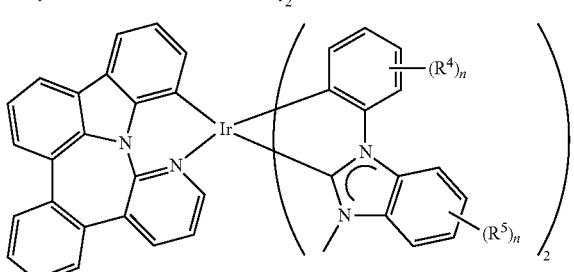
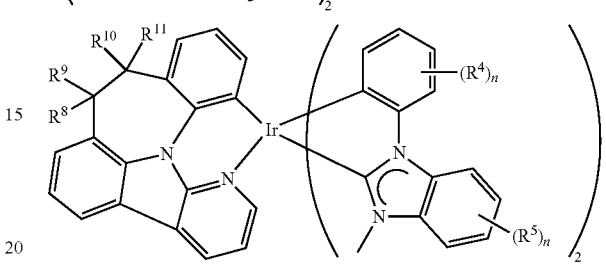
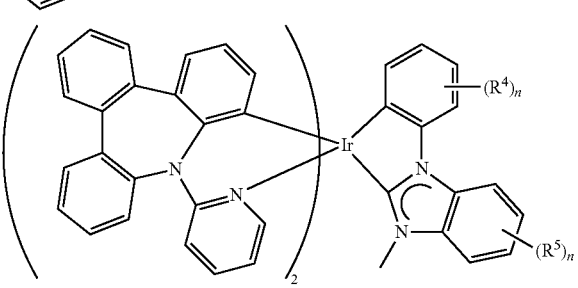
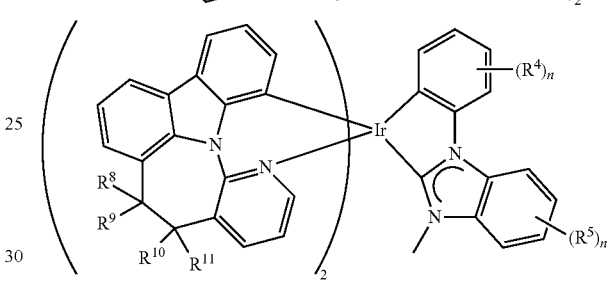
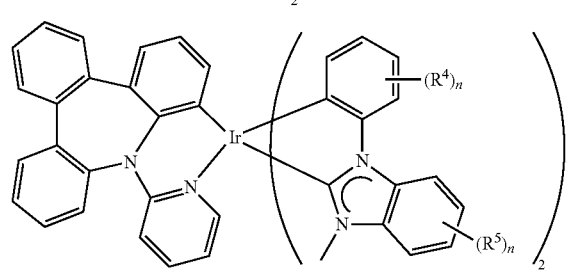
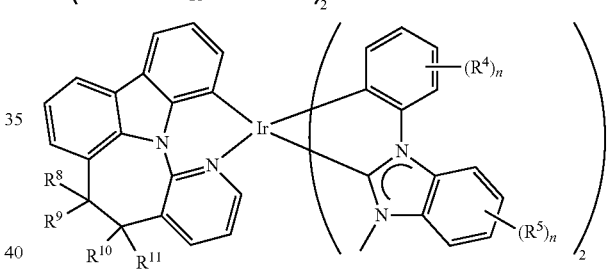
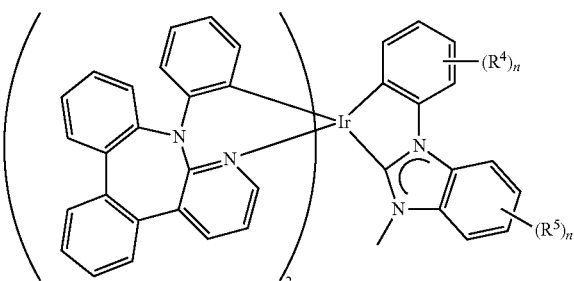
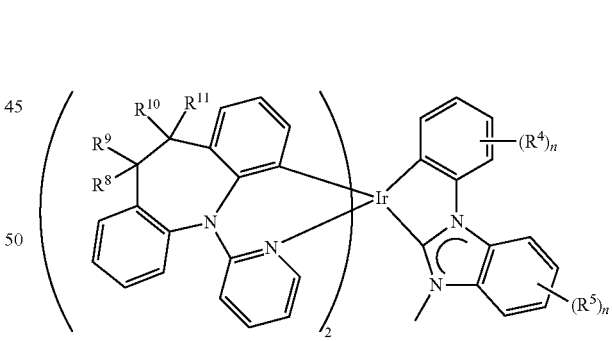
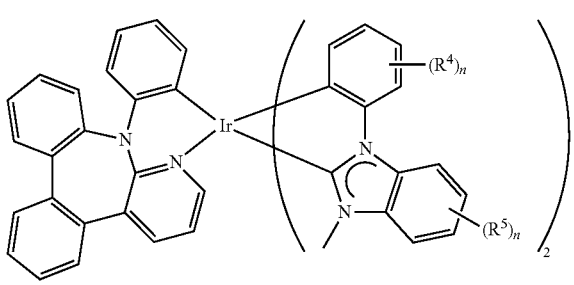
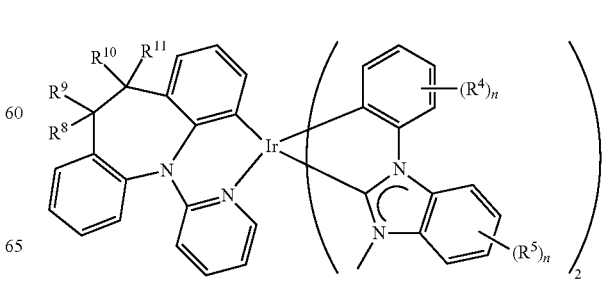

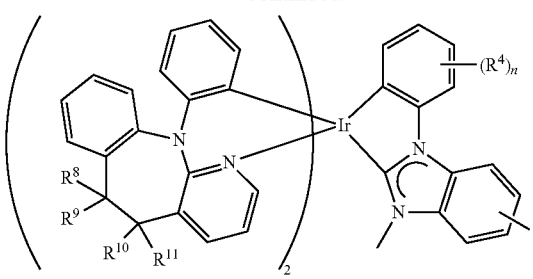
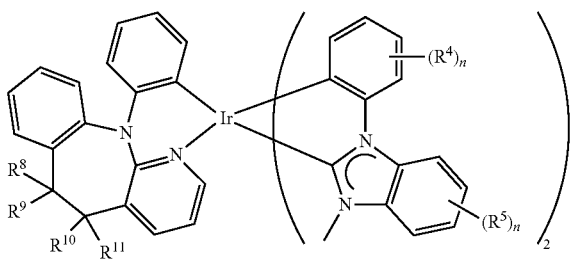
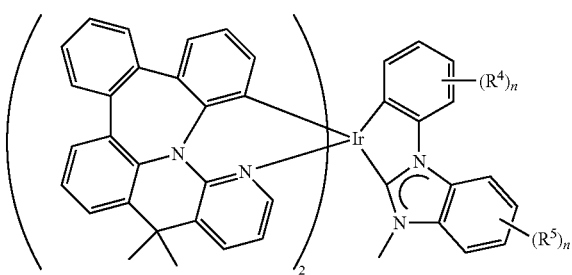
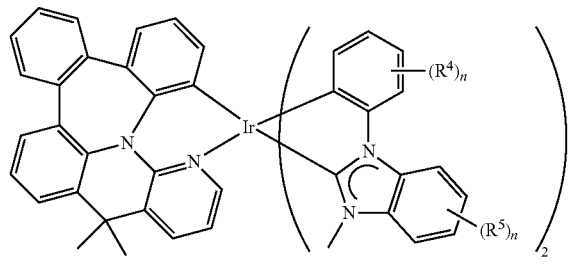
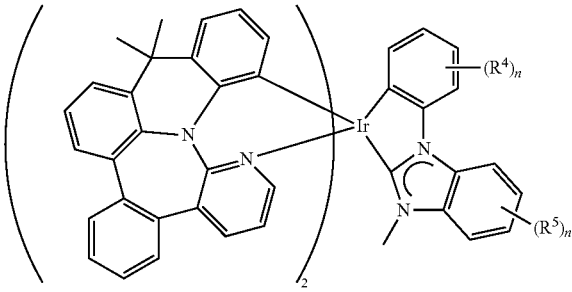
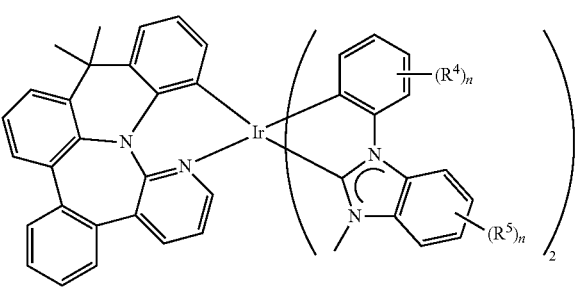
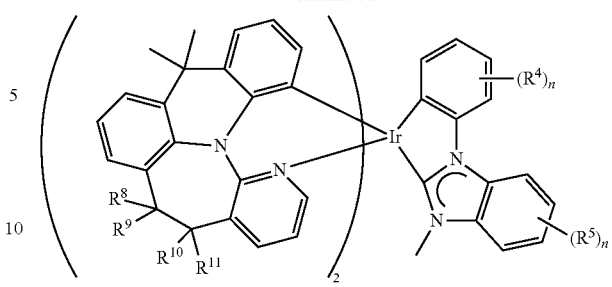
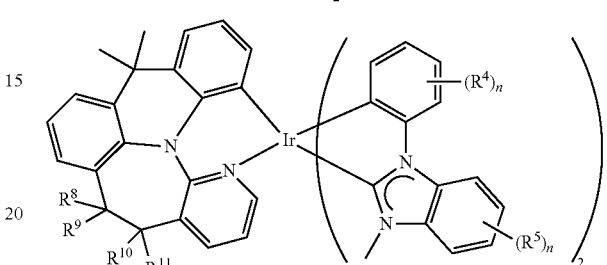
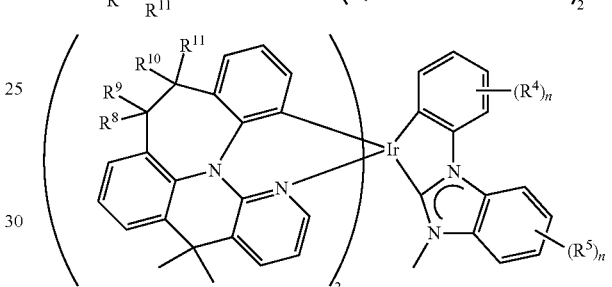
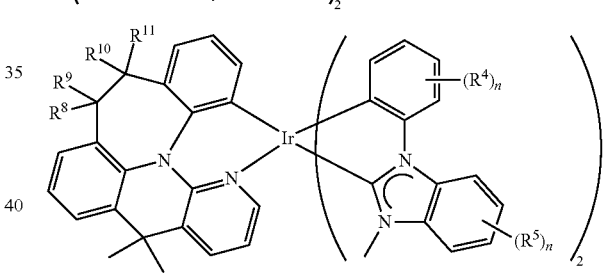
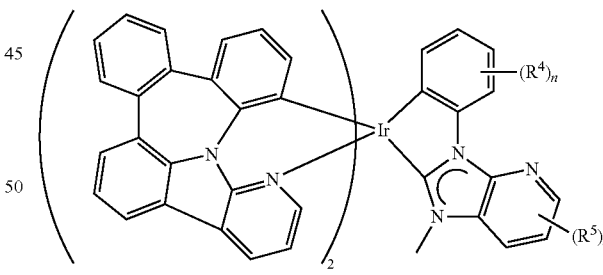
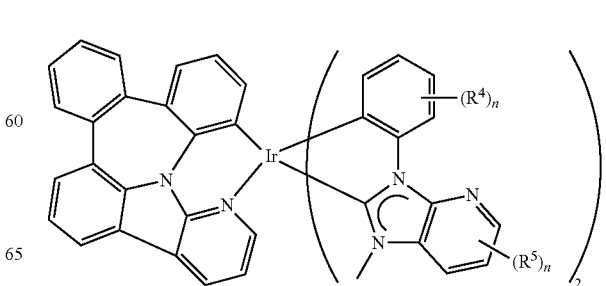

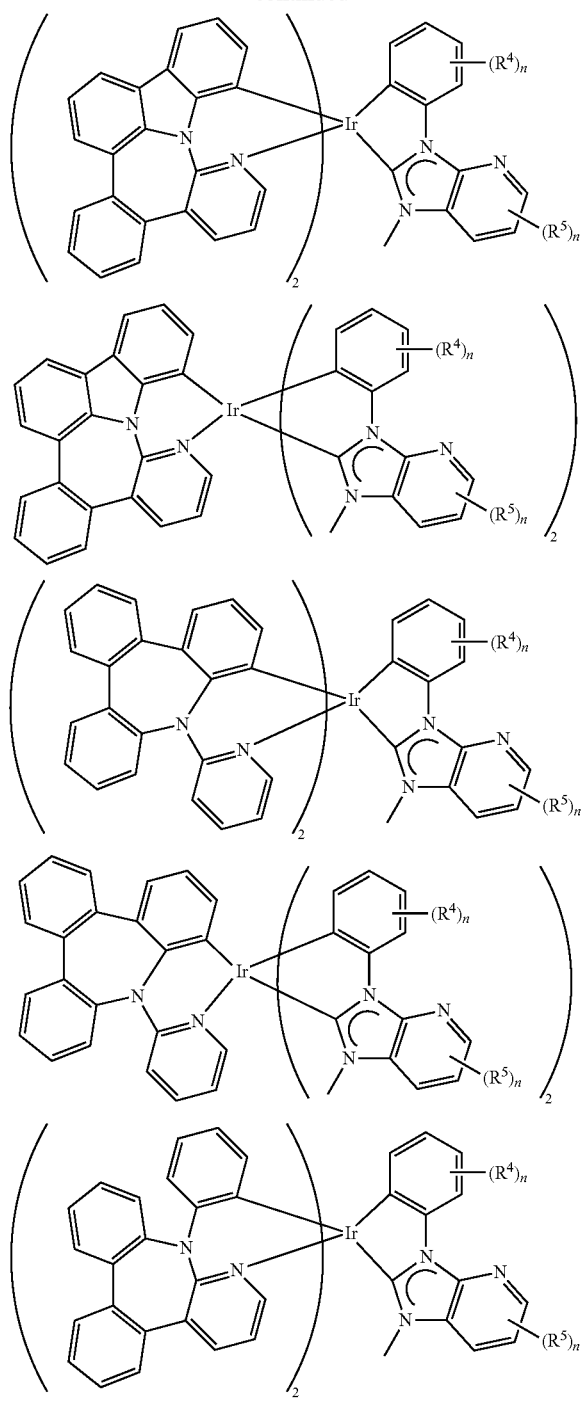
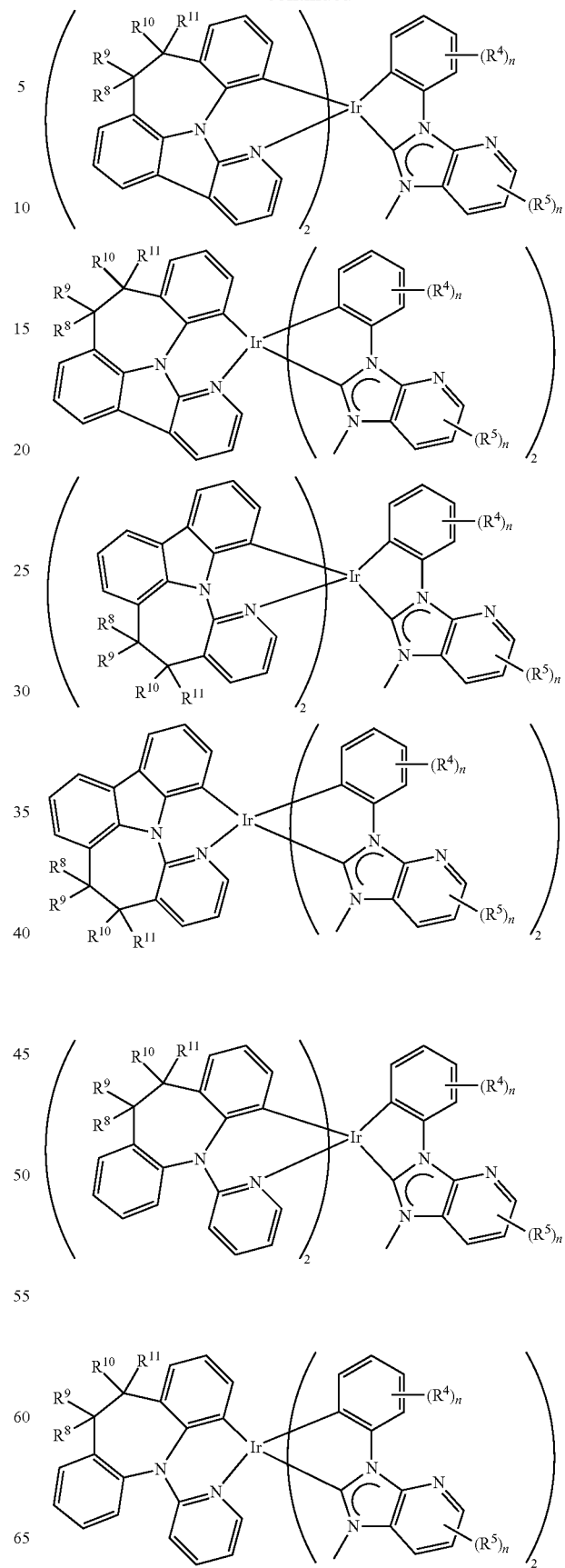

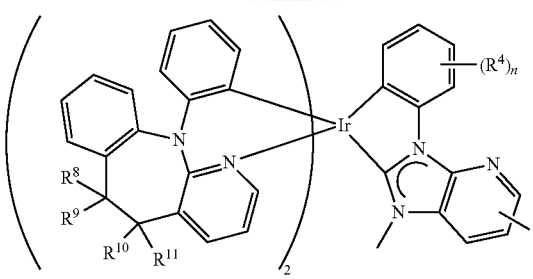
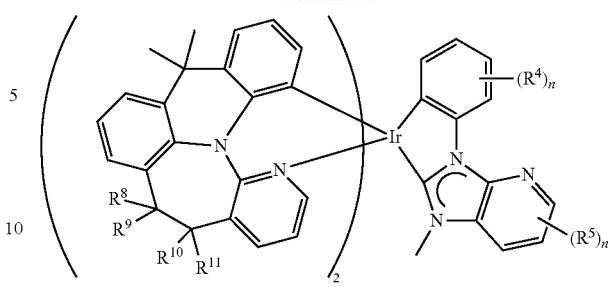
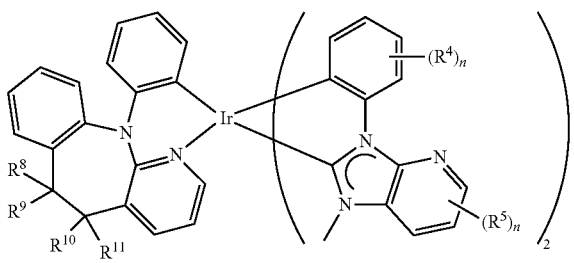
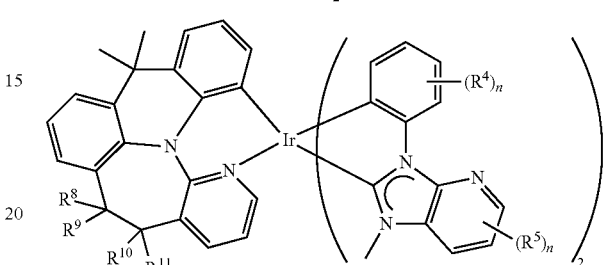
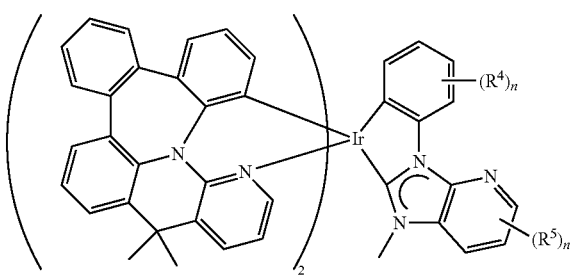
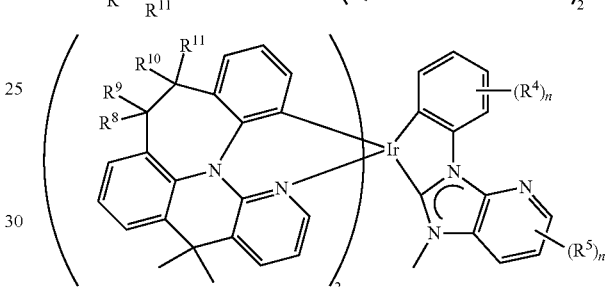
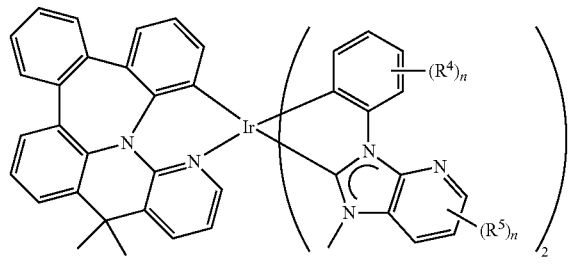
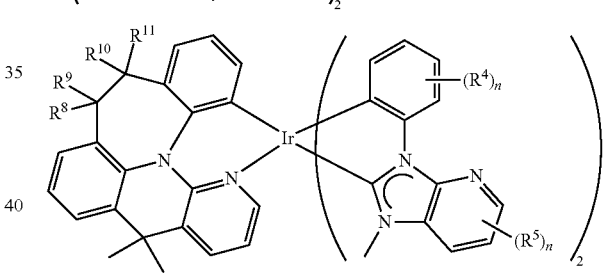
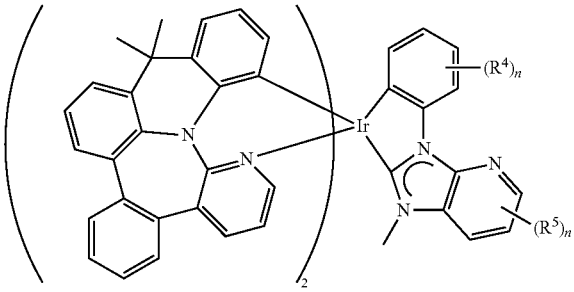
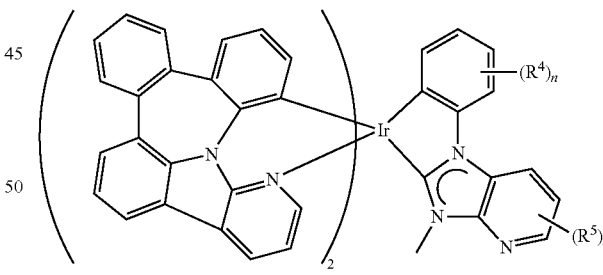
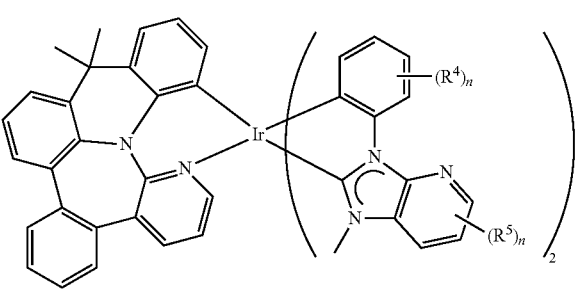
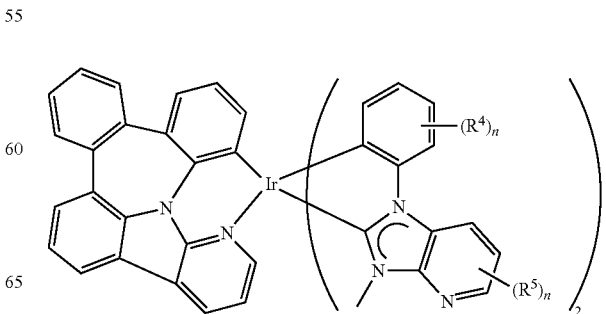

-continued
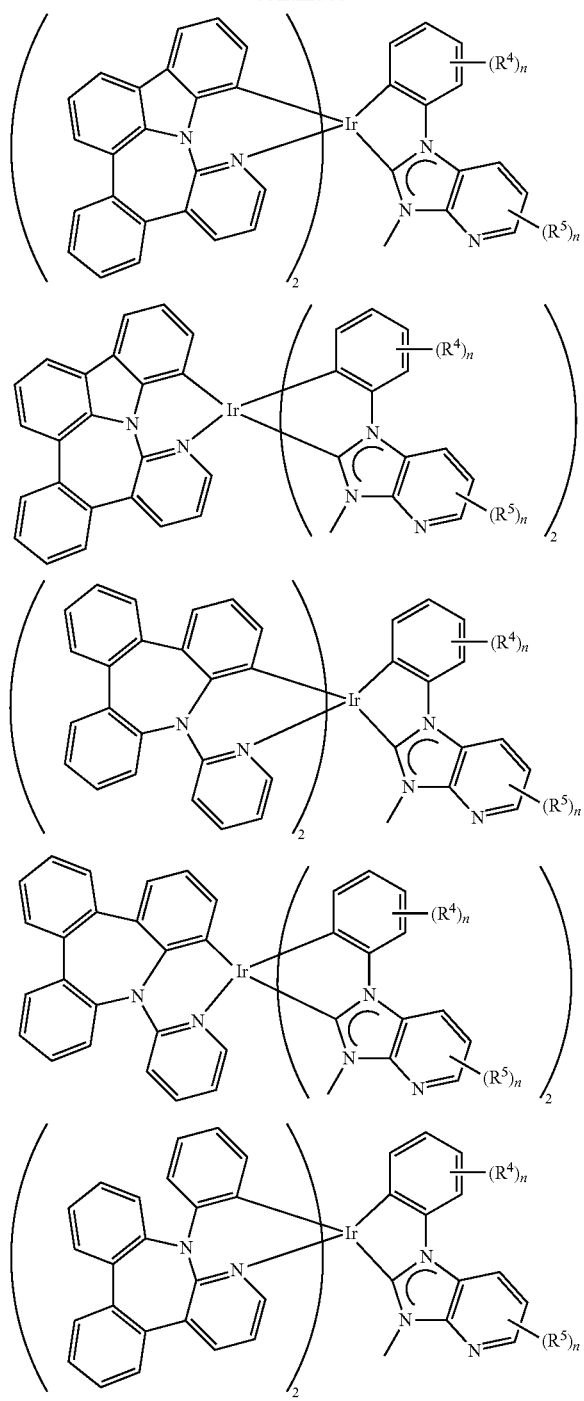
-continued
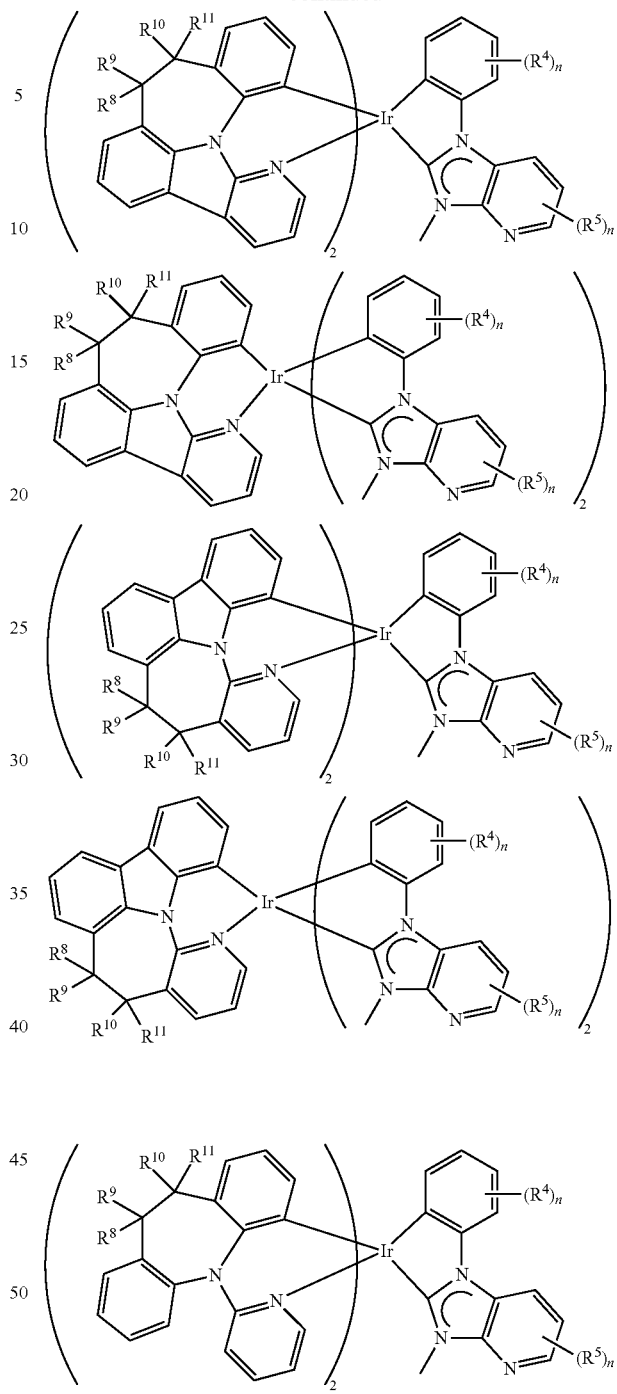
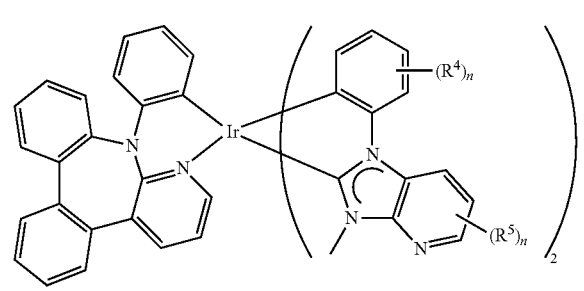
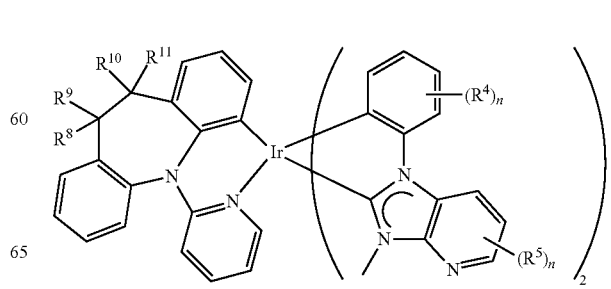

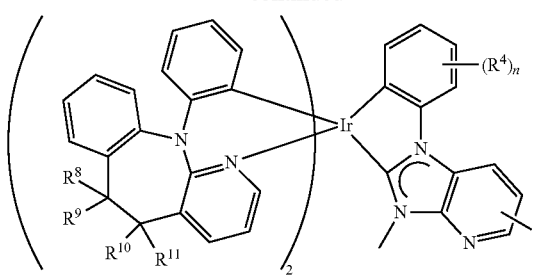
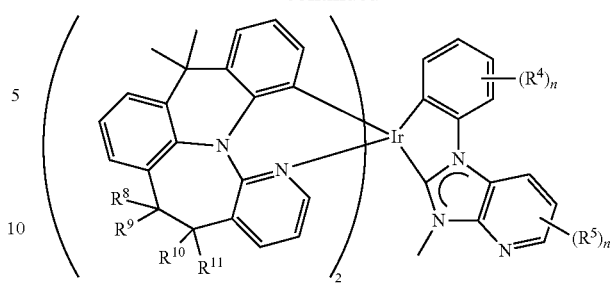
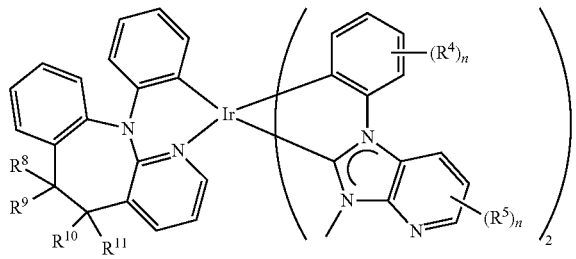
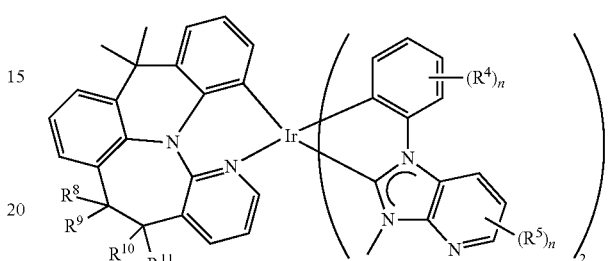
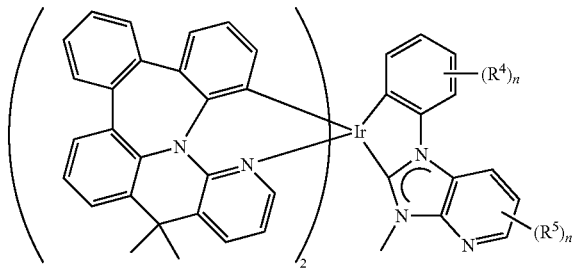
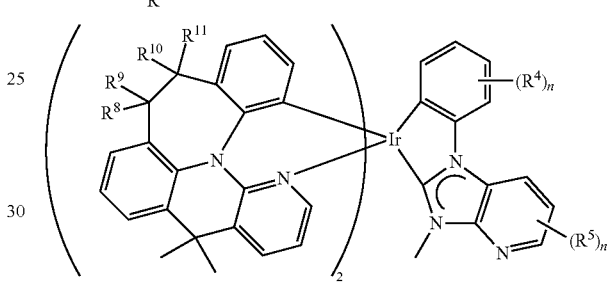
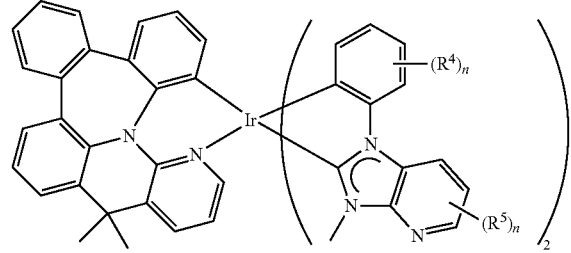
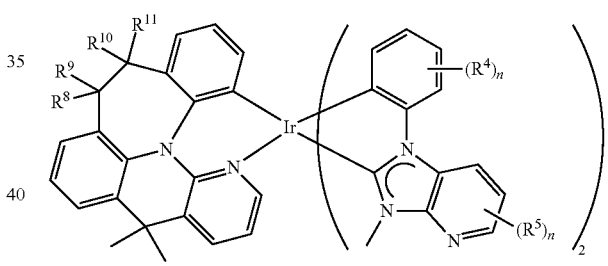
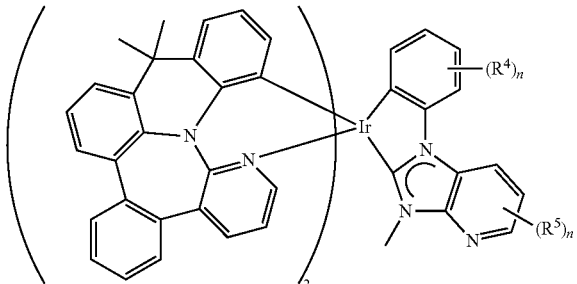
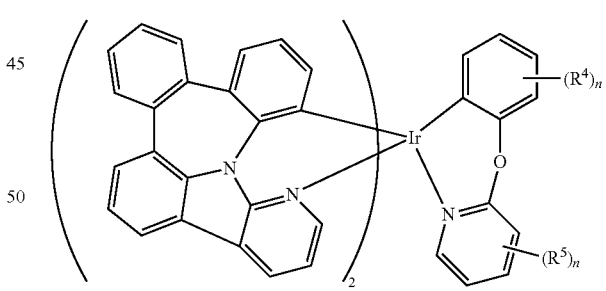
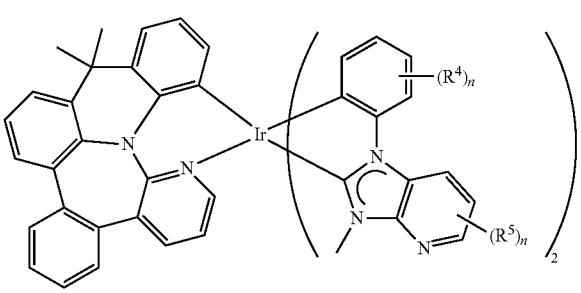
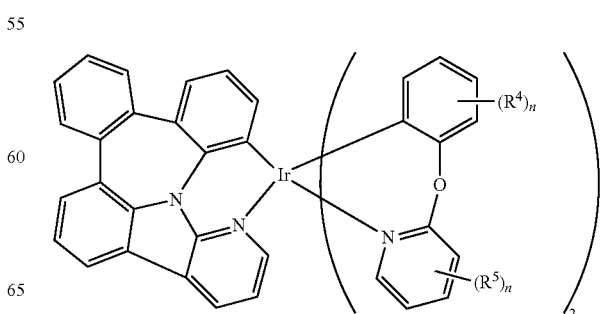

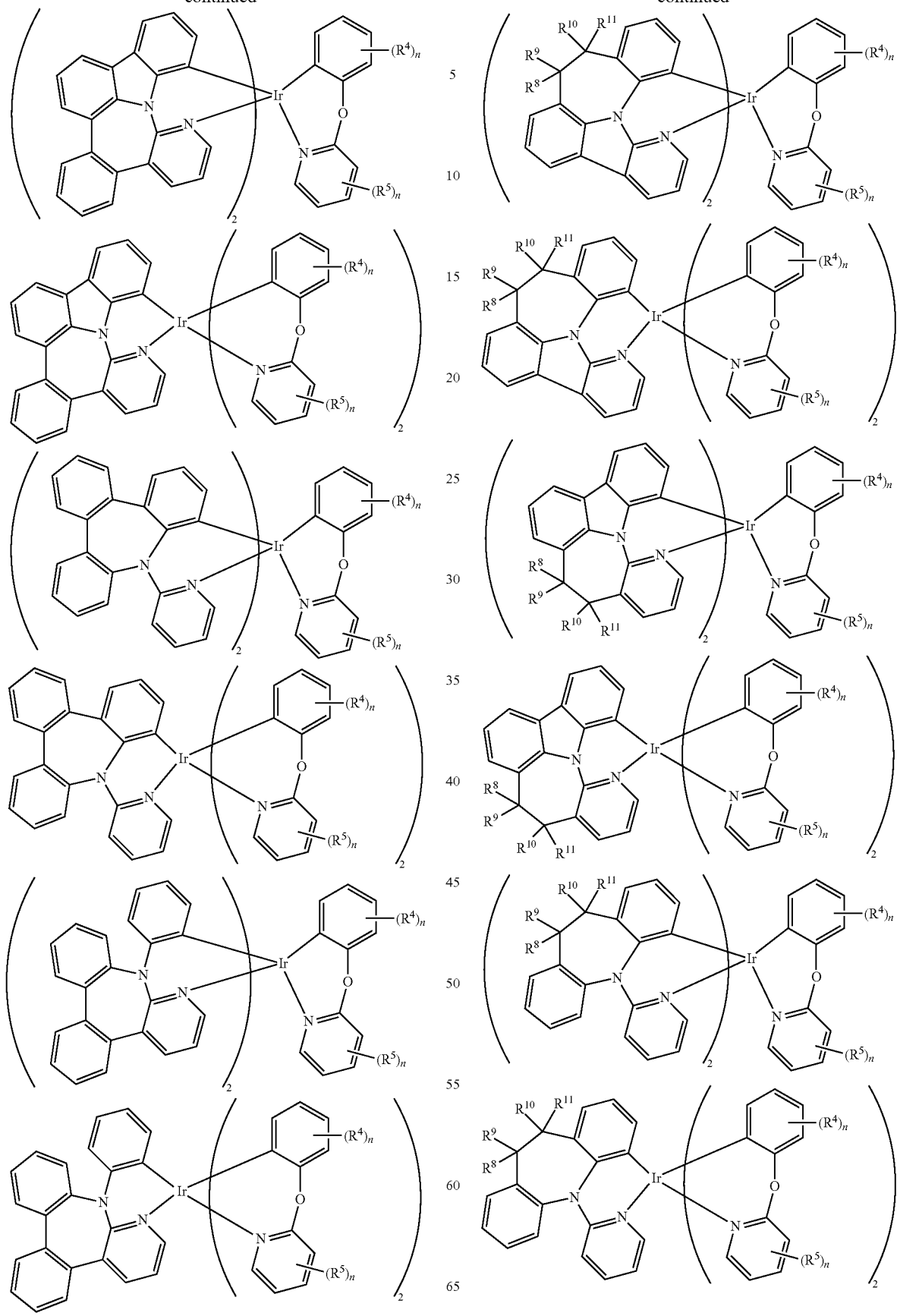

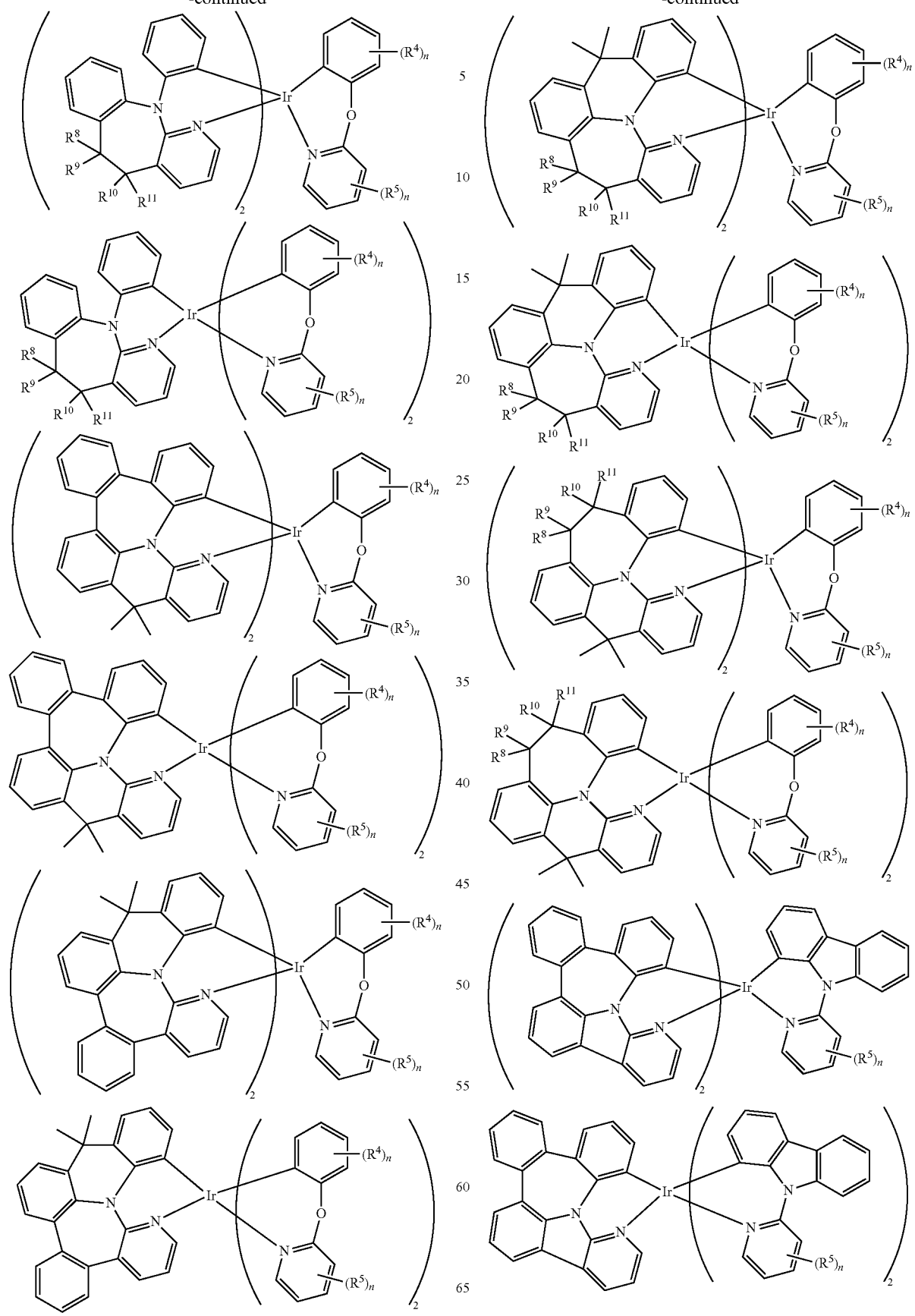

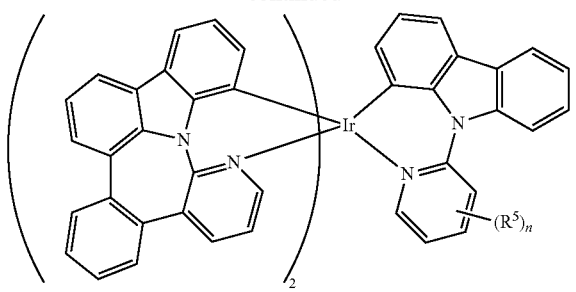
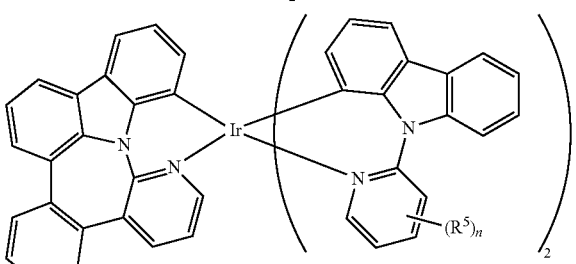
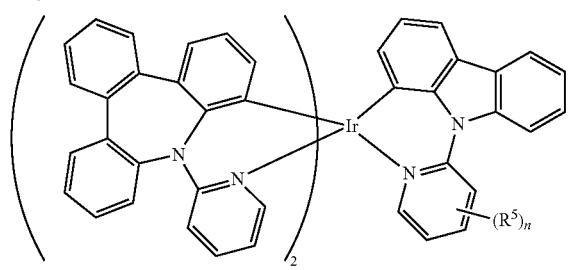
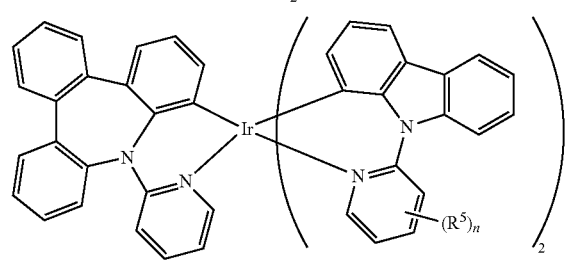
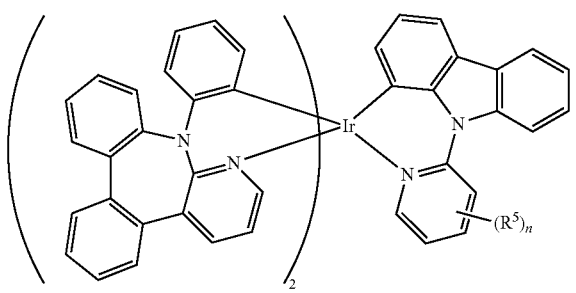
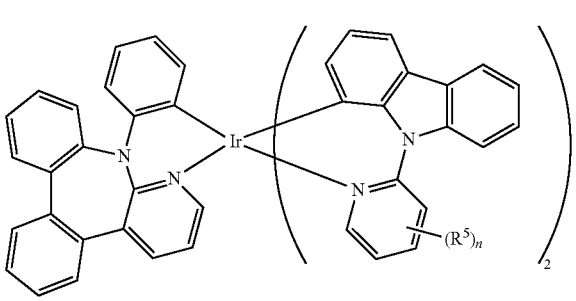
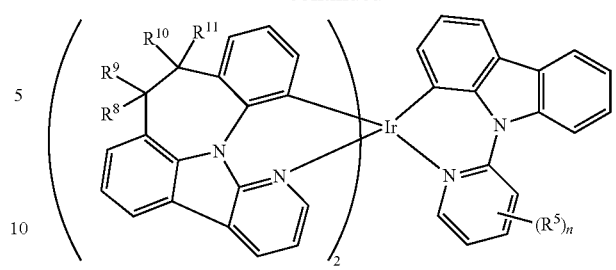
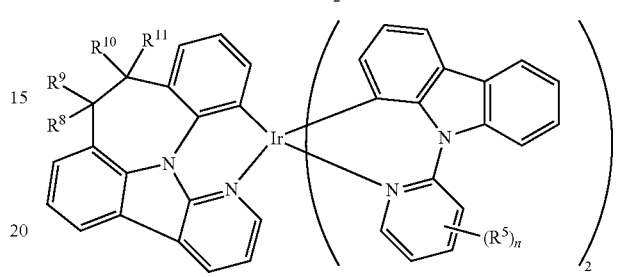
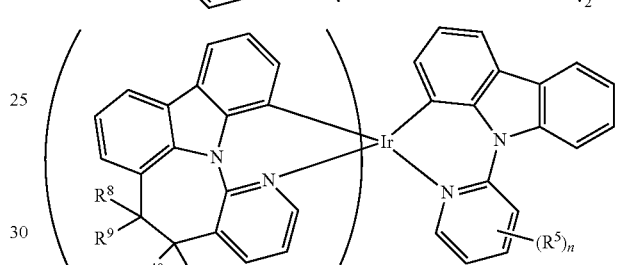
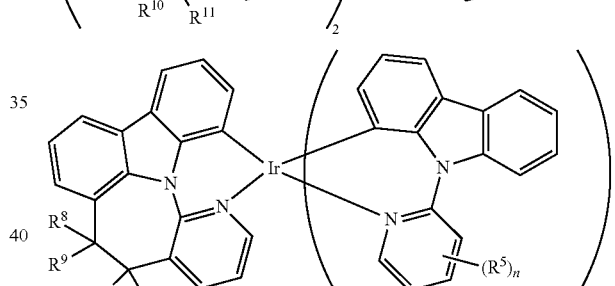
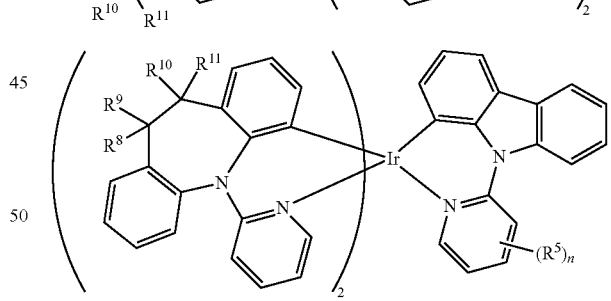
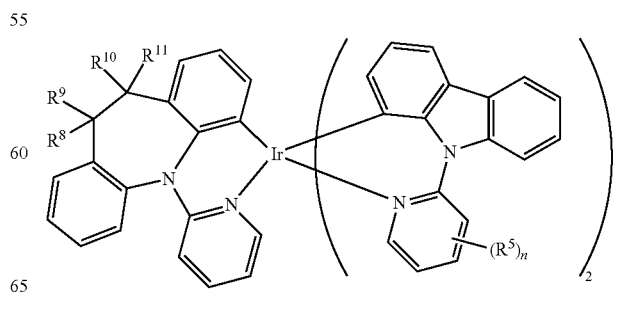

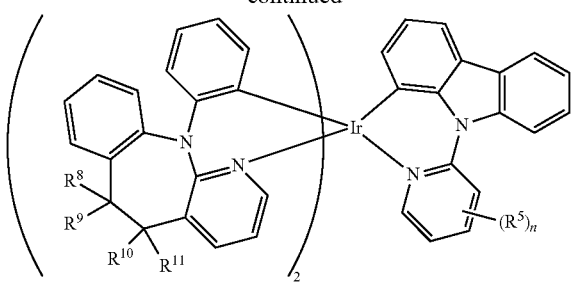
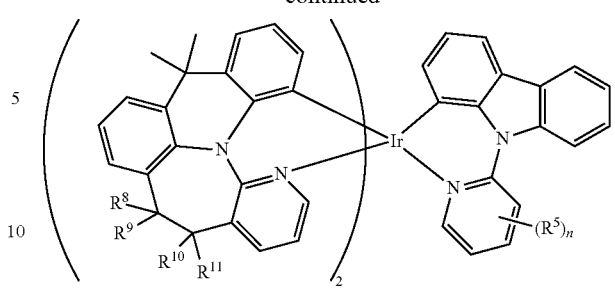
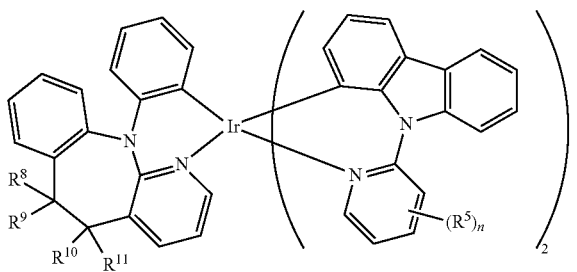
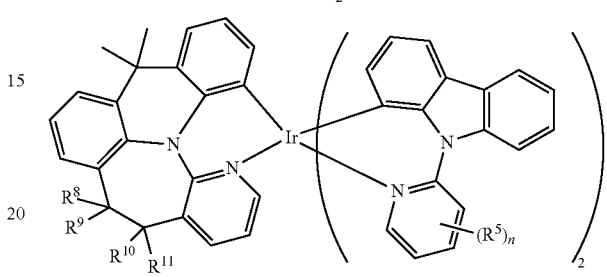
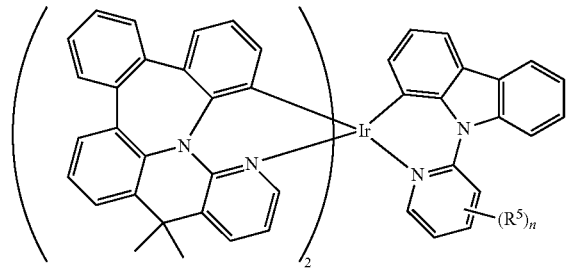
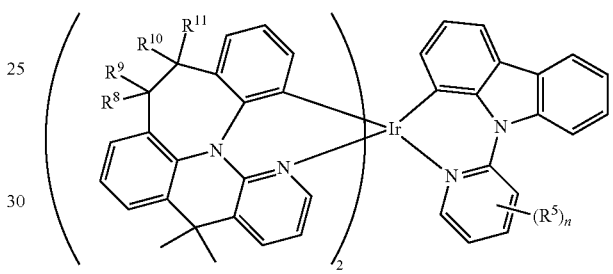
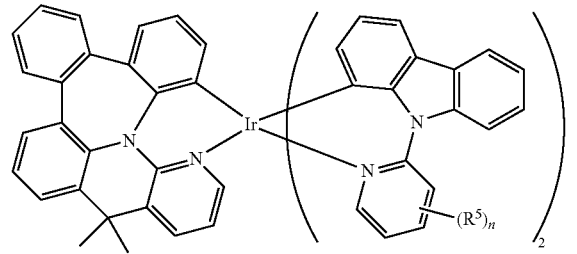
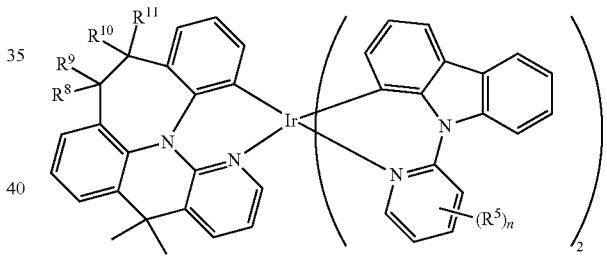
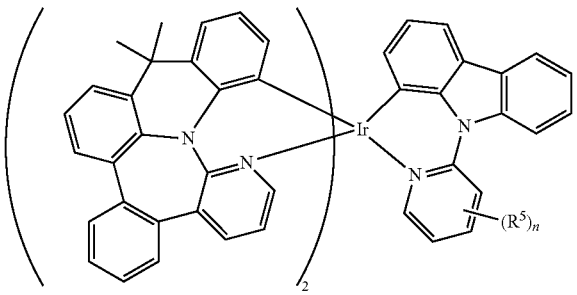
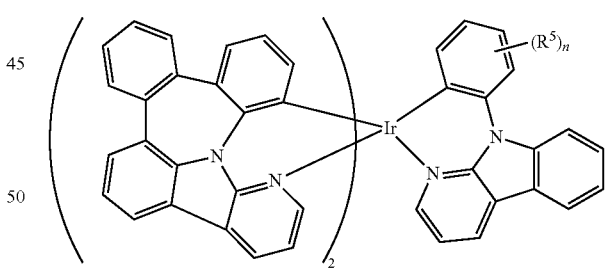
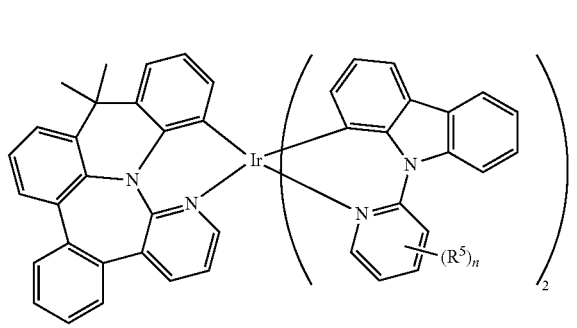
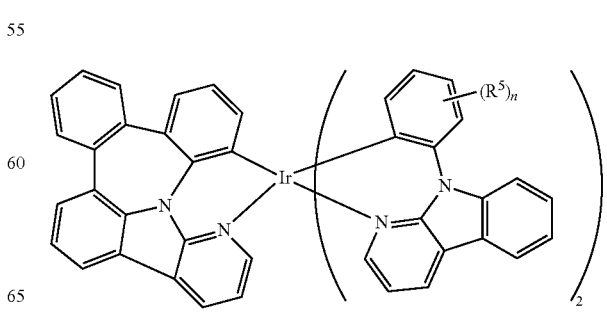

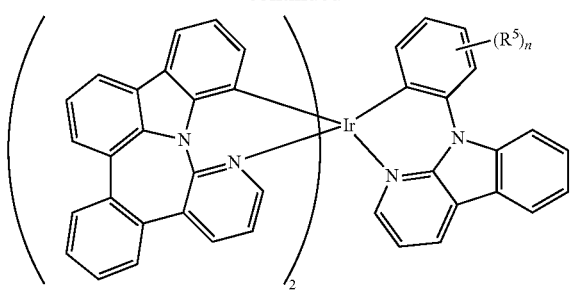
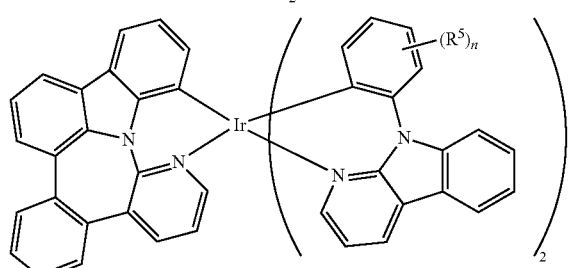
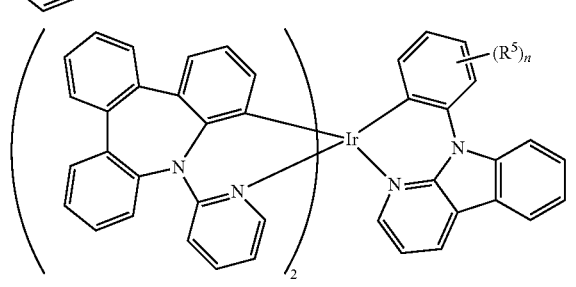
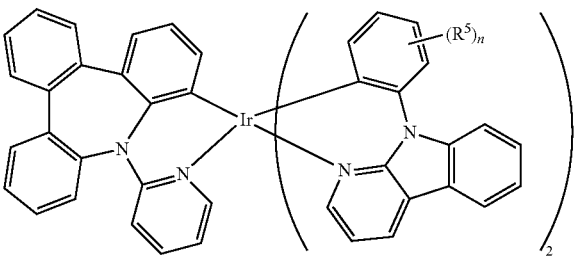
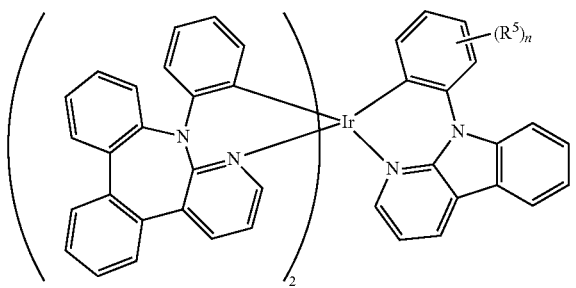
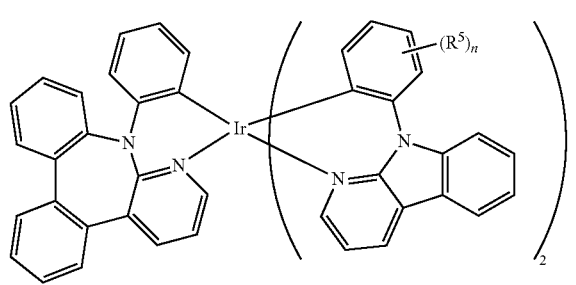
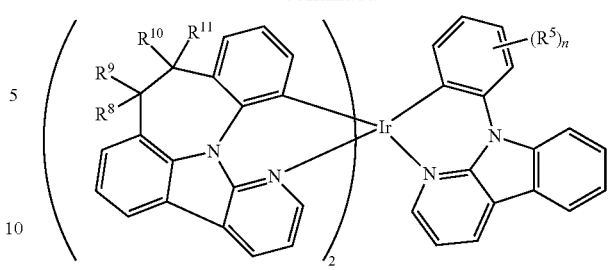
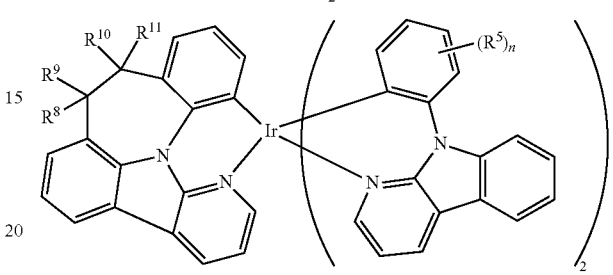
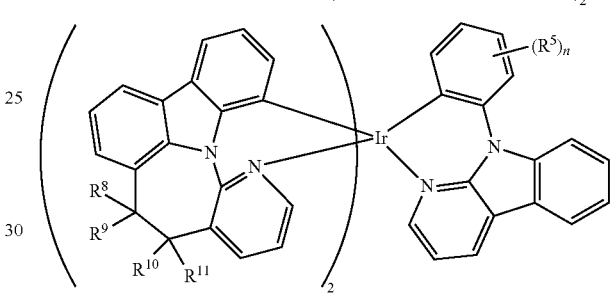
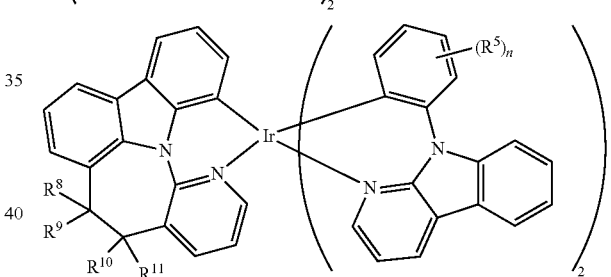
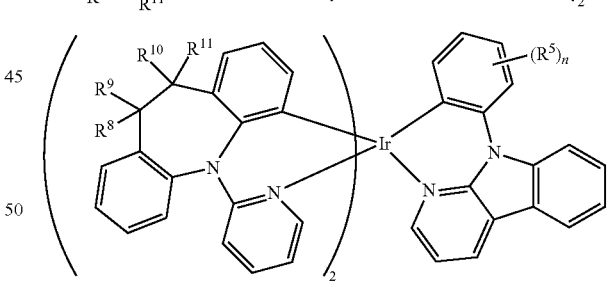
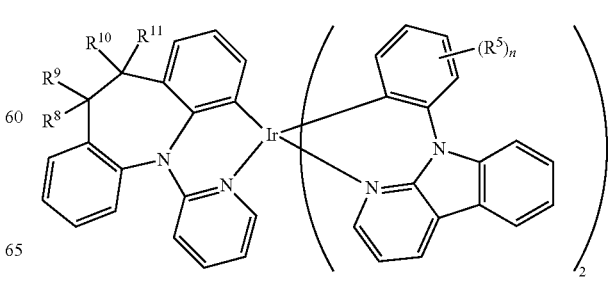

-continued
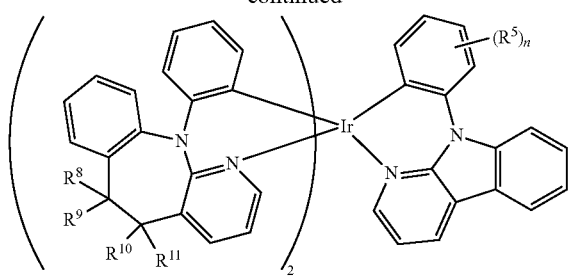
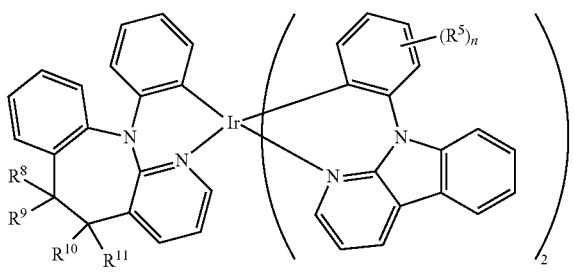
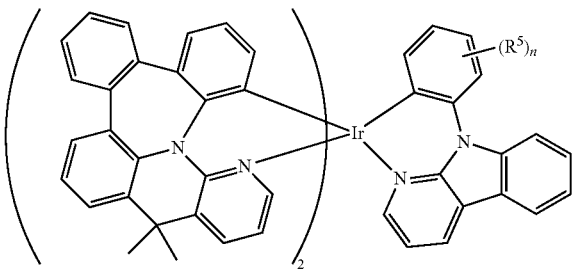
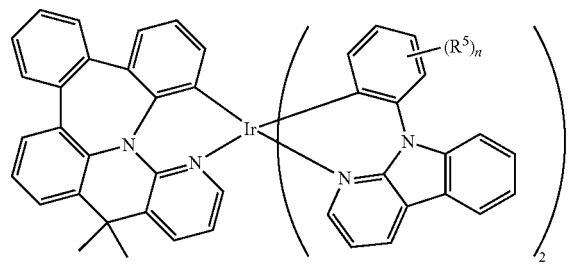
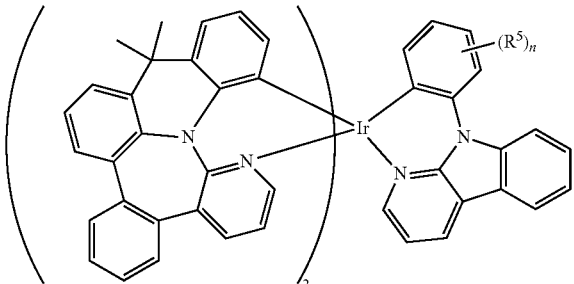
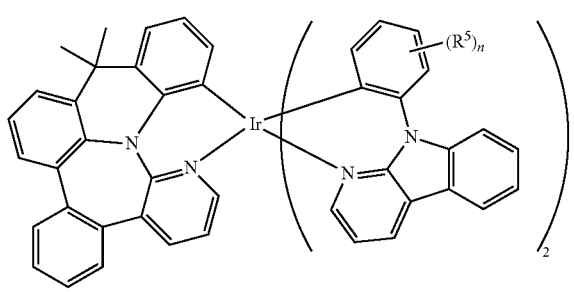
-continued
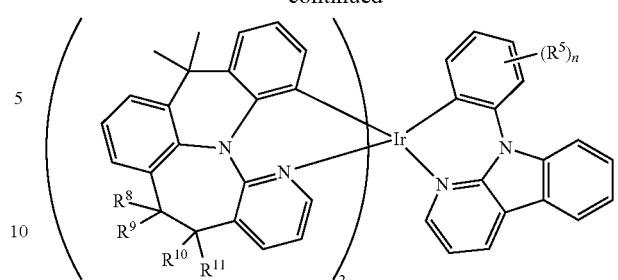
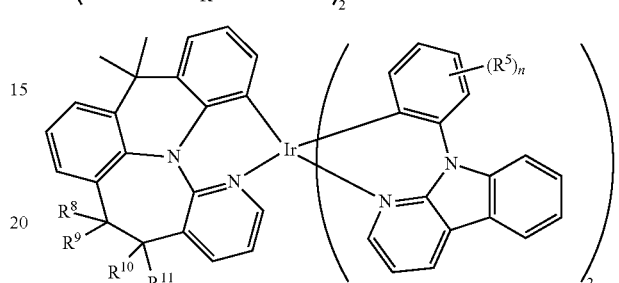
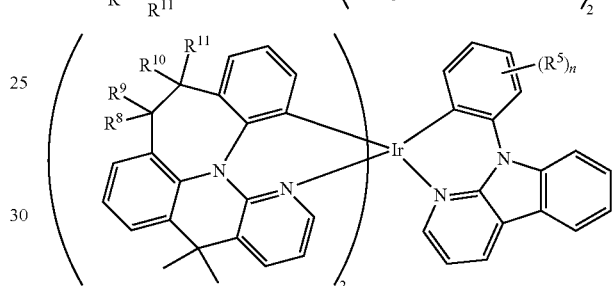
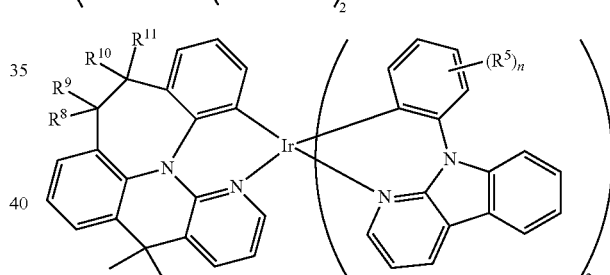
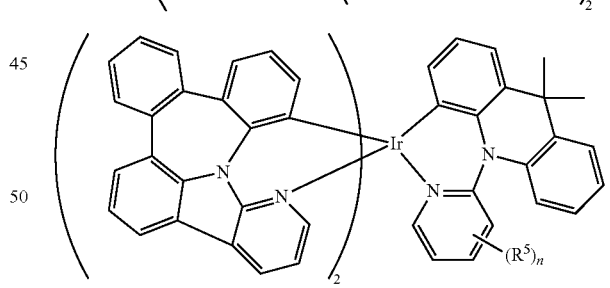
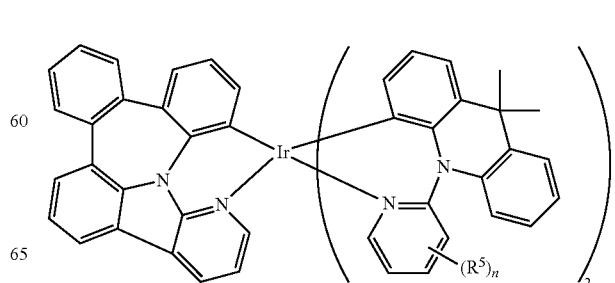

101
-continued
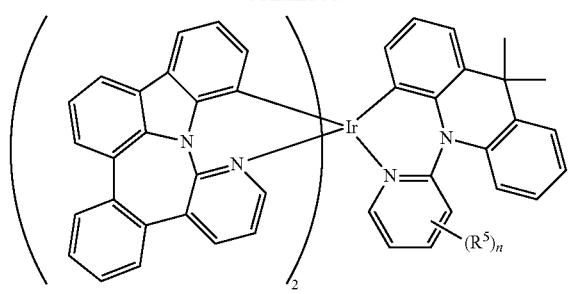
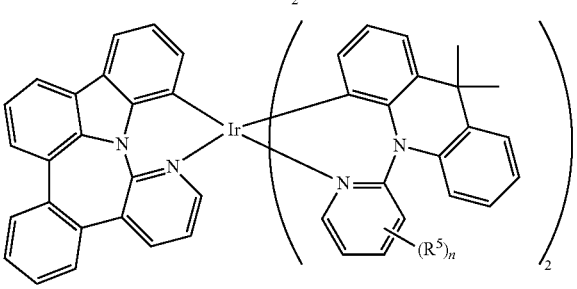
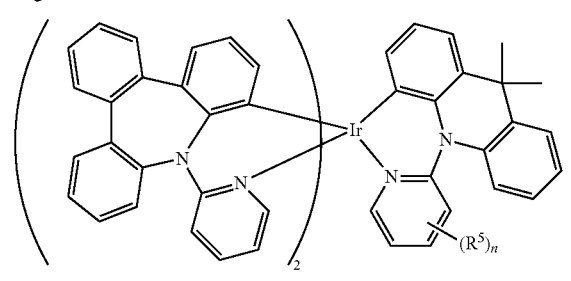
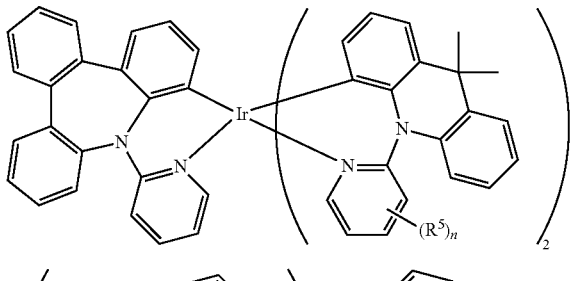
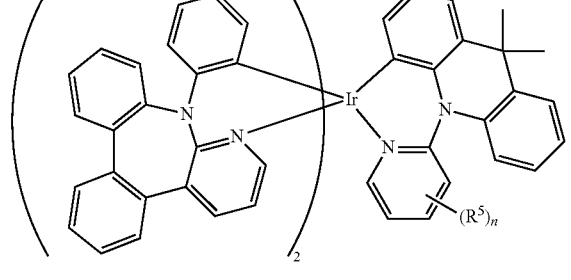
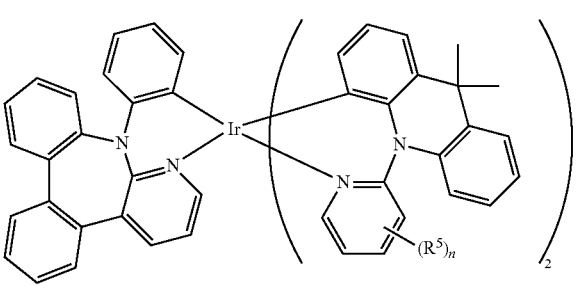
102
-continued
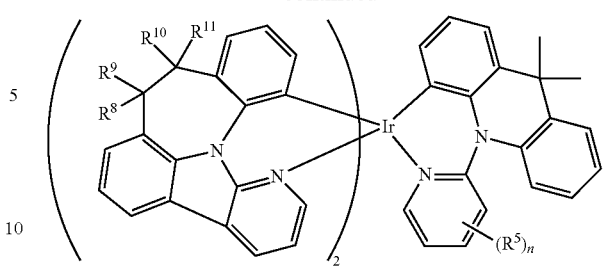
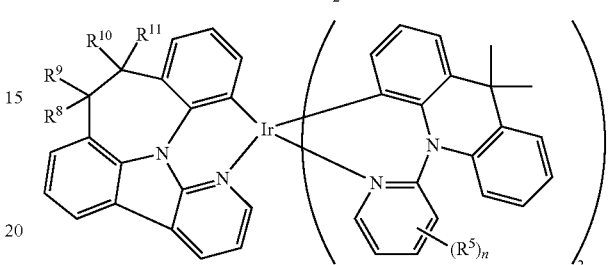
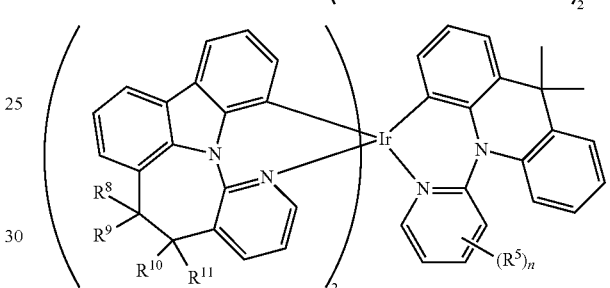
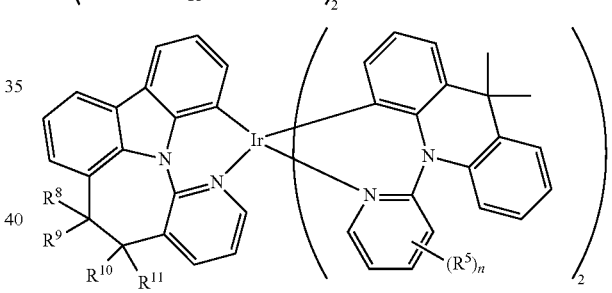
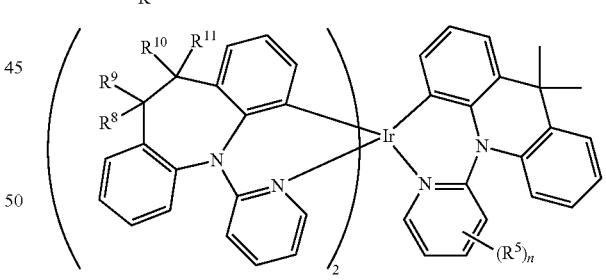
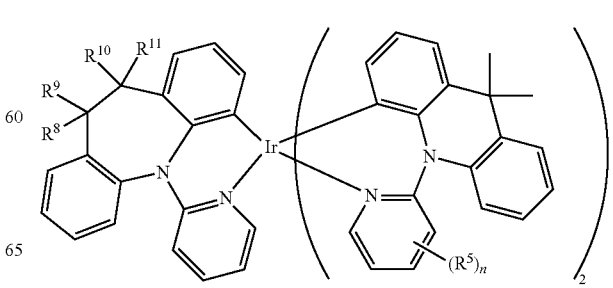

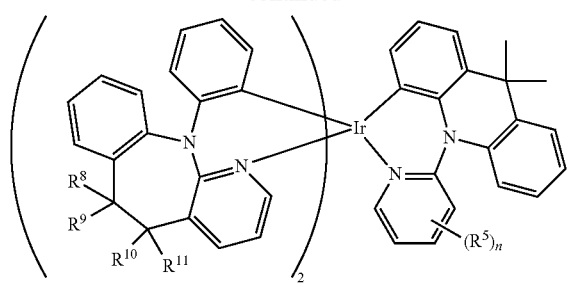
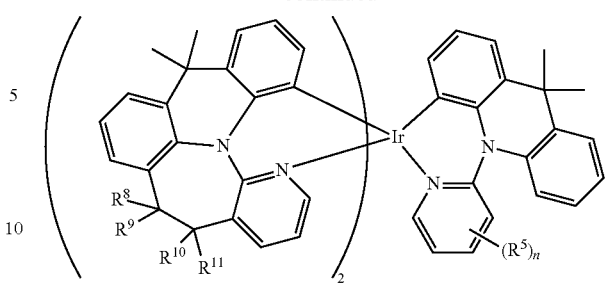
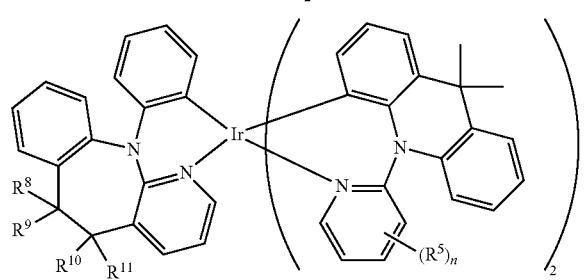
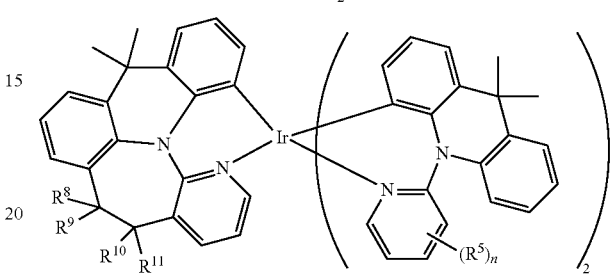
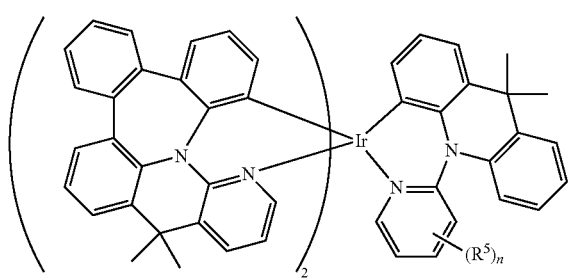
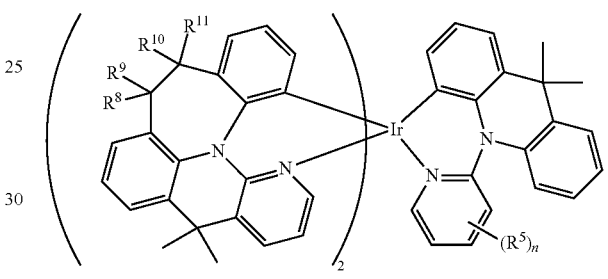
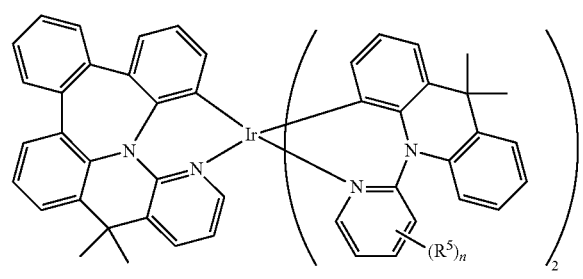
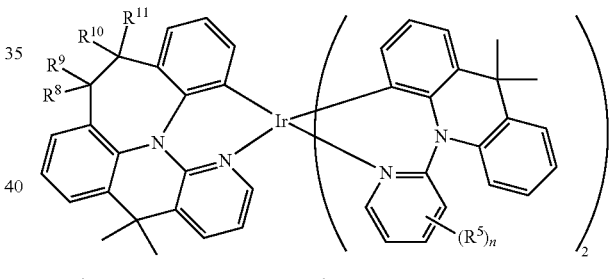
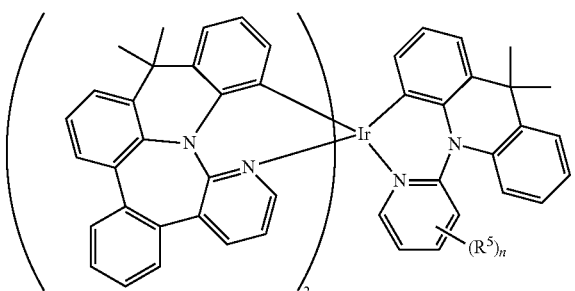
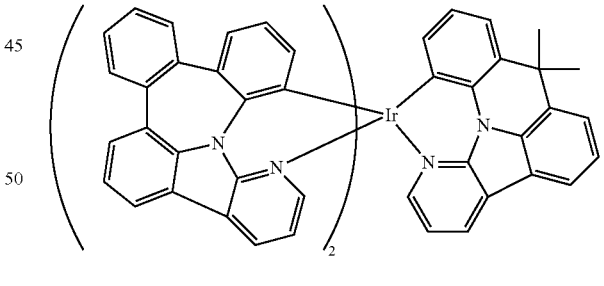
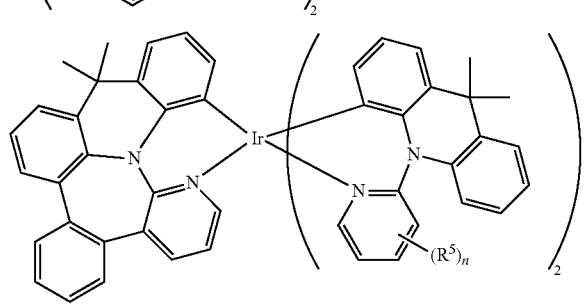
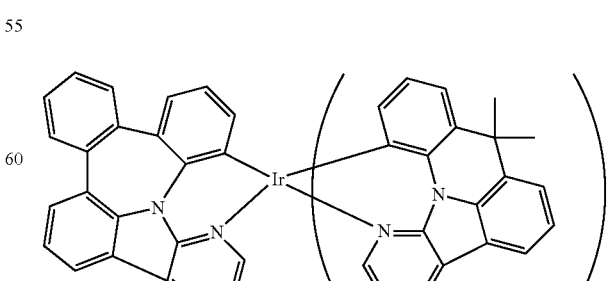

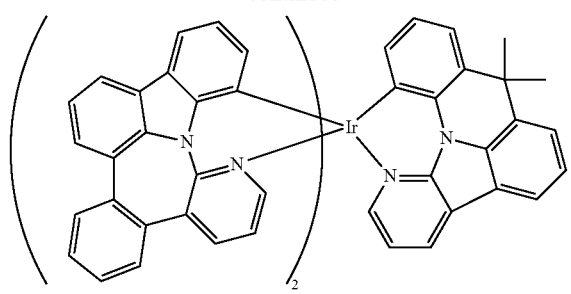
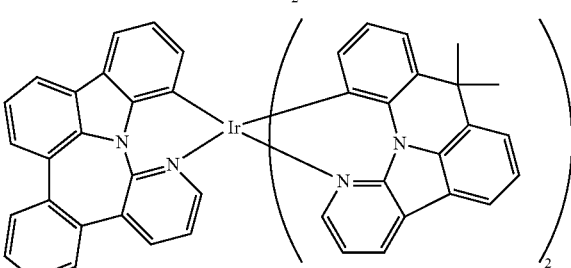
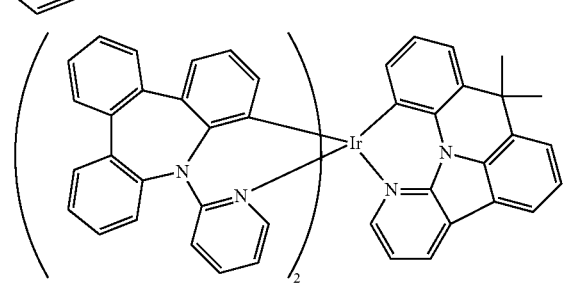
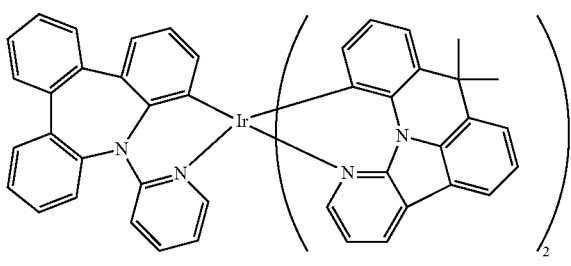
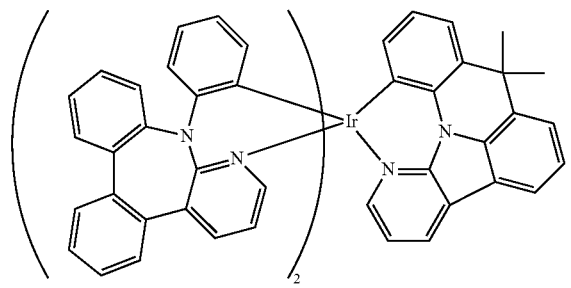
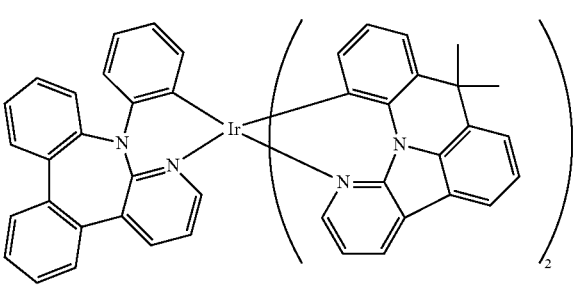
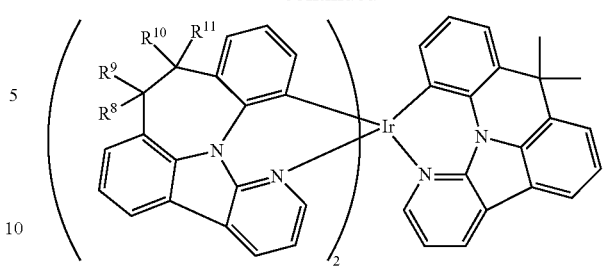
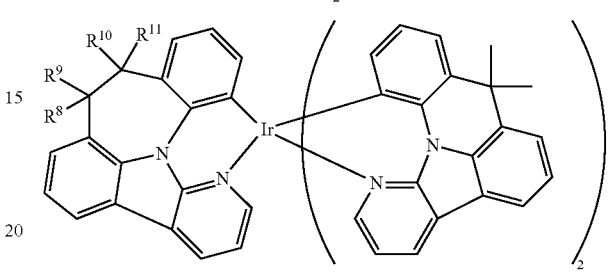
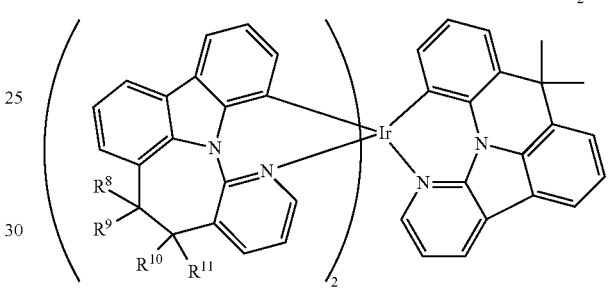
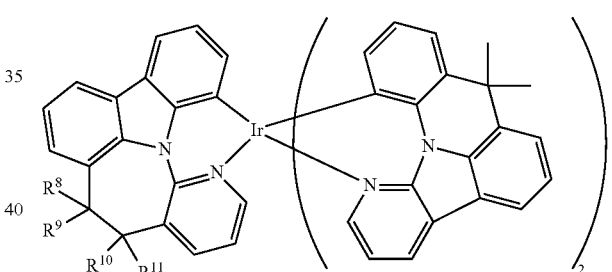
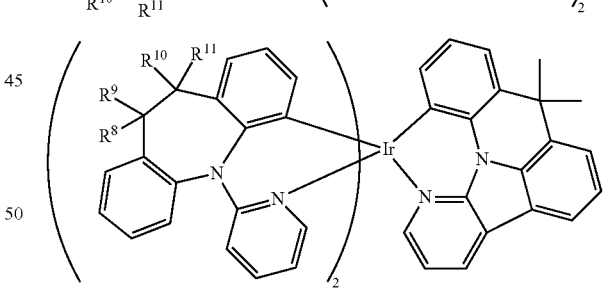
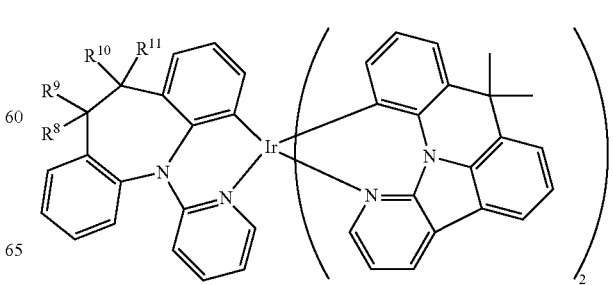

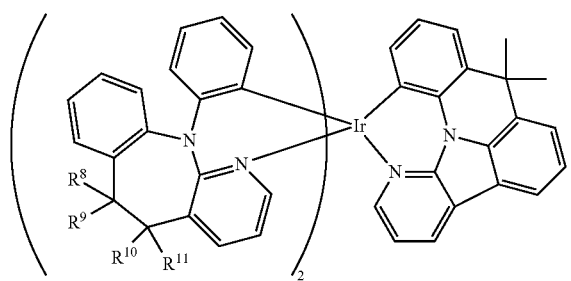
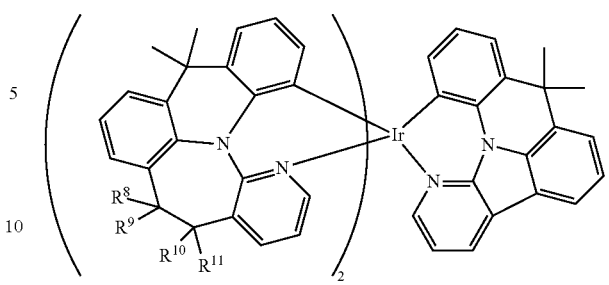
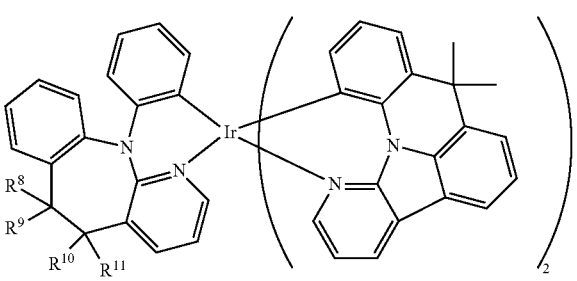
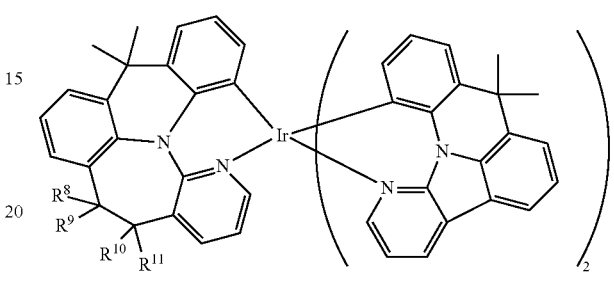
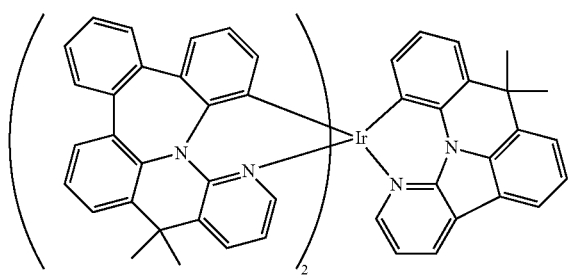
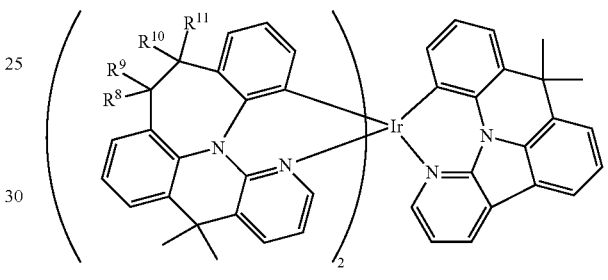
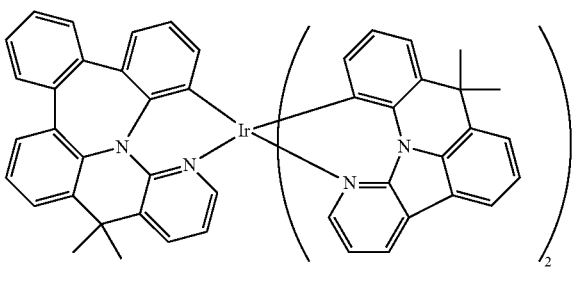
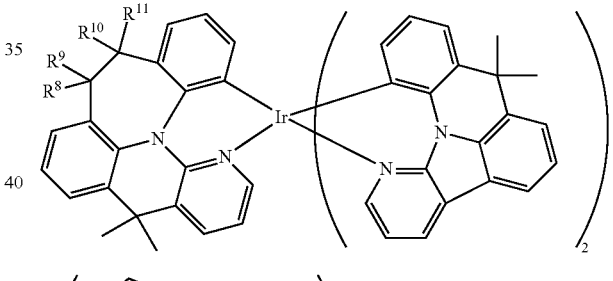
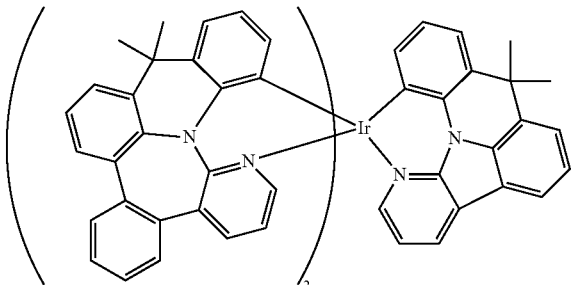
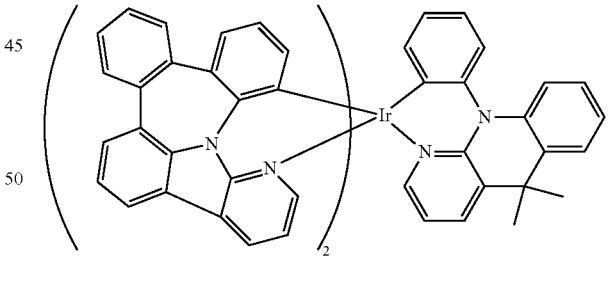
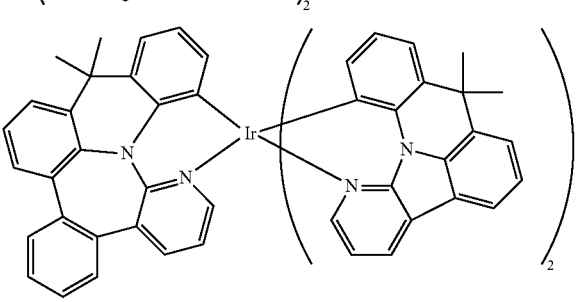
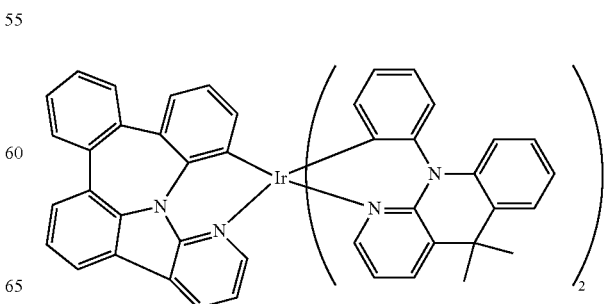

109
-continued
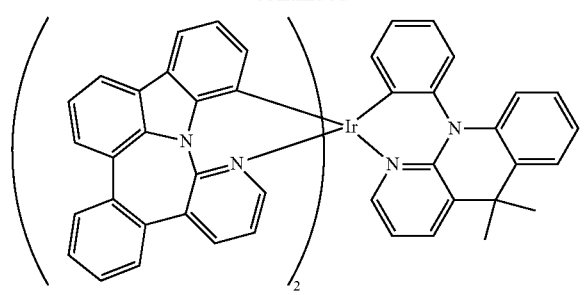
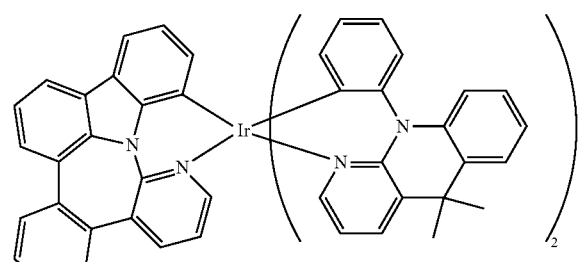
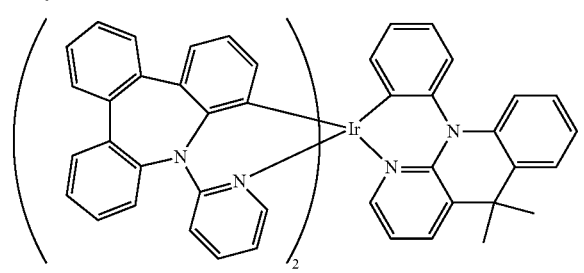
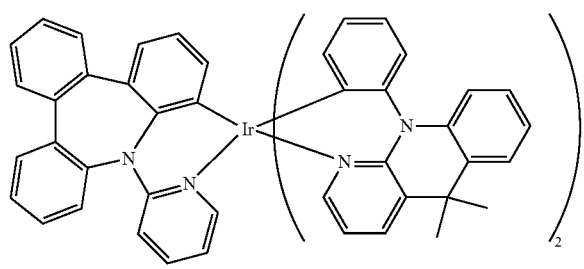
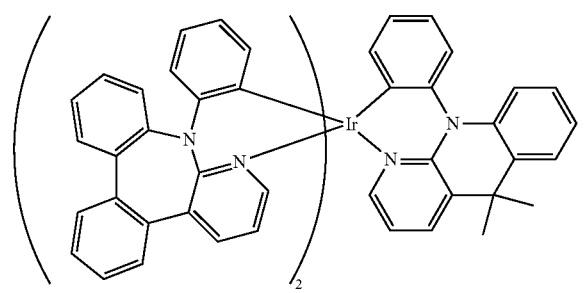
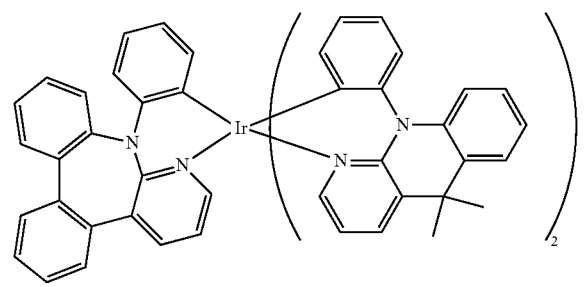
110
-continued
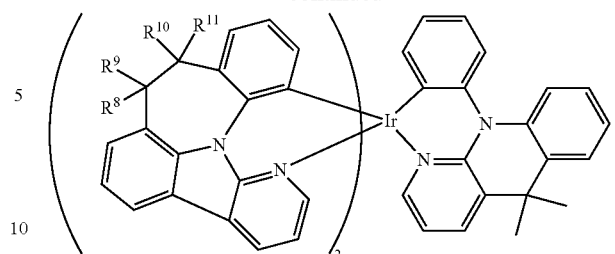
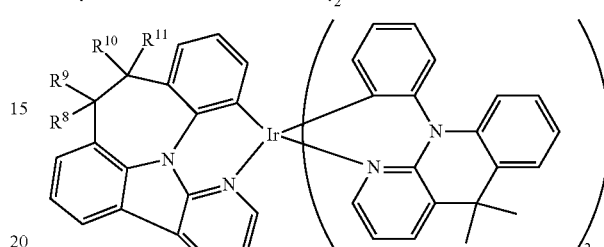
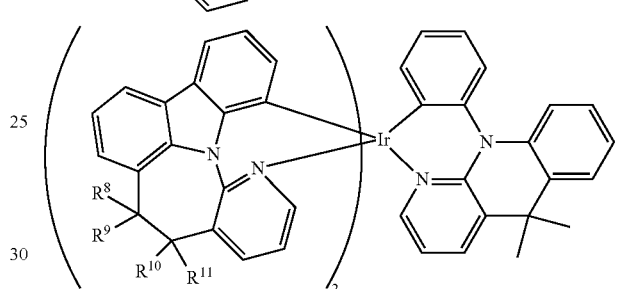
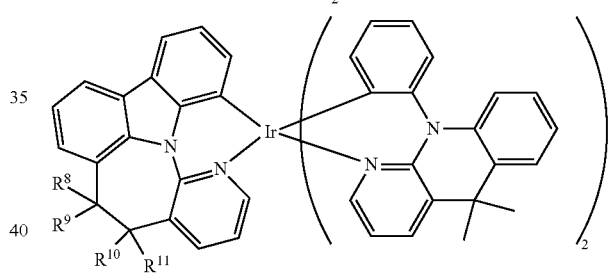
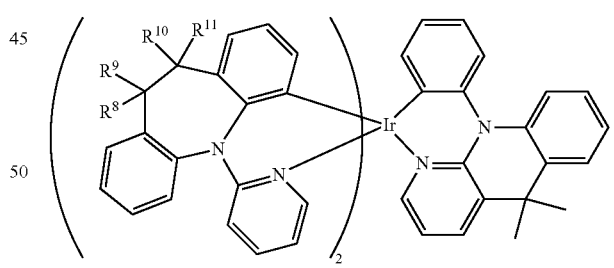
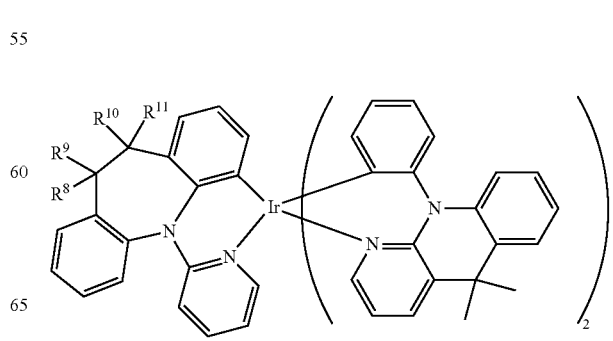

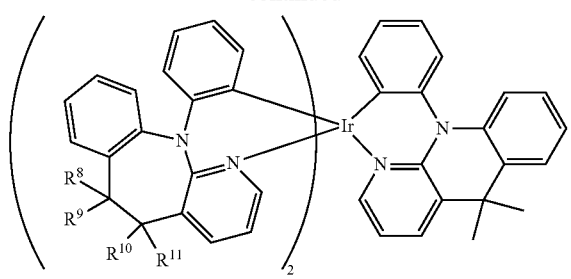
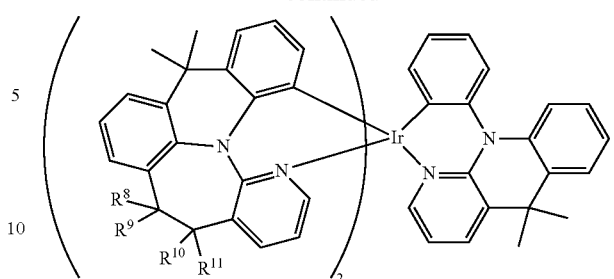
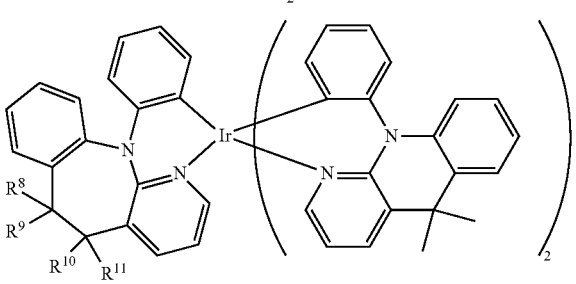
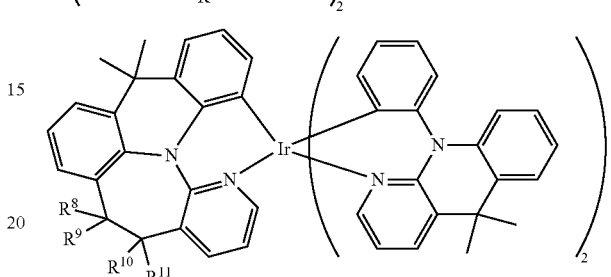
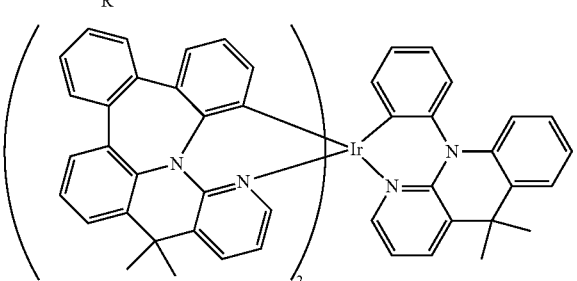
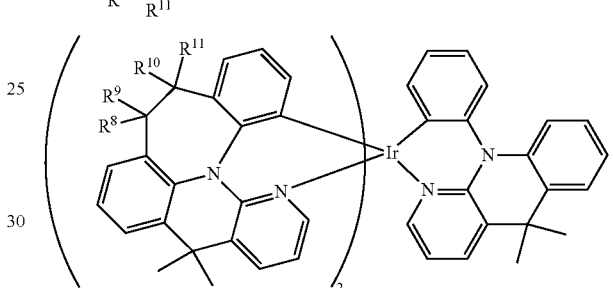
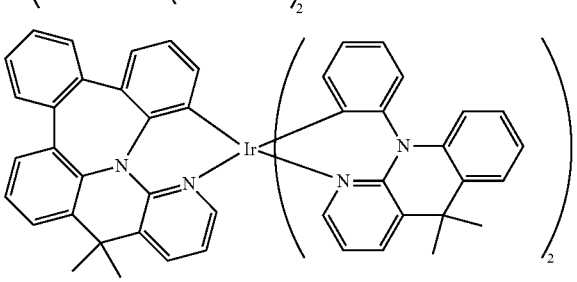
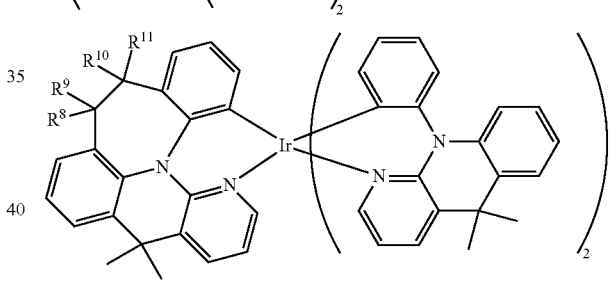
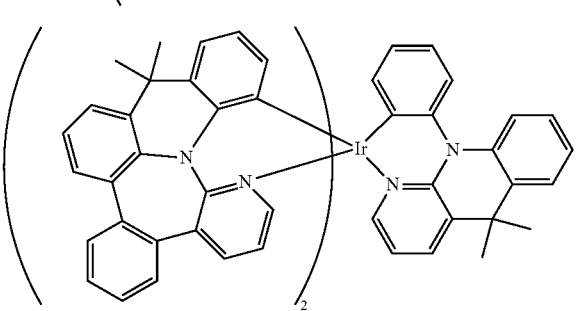
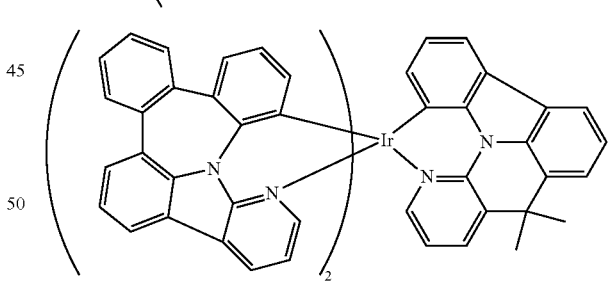
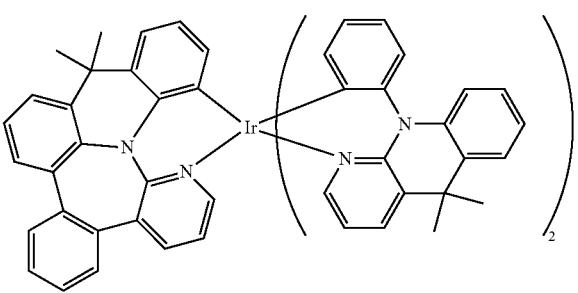
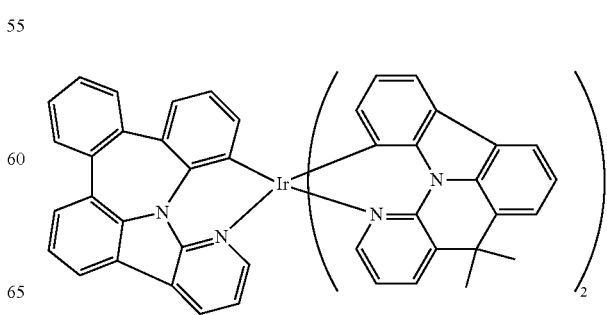

113
-continued
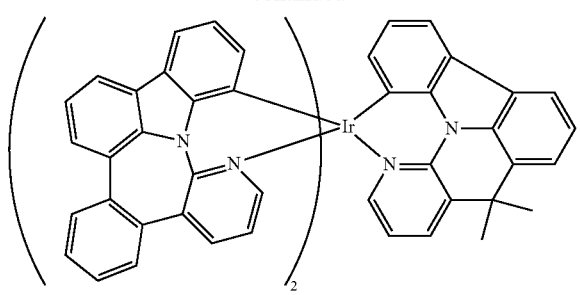
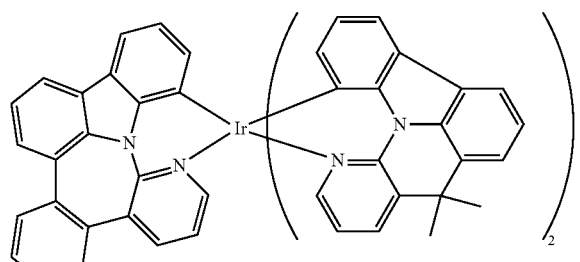
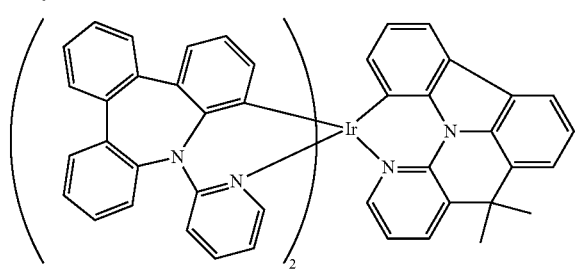
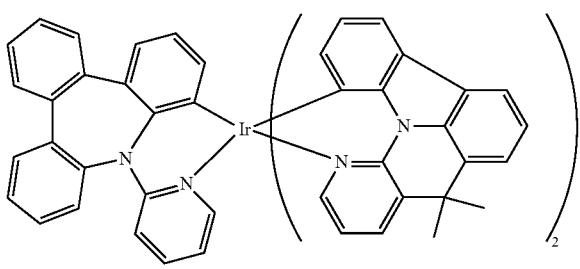
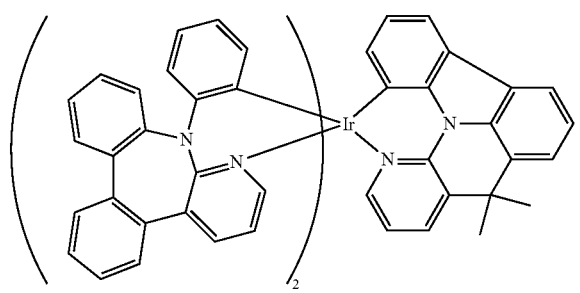
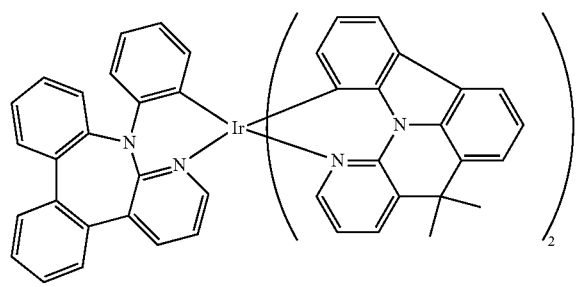
114
-continued
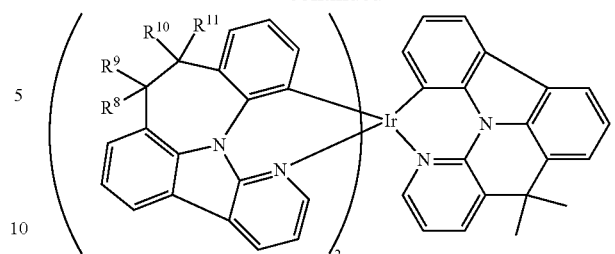
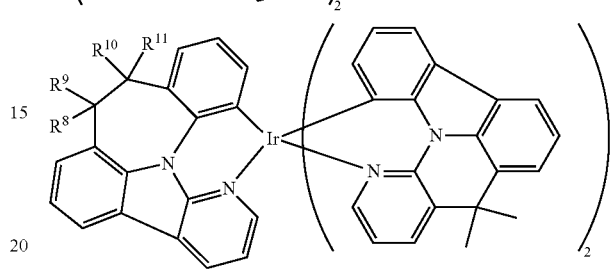
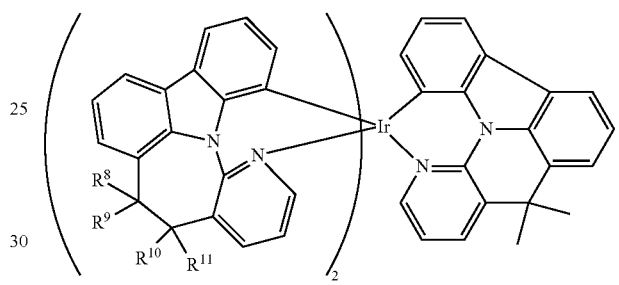
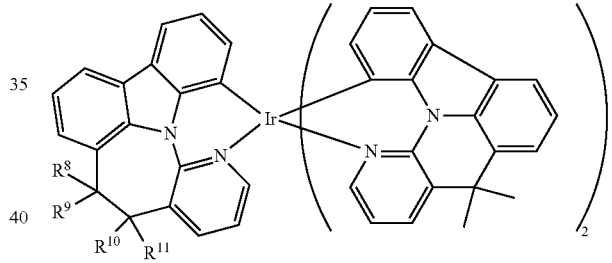
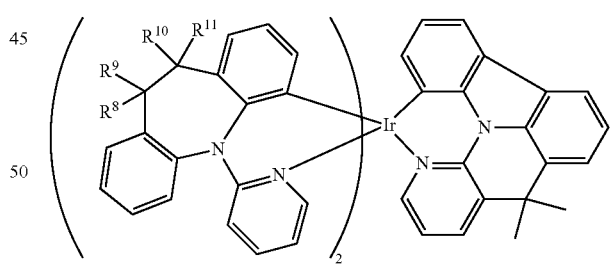
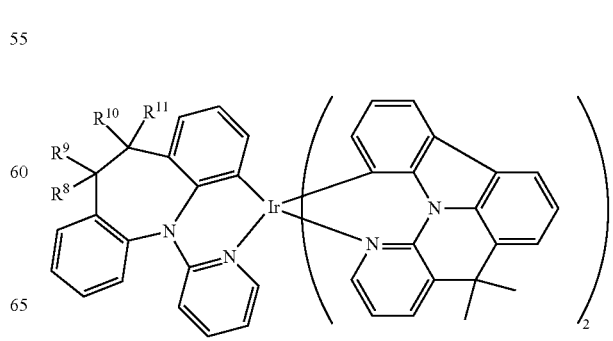

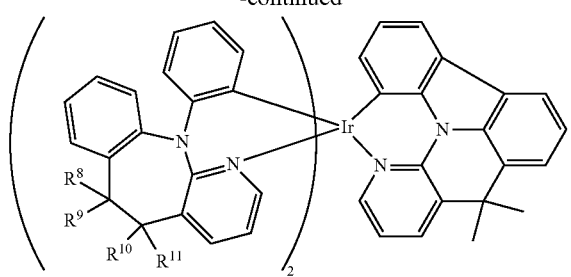
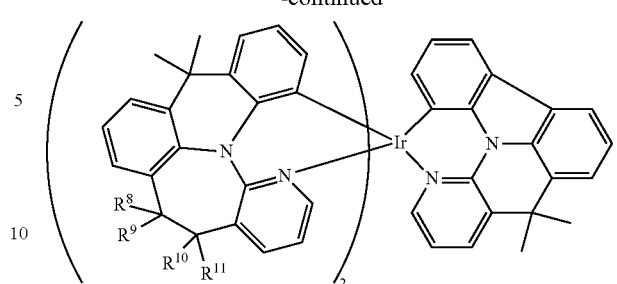
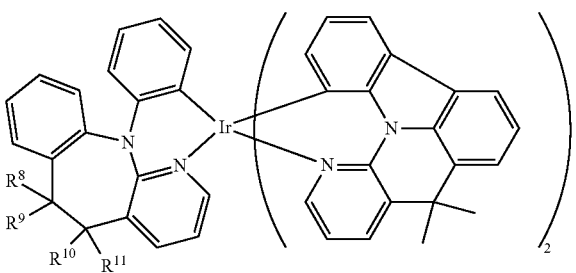
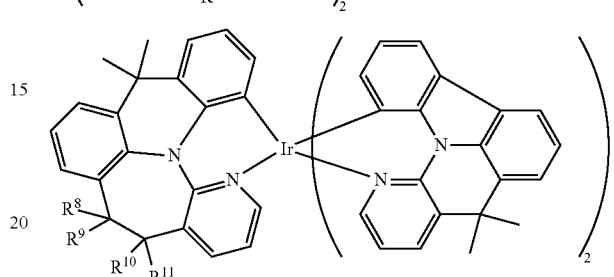
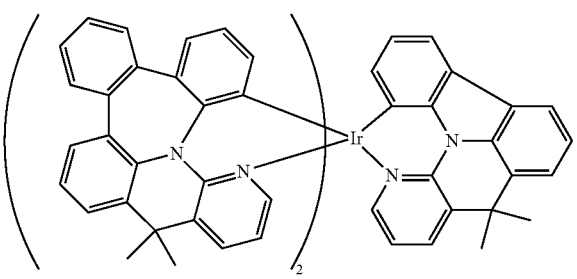
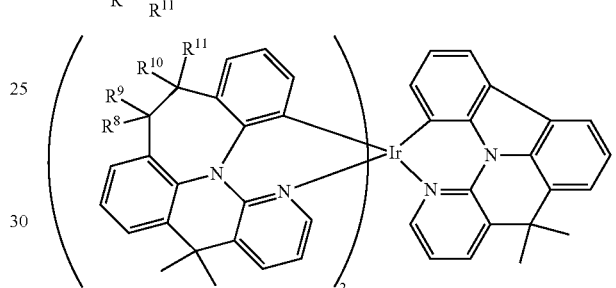
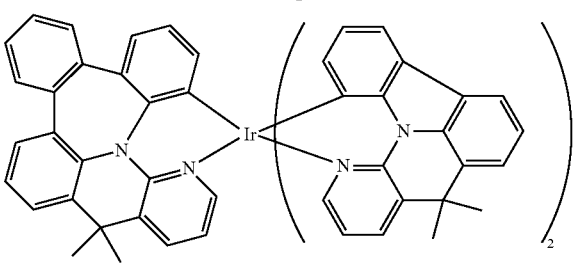
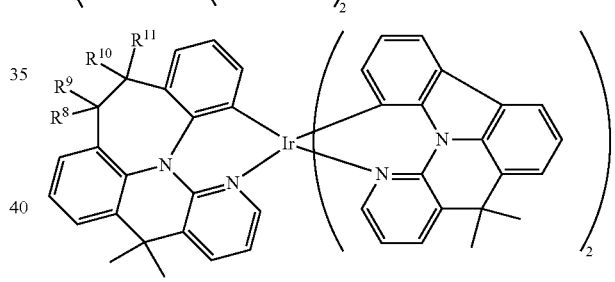
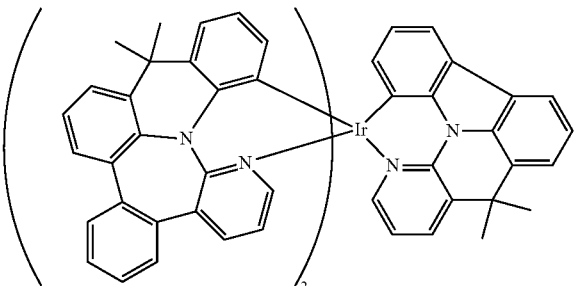
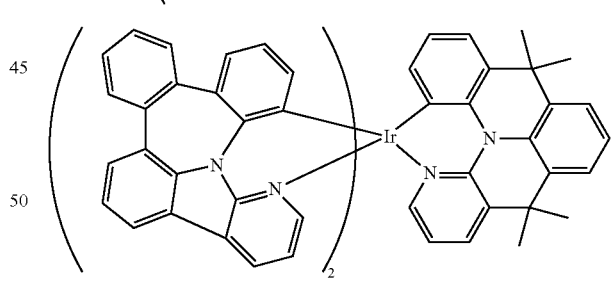
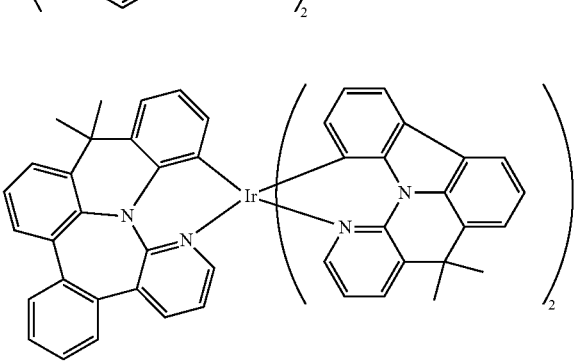
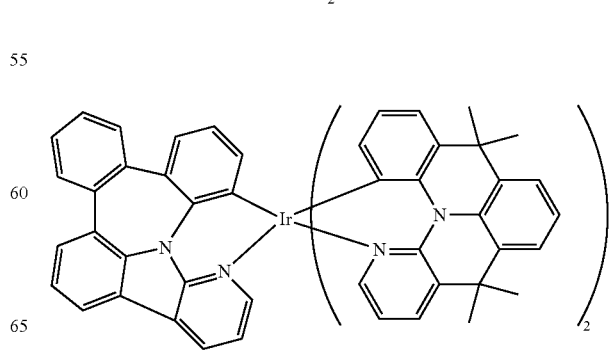

117
-continued
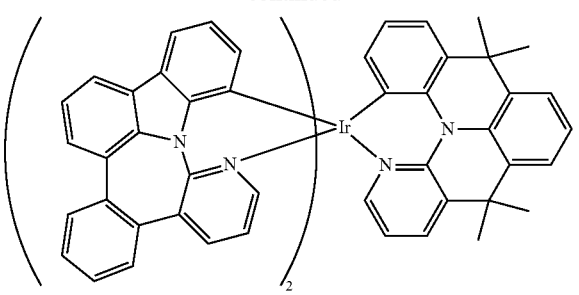
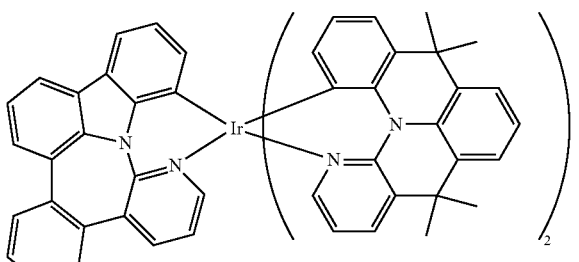
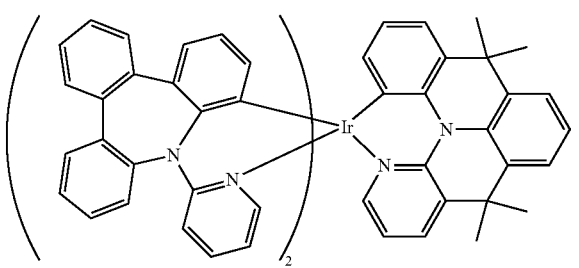
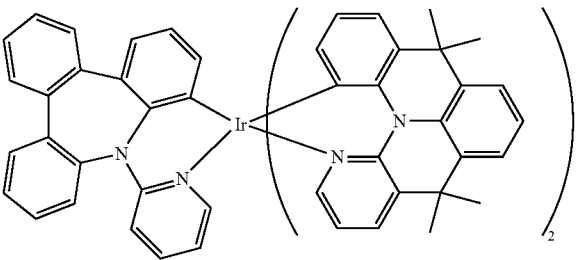
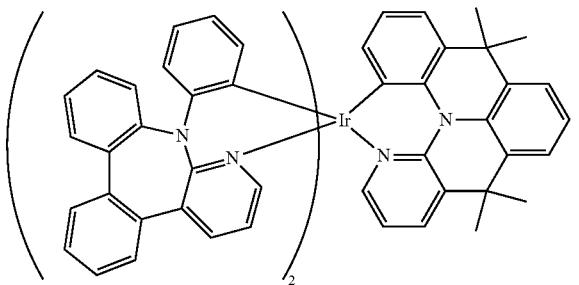
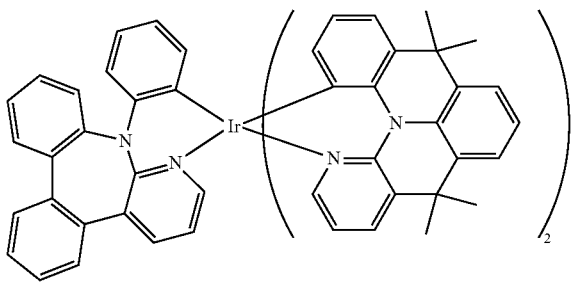
118
-continued
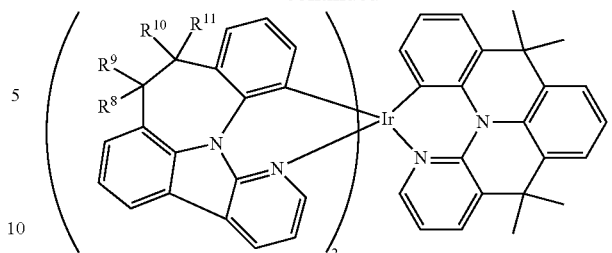
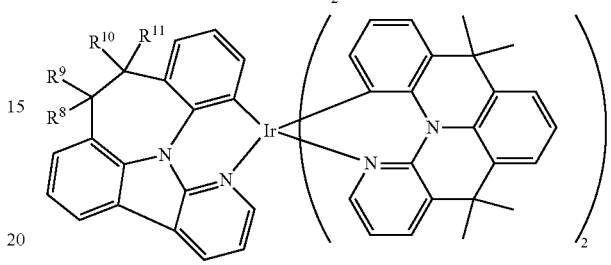
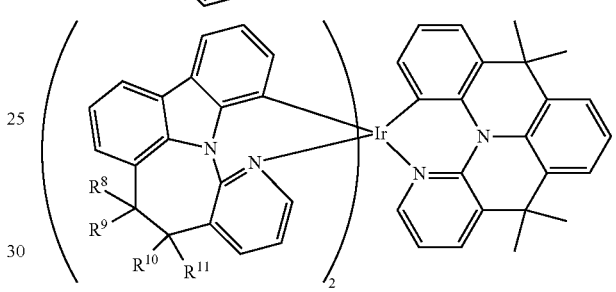
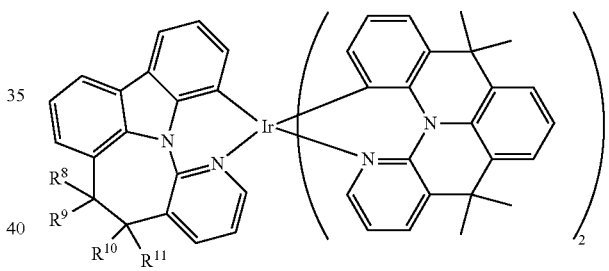
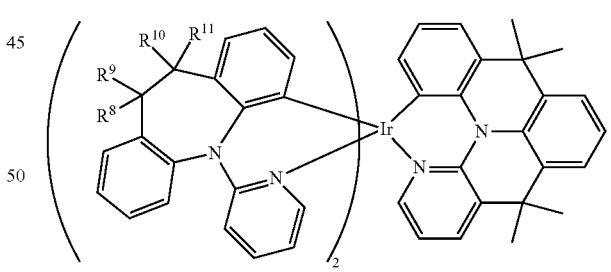
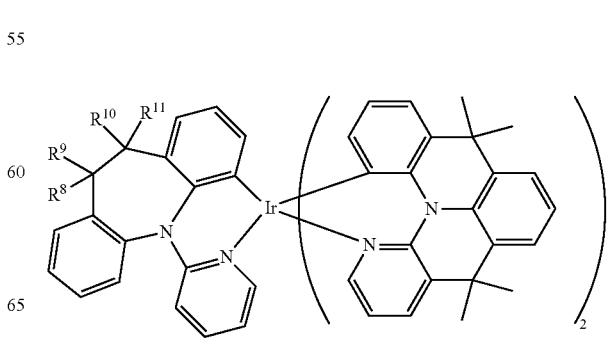

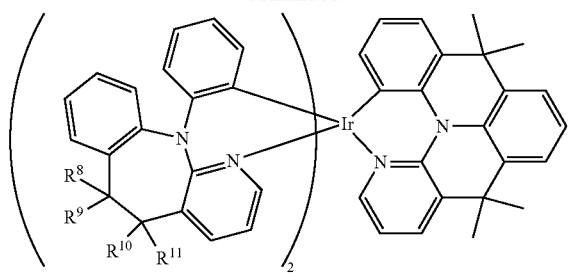
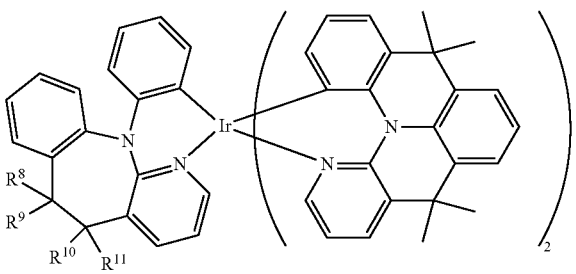
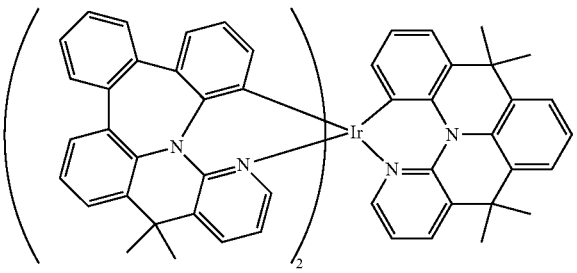
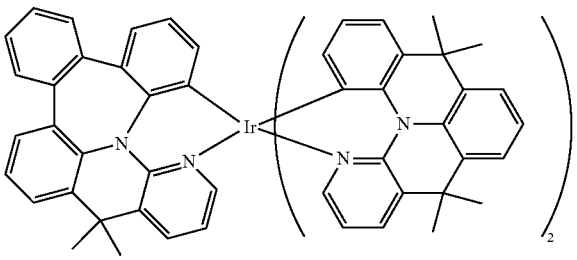
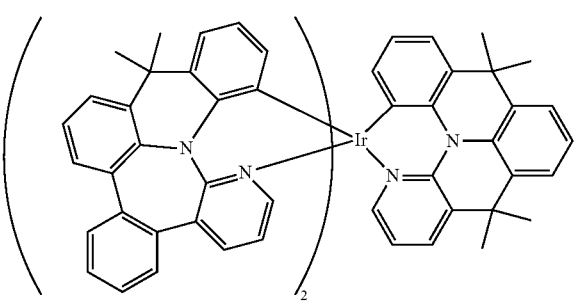
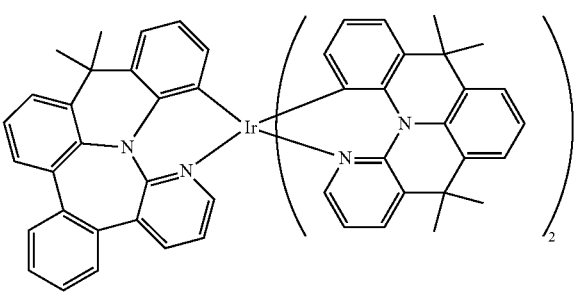
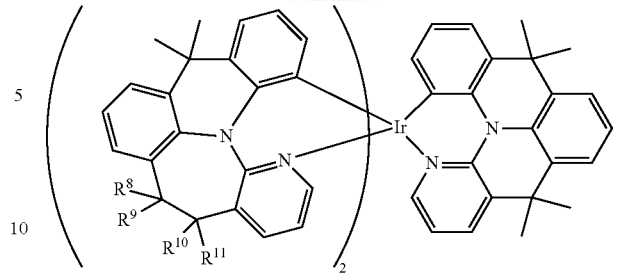
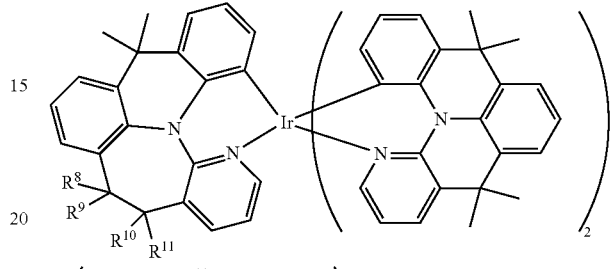
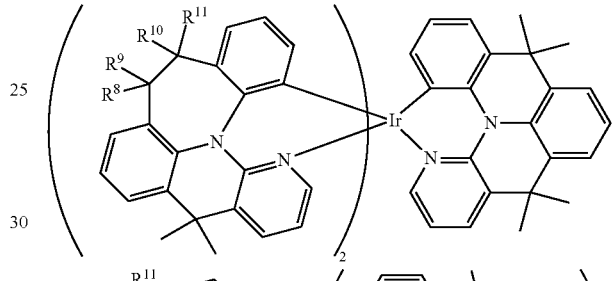
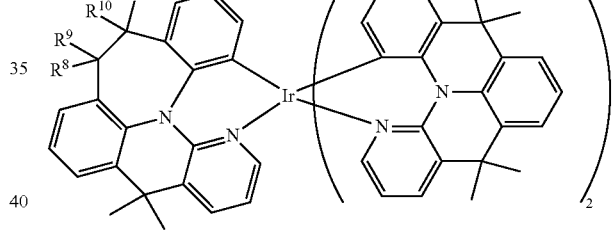

where:

each $R^4$ and $R^5$ present independently represents hydrogen, halogen, hydroxy, nitro, thiol, or substituted or unsubstituted $C_1$-$C_4$ alkyl, alkoxy, amino, or aryl;

each n is independently 1, 2, 3, 4, or 5, valency permitting;

U, $U^1$, and $U^2$, valency permitting, each independently represents N, P, N=O, P=O, NR, PR, CR, SiR, $CR_2$, $SiR_2O$, or S; and R represents substituted or unsubstituted $C_1$-$C_4$ alkyl, aryl, or heteroaryl.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C is disclosed as well as a class of molecules D, E, and F, and an example of a combination molecule, A-D is disclosed, then even if each is not individually recited, each is individually and collectively contemplated, meaning combinations A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed, it is understood that each of these additional steps can be performed with any specific embodiment or combination of embodiments of the methods described herein.

As referred to herein, a linking atom or linking group connects two atoms such as, for example, an N atom and a C atom. A linking atom or linking group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amino, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neo-pentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulas herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1O A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

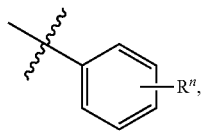

which is understood to be equivalent to a formula:

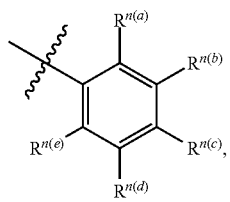

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

EXAMPLES

The complexes, devices, and methods described herein are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of compounds of the present disclosure, example methods and materials are now described.

Platinum and palladium complexes of Formulas A and B may be synthesized by synthetic procedures such as those depicted below.

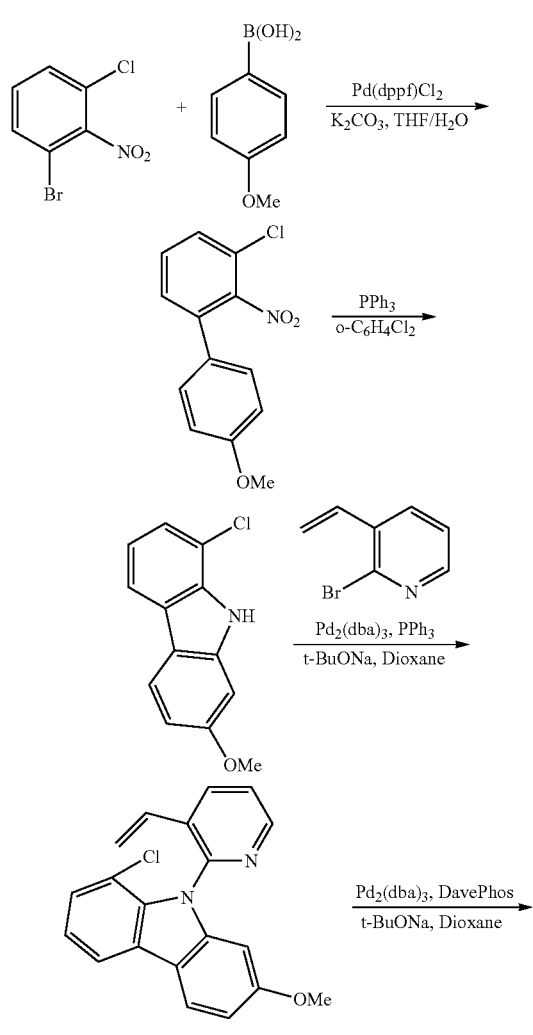
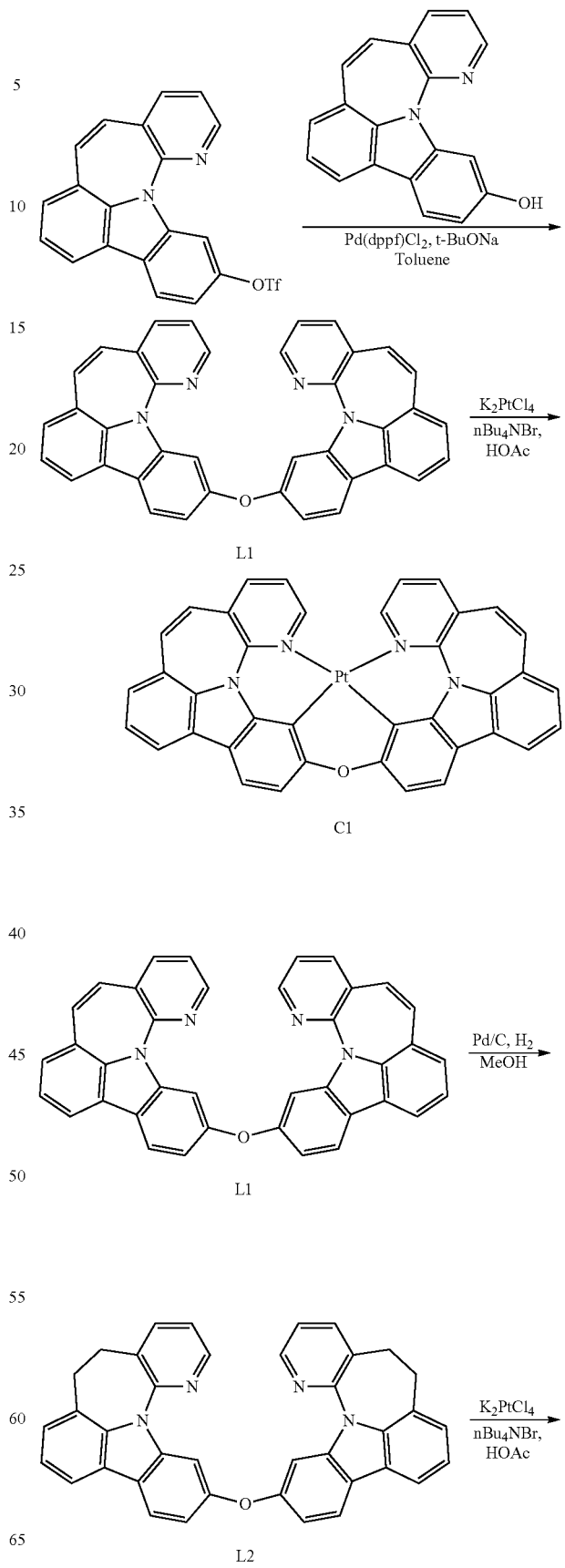

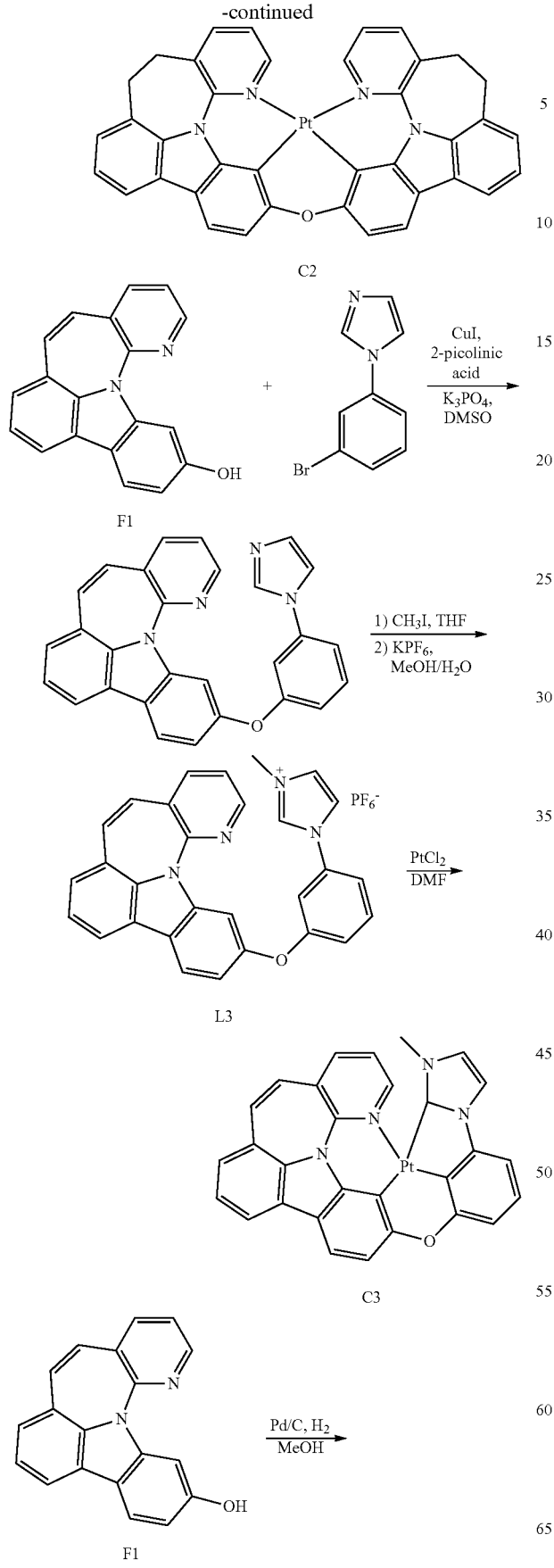
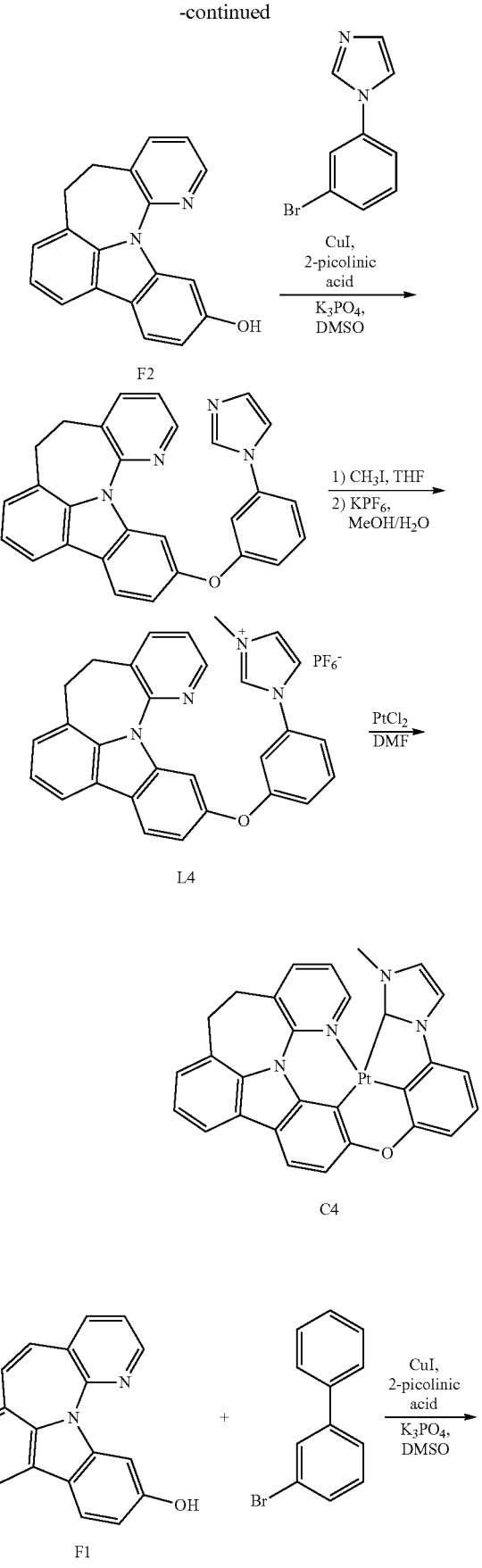

-continued
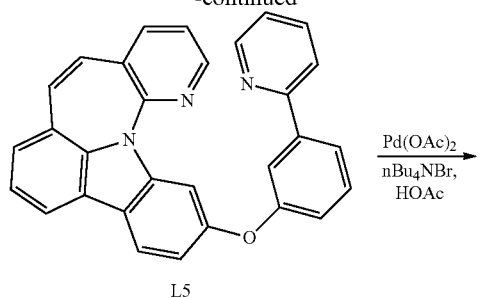
L5
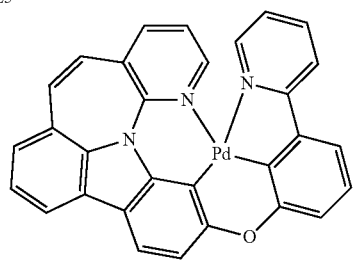
C5
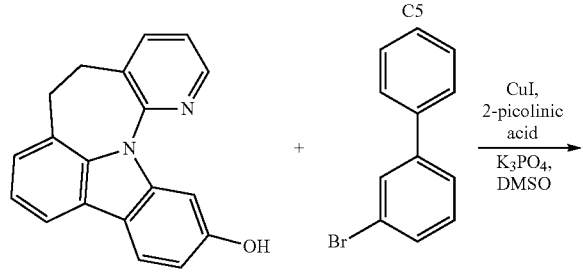
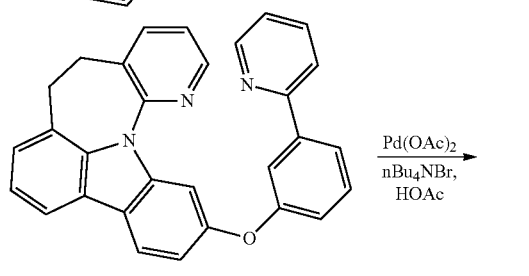
L6
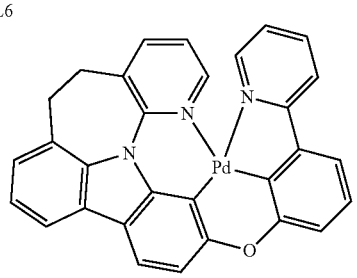
C6
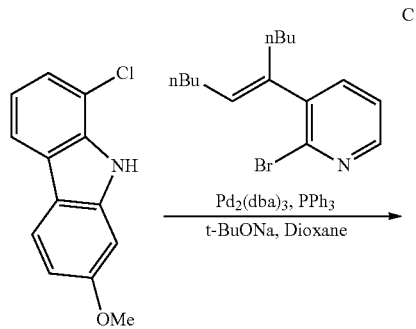
-continued
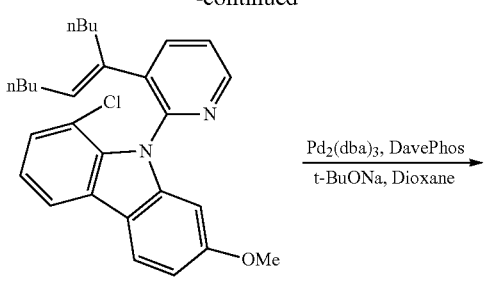
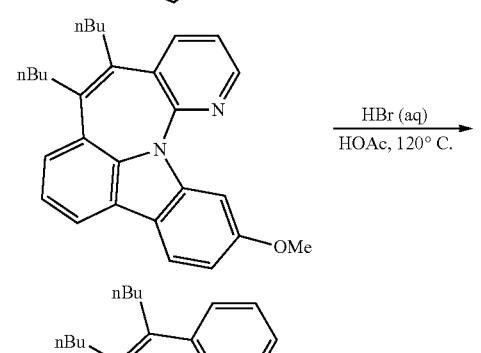
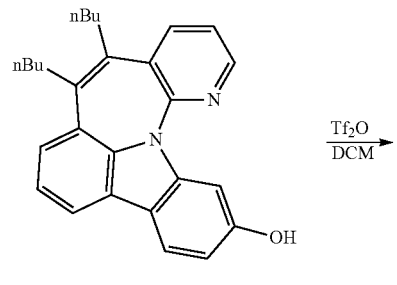
F3
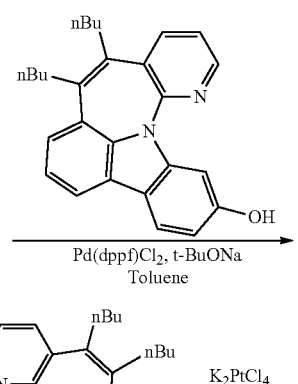
L7
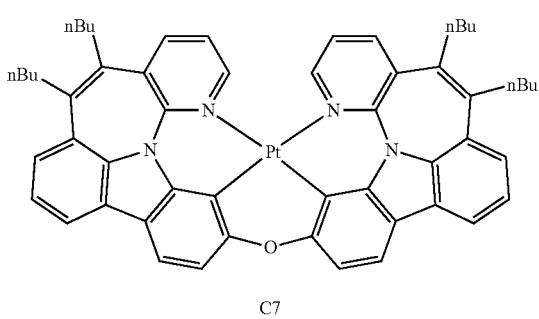
C7

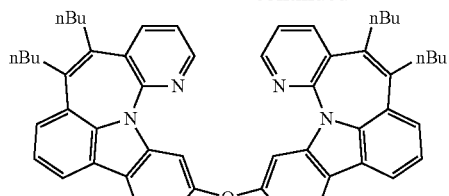

L7

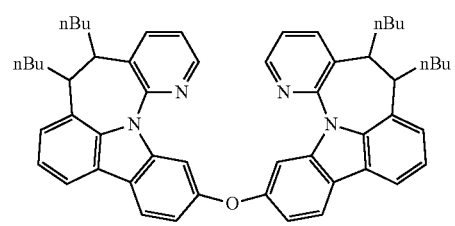

L8

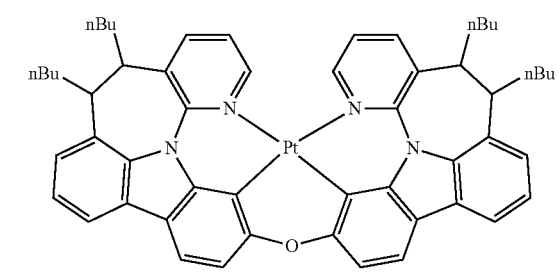

C8

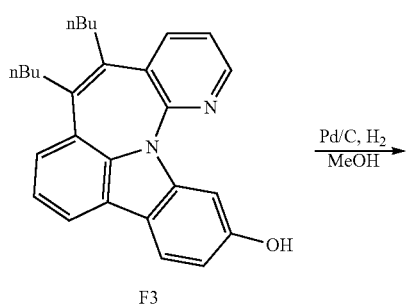

F3

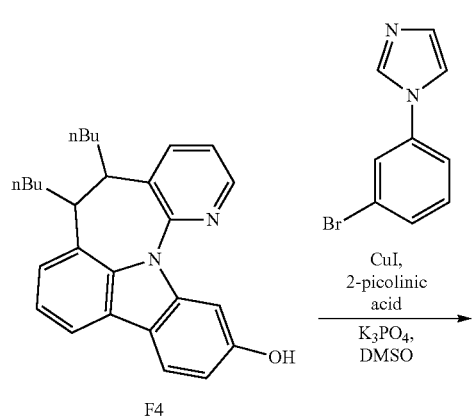

F4

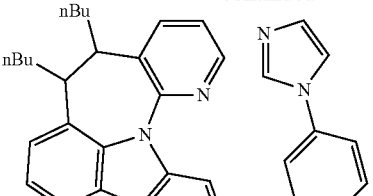

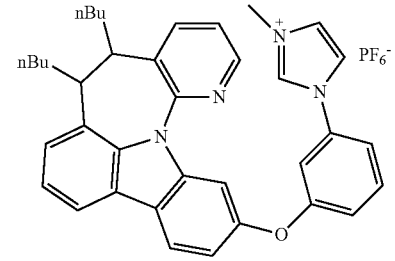

L9

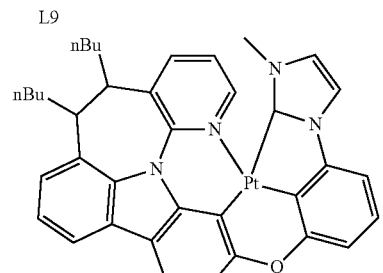

C9

General procedures for the synthesis of platinum complexes of Formulas A and B are described below, with reference to ligands L1-L4 and L7-L9 above.

Procedure A: To a solution of ligand (L1, L2, L7, or L8, 1 eq) in acetic acid (0.02 M) were added $K_2PtCl_4$ (1.05 eq) and n-$Bu_4NBr$ (0.1 eq). The mixture was heated to reflux for 3 days. The reaction mixture was cooled to room temperature and filtered through a short pad of silica gel. The filtrate was concentrated under reduced pressure. Purification by column chromatography (hexanes:dichloromethane) gave the complexes.

Procedure B: To a solution of ligand (L3, L4, or L9, 1 eq) in dimethylformamide (0.02 M) were added $PtCl_2$ (1.05 eq). The mixture was heated to reflux for 3 days. The reaction mixture was cooled to room temperature and the dimethylformamide was removed under reduced pressure. The residue was further purified by column chromatography (hexanes:dichloromethane) gave the complexes.

A general procedure for the synthesis of palladium complexes of Formulas A and B is described below, with reference to ligands L5 and L6 above.

To a solution of ligand (L5 or L6, 1 eq) in acetic acid (0.02 M) were added Pd(OAc)$_2$ (1.05 eq) and n-Bu$_4$NBr (0.1 eq). The mixture was heated to reflux for 3 days. The reaction mixture was cooled to room temperature and filtered through a short pad of silica gel. The filtrate was concentrated under reduced pressure. Purification by column chromatography (hexanes:dichloromethane) gave the complexes.

Iridium complexes of Formula C may be synthesized by synthetic procedures such as those depicted below.

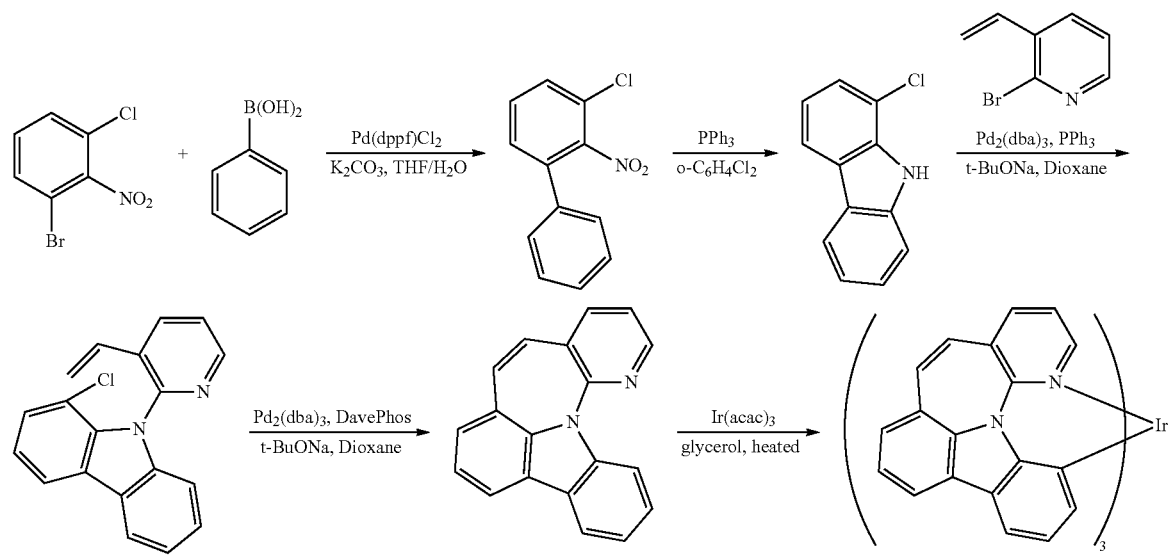
i)
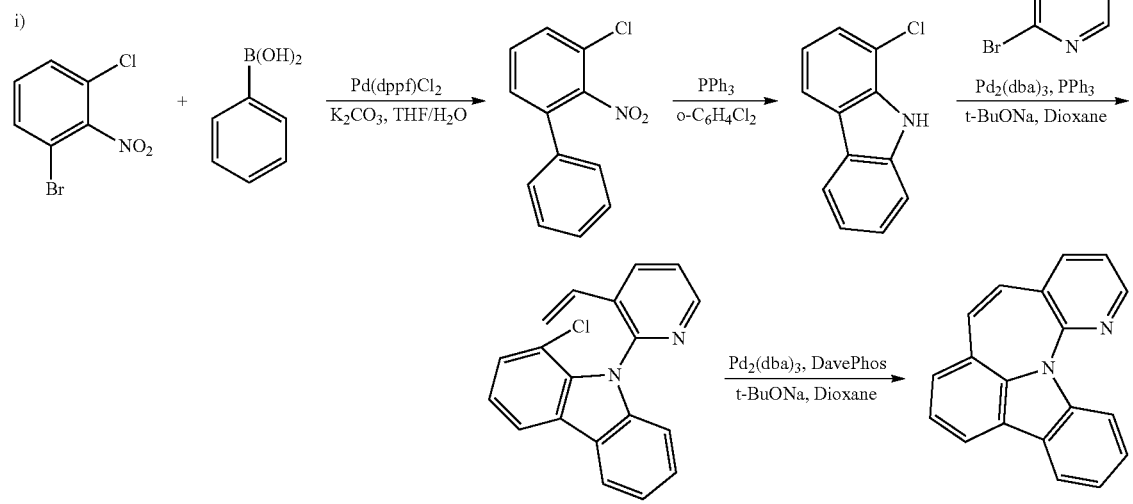
ii)
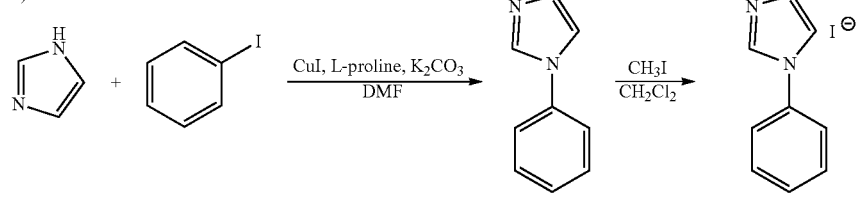
iii)
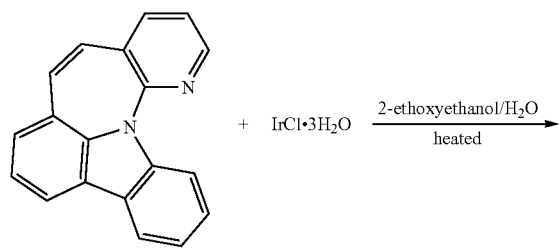

-continued
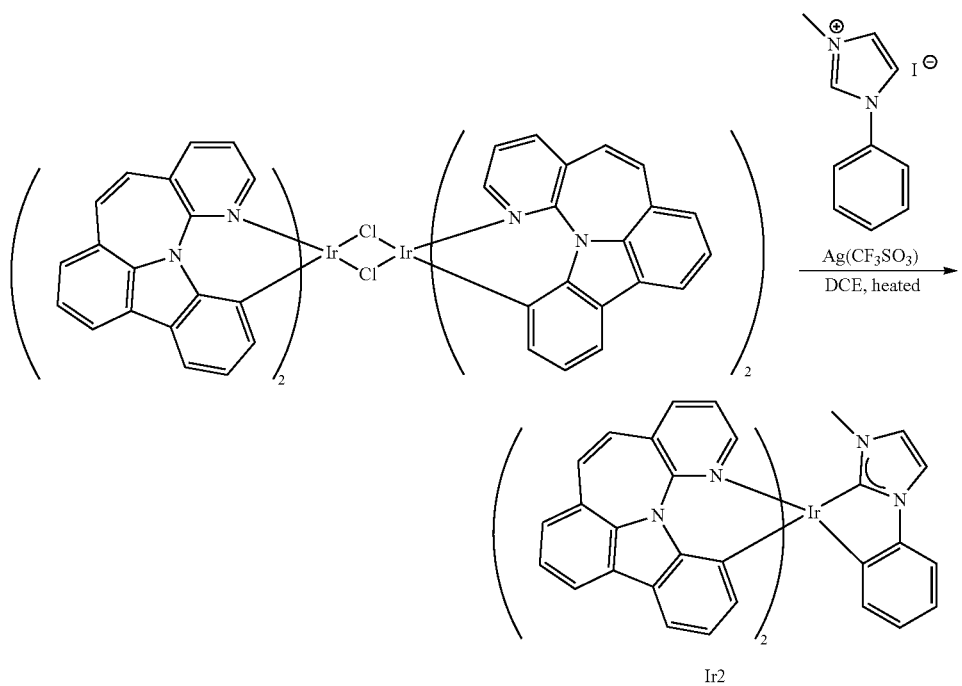
Ir2
i) 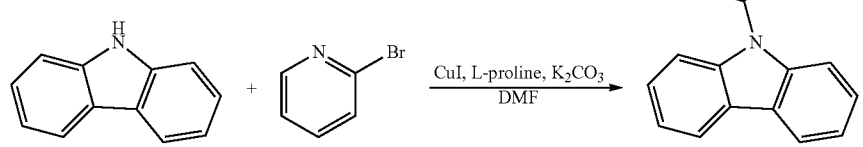
ii) 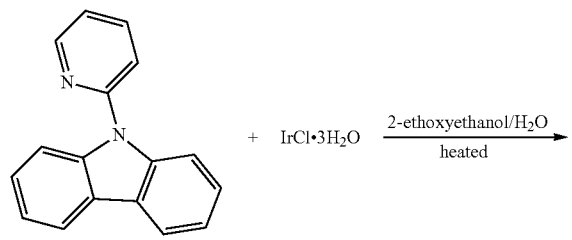
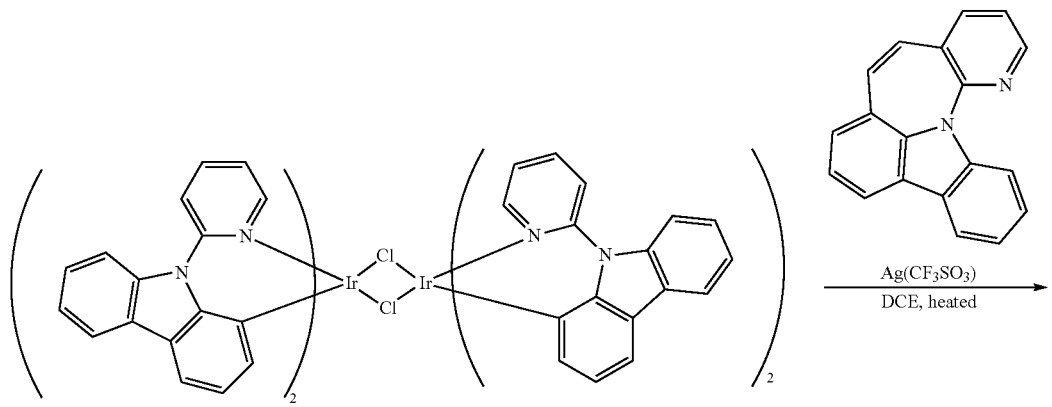

-continued
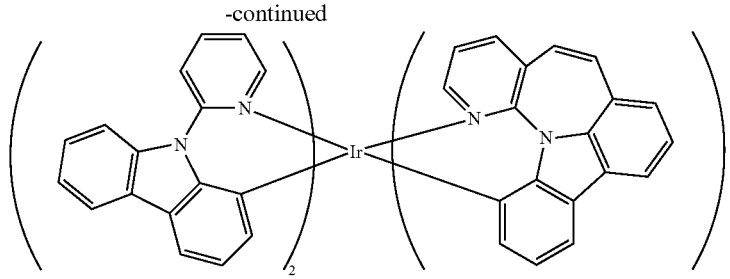
Ir3
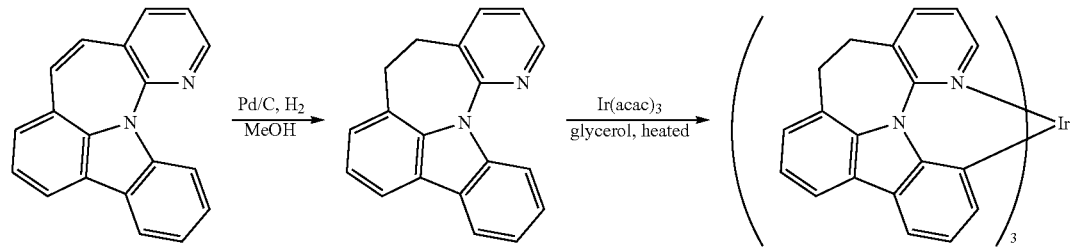
Ir4
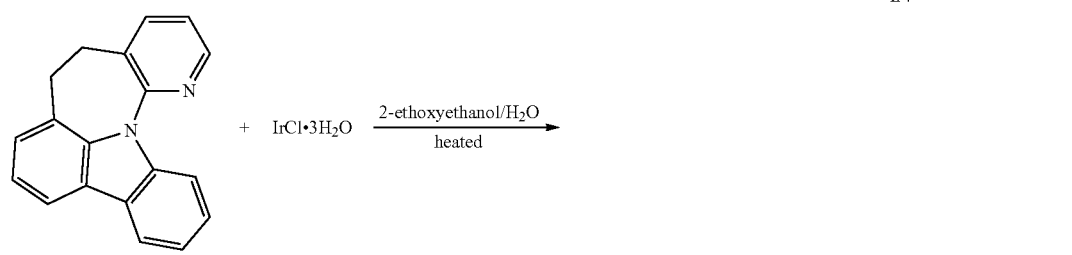
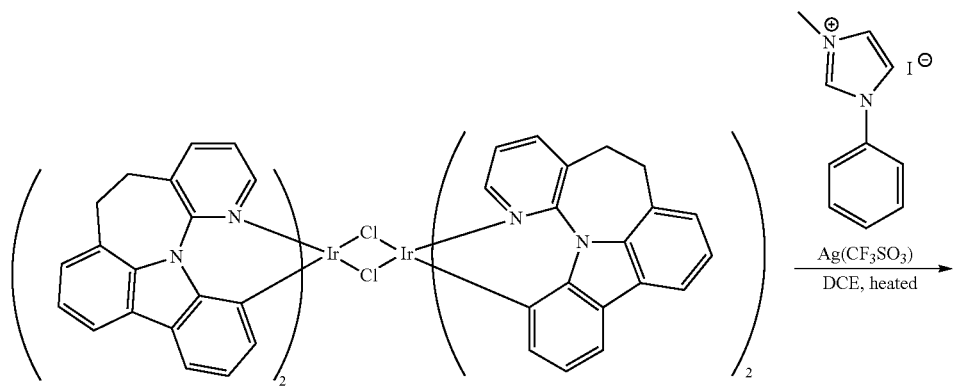
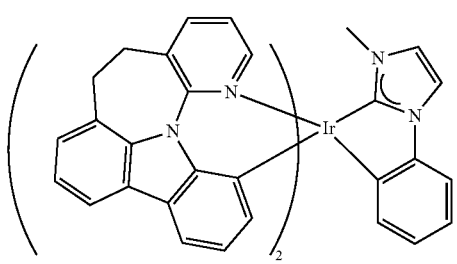
Ir5

-continued
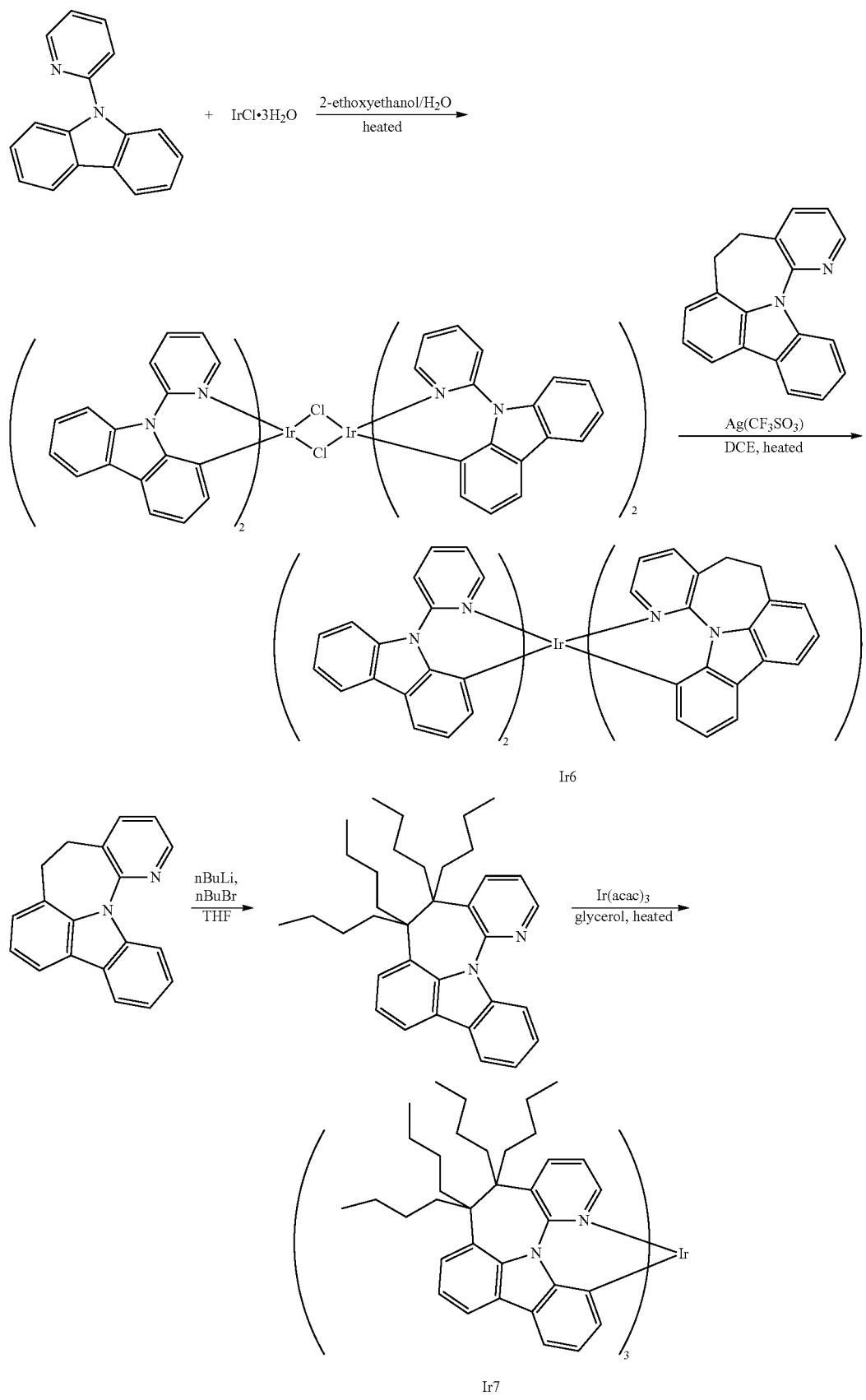

-continued
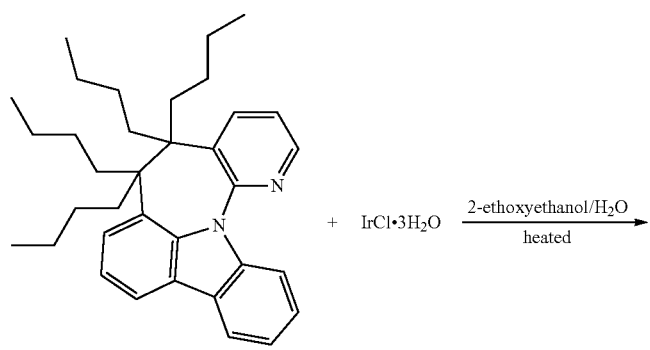
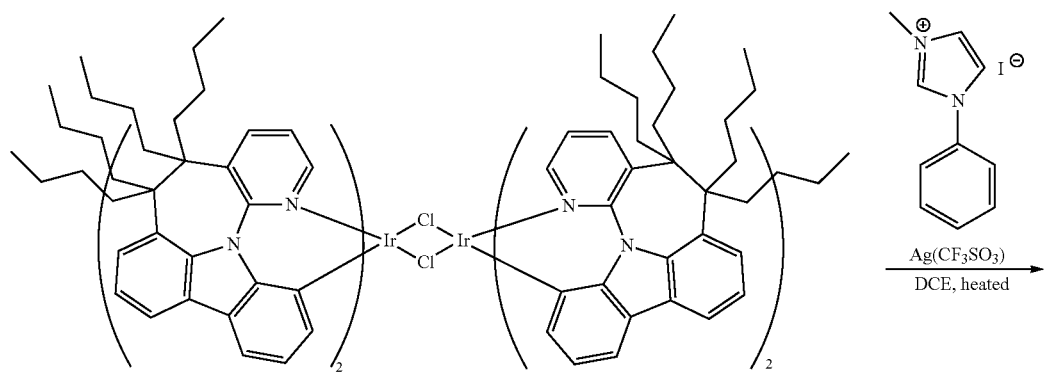
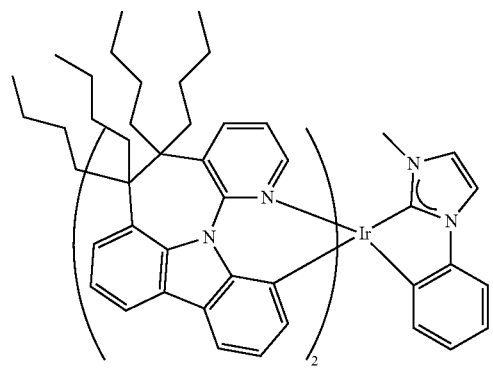
Ir8
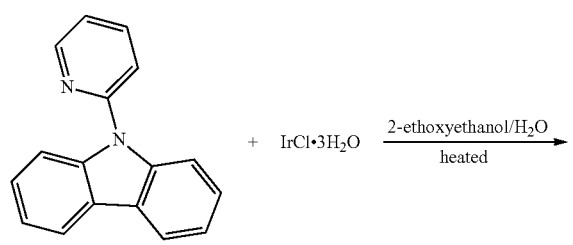

-continued

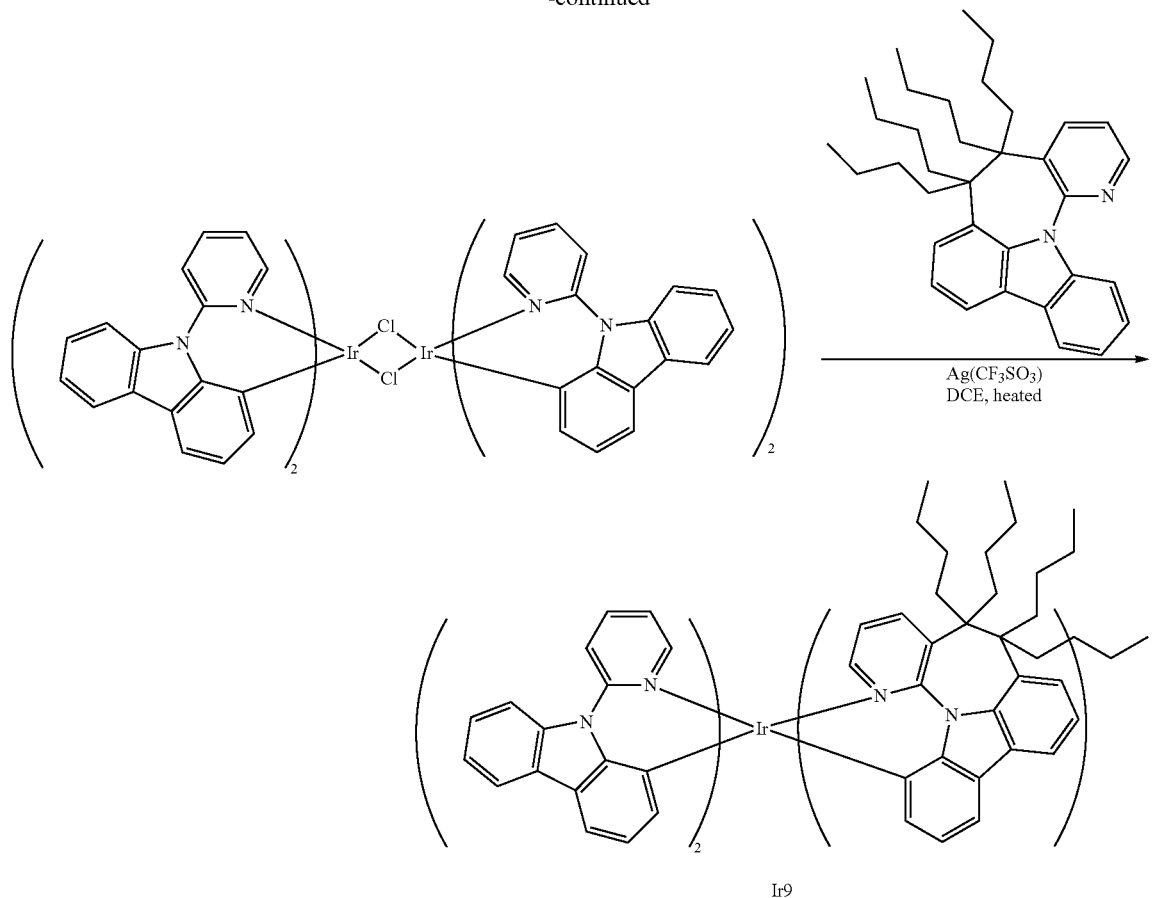

Ir9

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include OLEDs, organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

The complexes disclosed herein are suited for use in a wide variety of devices, including, for example, optical and electro-optical devices, including, for example, photo-absorbing devices such as solar- and photo-sensitive devices, OLEDs, photo-emitting devices, devices capable of both photo-absorption and emission, and markers for bio-applications.

Also disclosed herein are compositions including one or more complexes disclosed herein. The present disclosure provides light emitting device that include one or more complexes or compositions described herein. The light emitting device can be an OLED (e.g., a phosphorescent OLED device). The present disclosure also provides a photovoltaic device comprising one or more complexes or compositions described herein. Further, the present disclosure also provides a luminescent display device comprising one or more complexes or compositions described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N-di-1-naphthyl-N,N-diphenyl-1,1'-biphenyl-4,4'diamine (NPD), 1,1-bis((di-4-tolylamino)phenyl)cyclohexane (TAPC), 2,6-bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

Only a few implementations are described and illustrated. Variations, enhancements and improvements of the described implementations and other implementations can be made based on what is described and illustrated in this document.

What is claimed is:

1. A complex of Formula A or Formula B:

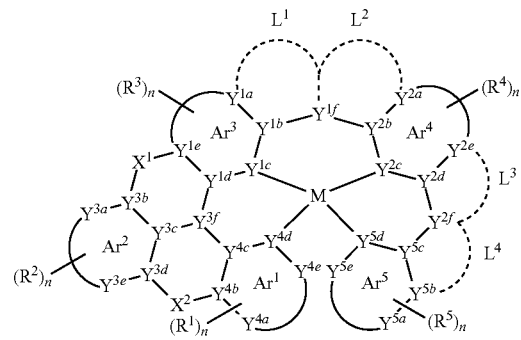

Formula A

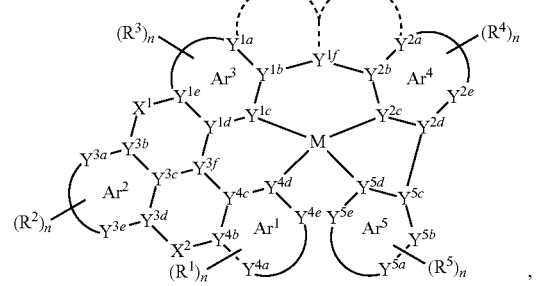

Formula B wherein:
M represents $Pt^{2+}$ or $Pd^{2+}$;
$Ar^1$, $Ar^2$, $Ar^3$, $Ar^4$, and $Ar^5$ each independently represents an aryl or heteroaryl;
$R^1$, $R^2$, $R^3$, $R^4$, and $R^5$ each independently represents hydrogen, halogen, hydroxyl, nitro, thiol, or substituted or unsubstituted $C_1$-$C_4$ alkyl, alkoxy, amino, or aryl;
each n is independently 0, 1, 2, 3, 4, or 5, valency permitting;
$Y^{1a}$, $Y^{1b}$, $Y^{1c}$, $Y^{1d}$, $Y^{1e}$, $Y^{2a}$, $Y^{2b}$, $Y^{2c}$, $Y^{2d}$, $Y^{2e}$, $Y^{3a}$, $Y^{3b}$, $Y^{3c}$, $Y^{3d}$, $Y^{3e}$, $Y^{4a}$, $Y^{4b}$, $Y^{4c}$, $Y^{4d}$, $Y^{4e}$, $Y^{5a}$, $Y^{5b}$, $Y^{5c}$, $Y^{5d}$, and $Y^{5e}$ each independently represents C, N, Si, O, or S;
each $Y^{1f}$, $Y^{2f}$, and $Y^{3f}$ present, valency permitting, independently represents N, P, N=O, P=O, NR, PR, CR, SiR, $CR_2$, $SiR_2$, O, or S;
at least one of $X^1$ and $X^2$ independently represents one of the following moieties:

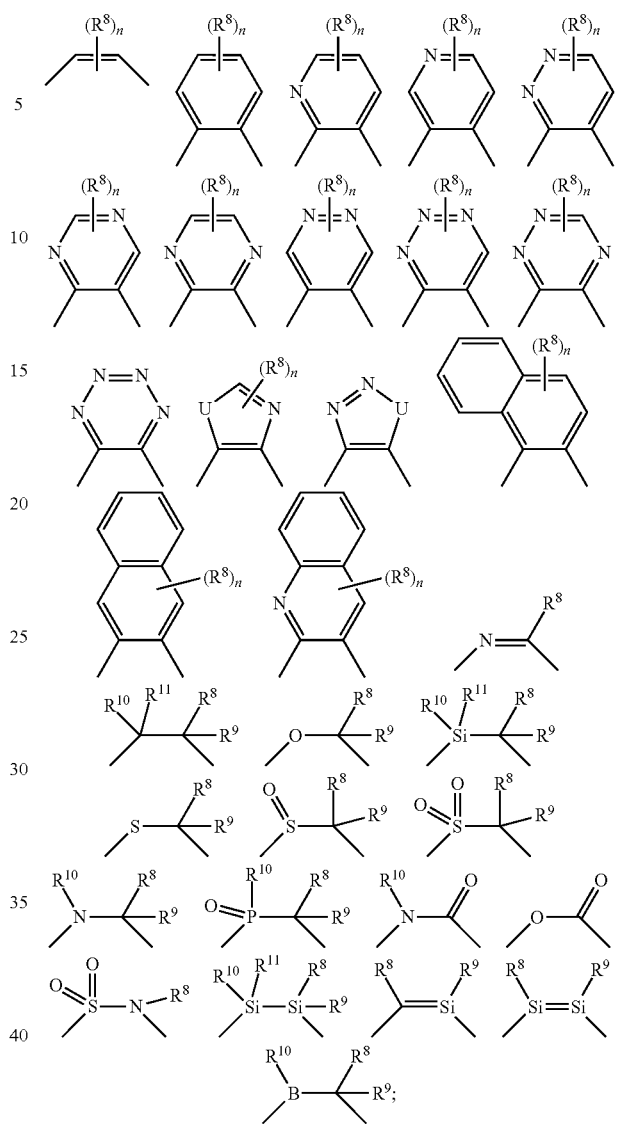

the other of $X^1$ and $X^2$, if not one of the moieties above, is independently present or absent, and each $X^1$ and $X^2$ present independently represents a single bond, NR, PR, BR, CRR', SiRR', O, S, S=O, O=S=O, Se, Se=O, or O=Se=O;
each of R and R' is independently present or absent, and each R and R' present independently represents substituted or unsubstituted $C_1$-$C_4$ alkyl, aryl, or heteroaryl;
$R^8$, $R^9$, $R^{10}$, and $R^{11}$ each independently represents hydrogen, halogen, hydroxyl, nitro, thiol, or substituted or unsubstituted $C_1$-$C_4$ alkyl, alkoxy, amino, or aryl;
each of $L^1$, $L^2$, $L^3$, and $L^4$ is independently present or absent, and each $L^1$, $L^2$, $L^3$, and $L^4$ present represents a linking atom or linking group.

2. The complex of claim 1, wherein at least one of $L^1$, $L^2$, $L^3$, and $L^4$ represents a linking group, and the linking group comprises a hydroxy, amide, thiol, or substituted or unsubstituted alkyl, alkoxy, alkenyl, alkynyl, amino, aryl, heteroaryl, cycloalkyl, or heterocyclyl moiety.

3. The complex of claim 1, comprising a complex of Formula A represented by one of the following structures:

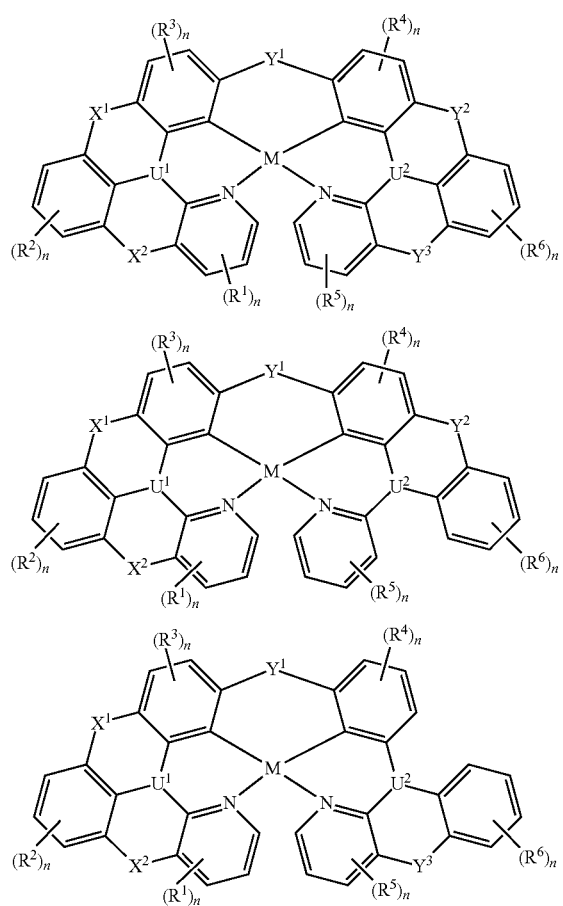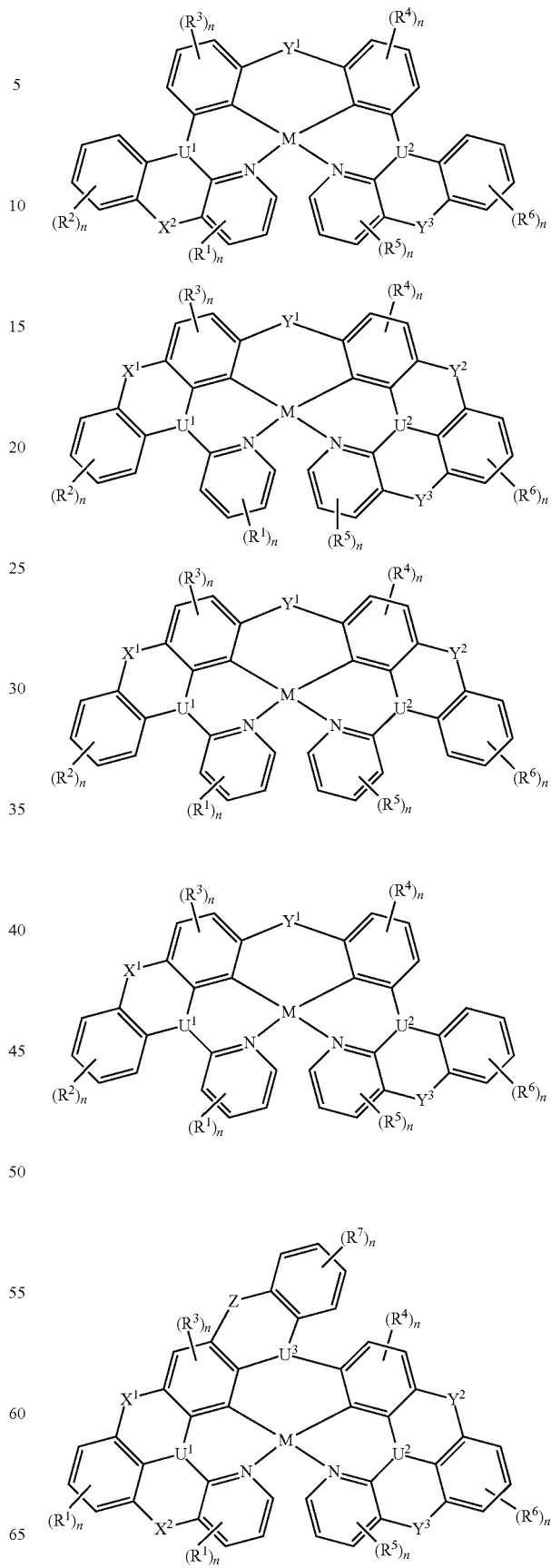

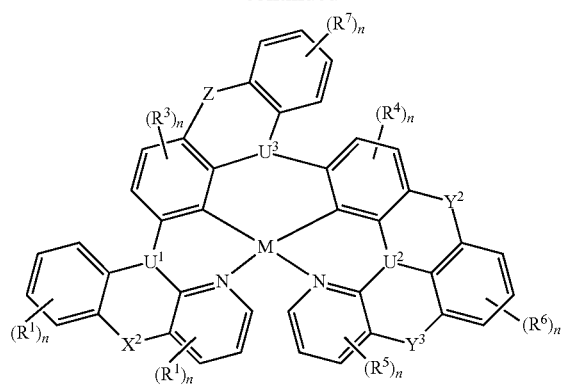
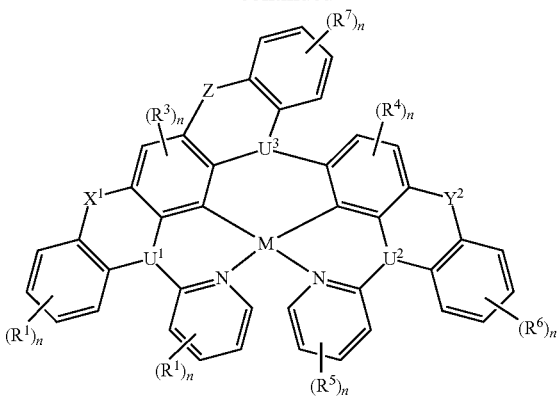
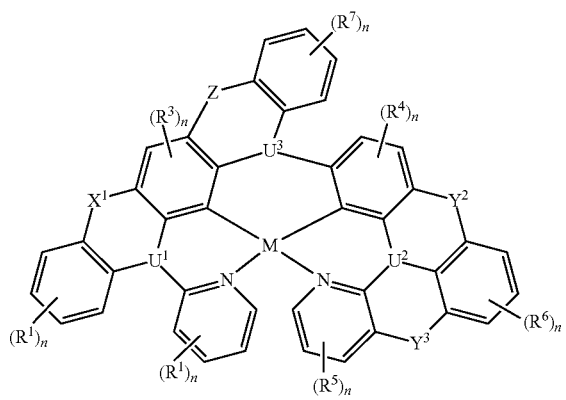
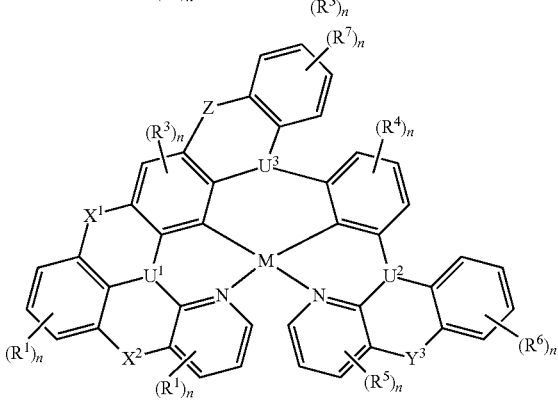
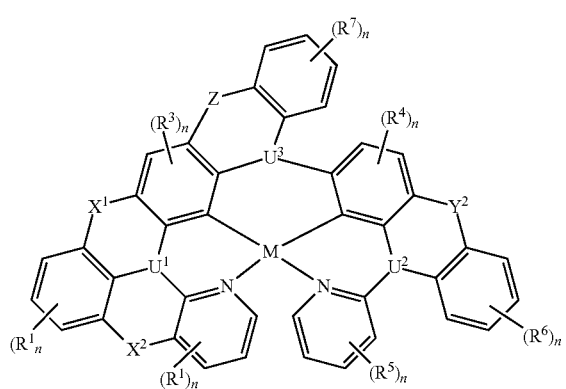
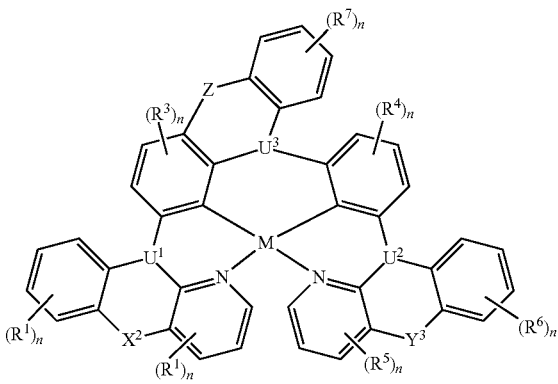
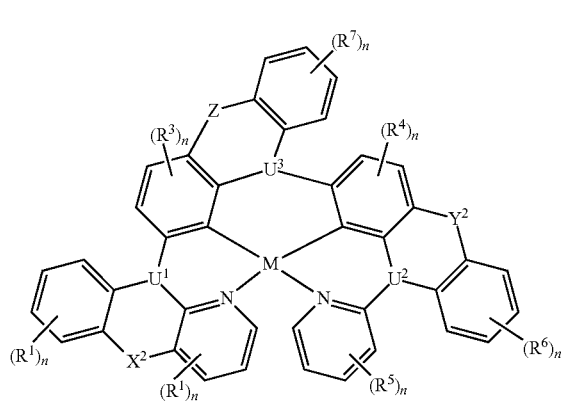
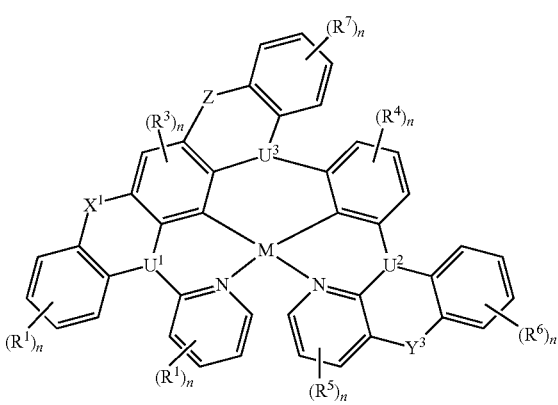

153
-continued

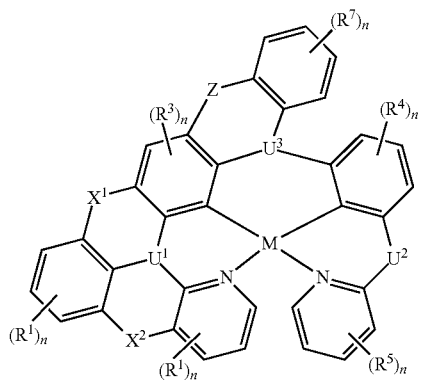

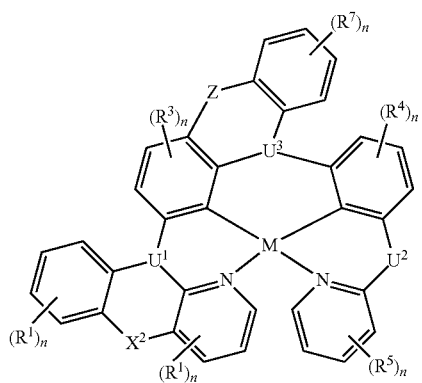

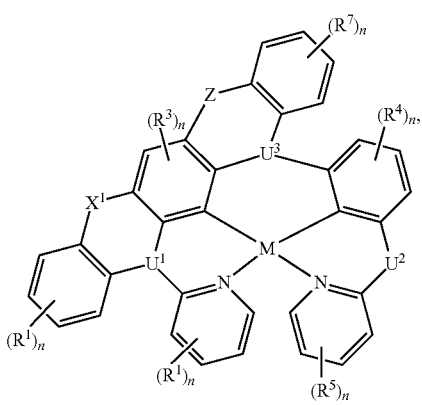

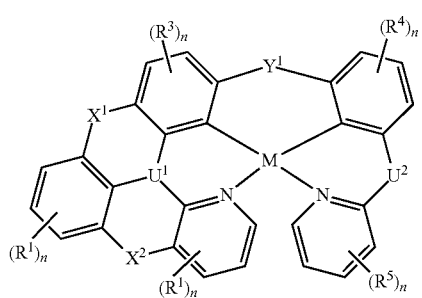

154
-continued

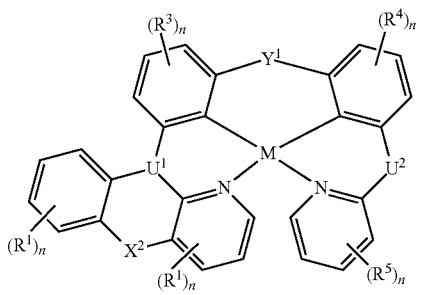

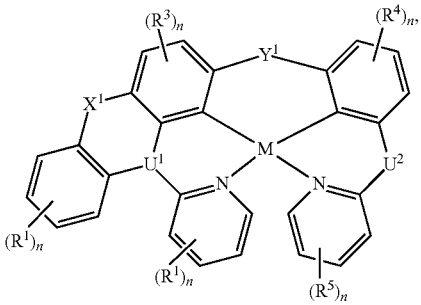

where:
U$^1$ is Y$^{3f}$;
U$^2$ is Y$^{2f}$;
U$^3$ and Y$^1$ are Y$^{1f}$;
Y$^2$ and Y$^3$ each independently represents a single bond, CR$_2$,

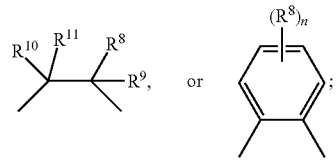

Z represents O, S, SO, S(O)$_2$, NR, PR, CR$_2$, SiR$_2$, or BR; and

R$^6$ and R$^7$ each independently represents hydrogen, halogen, hydroxyl, nitro, thiol, or substituted or unsubstituted C$_1$-C$_4$ alkyl, alkoxy, amino, or aryl.

4. The complex of claim 1, comprising a complex of Formula B represented by one of the following structures:

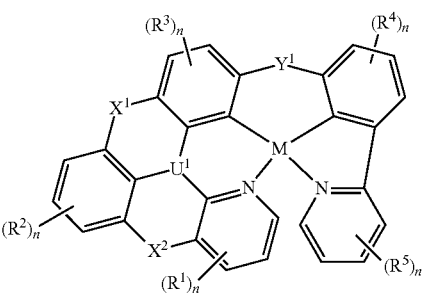

-continued
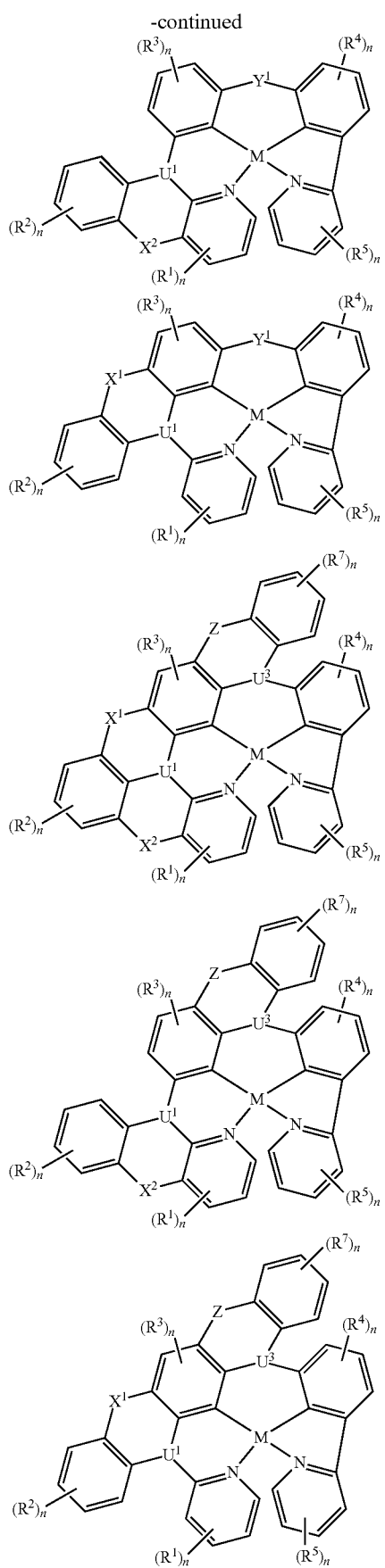
-continued
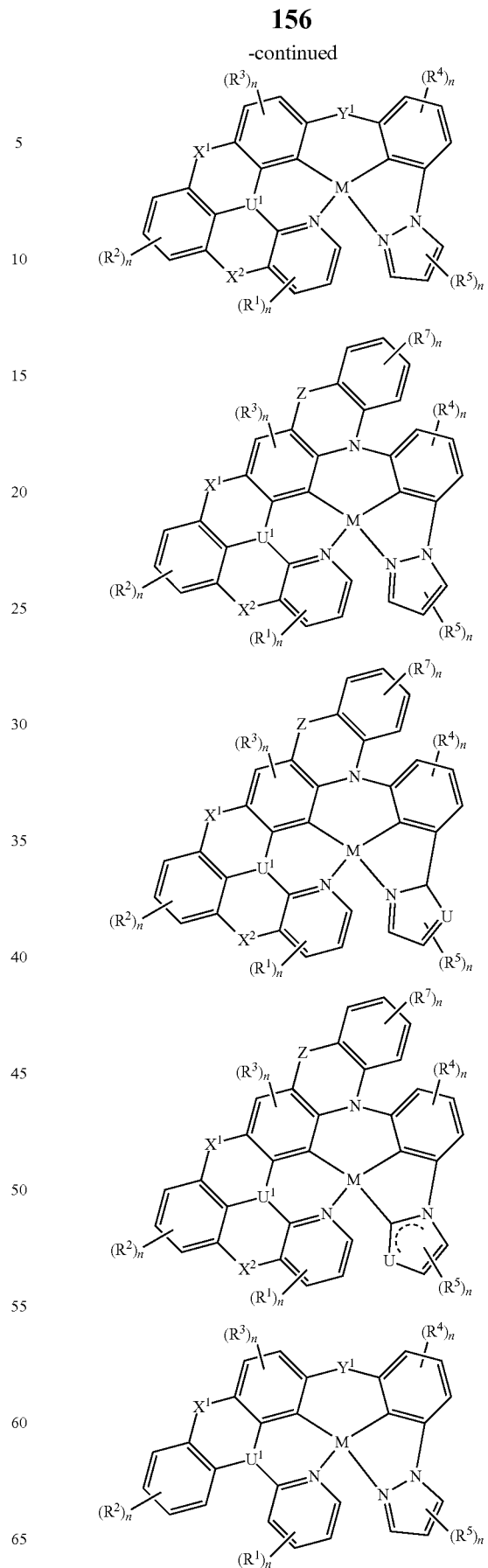

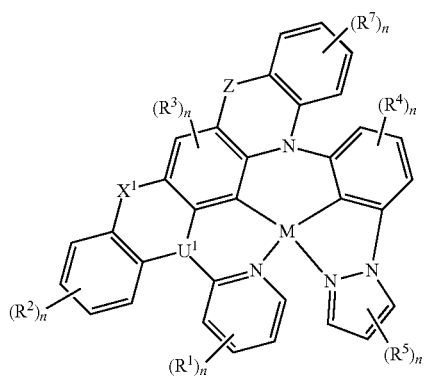
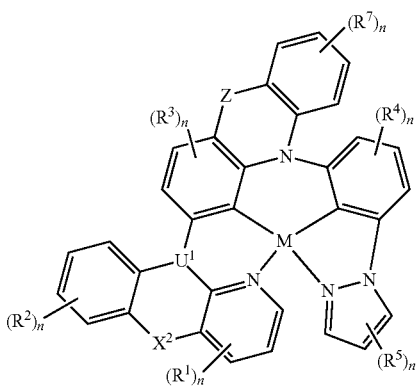
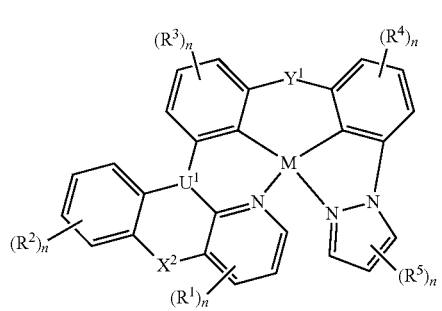

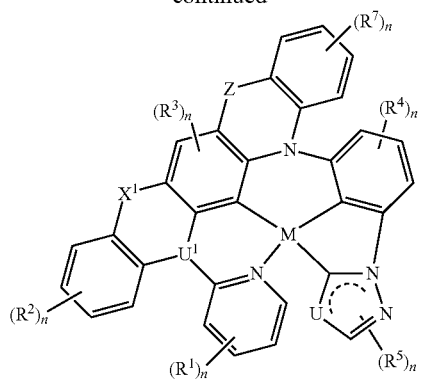
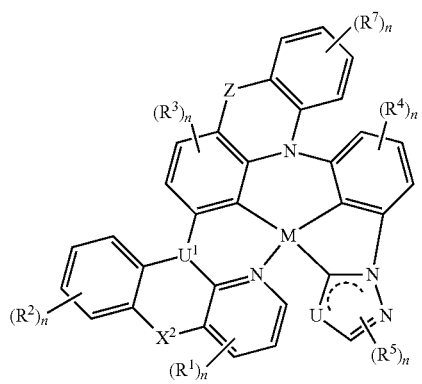
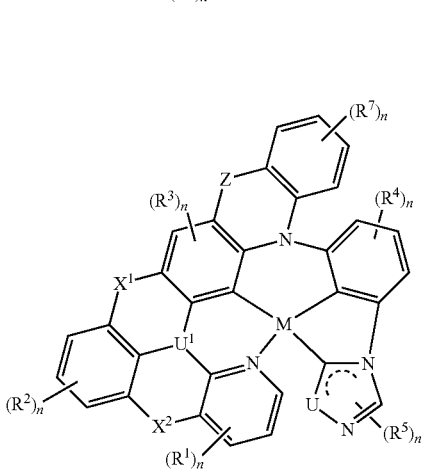
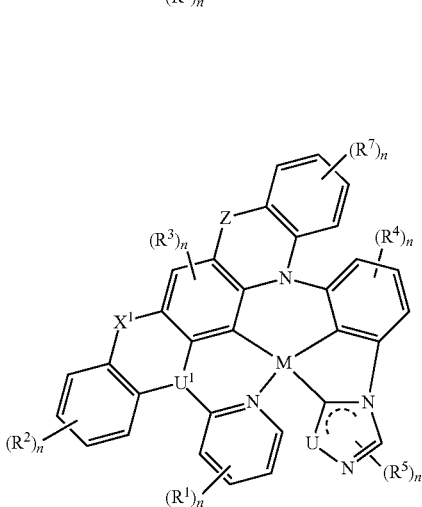
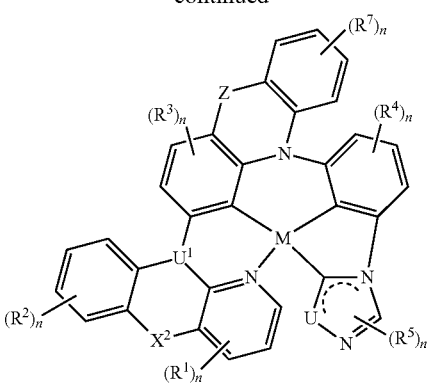
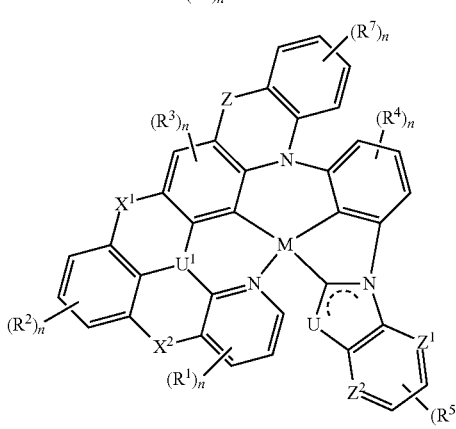
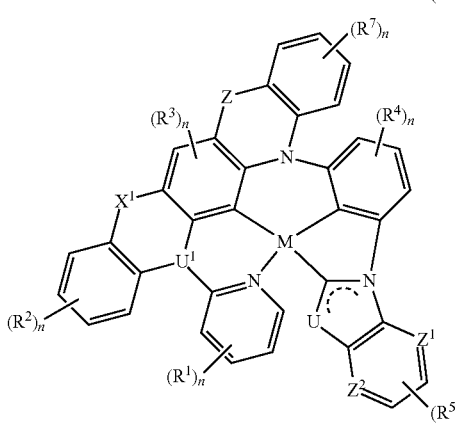
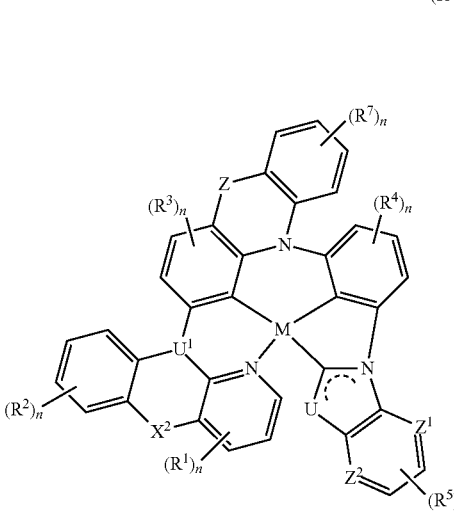

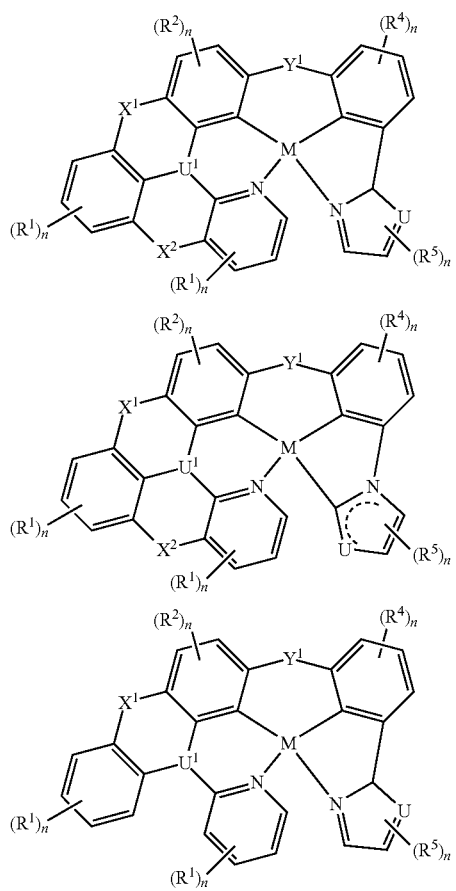
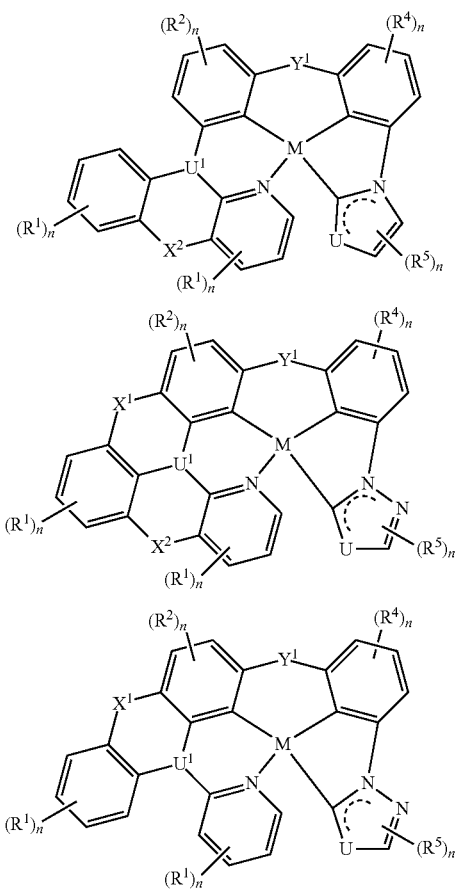
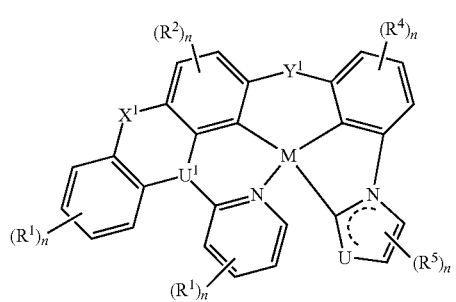
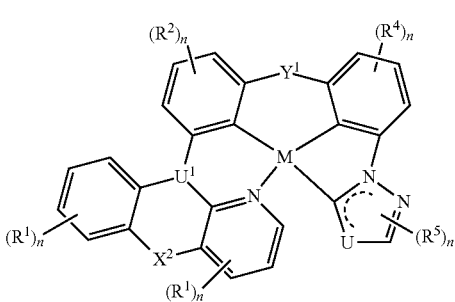
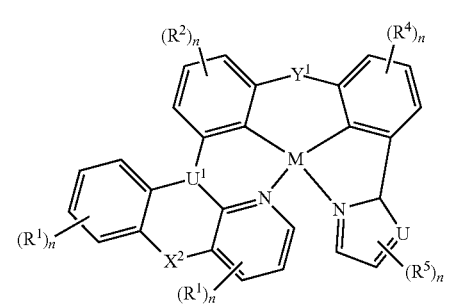
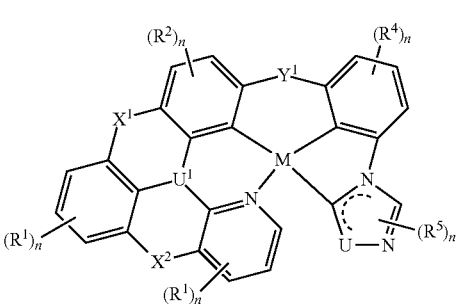

-continued
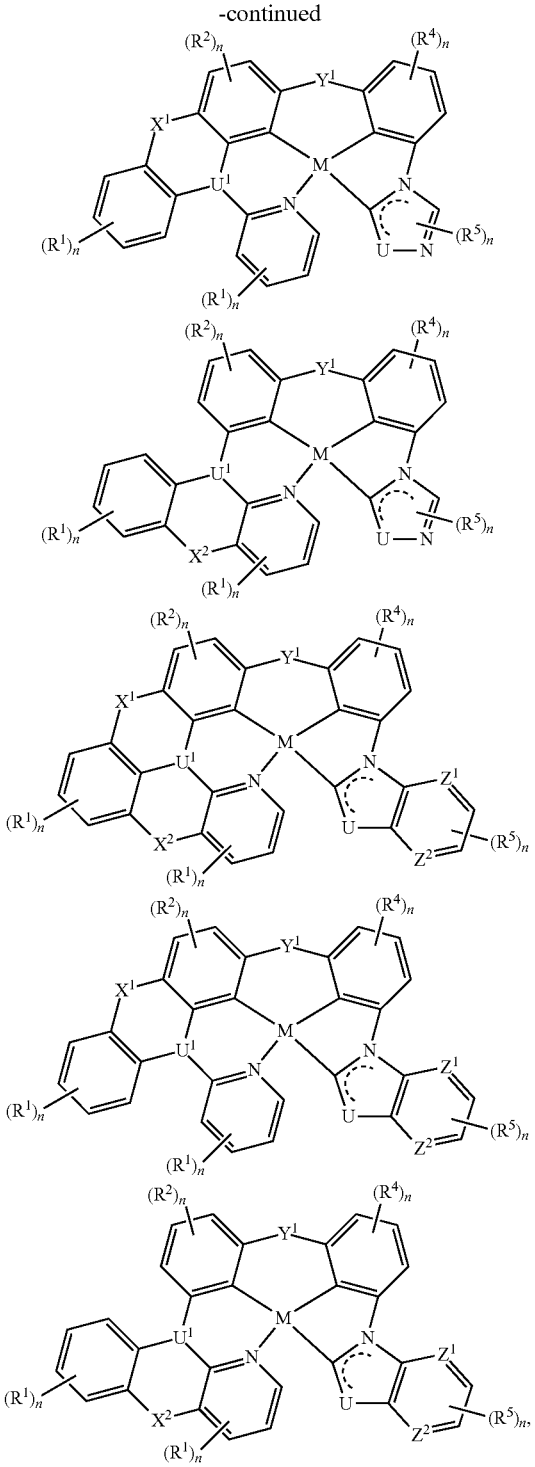
where:
U represents O, S, NR, or PR;
$Y^1$ is $Y^{1f}$;
$U^1$ is $Y^{3f}$;
Z represents O, S, SO, S(O)$_2$, NR, PR, CR$_2$, SiR$_2$, or BR;
$Z^1$ represents CH or N;
$Z^2$ represents CH or N; and
$R^7$ represents hydrogen, halogen, hydroxyl, nitro, thiol, or substituted or unsubstituted C$_1$-C$_4$ alkyl, alkoxy, amino, or aryl.
5. The complex of claim 1, represented by one of the following structures:
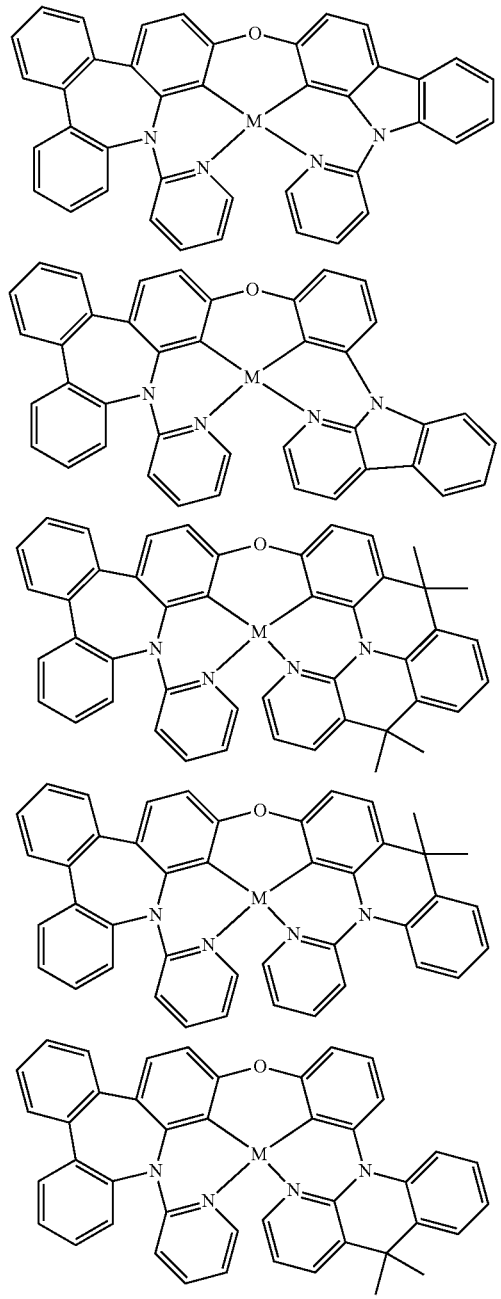
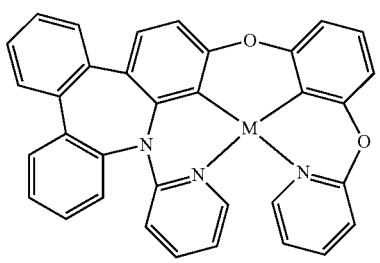

165
-continued
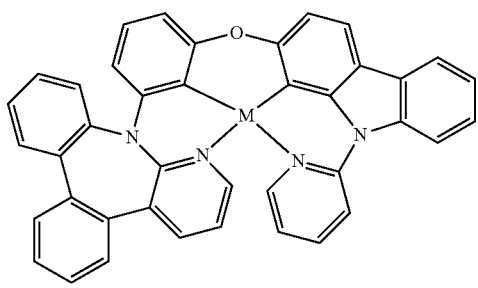
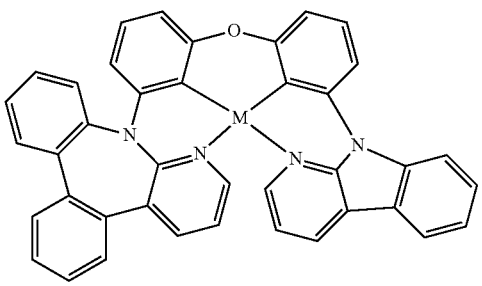
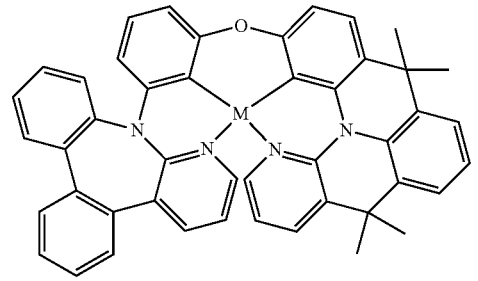
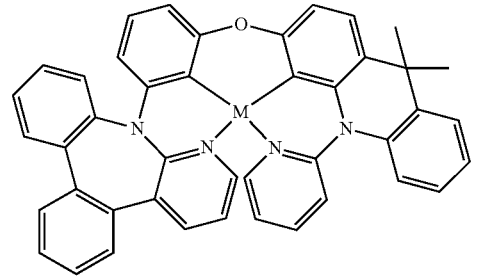
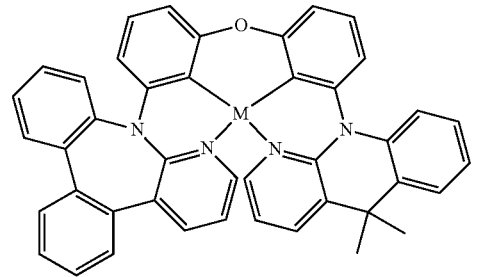
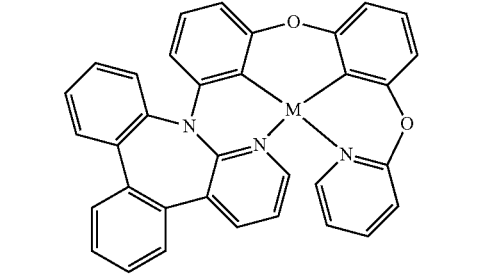
166
-continued
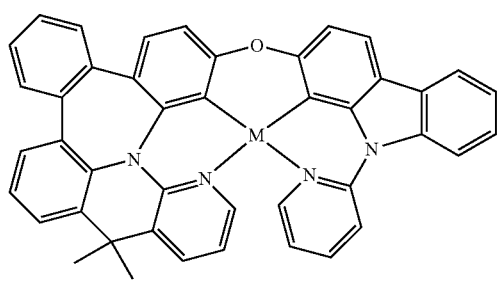
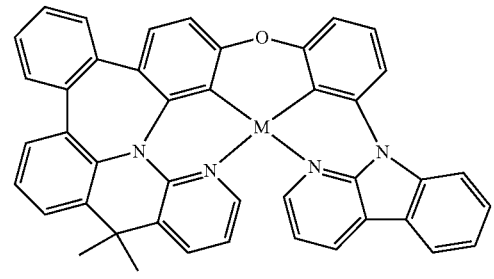
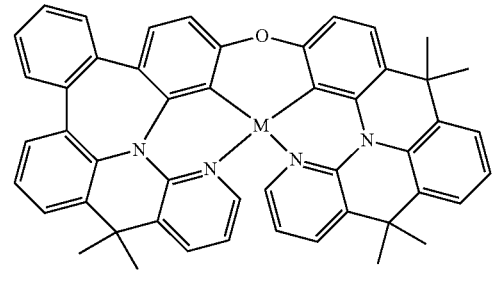
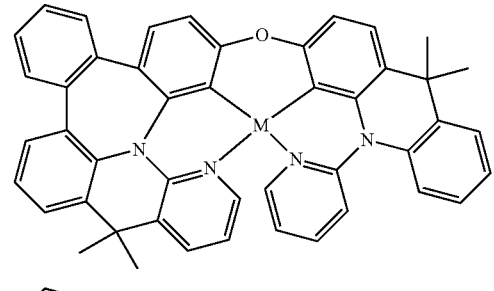
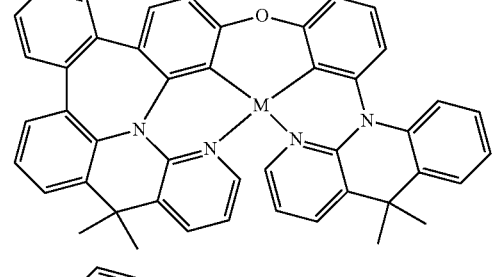
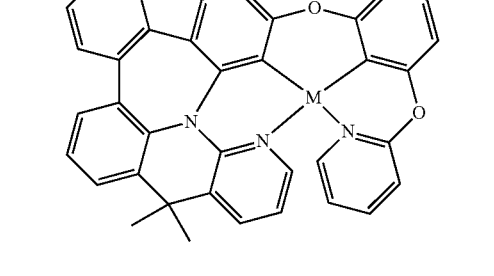

167
-continued
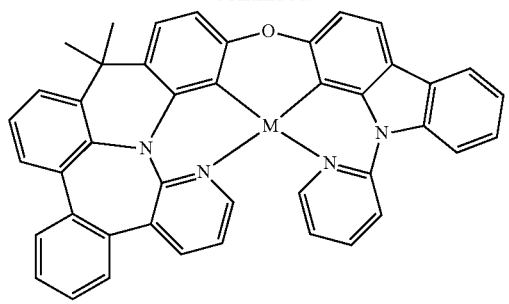
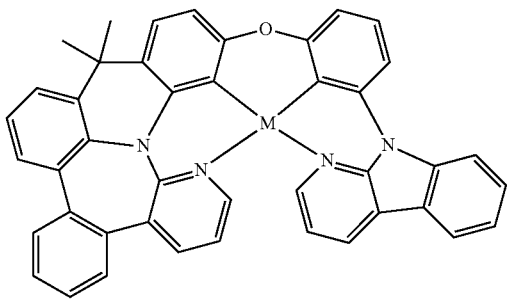
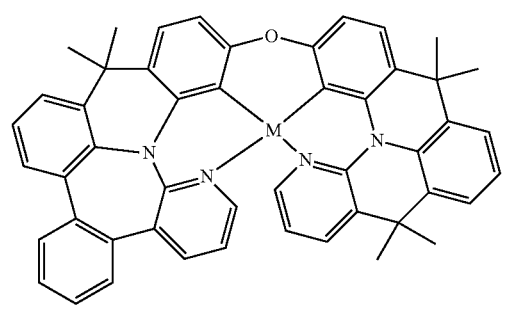
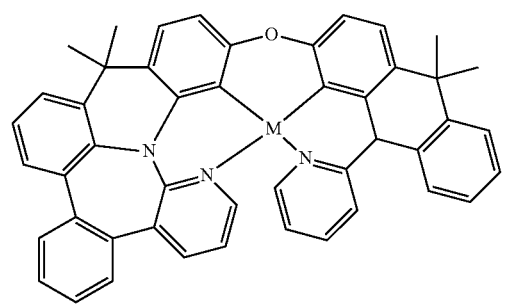
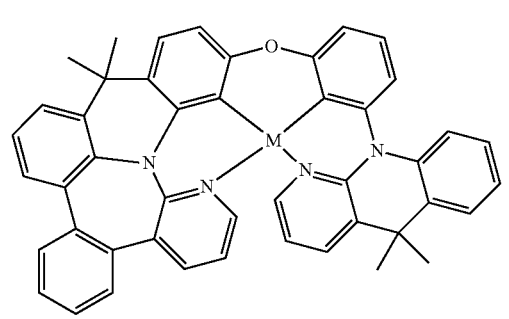
168
-continued
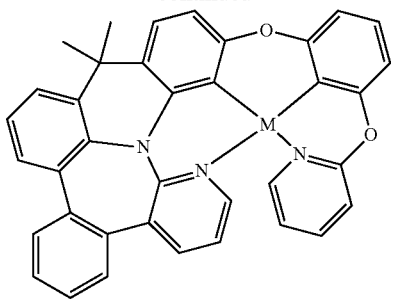
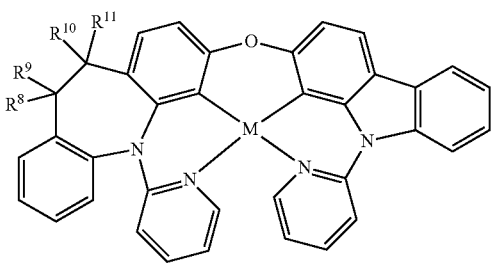
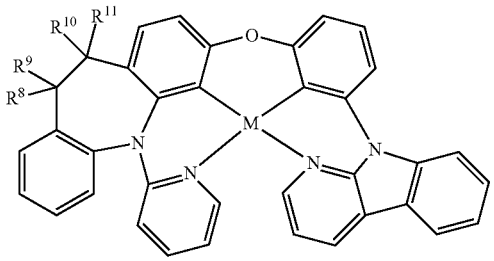
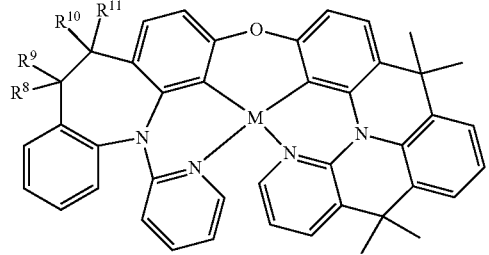
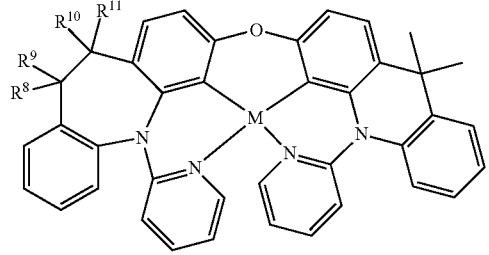
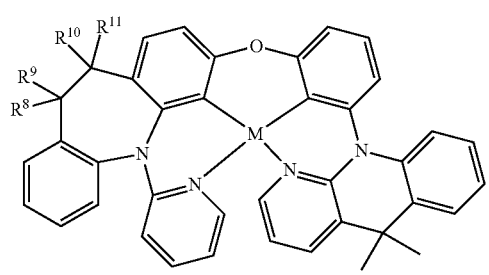

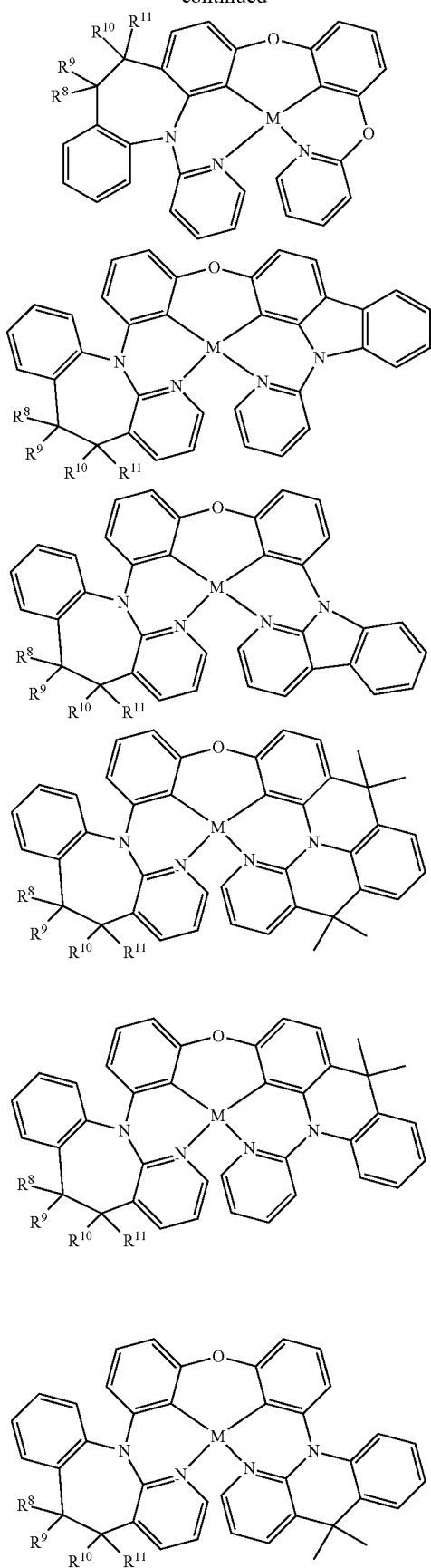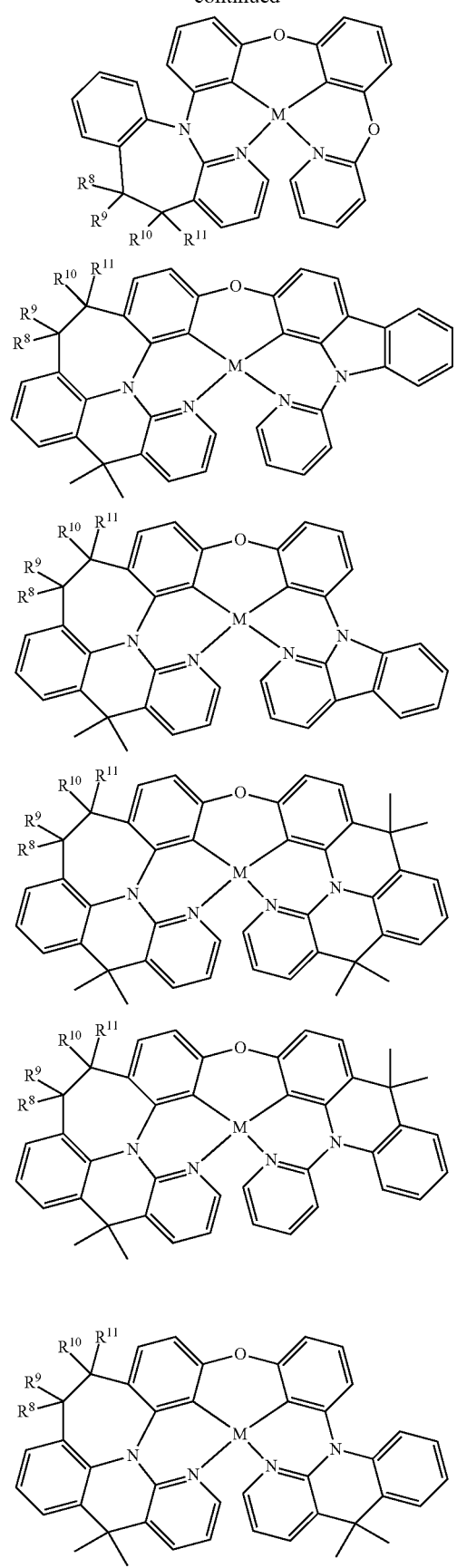

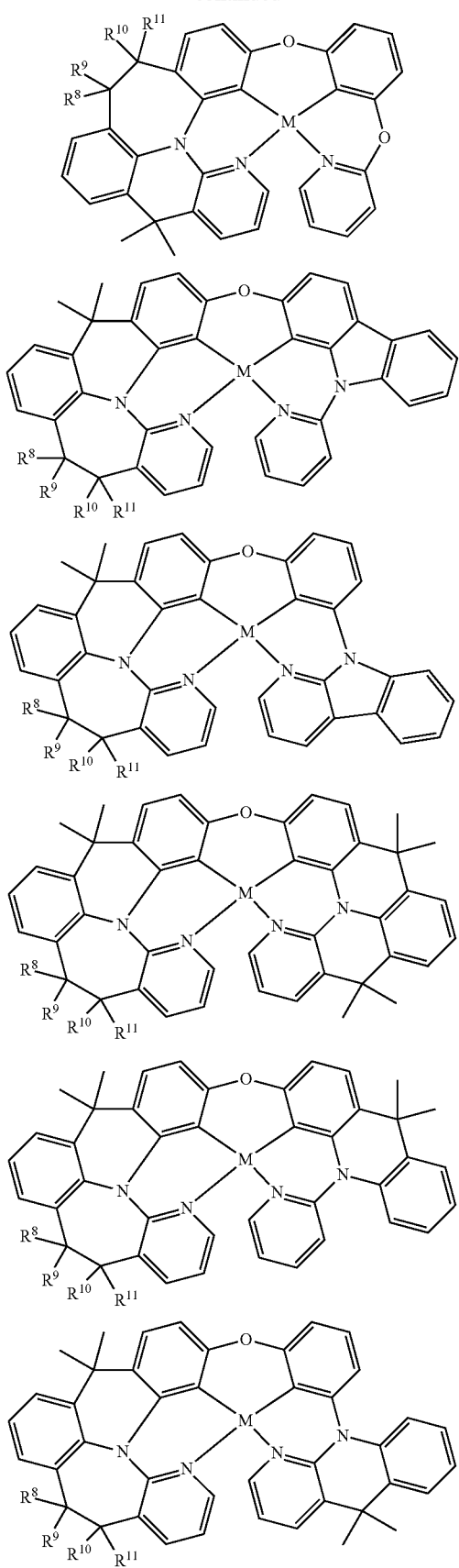
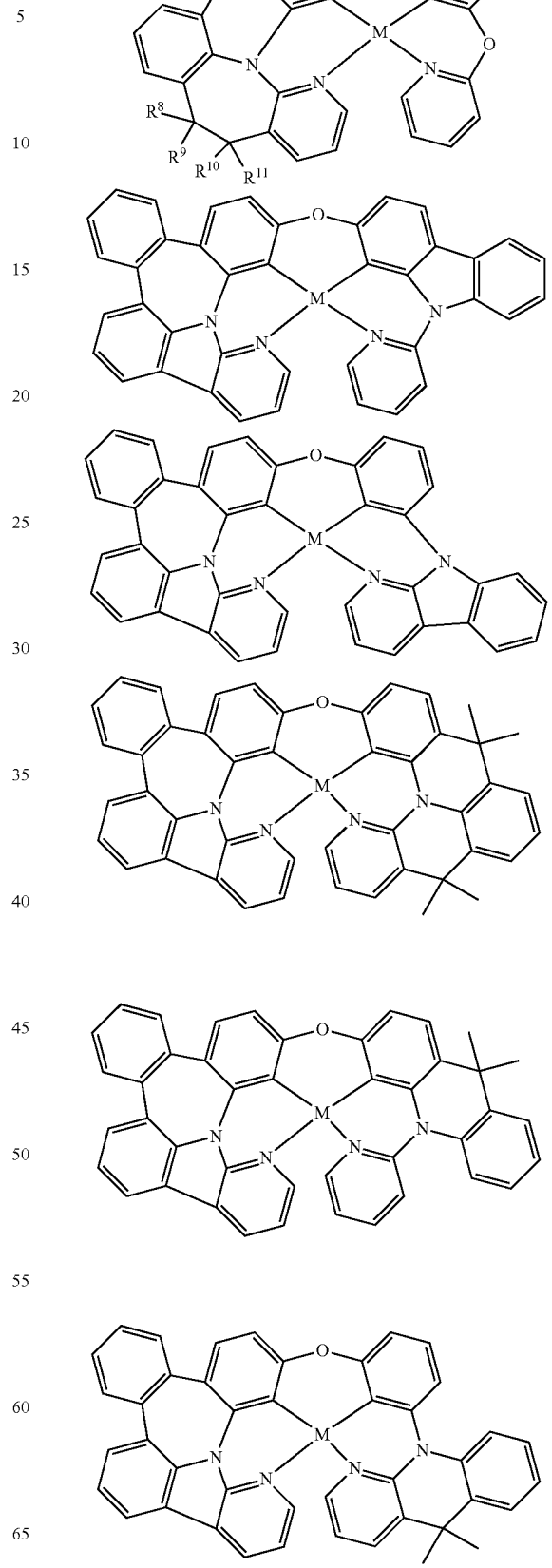

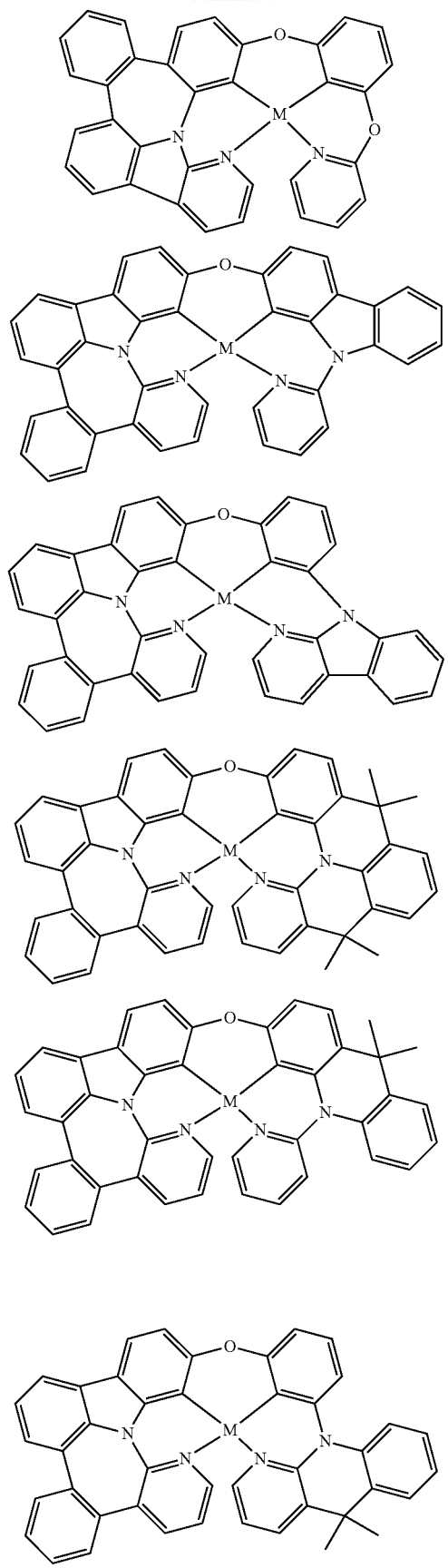

175
-continued
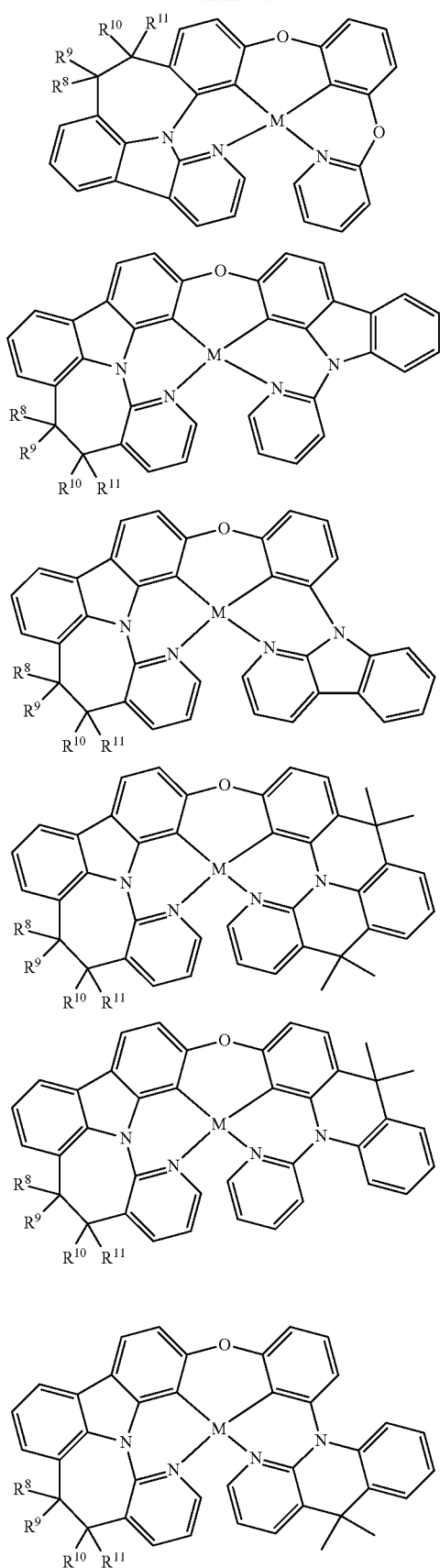
176
-continued
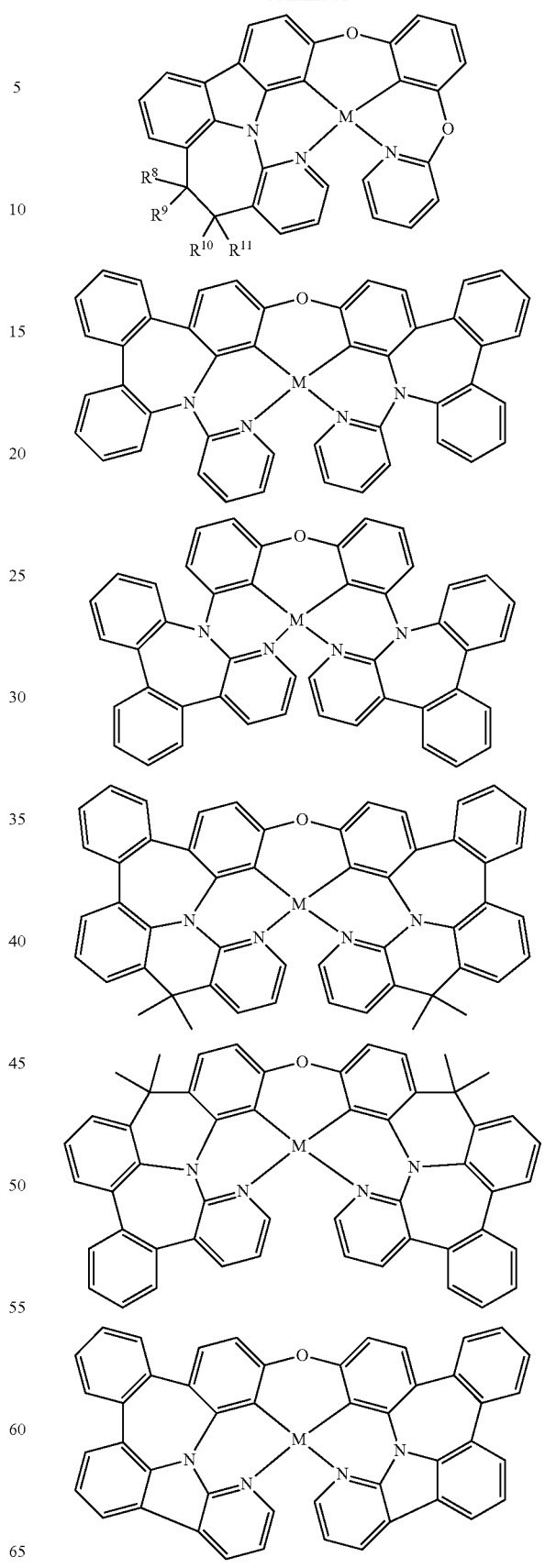

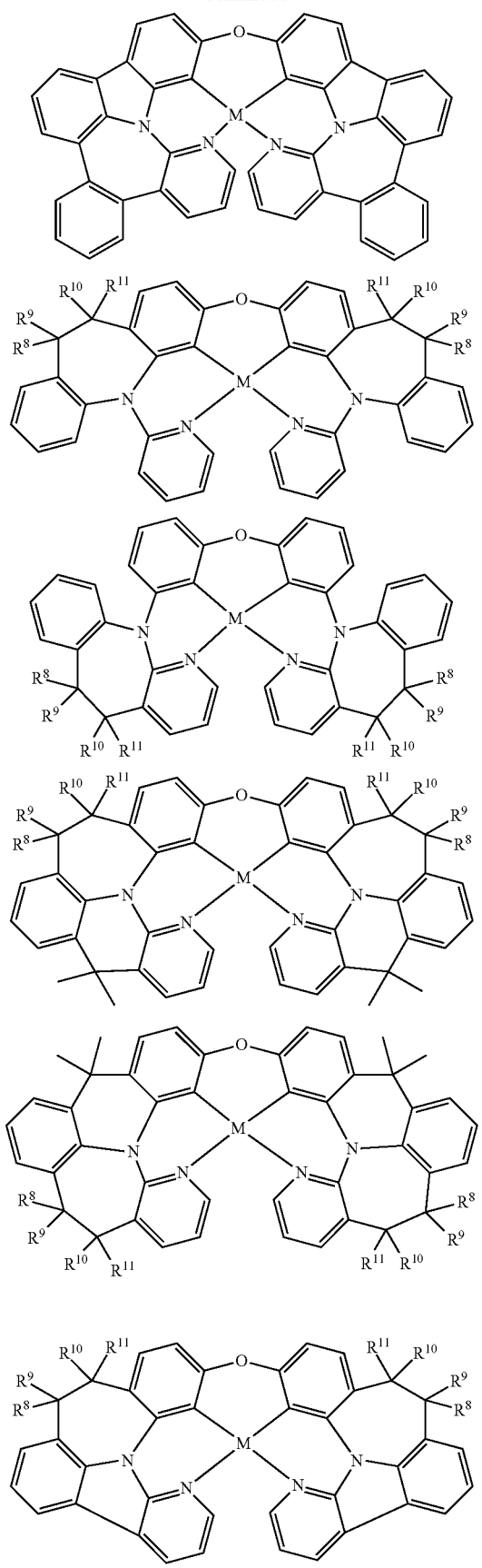
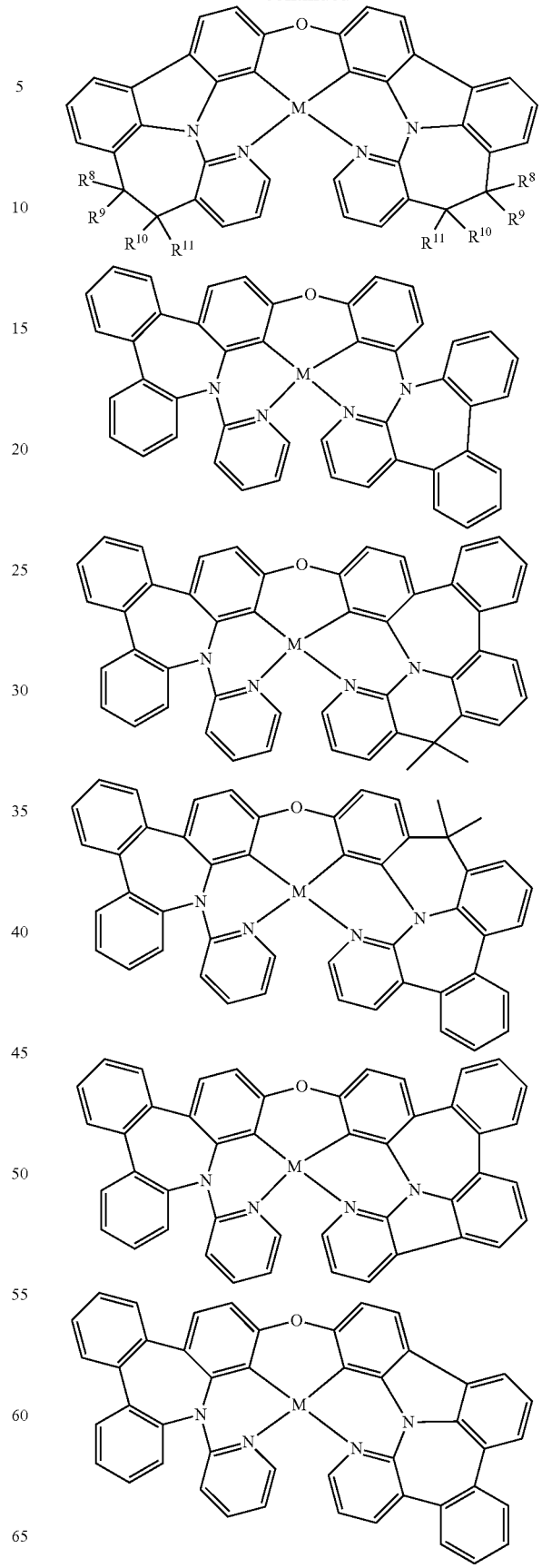

179
-continued
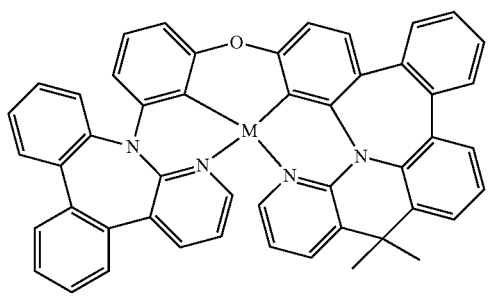
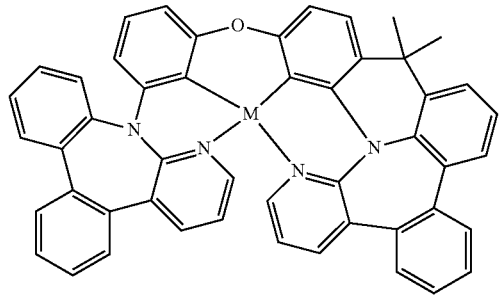
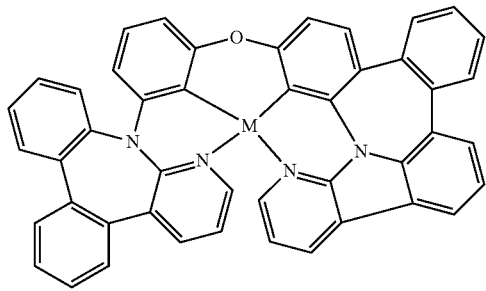
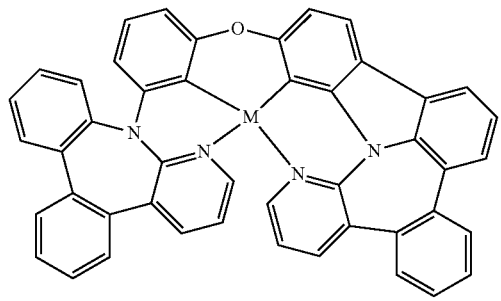
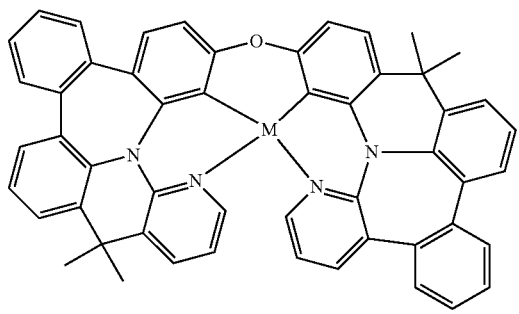
180
-continued
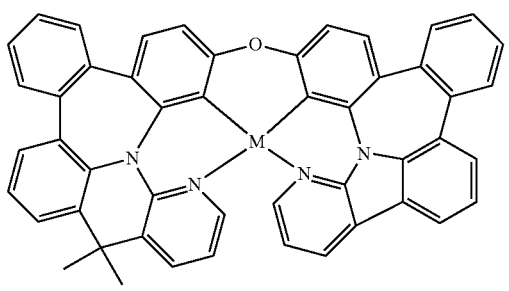
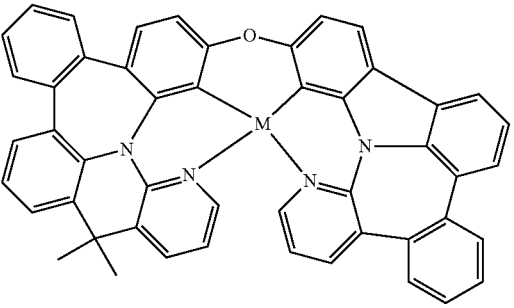
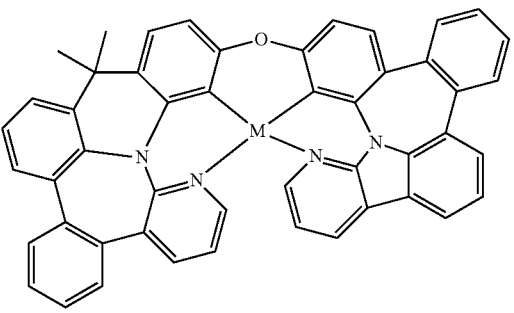
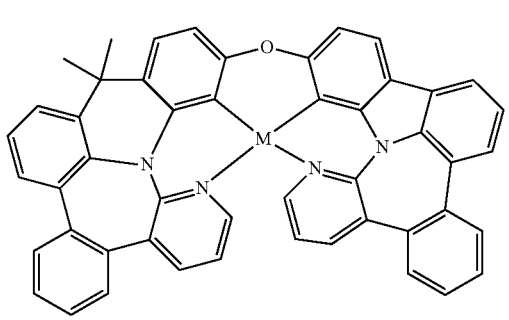
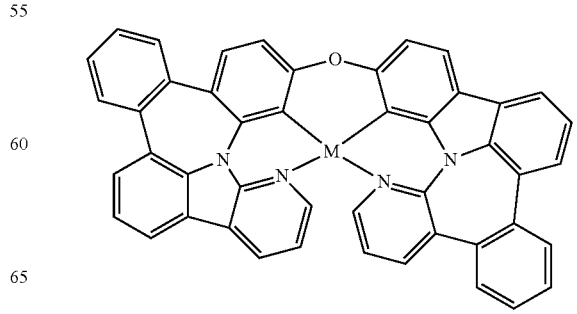

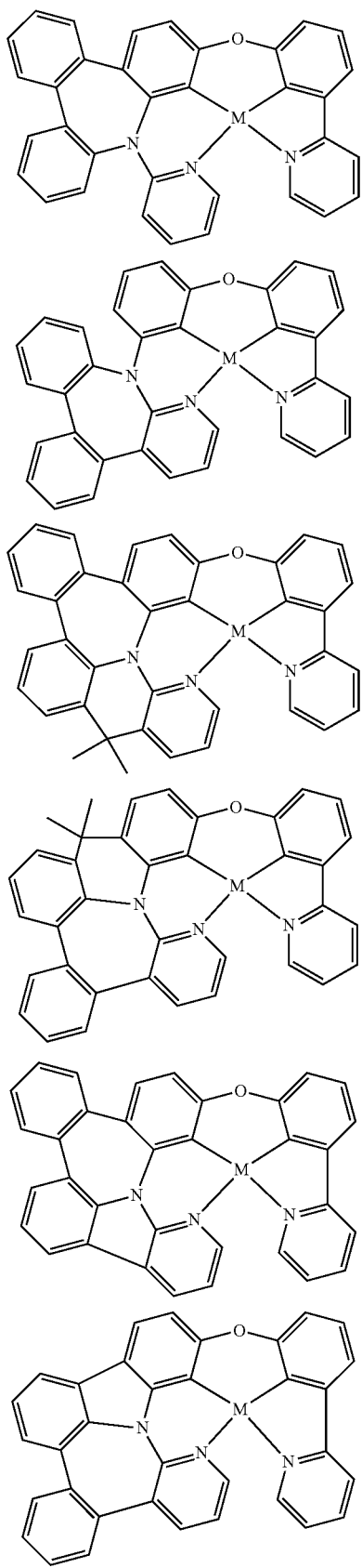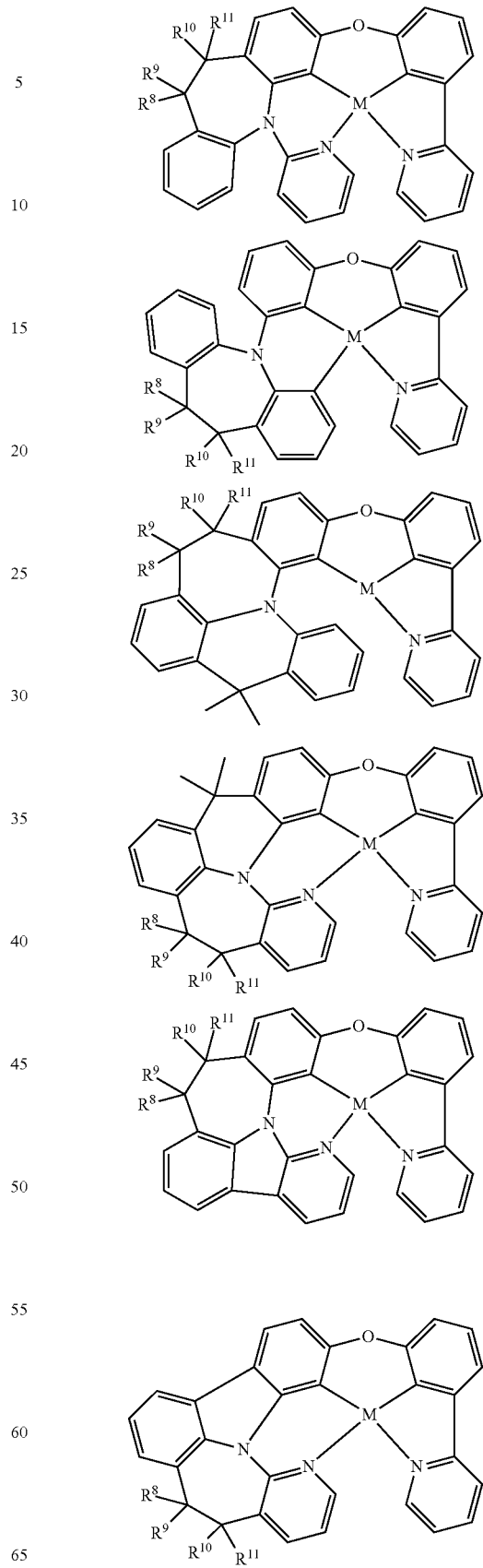

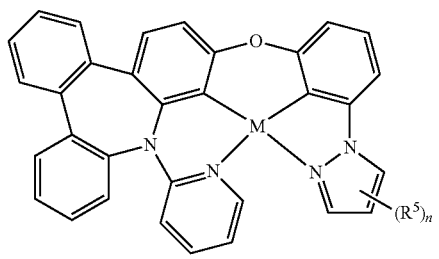
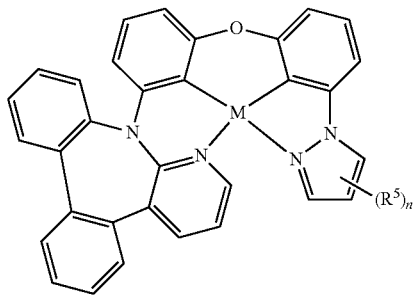
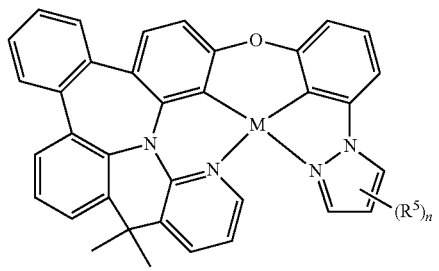
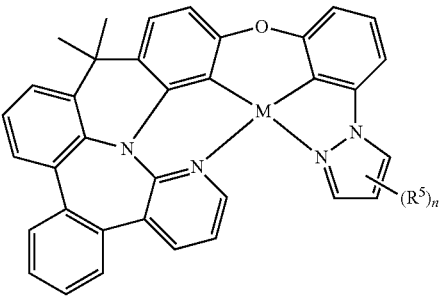
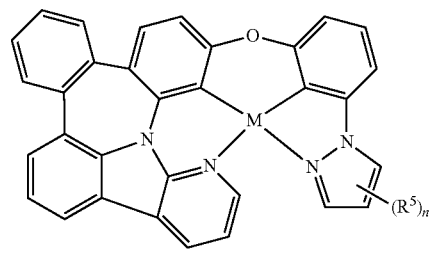
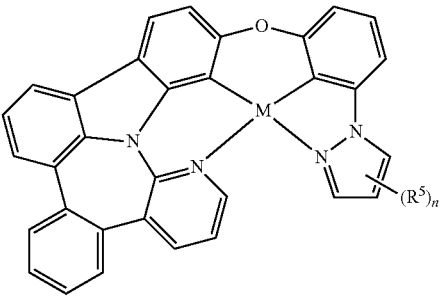
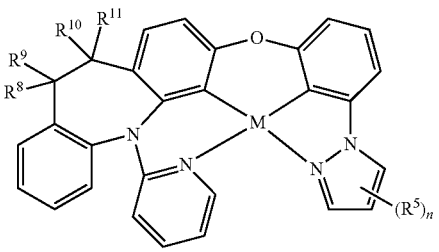
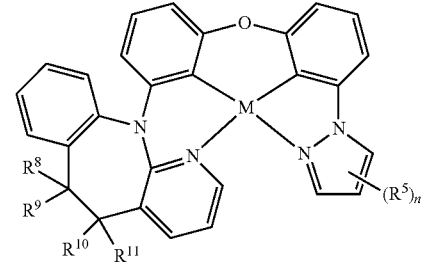
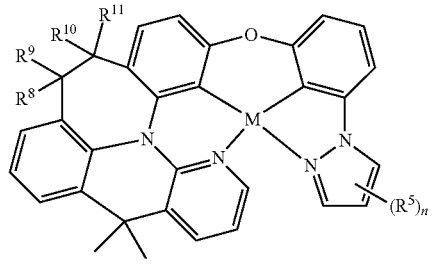
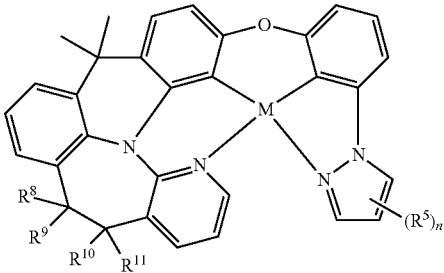
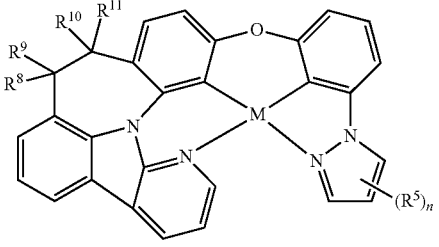
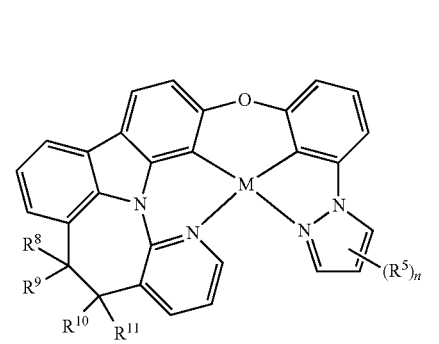

185
-continued
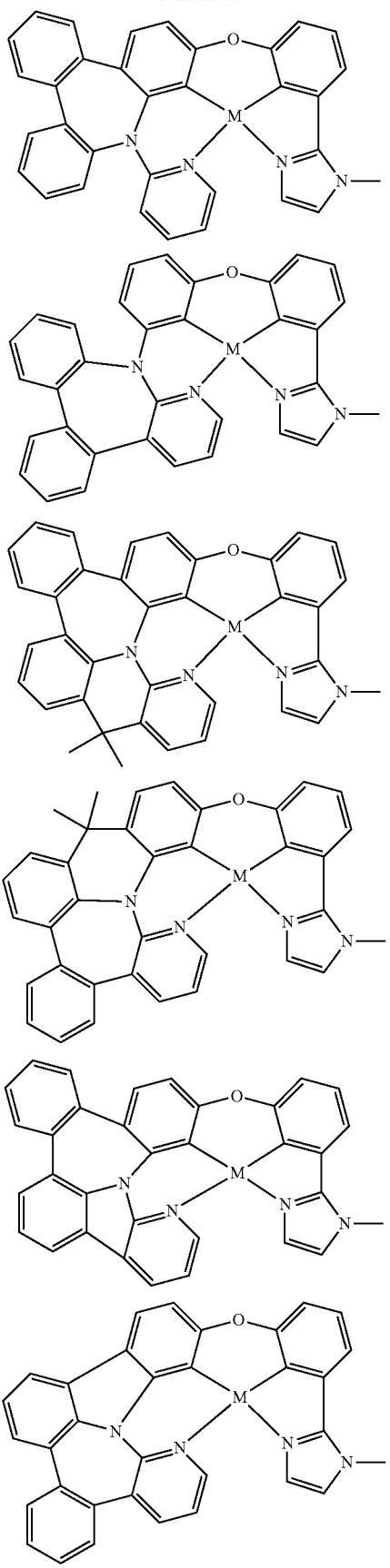
186
-continued
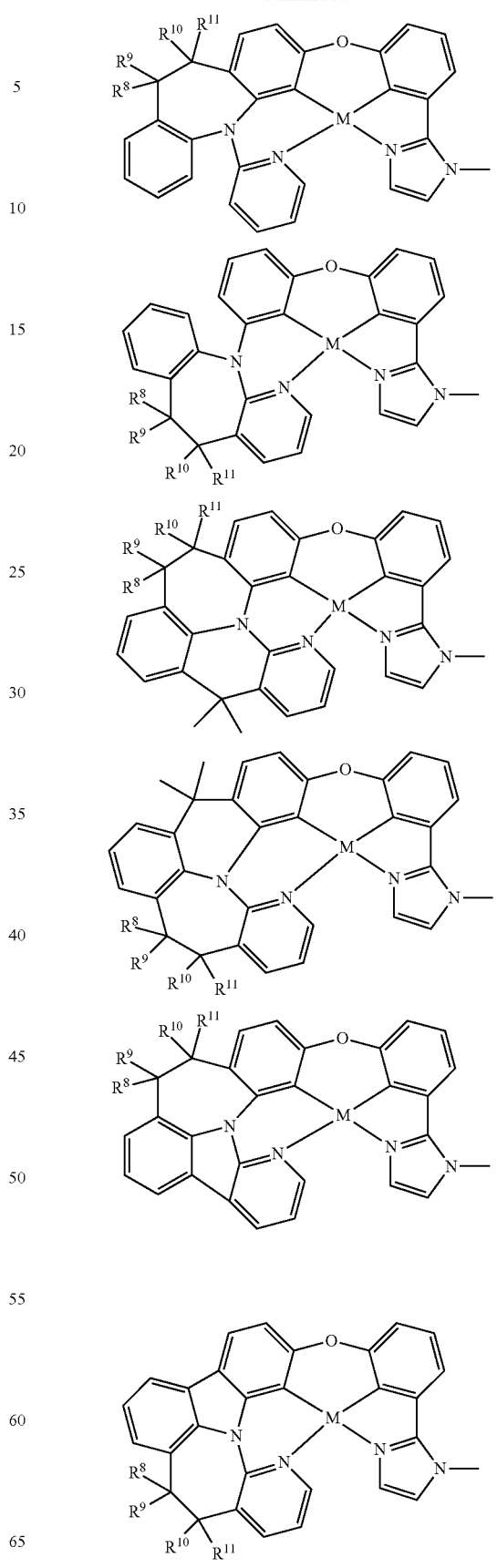

187
-continued
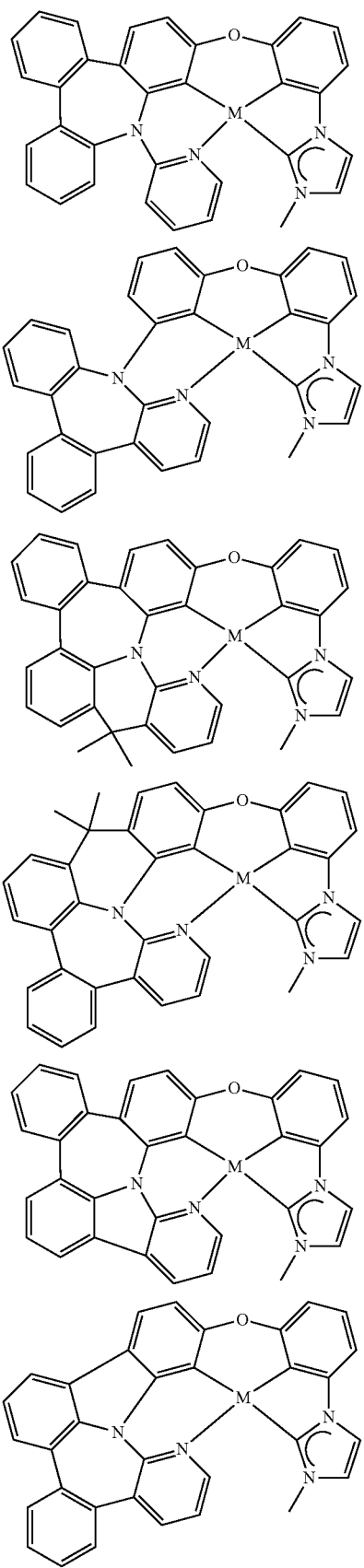
188
-continued
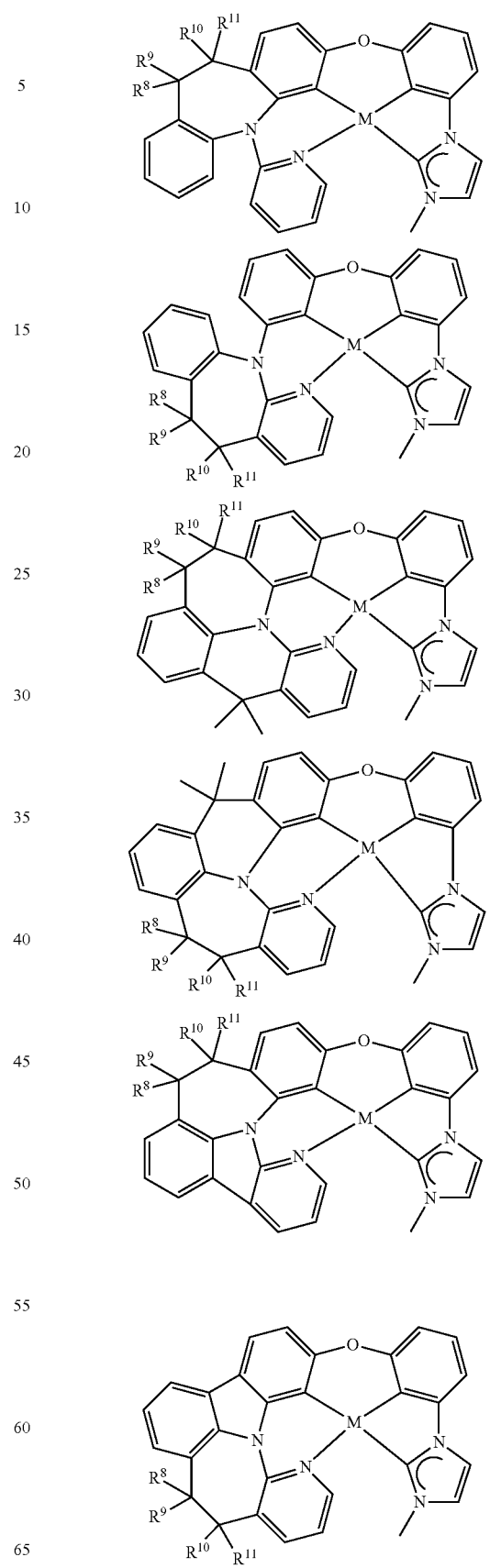

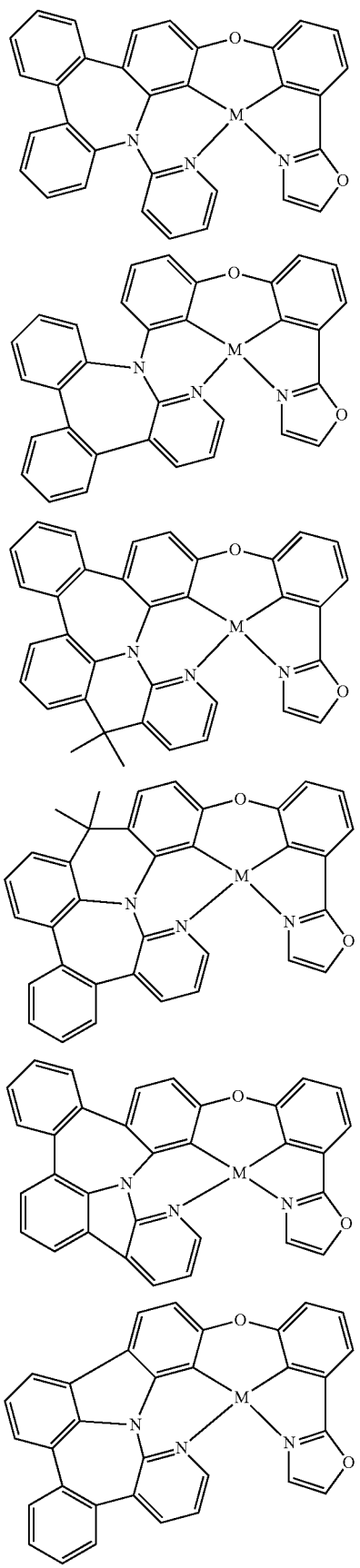
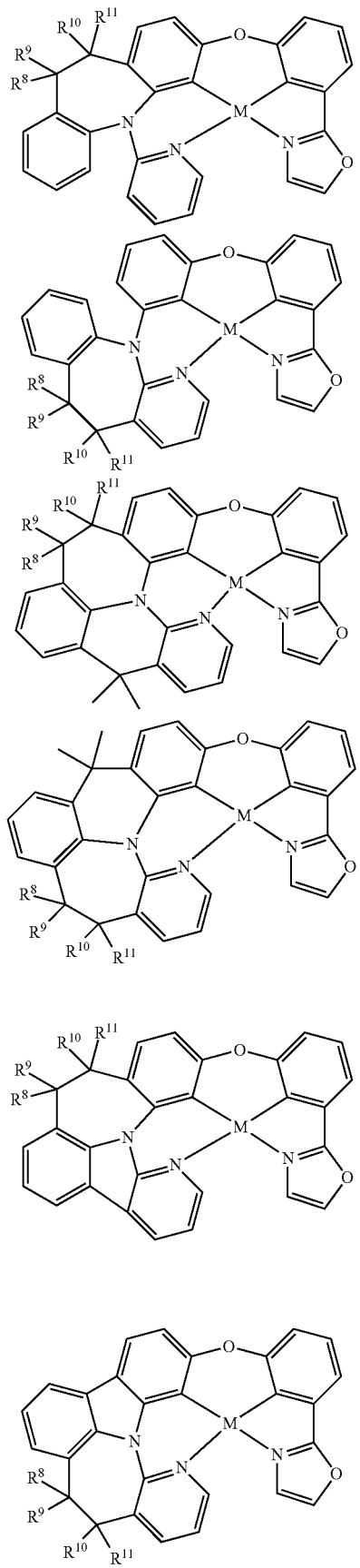

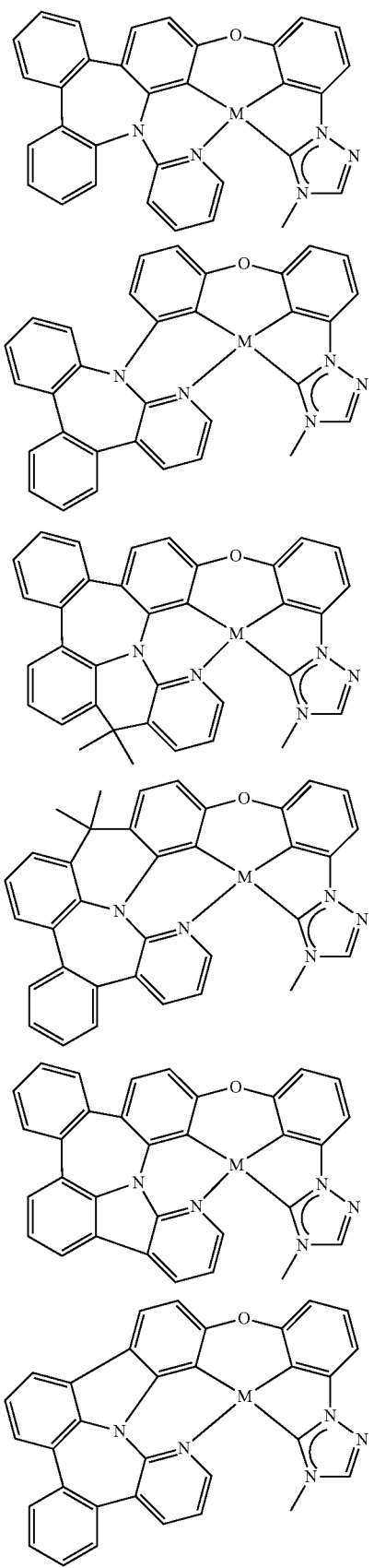
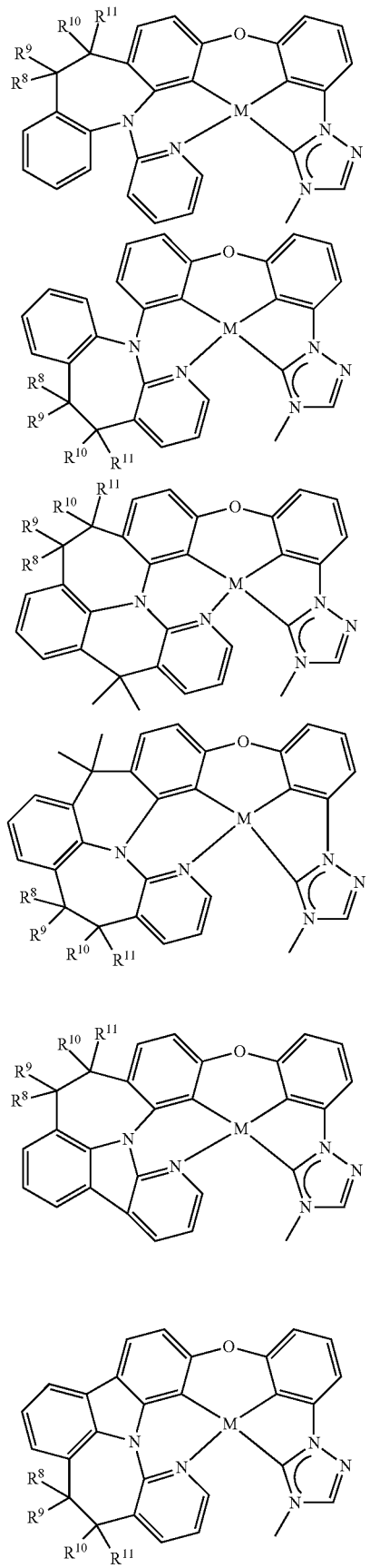

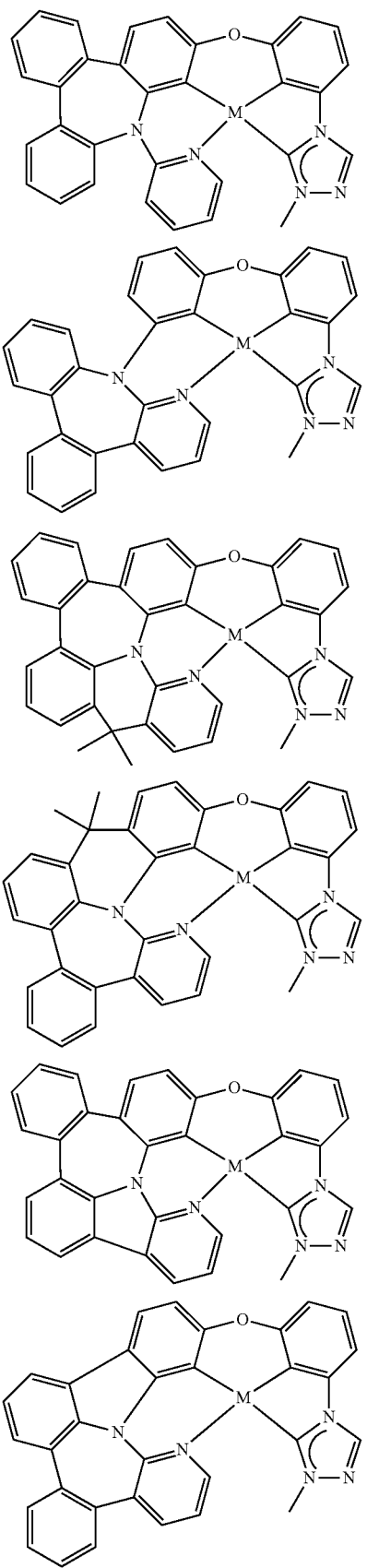
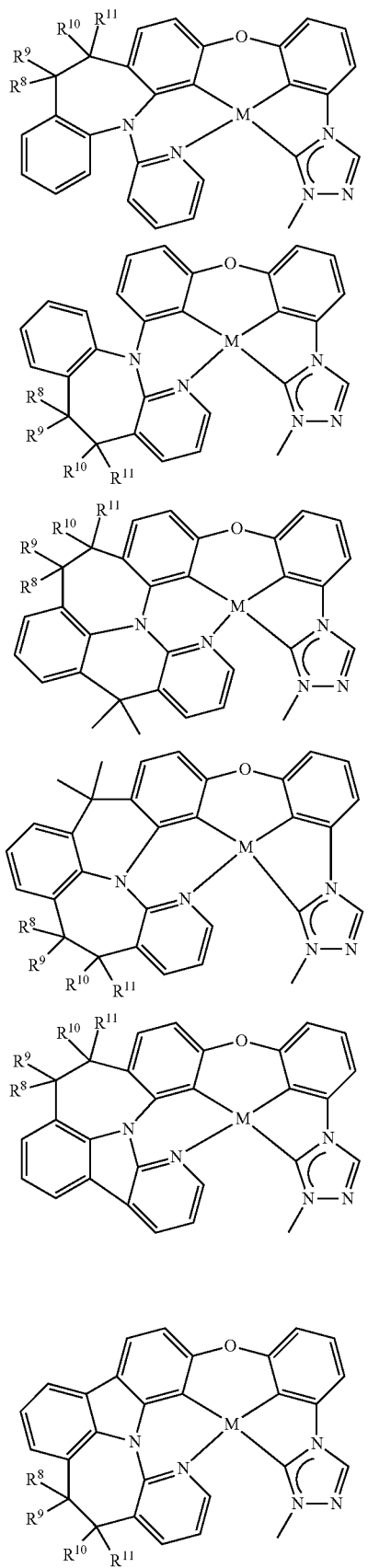

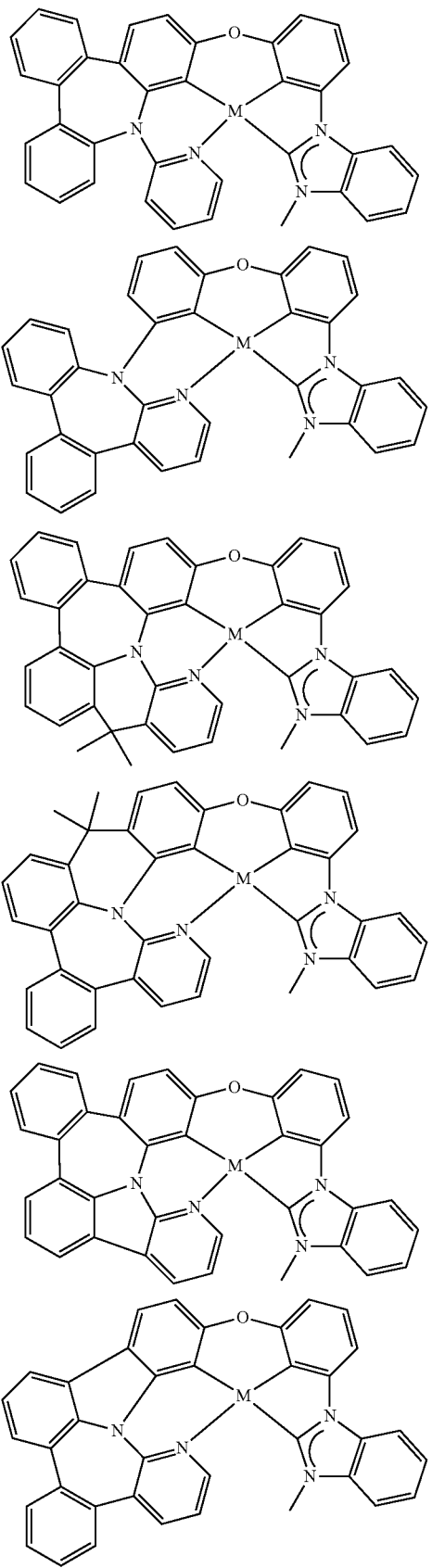
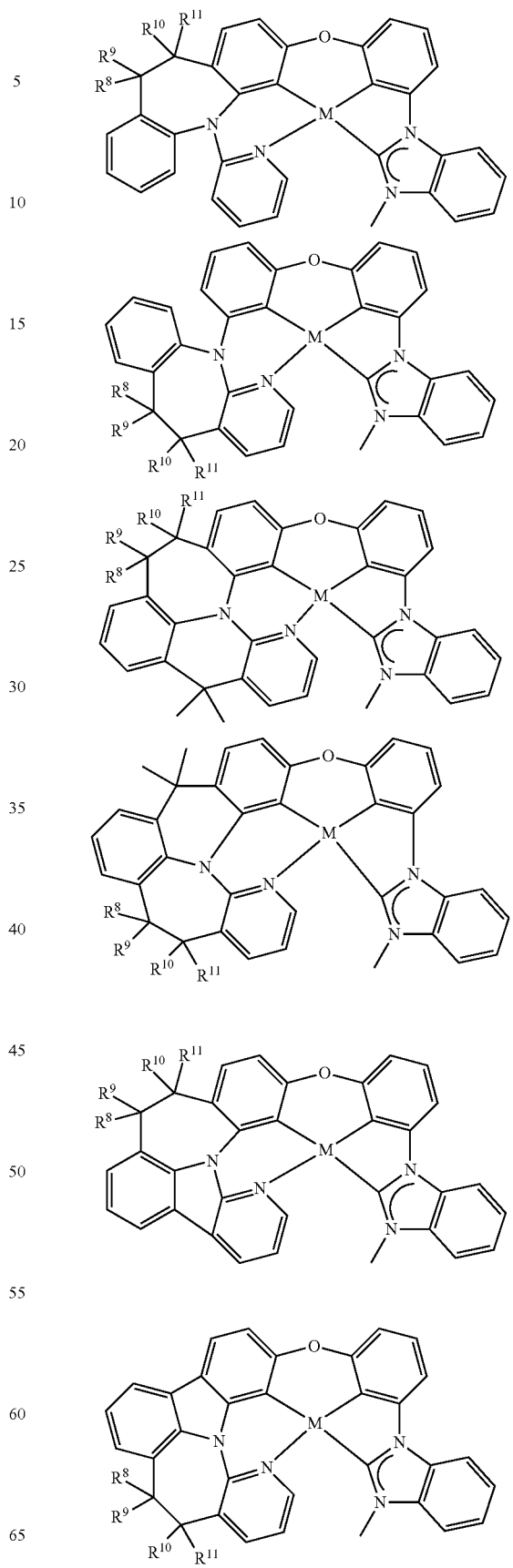

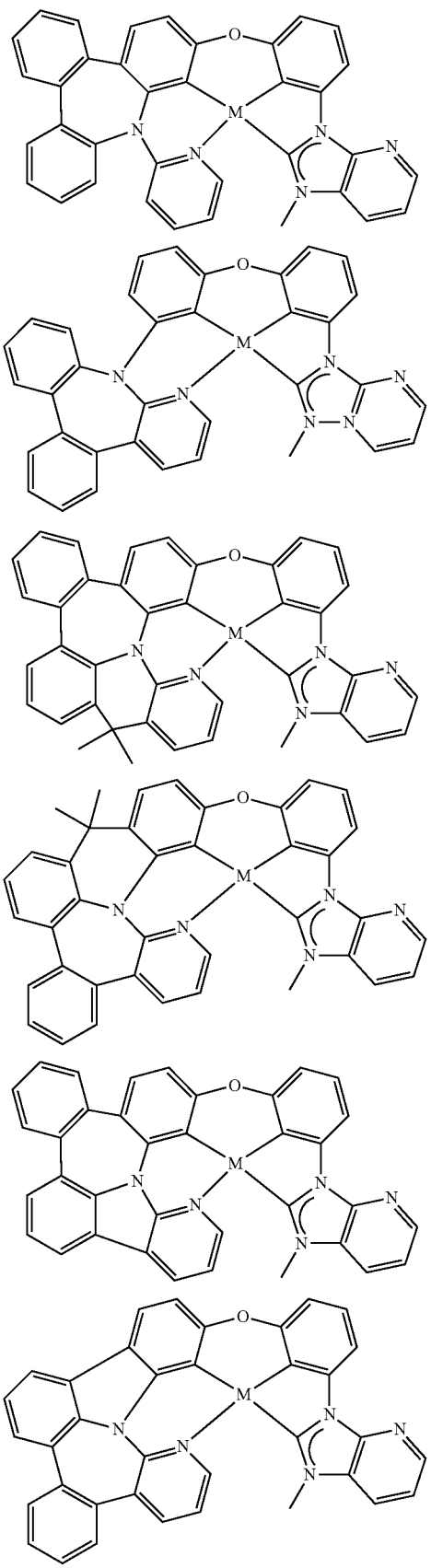
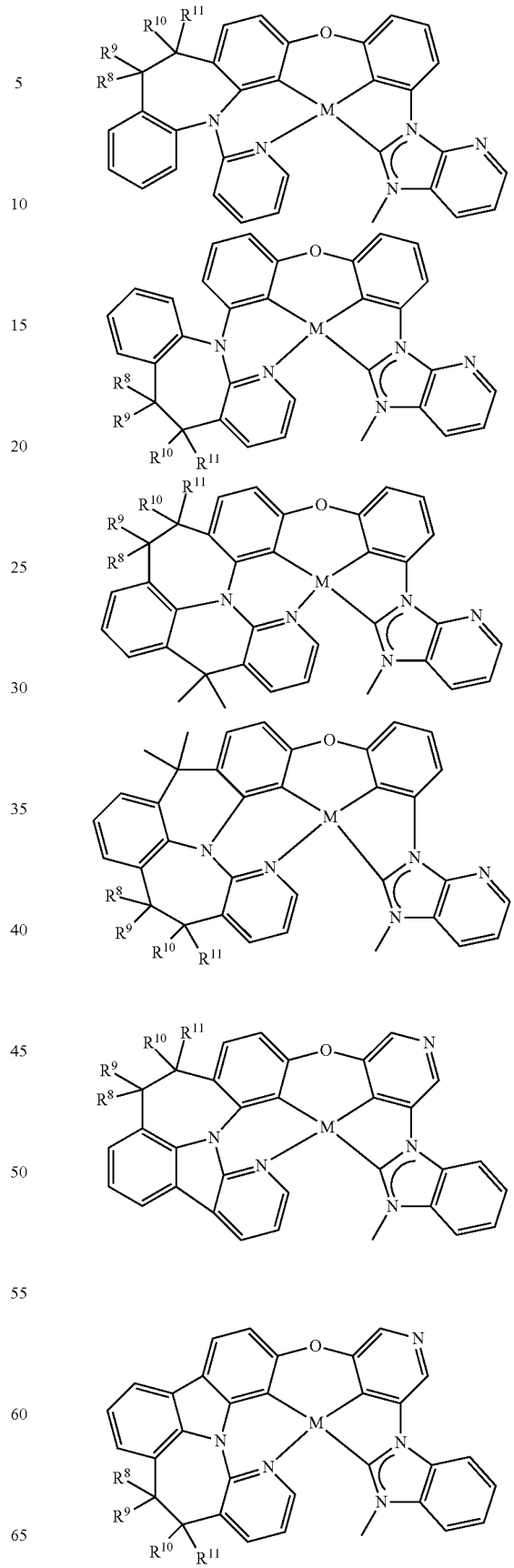

199
-continued
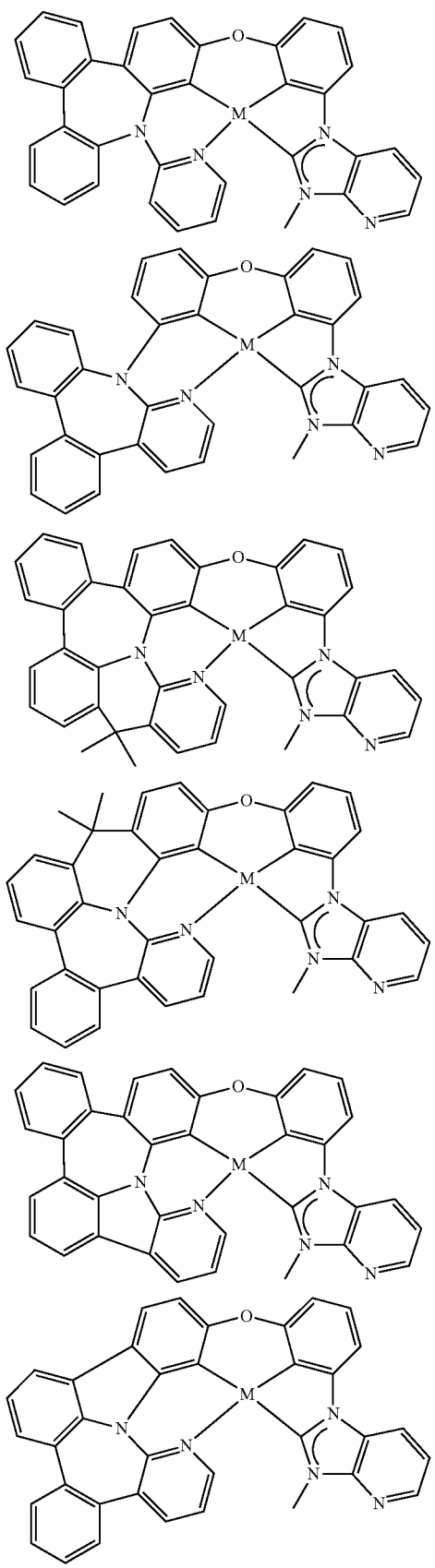
200
-continued
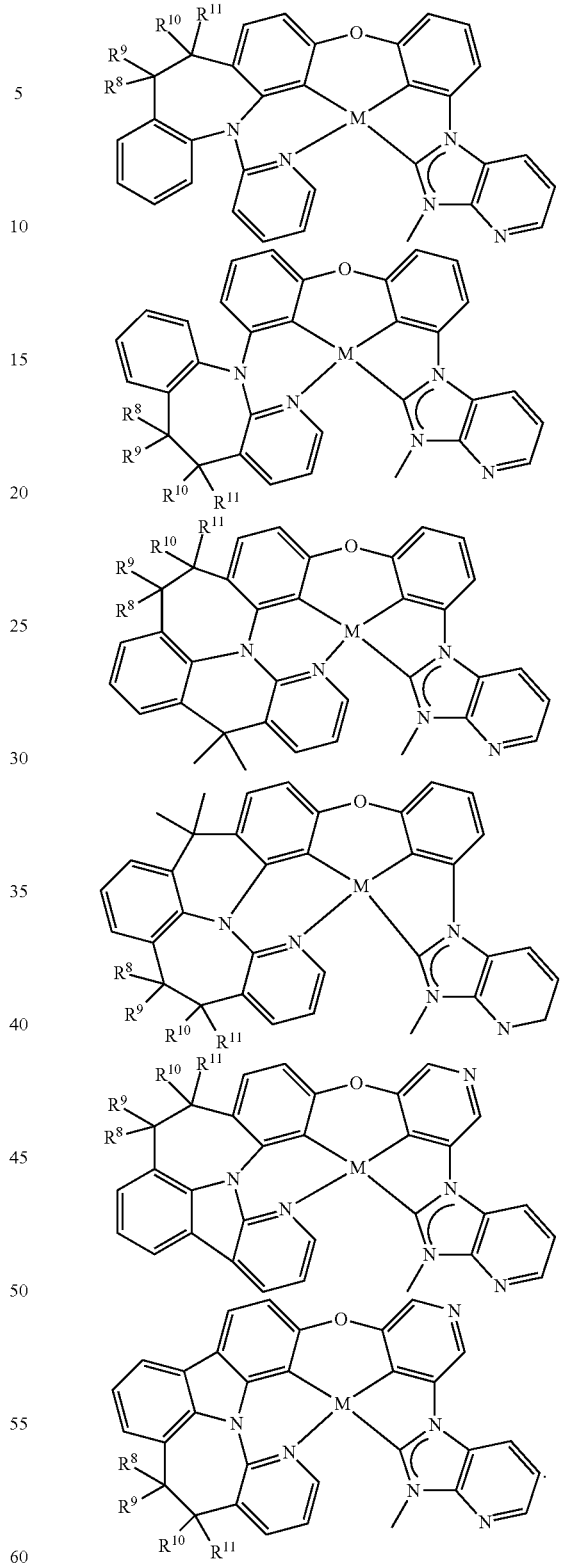
6. A light emitting device comprising the complex of claim 1.
7. An organic light emitting device comprising the complex of claim 1.
8. The organic light emitting device of claim 7, wherein the device is a phosphorescent organic light emitting device.

9. A photovoltaic device comprising the complex of claim 1.

10. A luminescent display device comprising the complex of claim 1.

* * * * *